(12) United States Patent
Barton et al.

(10) Patent No.: US 11,441,128 B2
(45) Date of Patent: Sep. 13, 2022

(54) METHANOL DEHYDROGENASE FUSION PROTEINS

(71) Applicant: Genomatica, Inc., San Diego, CA (US)

(72) Inventors: Nelson R. Barton, San Diego, CA (US); Jingyi Li, San Diego, CA (US); Joseph R. Warner, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 449 days.

(21) Appl. No.: 15/771,973

(22) PCT Filed: Oct. 27, 2016

(86) PCT No.: PCT/US2016/059096
§ 371 (c)(1),
(2) Date: Apr. 27, 2018

(87) PCT Pub. No.: WO2017/075208
PCT Pub. Date: May 4, 2017

(65) Prior Publication Data
US 2019/0085303 A1    Mar. 21, 2019

Related U.S. Application Data

(60) Provisional application No. 62/260,189, filed on Nov. 25, 2015, provisional application No. 62/249,032, filed on Oct. 30, 2015.

(51) Int. Cl.
| | |
|---|---|
| *C12N 9/00* | (2006.01) |
| *C12N 9/10* | (2006.01) |
| *C12N 9/90* | (2006.01) |
| *C12N 9/88* | (2006.01) |
| *C12N 15/52* | (2006.01) |
| *C12N 9/04* | (2006.01) |
| *C12P 7/24* | (2006.01) |

(52) U.S. Cl.
CPC ......... *C12N 9/0006* (2013.01); *C12N 9/1029* (2013.01); *C12N 9/88* (2013.01); *C12N 9/90* (2013.01); *C12N 15/52* (2013.01); *C12P 7/24* (2013.01); *C12Y 101/02007* (2013.01); *C12Y 203/01085* (2013.01); *C12Y 401/02013* (2013.01); *C12Y 401/02043* (2013.01); *C12Y 503/01027* (2013.01); *C07K 2319/00* (2013.01)

(58) Field of Classification Search
CPC .... C12N 15/52; C12P 7/62; C12P 7/16; C12P 7/40
See application file for complete search history.

(56) References Cited

U.S. PATENT DOCUMENTS

| | | | |
|---|---|---|---|
| 6,280,972 B1 | 8/2001 | Yaseuda | |
| 6,440,711 B1 | 8/2002 | Dave | |
| 6,558,933 B2 | 5/2003 | Donald et al. | |
| 9,346,902 B2 | 5/2016 | Burgard et al. | |
| 9,518,278 B2 | 12/2016 | Liao et al. | |
| 2015/0050708 A1* | 2/2015 | Burgard | C12N 15/52 435/158 |
| 2015/0104854 A1 | 4/2015 | Singh et al. | |
| 2016/0060635 A1* | 3/2016 | Liao | C12Y 202/01003 435/190 |

FOREIGN PATENT DOCUMENTS

| | | |
|---|---|---|
| CN | 105 255 804 A | 1/2016 |
| WO | 2009141607 A1 | 11/2009 |
| WO | 2013110797 A1 | 8/2013 |

(Continued)

OTHER PUBLICATIONS

Elleuche et al. (2015) "Bringing functions together with fusion enzymes—from nature's inventions to biotechnological applications", Appl. Microbiol. Biotechnol., 99:1545-1556.
Anthony, C. (1991) "Assimilation of Carbon by Methylotrophs", Biology of Methylotrophs, 18; pp. 79-109.
Brautaset, et al. (2004) "Plasmid-Dependent Methylotrophy in Thermotolerant Bacillus methanolicus", Journal of Bacteriology, 186(5); pp. 1229-1238.
Krog et al. (2013) "Methylotrophic Bacillus Methanolicus Encodes Two Chromosomal and One Plasmid Born NAD+ Dependent Methanol Dehydrogenase Paralogs with Different Catalytic and Biochemical Properties", PLOS ONE, 8(3), pp. 1-11.

(Continued)

*Primary Examiner* — Maryam Monshipouri
(74) *Attorney, Agent, or Firm* — Kagan Binder, PLLC

(57) ABSTRACT

Described herein are fusion proteins including methanol dehydrogenase (MeDH) and at least one other polypeptide such as 3-hexulose-6-phosphate dehydrogenase (HPS) or 6-phospho-3-hexuloisomerase (PHI), such as DHAS synthase or fructose-6-Phosphate aldolase or such as DHA synthase or DHA kinase. In a localized manner, the fusion protein can promote the conversion of methanol to formaldehyde and then to a ketose phosphate such as hexulose 6-phosphate or then to DHA and G3P. When expressed in cells, the fusion proteins can promote methanol uptake and rapid conversion to the ketose phosphate or to the DHA and D3P, which in turn can be used in a pathway for the production of a desired bioproduct. Beneficially, the rapid conversion to the ketose phosphate or to the DHA and G3P can avoid the undesirable accumulation of formaldehyde in the cell. Also described are engineered cells expressing the fusion protein, optionally include one or more additional metabolic pathway transgene(s), methanol metabolic pathway genes, target product pathway genes, cell culture compositions including the cells, methods for promoting production of the target product or intermediate thereof from the cells, compositions including the target product or intermediate, and products made from the target product or intermediate.

13 Claims, 10 Drawing Sheets
Specification includes a Sequence Listing.

(56) References Cited

FOREIGN PATENT DOCUMENTS

| WO | 2014/152434 A2 | 9/2014 |
| WO | 2015051298 A2 | 4/2015 |
| WO | 2015/108777 A1 | 7/2015 |

OTHER PUBLICATIONS

Kloosterman et al. (2002) "Molecular, Biochemical, and Functional Characterization of a Nudix Hydrolase Protein That Stimulates the Activity of a Nicotinoprotein Alcohol Dehydrogenase", J. Biol. Chem. 277, pp. 34785-34792.
Culpepper et al. (2014) "Structure and Protein-Protein Interactions of Methanol Dehydrogenase from Methylococcus capsulatus (Bath)", Biochemistry, 53, pp. 6211-6219.
Song et al. (2010) "Overexpression of an HPS/PHI fusion enzyme from Mycobacterium gastri in chloroplasts of geranium enhances its ability to assimilate and phytoremediate formaldehyde", Biotechnol Lett, 32, pp. 1541-1548.
Orita et al. (2007) "Bifunctional enzyme fusion of 3-hexulose-6-phosphate synthase and 6-phospho-3-hexuloisomerase", Appl. Microbiol Biotechnol., 76, pp. 439-444.
Hektor, H.J., et al. (2002) "Identification of a Magnesium-dependent NAD(P)(H)-binding Domain in the Nicotinoprotein Methanol Dehydrogenase from Bacillus methanolicus", Journal of Biological Chemistry, 277, pp. 46966-46973.
Ochsner, et al. (2014) "In Vitro Activation of NAD-Dependent Alcohol Dehydrogenases by Nudix Hydrolases is more widespread than assumed", Federation of European Biochemcial Societies, 588, pp. 2993-2999.

* cited by examiner

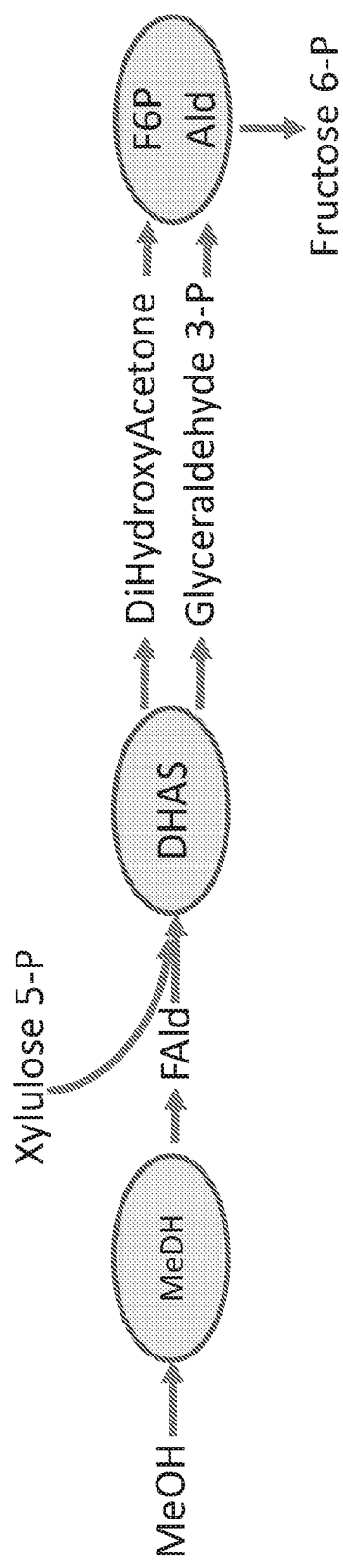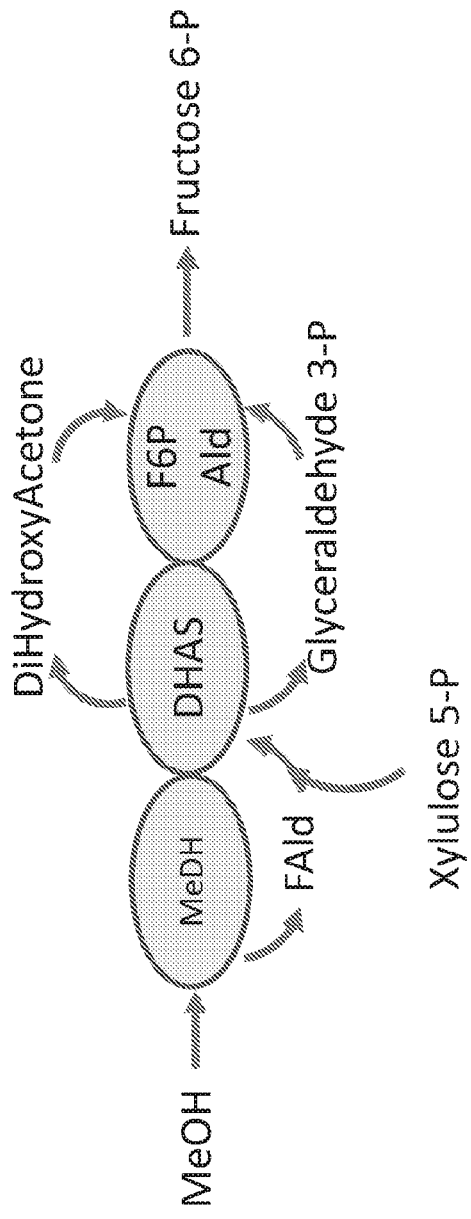
Figure 10A
Figure 10B

METHANOL DEHYDROGENASE FUSION PROTEINS

PRIORITY CLAIM

This application claims priority to International Application No. PCT/US2016/059096, filed Oct. 27, 2016, and titled "METHANOL DEHYDROGENASE FUSION PROTEINS", which claims the benefit of U.S. Provisional Patent Application Ser. No. 62/249,032, filed Oct. 30, 2015, and U.S. Provisional Patent Application Ser. No. 62/260,189, filed Nov. 25, 2015 the disclosures of which are incorporated in their entireties herein by reference. Also, the entire content of the ASCII text file entitled "GN00027US Sequence_Listing_V6.txt" created on Feb. 8, 2022, having a size of 243 kilobytes is incorporated herein by reference.

FIELD OF INVENTION

The disclosure is directed to fusion proteins containing methanol dehydrogenase and engineered cells expressing these fusions and methods for using methanol for production of a bioproduct.

BACKGROUND

In an intracellular metabolic pathway, metabolic intermediates are molecules which are the precursors of the pathway products, which are typically biologically significant molecules.

Various factors can affect the processing of metabolic intermediates in a product pathway. When there is a rate limiting event in the conversion of an intermediate into a subsequent metabolite, that intermediate may accumulate in the cell. In some cases the accumulation of an intermediate may adversely affect the cell. For example, accumulation of an intermediate may indirectly affect the cell by diverting intracellular energy resources, or by reducing the production of a biologically important product. In other cases, the accumulation of metabolic intermediates may have a direct adverse effect on the cell. For example, at elevated concentrations, small molecules such as methylglyoxal or formaldehyde can non-specifically modify intracellular proteins and have an adverse effect on cell health.

Alcohol dehydrogenases (ADHs; EC 1.1.1.1) promote the conversion of alcohols to and aldehydes or ketones, typically along with the reduction of nicotinamide adenine dinucleotide ($NAD^+$ to NADH). ADHs are instrumental in the generation of important compounds having aldehyde, ketone, and alcohol groups during biosynthesis of various metabolites. However, some of these compounds, such as aldehyde-containing compounds, include formaldehyde which, when accumulated in the cell, can be problematic.

One class of alcohol dehydrogenase is methanol dehydrogenases (MeDHs). MeDHs, converts methanol (MeOH) to formaldehyde (Fald), may be used in an enzymatic pathway engineered into a microbe to enable MeOH as a sole carbon source or as a co-carbon source with other feed stocks such as, for example, glucose, dextrose, plant biomass or syngas, to produce valuable products. Microorganisms have been that metabolize methanol, and in some instances do so via methanol dehydrogenase, and in even fewer instances produce valuable products. Increasing MeDH activity will enable improved use of MeOH, improving MeOH as a sole carbon source, decreasing production costs, decreasing amounts of any more expensive secondary or co-carbon source, e.g. glucose, increasing product yields, and providing faster rate of MeOH use.

SUMMARY

The current invention is directed towards fusion proteins that include methanol dehydrogenase activity and at least one other activity that promotes formaldehyde fixation. For example, the fusion can include activities which promote the conversion of methanol to formaldehyde and then from formaldehyde to a ketose phosphate such as hexulose 6-phosphate, or fructose-6-phosphate. Alternatively, for example, the fusion can include activities which promote the conversion of methanol to formaldehyde and then from formaldehyde to dihydroxyacetone (DHA) and glycerladehyde-3-phosphate (G3P), and then to fructose-6-phosphate. The current invention is also directed to engineered cells that express such fusion proteins, as well as engineered cells having a heterologous methanol dehydrogenase in combination with a fusion protein that promotes formaldehyde fixation. The engineered cells can display increased methanol uptake, through increased expression of the methanol dehydrogenase fusion and/or by using active variants, or through increased efficiency of fixation of formaldehyde into ketose phosphate compounds as a result of the fusion. And while this promotes increased formation of formaldehyde, the formaldehyde is more rapidly fixed into ketose phosphate compounds such as hexulose 6-phosphate, or fructose-6-phosphate, or to DHA and G3P, due to the localization of the enzymatic activities because of the fusion proteins. Therefore, undesirable levels of formaldehyde do not build up in the cell and cause adverse effects on growth.

Further, the increased flux and formation of ketose phosphate compounds, or to DHA and G3P, can provide precursors to the glycolysis pathway. In turn, increased glycolysis can provide increases in the pools of subsequent intermediate compounds such as glycerol 3-phosphate, pyruvate, and acetyl-CoA. These intermediate compounds can be used by product pathways for forming desired (target) bioproducts such as butanediols (BDOs) like 1,3-butanediol (1,3-BDO) and 1,4-butanediol (1,4-BDO), 4-hydroxybutyrate (4-HB), butadiene, 6-amino caproic acid (6ACA), hexamethylenediamine (HMDA), adipic acid, croytl alcohol, methyl vinyl carbinol, 3-buten-1-ol, 1,2-propanediol (propylene glycol), n-propanol, 1,3-propanediol, etc. Therefore, the fusions can be expressed in cells that naturally have such product pathways, or cells engineered to express the fusion proteins can further be engineered to include target product pathway enzymes that use the increased amounts of intermediate products available when the fusion proteins of the disclosure are expressed.

The fusion proteins of the invention improve the ability of a microorganism to grow on methanol as a carbon source. The improved growth on methanol using methanol pathway fusions is likely due to several benefits the fusions provide: 1) rapid conversion of formaldehyde, a potentially toxic product of the MeDH reaction, to hexulose-6-phosphate (or alternatively to DHA and G3P) due to the localized presence of fused HPS; 2) increased efficiency of the fusion protein(s) in the methanol pathway reduces the amount of total methanol pathway protein required for efficient methanol utilization; 3) the presence of methanol pathway fusion proteins pushes the reaction in the forward, desired direction with respect to methanol utilization.

In embodiments the invention provides a fusion protein comprising: (1a) a first region comprising methanol dehydrogenase or an enzymatically active portion thereof, and (1b) a second region comprising 3-hexulose-6-phosphate dehydrogenase or an enzymatically active portion thereof; (2a) a first region comprising methanol dehydrogenase or an enzymatically active portion thereof, (2b) a second region comprising 3-hexulose-6-phosphate dehydrogenase or an enzymatically active portion thereof; and (2c) a third region comprising methanol dehydrogenase activator or an enzymatically active portion thereof; (3a) a first region comprising methanol dehydrogenase or an enzymatically active portion thereof, and (3b) a second region comprising 6-phospho-3-hexuloisomerase or an enzymatically active portion thereof; (4a) a first region comprising methanol dehydrogenase or an enzymatically active portion thereof, (4b) a second region comprising 3-hexulose-6-phosphate dehydrogenase or an enzymatically active portion thereof; and (4c) a third region comprising methanol dehydrogenase activator or an enzymatically active portion thereof; (5a) a first region comprising methanol dehydrogenase or an enzymatically active portion thereof, (5b) a second region comprising 3-hexulose-6-phosphate dehydrogenase or an enzymatically active portion thereof; and (5c) a third region comprising 6-phospho-3-hexuloisomerase or an enzymatically active portion thereof; or (6a) a first region comprising methanol dehydrogenase or an enzymatically active portion thereof, (6b) a second region comprising 3-hexulose-6-phosphate dehydrogenase or an enzymatically active portion thereof; (6c) a third region comprising 6-phospho-3-hexuloisomerase or an enzymatically active portion thereof; and (6d) a fourth region comprising methanol dehydrogenase activator or an enzymatically active portion thereof; wherein the fusion protein optionally comprises one or more linker amino acid sequence(s) positioned between two or more of the first, second, and third regions of the fusion protein.

In an alternative embodiment directed to MeDH with one or more DHA pathway enzyme(s) fusion proteins, the invention provides a fusion protein comprising: (7a) a first region comprising methanol dehydrogenase or an enzymatically active portion thereof and (7b) a second region comprising DHA synthase or an enzymatically active portion thereof; (8a) a first region comprising methanol dehydrogenase or an enzymatically active portion thereof, (8b) a second region comprising DHA synthase or an enzymatically active portion thereof; and (8c) a third region comprising methanol dehydrogenase activator or an enzymatically active portion thereof; (9a) a first region comprising methanol dehydrogenase or an enzymatically active portion thereof, and (9b) a second region comprising a F6P aldolase or an enzymatically active portion thereof; (10a) a first region comprising methanol dehydrogenase or an enzymatically active portion thereof, (10b) a second region comprising DHA synthase or an enzymatically active portion thereof; and (10c) a third region comprising methanol dehydrogenase activator or an enzymatically active portion thereof; (11a) a first region comprising methanol dehydrogenase or an enzymatically active portion thereof, (11b) a second region comprising DHA synthase or an enzymatically active portion thereof; and (11c) a third region comprising F6P aldolase or an enzymatically active portion thereof; or (12a) a first region comprising methanol dehydrogenase or an enzymatically active portion thereof, (12b) a second region comprising DHA synthase or an enzymatically active portion thereof; (12c) a third region comprising F6P aldolase or an enzymatically active portion thereof; and (12d) a fourth region comprising methanol dehydrogenase activator or an enzymatically active portion thereof; wherein the fusion protein optionally comprises one or more linker amino acid sequence(s) positioned between two or more of the first, second, and third regions of the fusion protein.

Embodiments of the invention also include a nucleic acid encoding the MeDH-containing fusion protein (1-6) or (7-12), expression constructs comprising the nucleic acid, engineered cells comprising the MeDH-containing fusion protein (1-6) or (7-12), such as engineered cells comprising exogenous nucleic acids that express the fusion protein (1-6) or (7-12), and methods for producing a target product or an intermediate thereof comprising culturing the engineered cell comprising the MeDH-containing fusion protein (1-6) or (7-12).

The invention also provides fusion proteins where the methanol dehydrogenase is split into at least two portions separated by at least one regions of 3-hexulose-6-phosphate dehydrogenase, 6-phospho-3-hexuloisomerase, or/and methanol dehydrogenase activator, or alternatively separated by at least one region(s) of DHAS, F6P aldolase, or/and methanol dehydrogenase activator. In this embodiment the invention provides a fusion protein comprising first and second portions of a methanol dehydrogenase, and one or more of 3-hexulose-6-phosphate dehydrogenase or an enzymatically active portion thereof, 6-phospho-3-hexuloisomerase or an enzymatically active portion thereof, or methanol dehydrogenase activator or an enzymatically active portion thereof, positioned between the first and second portions of a methanol dehydrogenase; or alternatively in this embodiment the invention provides a fusion protein comprising first and second portions of a methanol dehydrogenase, and one or more of DHAS or an enzymatically active portion thereof, F6P aldolase or an enzymatically active portion thereof, or methanol dehydrogenase activator or an enzymatically active portion thereof, positioned between the first and second portions of a methanol dehydrogenase. Optionally, the fusion protein includes one or more linker amino acid sequence(s) positioned between two or more of the first, second, and third regions of the fusion protein Embodiments of the invention also include a nucleic acid encoding the fusion protein with a split MeDH sequence, expression constructs comprising the nucleic acid, engineered cells comprising the fusion protein with a split MeDH sequence, such as engineered cells comprising exogenous nucleic acids that express the fusion protein, and methods for producing a target product or an intermediate thereof comprising culturing the engineered cell comprising the fusion protein with a split MeDH sequence.

Other embodiments of the disclosure are directed to products made from the target product obtained from methods using the engineered cell with the fusion protein. Exemplary products include polymers made with a target bioproducts, such as polymers made from diol target products combined with diacids.

DESCRIPTION OF THE DRAWINGS

FIGS. 10A and 10B are schematic illustrations of a methanol pathway for formation of fructose-6-phosphate comparing a non-fusion (10A) and an exemplary fusion (10B) MeDH-DHAS-F6PALd proteins in which less diffusion of an intermediate (Fald, DHA, G3P) occurs.

DETAILED DESCRIPTION

The embodiments of the description described herein are not intended to be exhaustive or to limit the disclosure to the precise forms disclosed in the following detailed description. Rather, the embodiments are chosen and described so that others skilled in the art can appreciate and understand the principles and practices of the description.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

In methanotrophic bacteria formaldehyde made from methane and methanol oxidation is used to form metabolic intermediates in pathways leading to the formation of cellular products (Anthony, C. (1991) Biotechnology 18:79-109). The serine and D-ribulose 5-phosphate (RuMP) pathways use formaldehyde to produce carbon-containing intermediate compounds which are subsequently converted into other downstream products.

The RuMP pathway hexulose-6-phosphate synthase (HPS) enzymatically condenses formaldehyde and D-ribulose 5-phosphate (RuMP) to form hexulose 6-phosphate (HuMP). 6-phospho-3-hexuloisomerase (HPI) enzymatically converts HuMP to β-D-fructofuranose 6-phosphate (FMP). HPS and HPI are unique to natural organisms that have the RuMP pathway. For every one molecule of formaldehyde assimilated, one molecule of FMP is created.

FMP can then be cleaved to 3-carbon compounds by either of two routes. Enzymes of these other routes are not exclusive to those methanotrophic bacteria expressing HPS and HPI In one route 6-phosphofructokinase (EC 2.7.1.11) phosphorylates FMP to fructose 1,6-bisphosphate (FDP). Fructose-bisphosphate aldolase (EC 4.1.2.13) then cleaves FDP into dihydroxy acetone phosphate (DHAP) and glyceraldehyde 3-phosphate.

In another route glucose-6-phosphate isomerase (EC 5.3.1.9) isomerizes FMP to glucose 6-phosphate (GMP). Glucose-6-phosphate 1-dehydrogenase (EC 1.1.1.49) then dehydrogenates GMP to D-glucono-1,5-lactone 6-phosphate which is further dehydrogenated to 6-phospho-gluconate by 6-phosphogluconolactonase (EC 3.1.1.31). Phosphogluconate dehydratase (EC 4.2.1.12) then converts 6-phosphogluconate to 2-keto-3-deoxy-6-phospho-D-gluconate (KDPG). Subsequently, KDPG aldolase (EC 4.1.2.14) cleaves KDPG into glyceraldehyde 3-phosphate and pyruvate. Pyruvate and DHAP formed through this pathway can be used in cellular pathways for the synthesis of biomolecules.

Figure 5:
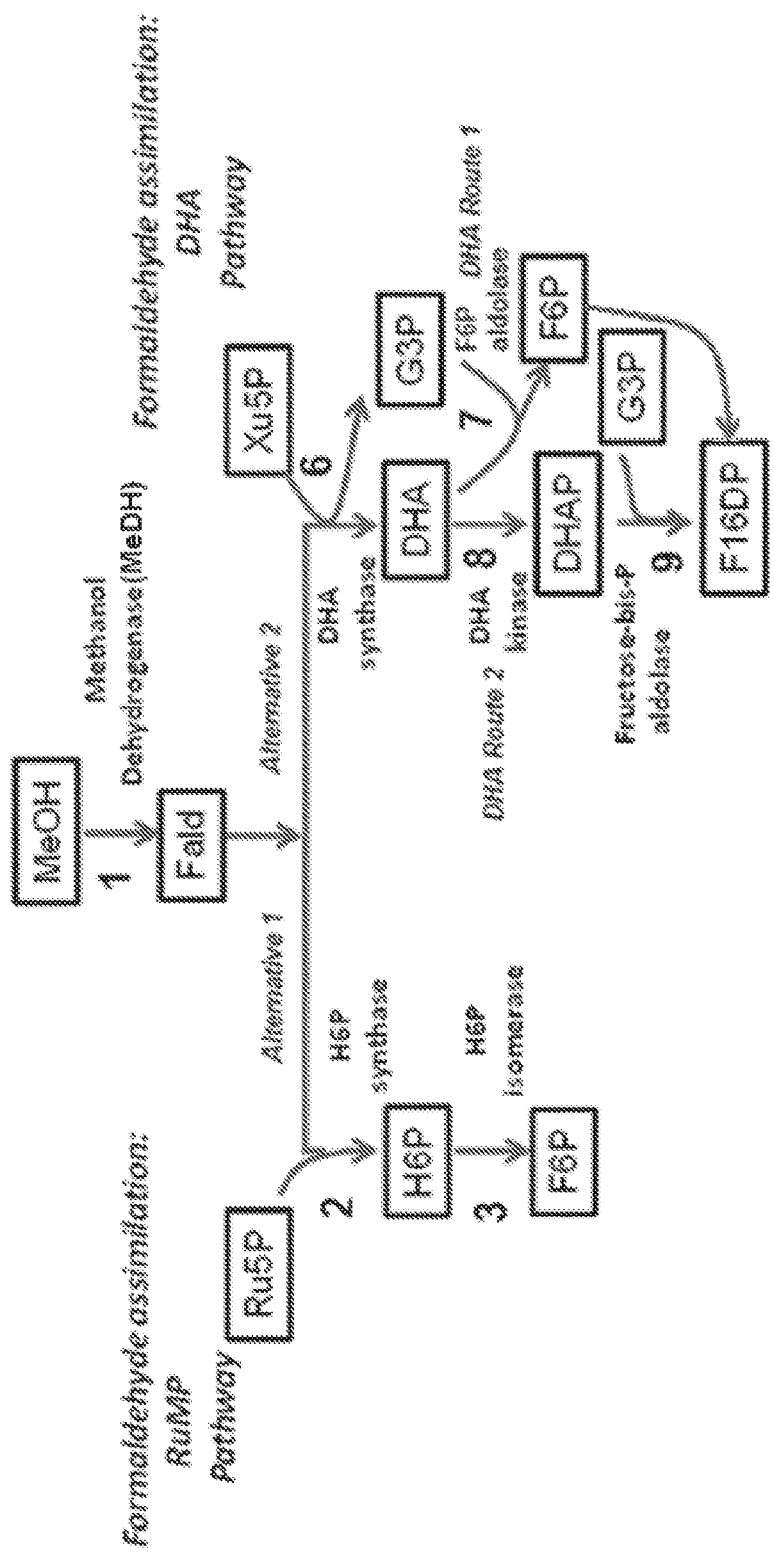
FIG. 5 illustrates alternative formaldehyde assimilation pathways (RuMP and DHA) and metabolic intermediates from each that can be used in a product pathway. Enzymes catalyzing the reactions are (1) methanol dehydrogenase, e.g. EC 1.1.1, (2) hexulose-6-phosphate synthase, e.g. EC 4.1.2.43, (3) 6-phospho-3-hexuloisomerase, e.g. EC 5.3.1.27, (6) DHA (dihydroxyacetone) synthase, e.g. EC 2.2.1.3, (7) F6P (fructose-6-phosphate) aldolase, e.g. EC 4.1.2, (8) DHA kinase, e.g. EC 2.7.1.121, (9) fructose-bisphosphate aldolase, e.g. EC 4.1.2.13. The fusions described herein can catalyze two or more of the reactions.

In engineered cells of the disclosure, methanol consumption minimally requires the heterologous expression of three genes: methanol dehydrogenase (MeDH), 3-hexulose-6-phosphate dehydrogenase (HPS or rmpA), and 6-phospho-3-hexuloisomerase (PHI or rmpB). In another embodiment the engineered cells of the disclosure, methanol consumption minimally requires the heterologous expression of three genes: methanol dehydrogenase (MeDH), DHA (dihydroxyacetone) synthase (DHAS) and F6P (fructose-6-phosphate) aldolase (F6P Ald) (e.g., see DHA Route of FIG. 5) or alternatively, less preferably, MeDH, DHA (dihydroxyacetone) synthase, and DHA kinase optionally with fructose-bisphosphate aldolase (FIG. 5, DHA Route 2). The MeDH protein catalyzes the inter-conversion of methanol and formaldehyde. As noted herein, the HPS protein catalyzes bond formation between formaldehyde and D-ribulose 5-phosphate, forming hexulose-6-phosphate and the PHI protein catalyzes isomerization of hexulose-6-phosphate to fructose-6-phosphate, which is an intermediate in glycolysis. In addition, the presence of an accessory protein, the MeDH Activator (ACT), may increase the activity of MeDH and improve methanol uptake. It is generally recognized that the activity of this heterologous pathway limits the ability of the non-native organism to consume methanol and grow on methanol as a carbon source. One of the issues associated with converting an organism to methylotrophy, is the potential toxic build-up of formaldehyde, the product of MeDH.

The fusion proteins of the disclosure provide approaches to avoid unwanted accumulation of formaldehyde by increasing the efficiency of the HPS reaction that uses formaldehyde and D-ribulose 5-phosphate as substrates, forming hexulose-6-phosphate. Increasing HPS efficiency could be accomplished such as by co-localization of the MeDH and HPS so HPS has easy access to higher local concentrations of formaldehyde. The fusion proteins of MeDH with a DHA Route 1 or Route 2 enzyme or enzymes avoid unwanted accumulation of formaldehyde by providing increased efficiency of the DHA synthase reaction that uses formaldehyde and xylulose-5-phosphate, forming DHA and G3P. Increased rate of MeOH use is also obtained.

Generally, the disclosure provides fusion proteins having at least (i) methanol dehydrogenase activity and (ii) 3-hexulose-6-phosphate dehydrogenase activity and/or 6-phospho-3-hexuloisomerase activity. Generally, in another embodiment the disclosure provides fusion proteins having at least (i) methanol dehydrogenase activity and (ii) DHA synthase activity and/or fructose-6-phosphate aldolase activity; or in yet another embodiment at least (i) methanol dehydrogenase activity and (ii) DHA synthase activity and/or DHA kinase activity. The fusion proteins can also include methanol dehydrogenase activator activity. Therefore, fusion proteins of the disclosure can include two, three, or four or more regions each providing a different activity. The regions can include the full (e.g., native) sequence of the enzyme, or can include an active portion thereof. Optionally, one or more linker sequences can bond one region to another in the fusion protein.

Methanol dehydrogenase activity, 3-hexulose-6-phosphate dehydrogenase activity, 6-phospho-3-hexuloisomerase activity, and methanol dehydrogenase activator activity can be provided by methanol dehydrogenase, 3-hexulose-6-phosphate dehydrogenase, 6-phospho-3-hexuloisomerase activity, and methanol dehydrogenase activator enzymes and active portions thereof, including those polypeptide sequence that are known in the art, as well as those described herein. Methanol dehydrogenase activity, DHA synthase, F6P aldolase, and DHA kinase activity and methanol dehydrogenase activator activity can be provided by methanol dehydrogenase, DHA synthase, F6P aldolase and DHA kinase and methanol dehydrogenase activator enzymes and active portions thereof, including those polypeptide sequence that are known in the art, as well as those described herein. In exemplary fusion protein diagrams the acronym "MeDH" can indicate a polypeptide region having methanol dehydrogenase activity; the acronym "HPS" can indicate a polypeptide region having 3-hexulose-6-phosphate dehydrogenase activity; the acronym "PHI" can indicate a polypeptide region having 6-phospho-3-hexuloisomerase activity; and the acronym "ACT" can indicate a polypeptide region having methanol dehydrogenase activator activity. The acronym "DHAS" can indicate a polypeptide region having DHA synthase activity; the acronym "F6P Ald" can indicate a polypeptide region having F6P aldolase activity; the acronym "DHAK" can indicate a polypeptide region having DHA kinase activity. The fusion proteins can include one or more polypeptide linkers, positions between polypeptide regions of the fusion proteins.

Nucleic acids encoding the fusion proteins, as well as expression constructs including the nucleic acids, are described.

Also described are engineered cells expressing the fusion proteins, optionally including one or more additional metabolic pathway transgene(s), methanol metabolic pathway genes, and/or target product pathway genes; cell culture compositions including the cells; methods for promoting production of the target product or intermediate thereof from the cells; compositions including the target product or intermediate; and products made from the target product or intermediate.

The term "non-naturally occurring", when used in reference to an organism (e.g., microbial) is intended to mean that the organism has at least one genetic alteration not normally found in a naturally occurring organism of the referenced species. Naturally-occurring organisms can be referred to as "wild-type" such as wild type strains of the referenced species. Likewise, a "non-natural" polypeptide or nucleic acid can include at least one genetic alteration not normally found in a naturally-occurring polypeptide or nucleic acid. Fusion proteins of the current disclosure are considered non-natural polypeptides. Naturally-occurring organisms, nucleic acids, and polypeptides can be referred to as "wild-type" or "original" such as wild type strains of the referenced species. Likewise, amino acids found in the wild type organism can be referred to as "original" with regards to any amino acid position.

A genetic alteration that makes an organism non-natural can include, for example, modifications introducing expressible nucleic acids encoding metabolic polypeptides, other nucleic acid additions, nucleic acid deletions and/or other functional disruption of the organism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon.

In the fusion protein, the location of regions having 3-hexulose-6-phosphate dehydrogenase activity (HPS), 6-phospho-3-hexuloisomerase activity (PHI), and methanol dehydrogenase activator activity (ACT) relative to the polypeptide having methanol dehydrogenase activity (MeDH) can be explained relative to the amino (N) and/or carboxyl (C) terminus of the fusion protein. In another embodiment the fusion protein, the location of regions having DHAS, F6P Ald (or DHAK), and methanol dehydrogenase activator activity (ACT) relative to the polypeptide having methanol dehydrogenase activity (MeDH) can be explained relative to the amino (N) and/or carboxyl (C) terminus of the fusion protein. For example, regions of the fusion proteins may be described relative to one another as "at the N-terminal portion of the protein" or "at the C-terminal portion of the protein" of the fusion protein if desired. Regions of the fusion proteins may also alternatively be described as "extending inwards from the N-terminus" or "extending inwards from the C-terminus" of the fusion protein if desired. Some regions of the fusion proteins may be described as "between one region and the N-terminal portion of the protein," "between one region and the C-terminal portion of the protein," or, "between the N-terminal portion of the protein and the C-terminal portion of the protein."

The N-terminal and C-terminal portions of the fusion proteins, which, in various embodiments, can include MeDH, HPS, PHI, or ACT regions, or alternatively MeDH, DHAS, F6P ALd (or DHAK) or ACT regions, can optionally be described in terms of the number of amino acid residues extending inward from either N- or C-terminus of the fusion protein. For example, the N-terminal and C-terminal portions of the fusion proteins may encompass up to 50, 75, 100, 125, 150, 175, 200, 225, 250, 275, 300, 325, 350, 375, 400, 425, 450, 475, or 500 amino acids inwards in the fusion protein from either N- or C-terminus, respectively. Likewise, one or more regions between the N-terminal and C-terminal portions which may encompass one or more of MeDH, HPS, PHI, or ACT regions, can be described in terms of an amount of amino acid residues. For example, a region of the fusion protein between the N-terminal and C-terminal portions may encompass up to 50, 75, 100, 125, 150, 175, 200, 225, 250, 275, 300, 325, 350, 375, 400, 425, 450, 475, or 500 amino acids.

Embodiments of the disclosure include, but are not limited to the following fusion protein arrangements: (a) a fusion protein having a MeDH region and PHI region, where the PHI region is between MeDH region and the C-terminus of the fusion protein; (b) a fusion protein having a MeDH region and HPS region, where the HPS region is between MeDH region and the C-terminus of the fusion protein; (c) a fusion protein having a MeDH region and PHI region, where the PHI region is between MeDH region and the N-terminus of the fusion protein; (d) a fusion protein having a MeDH region and HPS region, where the HPS region is between MeDH region and the N-terminus of the fusion protein; (e) a fusion protein having MeDH, HPS and PHI regions, where the MeDH region is between HSP and PHI regions, and where the PHI region is between the MeDH region and the N-terminus of the fusion protein and where the HPS region is between the MeDH region and the C-terminus of the fusion protein; (f) a fusion protein having MeDH, HPS and PHI regions, where the MeDH region is between HSP and PHI regions, and where the HPS region is between the MeDH region and the N-terminus of the fusion protein and where the PHI region is between the MeDH region and the C-terminus of the fusion protein; (g) a fusion protein having MeDH, HPS and PHI regions, where the HPS region is between MeDH and PHI regions, and where the MeDH region is between the HPS region and the N-terminus of the fusion protein and where the PHI region is between the HPS region and the C-terminus of the fusion protein; (h) a fusion protein having MeDH, HPS and PHI regions, where the HPS region is between MeDH and PHI regions, and where the PHI region is between the HPS region and the N-terminus of the fusion protein and where the MeDH region is between the HPS region and the C-terminus of the fusion protein; and (i) a fusion protein having ACT, MeDH, HPS and PHI regions, where the MeDH and HPS regions are between ACT and PHI regions, and where the ACT region is between the MeDH region and the N-terminus of the fusion protein and where the PHI region is between the HPS region and the C-terminus of the fusion protein. Linker sequences can be present between any one or more regions of the fusion proteins of (a)-(i).

Figure 1:
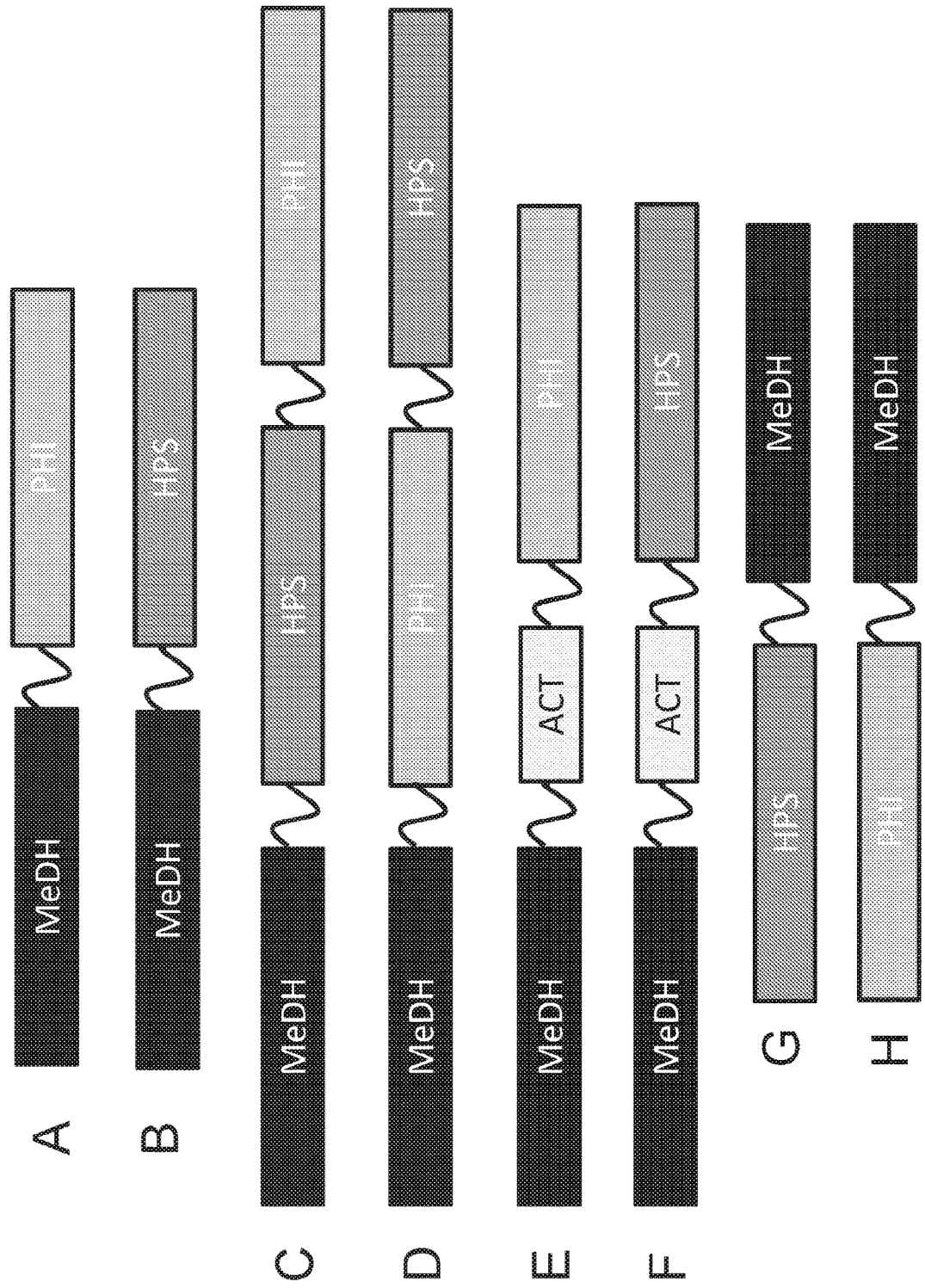
FIGS. 1A-1F are schematic diagrams of fusion proteins with a MeDH region that is at the N-terminal portion of the protein.
FIGS. 1G-1H are schematic diagrams of fusion proteins with a MeDH region that is at the C-terminal portion of the protein.

For example, FIG. 1A is a schematic diagram of a fusion protein with MeDH region that extends from the N-terminus and a PHI region that extends from the C-terminus. Such a fusion protein can be designated MeDH-PHI. Optionally, if a polypeptide linker is between the two regions the fusion protein designated MeDH-L$^1$-PHI.

As another embodiment, FIG. 1B is a schematic diagram of a fusion protein with a MeDH region that is at the N-terminal portion of the protein and a HPS region that is at the C-terminal portion of the protein. Such a fusion protein can be designated MeDH-HPS. Optionally, if a polypeptide linker is between the two regions the fusion protein designated MeDH-L$^1$-HPS.

As another embodiment, FIG. 1C is a schematic diagram of a fusion protein with a MeDH region that is at the N-terminal portion of the protein and a PHI region that is at the C-terminal portion of the protein, and a HPS region that is between the MeDH and PHI regions. Such a fusion protein can be designated MeDH-HPS-PHI. Optionally, if polypeptide linker(s) is/are between the different region(s) the fusion protein can be designated MeDH-L$^1$-HPS-PHI, MeDH-HPS-L$^1$-PHI, or MeDH-L$^1$-HPS-L$^2$-PHI.

As another embodiment, FIG. 1D is a schematic diagram of a fusion protein with a MeDH region that is at the N-terminal portion of the protein and a HPS region that is at the C-terminal portion of the protein, and a PHI region that is between the MeDH and HPS regions. Such a fusion protein can be designated MeDH-PHI-HPS. Optionally, if polypeptide linker(s) is/are between the different region(s) the fusion protein can be designated MeDH-L$^1$-PHI-HPS, MeDH-PHI-L$^1$-HPS, or MeDH-L$^1$-PHI-L$^2$-HPS.

As another embodiment, FIG. 1E is a schematic diagram of a fusion protein with a MeDH region that is at the N-terminal portion of the protein and a PHI region that is at the C-terminal portion of the protein, and an ACT region that is between the MeDH and PHI regions. Such a fusion protein can be designated MeDH-ACT-PHI. Optionally, if polypeptide linker(s) is/are between the different region(s) the fusion protein can be designated MeDH-L$^1$-ACT-PHI, MeDH-ACT-L$^1$-PHI, or MeDH-L$^1$-ACT-L$^2$-PHI.

As another embodiment, FIG. 1F a is a schematic diagram of a fusion protein with a MeDH region that is at the N-terminal portion of the protein and a HPS region that is at the C-terminal portion of the protein, and an ACT region that is between the MeDH and HPS regions. Such a fusion protein can be designated MeDH-ACT-HPS. Optionally, if polypeptide linker(s) is/are between the different region(s) the fusion protein can be designated MeDH-L$^1$-ACT-HPS, MeDH-ACT-L$^1$-HPS, or MeDH-L$^1$-ACT-L$^2$-HPS.

As another embodiment, FIG. 1G is a schematic diagram of a fusion protein with MeDH region that is at the C-terminal portion of the protein and a HPS region that is at the N-terminal portion of the protein. Such a fusion protein can be designated HPS-MeDH. Optionally, if a polypeptide linker is between the two regions the fusion protein designated HPS-L$^1$-MeDH.

As another embodiment, FIG. 1H is a schematic diagram of a fusion protein with MeDH region that is at the C-terminal portion of the protein and a PHI region that is at the N-terminal portion of the protein. Such a fusion protein can be designated PHI-MeDH. Optionally, if a polypeptide linker is between the two regions the fusion protein designated PHI-L$^1$-MeDH.

Figure 2:
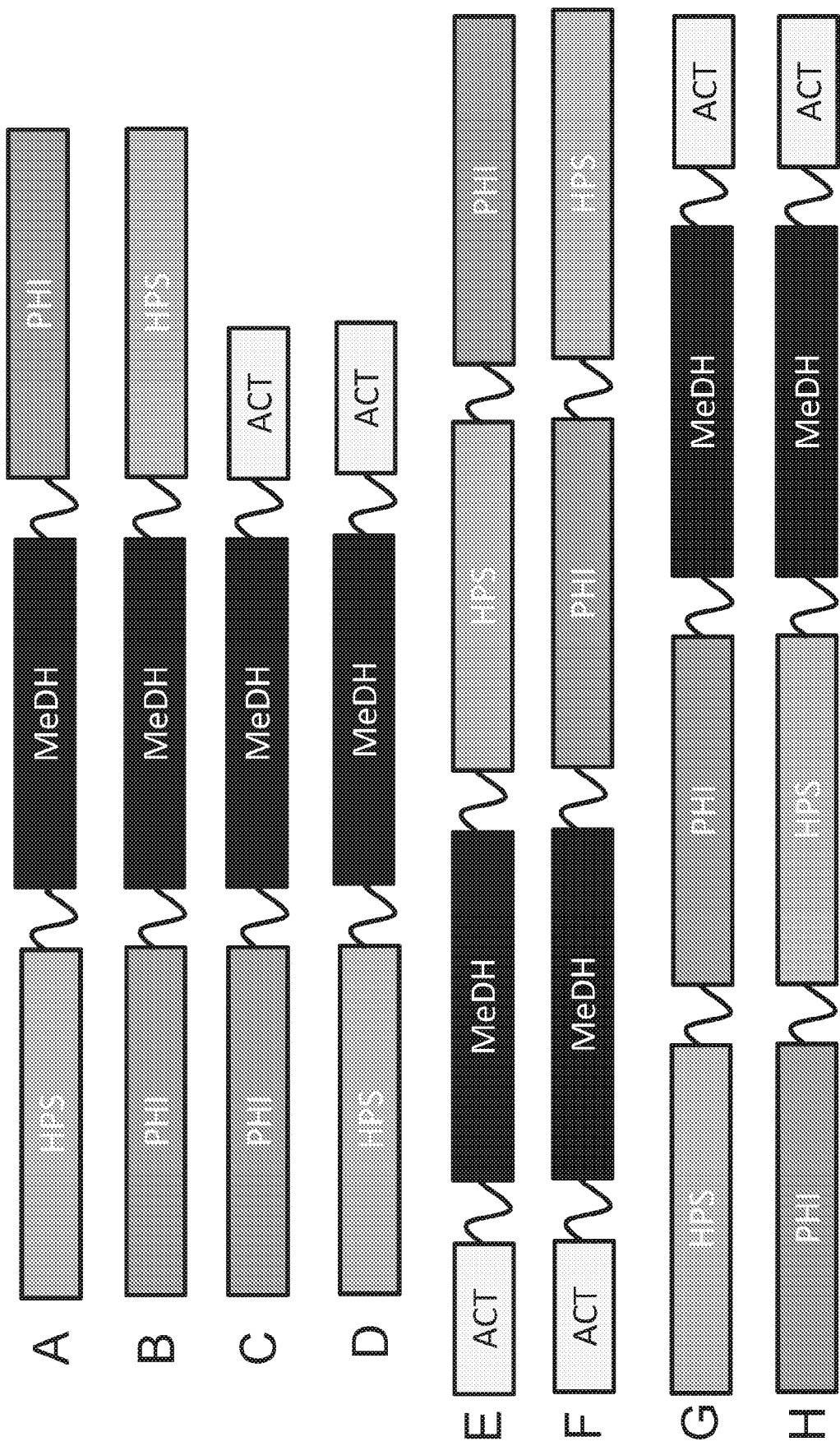
FIGS. 2A-2H are schematic diagrams of fusion proteins with a MeDH region that is between N- and C-terminal portions of the protein.

In other embodiments MeDH is positioned between two other regions of amino acid sequence. As another embodiment, FIG. 2A is a schematic diagram of a fusion protein with HPS region that is at the N-terminal portion of the protein and a PHI region that is at the C-terminal portion of the protein, and a MeDH region between the HPS and PHI regions. Such a fusion protein can be designated HPS-MeDH-PHI. Optionally, if polypeptide linker(s) is/are between the different region(s) the fusion protein can be designated HPS-MeDH-L$^1$-PHI, HPS-L$^1$-MeDH-PHI, or HPS-L$^L$-MeDH-L$^2$-PHI.

As another embodiment, FIG. 2B is a schematic diagram of a fusion protein with PHI region that is at the N-terminal portion of the protein and a HPS region that is at the C-terminal portion of the protein, and a MeDH region between the PHI and HPS regions. Such a fusion protein can be designated PHI-MeDH-HPS. Optionally, if polypeptide linker(s) is/are between the different region(s) the fusion protein can be designated PHI-MeDH-L$^1$-HPS, PHI-L$^1$-MeDH-HPS, or PHI-L$^1$-MeDH-L$^2$-HPS.

As another embodiment, FIG. 2C is a schematic diagram of a fusion protein with PHI region that is at the N-terminal portion of the protein and an ACT region that is at the C-terminal portion of the protein, and a MeDH region between the PHI and ACT regions. Such a fusion protein can be designated PHI-MeDH-ACT. Optionally, if polypeptide linker(s) is/are between the different region(s) the fusion protein can be designated PHI-MeDH-$L^1$-ACT, PHI-$L^1$-MeDH-ACT, or PHI-$L^1$-MeDH-$L^2$-ACT.

As another embodiment, FIG. 2D is a schematic diagram of a fusion protein with HPS region that is at the N-terminal portion of the protein and an ACT region that is at the C-terminal portion of the protein, and a MeDH region between the HPS and ACT regions. Such a fusion protein can be designated HPS-MeDH-ACT. Optionally, if polypeptide linker(s) is/are between the different region(s) the fusion protein can be designated HPS-MeDH-$L^1$-ACT, HPS-$L^1$-MeDH-ACT, or HPS-$L^1$-MeDH-$L^2$-ACT.

As another embodiment, FIG. 2E is a schematic diagram of a fusion protein with ACT region that is at the N-terminal portion of the protein and a PHI region that is at the C-terminal portion of the protein, and MeDH and HPS regions between the ACT and PHI regions, with MeDH being closer to the ACT region and HPS being closer to the PHI region. Such a fusion protein can be designated ACT-MeDH-HPS-PHI. Optionally, if polypeptide linker(s) is/are between the different region the fusion protein can be designated ACT-$L^1$-MeDH-HPS-PHI, ACT-MeDH-$L^1$-HPS-PHI, ACT-MeDH-HPS-$L^1$-PHI, ACT-$L^1$-MeDH-$L^2$-HPS-PHI, ACT-$L^1$-MeDH-HPS-$L^2$-PHI, ACT-MeDH-$L^1$-HPS-$L^2$-PHI, and ACT-$L^1$-MeDH-$L^2$-HPS-$L^3$-PHI.

As another embodiment, FIG. 2F is a schematic diagram of a fusion protein with ACT region that is at the N-terminal portion of the protein and a HIPS region that is at the C-terminal portion of the protein, and MeDH and PHI regions between the ACT and HPS regions, with MeDH being closer to the ACT region and PHI being closer to the HPS region. Such a fusion protein can be designated ACT-MeDH-PHI-HPS. Optionally, if polypeptide linker(s) is/are between the different region the fusion protein can be designated ACT-$L^1$-MeDH-PHI-HPS, ACT-MeDH-$L^1$-PHI-HPS, ACT-MeDH-PHI-$L^1$-HPS, ACT-$L^1$-MeDH-$L^2$-PHI-HPS, ACT-$L^1$-MeDH-PHI-$L^2$-HPS, ACT-MeDH-$L^1$-PHI-$L^2$-HPS, and ACT-$L^1$-MeDH-$L^2$-PHI-$L^3$-HPS.

As another embodiment, FIG. 2G is a schematic diagram of a fusion protein with HPS region that is at the N-terminal portion of the protein and an ACT region that is at the C-terminal portion of the protein, and PHI and MeDH regions between the HPS and ACT regions, with PHI being closer to the HPS region and MeDH being closer to the ACT region. Such a fusion protein can be designated HPS-PHI-MeDH-ACT. Optionally, if polypeptide linker(s) is/are between the different region the fusion protein can be designated HPS-$L^1$-PHI-MeDH-ACT, HPS-PHI-$L^1$-MeDH-ACT, HPS-PHI-MeDH-$L^1$-ACT, HPS-$L^1$-PHI-$L^2$-MeDH-ACT, HPS-$L^1$-PHI-MeDH-$L^2$-ACT, HPS-PHI-$L^1$-MeDH-$L^2$-ACT, and HPS-$L^1$-PHI-$L^2$-MeDH-$L^3$-ACT.

As another embodiment, FIG. 2H is a schematic diagram of a fusion protein with PHI region that is at the N-terminal portion of the protein and an ACT region that is at the C-terminal portion of the protein, and HPS and MeDH regions between the PHI and ACT regions, with HPS being closer to the PHI region and MeDH being closer to the ACT region. Such a fusion protein can be designated PHI-HPS-MeDH-ACT. Optionally, if polypeptide linker(s) is/are between the different region the fusion protein can be designated PHI-$L^1$-HPS-MeDH-ACT, PHI-HPS-$L^1$-MeDH-ACT, PHI-HPS-MeDH-$L^1$-ACT, PHI-$L^1$-HPS-$L^2$-MeDH-ACT, PHI-$L^1$-HPS-MeDH-$L^2$-ACT, PHI-HPS-$L^1$-MeDH-$L^2$-ACT, and PHI-$L^1$-HPS-$L^2$-MeDH-$L^3$-ACT.

In other embodiments, in the fusion protein the methanol dehydrogenase is interrupted by at least one different region of amino acid sequence, such as a PHI or a HPS region. For example, the nucleic acid will encode, in frame, a polypeptide with a first portion of a MeDH, a PHI or a HPS region, and then a second portion of a MeDH. Although the MeDH sequence is interrupted, the fusion protein still maintains methanol dehydrogenase activity.

Figure 3:
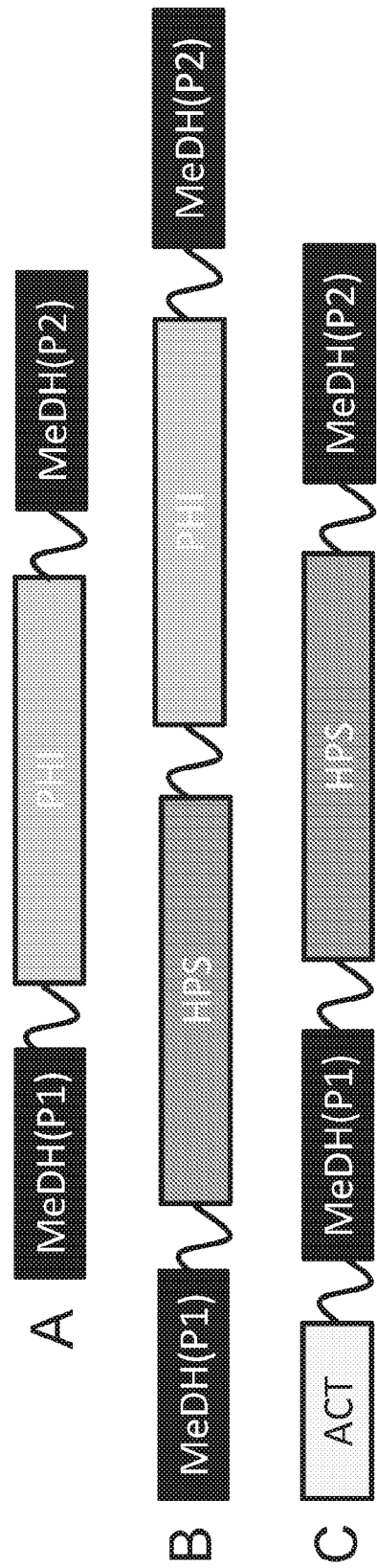
FIGS. 3A-3C are schematic diagrams of fusion proteins with a MeDH region that is split into two portions in the fusion protein.
Figure 4A:
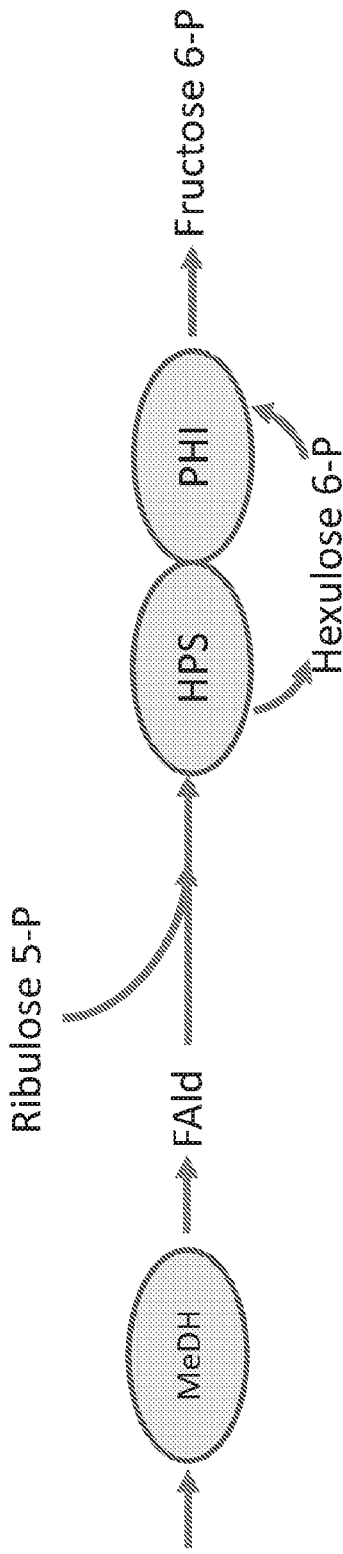
FIGS. 4A and 4B are schematic illustrations of HPS-PHI and MeDH-HPS-PHI fusion proteins in a methanol pathway for formation of fructose-6-phosphate.
Figure 4B:
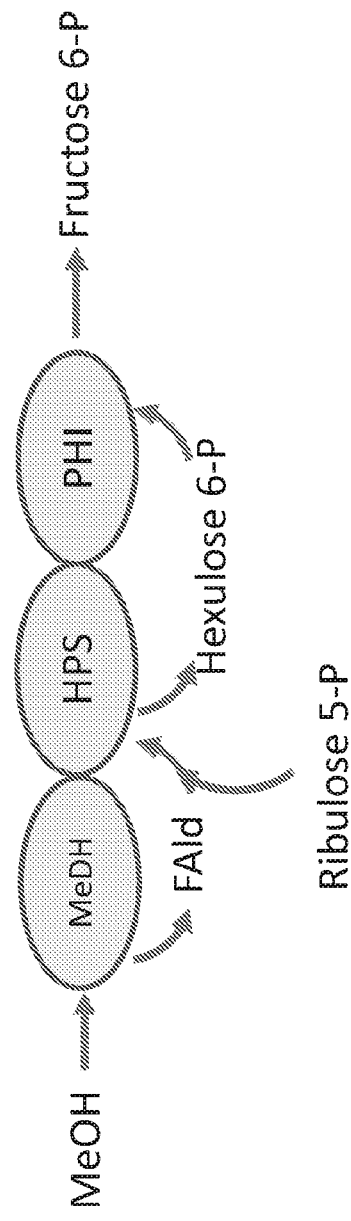

For example, FIG. 3A is a schematic diagram of a fusion protein having a first portion of a MeDH that is at the N-terminal portion of the protein, a second portion of a MeDH that is at the C-terminal portion of the protein, and PHI region between the first and second methanol dehydrogenase portions. Such fusion proteins can be designated MeDH(P1)-PHI-MeDH(P2), Optionally, if polypeptide linker(s) is/are between the different portions and region(s) the fusion protein can be designated MeDH(P1)-$L^1$-PHI-MeDH(P2), MeDH(P1)-PHI-$L^1$-MeDH(P2), or MeDH(P1)-$L^1$-PHI-$L^2$-MeDH(P2).

As another embodiment, FIG. 3B is a schematic diagram of a fusion protein having a first portion of a MeDH that is at the N-terminal portion of the protein, a second portion of a MeDH that is at the C-terminal portion of the protein, and HPS and PHI regions between the first and second MeDH portions, with HPS being closer to the first portion of the MeDH and PHI being closer to the second portion of the MeDH. Such a fusion protein can be designated MeDH(P1)-HPS-PHI-MeDH(P2). Optionally, if polypeptide linker(s) is/are between the different portions and region(s) the fusion protein can be designated MeDH(P1)-$L^1$-HPS-PHI-MeDH(P2), MeDH(P1)-HPS-$L^1$-PHI-MeDH(P2), MeDH(P1)-HPS-PHI-$L^1$-MeDH(P2), MeDH(P1)-$L^1$-HPS-$L^2$-PHI-MeDH(P2), MeDH(P1)-$L^1$-HPS-PHI-$L^2$-MeDH(P2), MeDH(P1)-HPS-$L^1$-PHI-$L^2$-MeDH(P2), or MeDH(P1)-$L^1$-HPS-$L^2$-PHI-$L^3$-MeDH(P2).

As another embodiment, FIG. 3C is a schematic diagram of a fusion protein having an ACT region that is at the N-terminal portion of the protein, a second portion of a MeDH that is at the C-terminal portion of the protein, a first portion of the MeDH and a HPS region between the ACT region and the second portion of a MeDH, with HPS being in between the first and second MeDH portions. Such a fusion protein can be designated ACT-MeDH(P1)-HPS-MeDH(P2). Optionally, if polypeptide linker(s) is/are between the different portions and region(s) the fusion protein can be designated ACT-$L^1$-MeDH(P1)-HPS-MeDH(P2), ACT-MeDH(P1)-$L^1$-HPS-MeDH(P2), ACT-MeDH(P1)-HPS-$L^1$-MeDH(P2), ACT-$L^1$-MeDH(P1)-$L^2$-HPS-MeDH(P2), ACT-MeDH(P1)-$L^1$-HPS-$L^2$-MeDH(P2), ACT-$L^1$-MeDH(P1)-HPS-$L^2$-MeDH(P2), or ACT-$L^1$-MeDH(P1)-$L^2$-HPS-$L^3$-MeDH(P2).

Additional embodiments of the disclosure include, but are not limited to the following fusion protein arrangements of MeDH with one or more DHA Pathway enzymes: (a) a fusion protein having a MeDH region and DHAS region, where the DHAS region is between MeDH region and the C-terminus of the fusion protein; (b) a fusion protein having a MeDH region and F6PALD region (alternatively written as "F6P Ald"), where the F6PALD region is between MeDH region and the C-terminus of the fusion protein; (c) a fusion protein having a MeDH region and DHAS region, where the DHAS region is between MeDH region and the N-terminus of the fusion protein; (d) a fusion protein having a MeDH region and F6PALD region, where the F6PALD region is between MeDH region and the N-terminus of the fusion protein; (e) a fusion protein having MeDH, F6PALD and DHAS regions, where the MeDH region is between DHAS and DHAS regions, and where the DHAS region is between the MeDH region and the N-terminus of the fusion protein and where the F6PALD region is between the MeDH region and the C-terminus of the fusion protein; (f) a fusion protein having MeDH, F6PALD and DHAS regions, where the MeDH region is between F6PALD and DHAS regions, and where the F6PALD region is between the MeDH region and the N-terminus of the fusion protein and where the DHAS region is between the MeDH region and the C-terminus of the fusion protein; (g) a fusion protein having MeDH, F6PALD and DHAS regions, where the F6PALD region is between MeDH and DHAS regions, and where the MeDH region is between the F6PALD region and the N-terminus of the fusion protein and where the DHAS region is between the F6PALD region and the C-terminus of the fusion protein; (h) a fusion protein having MeDH, F6PALD and DHAS regions, where the F6PALD region is between MeDH and DHAS regions, and where the DHAS region is between the F6PALD region and the N-terminus of the fusion protein and where the MeDH region is between the F6PALD region and the C-terminus of the fusion protein; and (i) a fusion protein having ACT, MeDH, F6PALD and DHAS regions, where the MeDH and F6PALD regions are between ACT and DHAS regions, and where the ACT region is between the MeDH region and the N-terminus of the fusion protein and where the DHAS region is between the F6PALD region and the C-terminus of the fusion protein. Linker sequences can be present between any one or more regions of the fusion proteins of (a)-(i).

Figure 7:
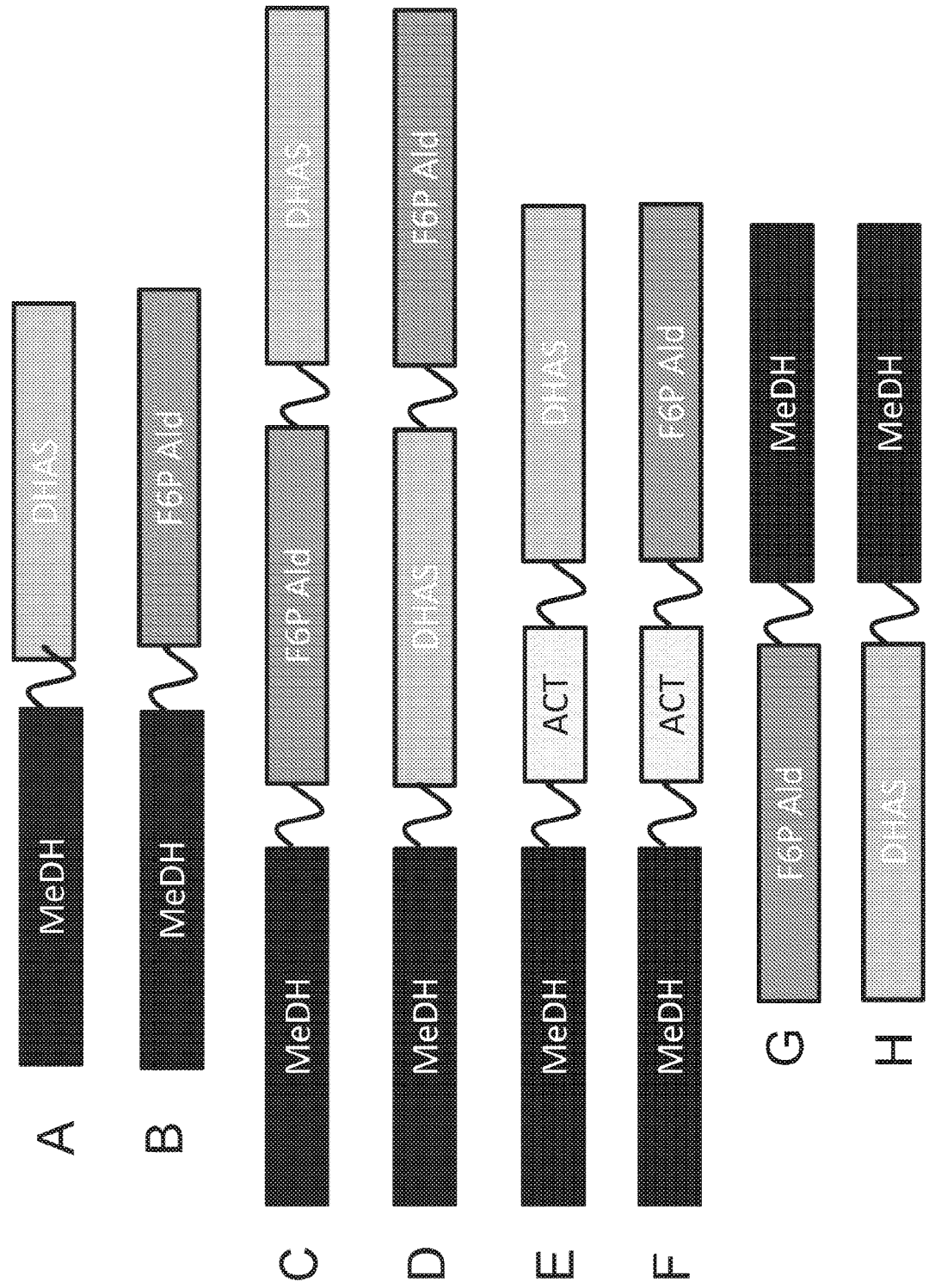
FIGS. 7A-7F are schematic diagrams of fusion proteins of DHA (dihydroxyacetone) synthase (DHAS) or F6P (fructose-6-phosphate) aldolase (F6P Ald) with a MeDH region that is at the N-terminal portion of the fusion protein.
FIGS. 7G-7H are schematic diagrams of fusion proteins with a MeDH region that is at the C-terminal portion of the fusion protein.

For example, FIG. 7A is a schematic diagram of a fusion protein with MeDH region that extends from the N-terminus and a DHAS region that extends from the C-terminus. Such a fusion protein can be designated MeDH-DHAS. Optionally, if a polypeptide linker is between the two regions the fusion protein designated MeDH-$L^1$-DHAS.

As another embodiment, FIG. 7B is a schematic diagram of a fusion protein with a MeDH region that is at the N-terminal portion of the protein and a F6PALD region that is at the C-terminal portion of the protein. Such a fusion protein can be designated MeDH-F6PALD. Optionally, if a polypeptide linker is between the two regions the fusion protein is designated MeDH-$L^1$-F6PALD.

As another embodiment, FIG. 7C is a schematic diagram of a fusion protein with a MeDH region that is at the N-terminal portion of the protein and a DHAS region that is at the C-terminal portion of the protein, and a F6PALD region that is between the MeDH and DHAS regions. Such a fusion protein can be designated MeDH-F6PALD-DHAS. Optionally, if polypeptide linker(s) is/are between the different region(s) the fusion protein can be designated MeDH-$L^1$-F6PALD-DHAS, MeDH-F6PALD-$L^1$-DHAS, or MeDH-$L^1$-F6PALD-$L^2$-DHAS.

As another embodiment, FIG. 7D is a schematic diagram of a fusion protein with a MeDH region that is at the N-terminal portion of the protein and a F6PALD region that is at the C-terminal portion of the protein, and a DHAS region that is between the MeDH and F6PALD regions. Such a fusion protein can be designated MeDH-DHAS-F6PALD. Optionally, if polypeptide linker(s) is/are between the different region(s) the fusion protein can be designated MeDH-$L^1$-DHAS-F6PALD, MeDH-DHAS-$L^1$-F6PALD, or MeDH-$L^1$-DHAS-$L^2$-F6PALD.

As another embodiment, FIG. 7E is a schematic diagram of a fusion protein with a MeDH region that is at the N-terminal portion of the protein and a DHAS region that is at the C-terminal portion of the protein, and an ACT region that is between the MeDH and DHAS regions. Such a fusion protein can be designated MeDH-ACT-DHAS. Optionally, if polypeptide linker(s) is/are between the different region(s) the fusion protein can be designated MeDH-$L^1$-ACT-DHAS, MeDH-ACT-$L^1$-DHAS, or MeDH-$L^1$-ACT-$L^2$-DHAS.

As another embodiment, FIG. 7F a is a schematic diagram of a fusion protein with a MeDH region that is at the N-terminal portion of the protein and a F6PALD region that is at the C-terminal portion of the protein, and an ACT region that is between the MeDH and F6PALD regions. Such a fusion protein can be designated MeDH-ACT-F6PALD. Optionally, if polypeptide linker(s) is/are between the different region(s) the fusion protein can be designated MeDH-$L^1$-ACT-F6PALD, MeDH-ACT-$L^1$-F6PALD, or MeDH-$L^1$-ACT-$L^2$-F6PALD.

As another embodiment, FIG. 7G is a schematic diagram of a fusion protein with MeDH region that is at the C-terminal portion of the protein and a F6PALD region that is at the N-terminal portion of the protein. Such a fusion protein can be designated F6PALD-MeDH. Optionally, if a polypeptide linker is between the two regions the fusion protein designated F6PALD-$L^1$-MeDH.

As another embodiment, FIG. 7H is a schematic diagram of a fusion protein with MeDH region that is at the C-terminal portion of the protein and a DHAS region that is at the N-terminal portion of the protein. Such a fusion protein can be designated DHAS-MeDH. Optionally, if a polypeptide linker is between the two regions the fusion protein designated DHAS-$L^1$-MeDH.

Figure 8:
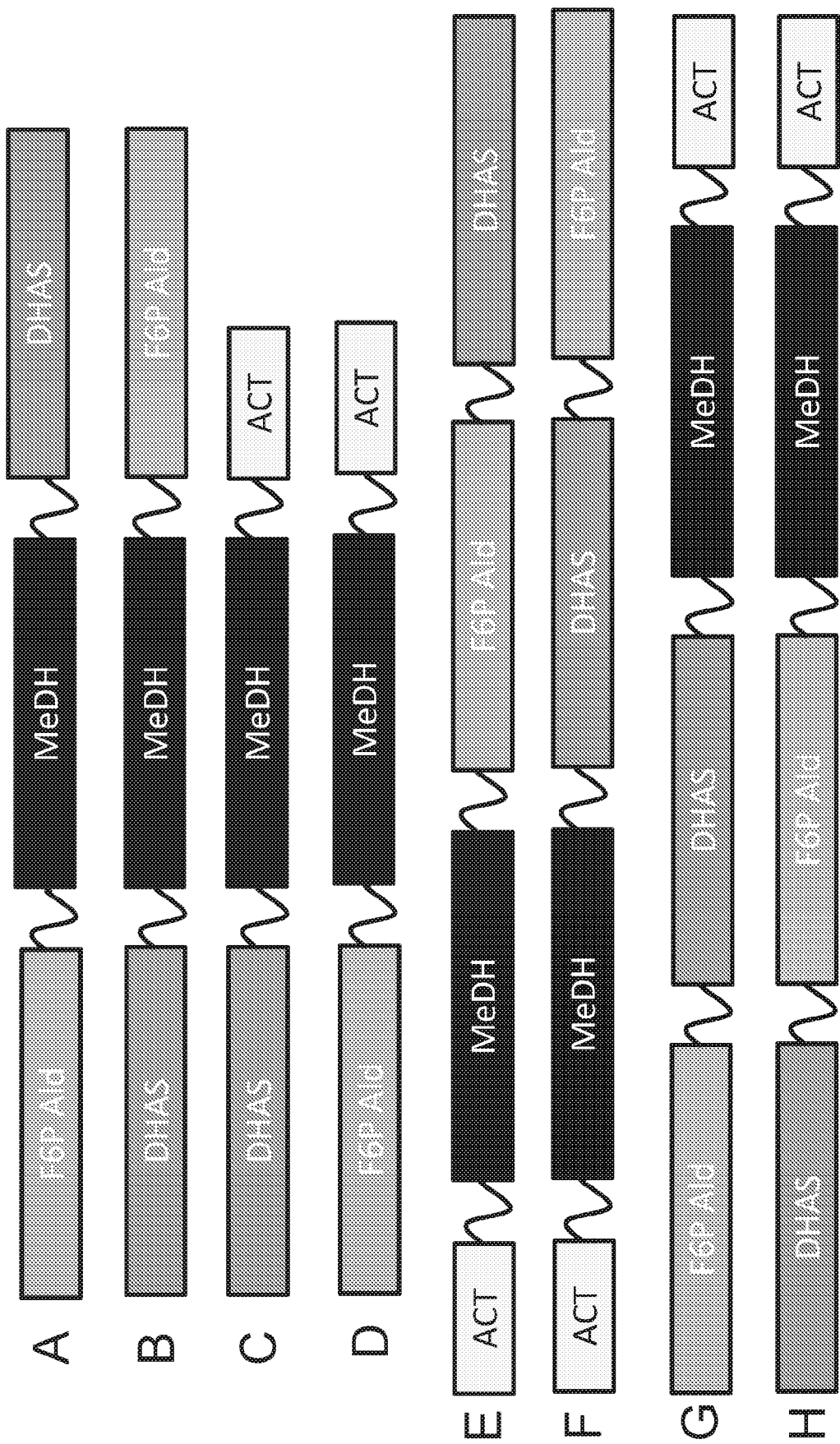
FIGS. 8A-8H are schematic diagrams of fusion proteins of DHA (dihydroxyacetone) synthase and F6P (fructose-6-phosphate) aldolase with a MeDH region that is between N- and C-terminal portions of the protein.

In other embodiments MeDH is positioned between two other regions of amino acid sequence. As another embodiment, FIG. 8A is a schematic diagram of a fusion protein with F6PALD region that is at the N-terminal portion of the protein and a DHAS region that is at the C-terminal portion of the protein, and a MeDH region between the F6PALD and DHAS regions. Such a fusion protein can be designated F6PALD-MeDH-DHAS. Optionally, if polypeptide linker(s) is/are between the different region(s) the fusion protein can be designated F6PALD-MeDH-$L^1$-DHAS, F6PALD-$L^1$-MeDH-DHAS, or F6PALD-$L^1$-MeDH-$L^2$-DHAS.

As another embodiment, FIG. 8B is a schematic diagram of a fusion protein with a DHAS region that is at the N-terminal portion of the protein and a F6PALD region that is at the C-terminal portion of the protein, and a MeDH region between the DHAS and F6PALD regions. Such a fusion protein can be designated DHAS-MeDH-F6PALD. Optionally, if polypeptide linker(s) is/are between the different region(s) the fusion protein can be designated DHAS-MeDH-$L^1$-F6PALD, DHAS-$L^1$-MeDH-F6PALD, or DHAS-$L^1$-MeDH-$L^2$-F6PALD.

As another embodiment, FIG. 8C is a schematic diagram of a fusion protein with DHAS region that is at the N-terminal portion of the protein and an ACT region that is at the C-terminal portion of the protein, and a MeDH region between the DHAS and ACT regions. Such a fusion protein can be designated DHAS-MeDH-ACT. Optionally, if polypeptide linker(s) is/are between the different region(s) the fusion protein can be designated DHAS-MeDH-$L^1$-ACT, DHAS-$L^1$-MeDH-ACT, or DHAS-$L^1$-MeDH-$L^2$-ACT.

As another embodiment, FIG. 8D is a schematic diagram of a fusion protein with F6PALD region that is at the N-terminal portion of the protein and an ACT region that is at the C-terminal portion of the protein, and a MeDH region between the F6PALD and ACT regions. Such a fusion protein can be designated F6PALD-MeDH-ACT. Optionally, if polypeptide linker(s) is/are between the different region(s) the fusion protein can be designated F6PALD-MeDH-L$^1$-ACT, F6PALD-L$^1$-MeDH-ACT, or F6PALD-L$^1$-MeDH-L$^2$-ACT.

As another embodiment, FIG. 8E is a schematic diagram of a fusion protein with ACT region that is at the N-terminal portion of the protein and a DHAS region that is at the C-terminal portion of the protein, and MeDH and F6PALD regions between the ACT and DHAS regions, with MeDH being closer to the ACT region and F6PALD being closer to the DHAS region. Such a fusion protein can be designated ACT-MeDH-F6PALD-DHAS. Optionally, if polypeptide linker(s) is/are between the different region the fusion protein can be designated ACT-L$^1$-MeDH-F6PALD-DHAS, ACT-MeDH-L$^1$-F6PALD-DHAS, ACT-MeDH-F6PALD-L$^1$-DHAS, ACT-L$^1$-MeDH-L$^2$-F6PALD-DHAS, ACT-L$^1$-MeDH-F6PALD-L$^2$-DHAS, ACT-MeDH-L$^1$-F6PALD-L$^2$-DHAS, and ACT-L$^1$-MeDH-L$^2$-F6PALD-L$^3$-DHAS.

As another embodiment, FIG. 8F is a schematic diagram of a fusion protein with ACT region that is at the N-terminal portion of the protein and a F6PALD region that is at the C-terminal portion of the protein, and MeDH and DHAS regions between the ACT and F6PALD regions, with MeDH being closer to the ACT region and DHAS being closer to the F6PALD region. Such a fusion protein can be designated ACT-MeDH-DHAS-F6PALD. Optionally, if polypeptide linker(s) is/are between the different region the fusion protein can be designated ACT-L$^1$-MeDH-DHAS-F6PALD, ACT-MeDH-L$^1$-DHAS-F6PALD, ACT-MeDH-DHAS-L$^1$-F6PALD, ACT-L$^1$-MeDH-L$^2$-DHAS-F6PALD, ACT-L$^1$-MeDH-DHAS-L$^2$-F6PALD, ACT-MeDH-L$^1$-DHAS-L$^2$-F6PALD, and ACT-L$^1$-MeDH-L$^2$-DHAS-L$^3$-F6PALD.

As another embodiment, FIG. 8G is a schematic diagram of a fusion protein with F6PALD region that is at the N-terminal portion of the protein and an ACT region that is at the C-terminal portion of the protein, and DHAS and MeDH regions between the F6PALD and ACT regions, with DHAS being closer to the F6PALD region and MeDH being closer to the ACT region. Such a fusion protein can be designated F6PALD-DHAS-MeDH-ACT. Optionally, if polypeptide linker(s) is/are between the different region the fusion protein can be designated F6PALD-L$^1$-DHAS-MeDH-ACT, F6PALD-DHAS-L$^1$-MeDH-ACT, F6PALD-DHAS-MeDH-L$^1$-ACT, F6PALD-L$^1$-DHAS-L$^2$-MeDH-ACT, F6PALD-L$^1$-DHAS-MeDH-L$^2$-ACT, F6PALD-DHAS-L$^1$-MeDH-L$^2$-ACT, and F6PALD-L$^1$-DHAS-L$^2$-MeDH-L$^3$-ACT.

As another embodiment, FIG. 8H is a schematic diagram of a fusion protein with DHAS region that is at the N-terminal portion of the protein and an ACT region that is at the C-terminal portion of the protein, and F6PALD and MeDH regions between the DHAS and ACT regions, with F6PALD being closer to the DHAS region and MeDH being closer to the ACT region. Such a fusion protein can be designated DHAS-F6PALD-MeDH-ACT. Optionally, if polypeptide linker(s) is/are between the different region the fusion protein can be designated DHAS-L$^1$-F6PALD-MeDH-ACT, DHAS-F6PALD-L$^1$-MeDH-ACT, DHAS-F6PALD-MeDH-L$^1$-ACT, DHAS-L$^1$-F6PALD-L$^2$-MeDH-ACT, DHAS-L$^1$-F6PALD-MeDH-L$^2$-ACT, DHAS-F6PALD-L$^1$-MeDH-L$^2$-ACT, and DHAS-L$^1$-F6PALD-L$^2$-MeDH-L$^3$-ACT.

In other embodiments, in the fusion protein the methanol dehydrogenase is interrupted by at least one different region of amino acid sequence, such as a DHAS or a F6PALD region. For example, the nucleic acid will encode, in frame, a polypeptide with a first portion of a MeDH and a DHAS and/or a F6PALD region, and then a second portion of a MeDH. Although the MeDH sequence is interrupted, the fusion protein still maintains methanol dehydrogenase activity.

Figure 9:
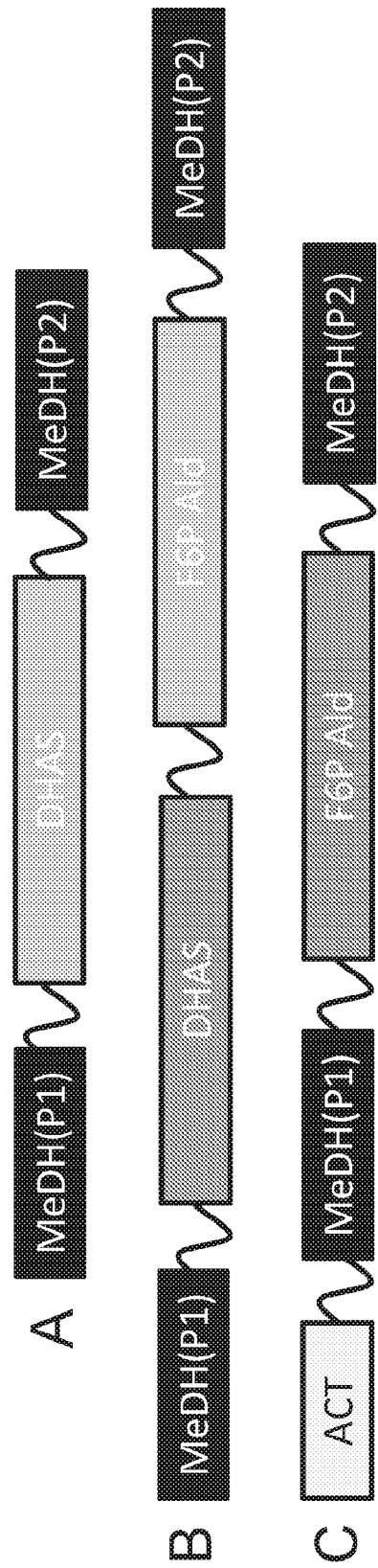
FIGS. 9A-9C are schematic diagrams of fusion proteins of DHA (dihydroxyacetone) synthase (DHAS) and/or F6P (fructose-6-phosphate) aldolase with a MeDH region that is split into two portions in the fusion protein.

For example, FIG. 9A is a schematic diagram of a fusion protein having a first portion of a MeDH that is at the N-terminal portion of the protein, a second portion of a MeDH that is at the C-terminal portion of the protein, and DHAS region between, and in frame with, the first and second methanol dehydrogenase portions. Such fusion proteins can be designated MeDH(P1)-DHAS-MeDH(P2), Optionally, if polypeptide linker(s) is/are between the different portions and region(s) the fusion protein can be designated MeDH(P1)-L$^1$-DHAS-MeDH(P2), MeDH(P1)-DHAS-L$^1$-MeDH(P2), or MeDH(P1)-L$^1$-DHAS-L$^2$-MeDH(P2).

As another embodiment, FIG. 9B is a schematic diagram of a fusion protein having a first portion of a MeDH that is at the N-terminal portion of the protein, a second portion of a MeDH that is at the C-terminal portion of the protein, and F6PALD and DHAS regions between the first and second MeDH portions, with DHAS being closer to the first portion of the MeDH and F6PALD being closer to the second portion of the MeDH. Such a fusion protein can be designated MeDH(P1)-DHAS-F6PALD-MeDH(P2). Optionally, if polypeptide linker(s) is/are between the different portions and region(s) the fusion protein can be designated MeDH(P1)-L$^1$-DHAS-F6PALD-MeDH(P2), MeDH(P1)-DHAS-L$^1$-F6PALD-MeDH(P2), MeDH(P1)-DHAS-F6PALD-L$^1$-MeDH(P2), MeDH(P1)-L$^1$-DHAS-L$^2$-F6PALD-MeDH(P2), MeDH(P1)-L$^1$-DHAS-F6PALD-L$^2$-MeDH(P2), MeDH(P1)-DHAS-L$^1$-F6PALD-L$^2$-MeDH(P2), or MeDH(P1)-L$^1$-DHAS-L$^2$-F6PALD-L$^3$-MeDH(P2).

As another embodiment, FIG. 9C is a schematic diagram of a fusion protein having an ACT region that is at the N-terminal portion of the protein, a second portion of a MeDH that is at the C-terminal portion of the protein, and a first portion of the MeDH and a F6PALD region between the ACT region and the second portion of a MeDH, with F6PALD being in between the first and second MeDH portions. Such a fusion protein can be designated ACT-MeDH(P1)-F6PALD-MeDH(P2). Optionally, if polypeptide linker(s) is/are between the different portions and region(s) the fusion protein can be designated ACT-L$^1$-MeDH(P1)-F6PALD-MeDH(P2), ACT-MeDH(P1)-L$^1$-F6PALD-MeDH(P2), ACT-MeDH(P1)-F6PALD-L$^1$-MeDH(P2), ACT-L$^1$-MeDH(P1)-L$^2$-F6PALD-MeDH(P2), ACT-MeDH(P1)-L$^1$-F6PALD-L$^2$-MeDH(P2), or ACT-L$^1$-MeDH(P1)-F6PALD-L$^2$-MeDH(P2).

In specifically contemplated fusion protein embodiments above and elsewhere herein DHA Kinase (DHAK) replaces F6P Aldolase.

Table 1 includes a list of amino acid domains in the MeDH sequence Bacillus methanolicus MGA3 MeDH (SEQ ID NO: 1) predicted to have a secondary structure consistent with a coil. These domains represent sites for splitting the MeDH sequence and insertion of another open reading frame (with or without flanking linker sequences), such as shown in FIGS. 3A-3C. For example, the sequence AGTGSETT corresponding to amino acids 139-146 in Bacillus methanolicus MGA3 MeDH (SEQ ID NO: 1) represent a first domain having a predicted coil. A fusion protein of the disclosure could have a sequence with a split in the MeDH sequence anywhere within this domain, and insertion of one or more sequences selected from PHI, HPS, and ACT, or alternatively DHAS, F6PAld (or alternatively DHAK) and ACT. For example, for this domain the MeDH sequence can be split between amino acids 139 and 140, 140 and 141, 141 and 142, 142 and 143, 143 and 144, 144 and 145, or 145-146.

TABLE 1

| Type | Sequence | Amino Acid positions |
|---|---|---|
| coil | AGTGSETT | 139-146 |
| coil | GIPSGY | 334-339 |
| coil | HSTGL | 42-46 |
| coil | AQPDP | 67-71 |
| coil | GSSHD | 97-101 |
| coil | VNSV | 122-125 |
| coil | IPP | 7-9 |
| coil | ITP | 167-169 |

The secondary structure of any MeDH can be predicted using EMBOSS (EMBOSS: The European Molecular Biology Open Software Suite (2000) Rice, P. Longden, I. and Bleasby, A. Trends in Genetics 16, (6) pp 276-277). The residues that constitute a predicted coil (residues which are not in any of the conformations such as helix, turn, or sheet) are proposed as sites where the MeDH sequence can be split and a second open reading frame inserted.

Embodiments of the invention include fusion proteins having a region with an amino acid sequence that provides methanol dehydrogenase (MeDH) activity. In the fusion protein, the MeDH amino acid sequence can be based on a full-length protein sequence, a partial sequence, such as one having N- and or C-terminal deletions, or a variant sequence, such as one having one or more amino acid substitutions that differ from the wild type sequence.

In some embodiments the fusion protein has first and second portions of a methanol dehydrogenase which are interrupted by another amino acid sequence that is different than the methanol dehydrogenase, such as a 3-hexulose-6-phosphate dehydrogenase or 6-phospho-3-hexuloisomerase (or alternatively DHAS or F6PAld; or in a further alternative DHAS or DHAK) amino acid sequence or an enzymatically active portion thereof, or methanol dehydrogenase activator or an enzymatically active portion thereof, positioned between the first and second portions of a methanol dehydrogenase.

The fusion protein can include a polypeptide sequence based on the NAD(P)+-dependent methanol dehydrogenase from Bacillus methanolicus MGA3 (Genbank Accession number EIJ77596.1, GI number: 387585261; designated herein as MeDH 2315, 382 amino acids long; SEQ ID NO: 1). MeDH 2315 is reported in the literature as an NAD(P)-dependent methanol dehydrogenase from Bacillus methanolicus MGA3 and its sequence was described in Brautaset et al., "Plasmid-Dependent Methylotrophy in Thermotolerant Bacillus methanolicus", Journal of Bacteriology, vol. 186, pp 1229-1238 (2004). It is also referred to as MeDH MGA3 in WO2013/110797 to Brautaset and MeDH "M" in Krog et al., "Methylotrophic Bacillus methanolicus Encodes Two Chromosomal and One Plasmid Born NAD+ Dependent Methanol Dehydrogenase Paralogs with Different Catalytic and Biochemical Properties", PLOS ONE, pp. 1-11, (2013), which report additional wild-type Bacillus MeDHs. SEQ ID NO: 2 is a nucleic acid sequence encoding SEQ ID NO: 1.

The fusion protein of the disclosure can optionally have a methanol dehydrogenase sequence that is less than 100% identical to Bacillus methanolicus MGA3 (SEQ ID NO: 1). For example, the methanol dehydrogenase region in the fusion polypeptide can have 50% or greater, 60% or greater, 70% or greater, 80% or greater, 85% or greater, 90% or greater, 95% or greater, 96% or greater, 97% or greater, 98% or greater, or 99% or greater identity to (SEQ ID NO: 1).

In some cases, variants having less than 100% identity of SEQ ID NO:1 can be generated by sequence alignment of SEQ ID NO:1 with other known methanol dehydrogenases or alcohol dehydrogenases to identify regions that are conserved and/or important for enzymatic functioning of the protein. Once these regions are identified, the methanol dehydrogenase can be modified at one or more amino acid locations outside of these conserved regions. Therefore, the methanol dehydrogenase region of the fusion protein can have one or more amino acid substitutions, deletions, or additions which cause the sequence to vary from a native methanol dehydrogenase while retaining certain sequence features. Table 2 is a table of pairwise sequence identity of various methanol dehydrogenases including Bacillus methanolicus MGA3 MeDH (SEQ ID NO: 1).

TABLE 2

| | Pairwise alignment (% ID) | | | | |
|---|---|---|---|---|---|
| MeDH | Bacillus methanolicus MGA3 [1] | Bacillus methanolicus MGA3 [2] | Bacillus methanolicus PB1 | Lysinibacillus fusiformis | Clostridium perfringens str. 13 |
| Bacillus methanolicus MGA3 [1] | 100 | 62 | 60.7 | 58.4 | 48.7 |
| Bacillus methanolicus MGA3 [2] | 62 | 100 | 92.7 | 72.2 | 53.2 |
| Bacillus methanolicus PB1 | 60.7 | 92.7 | 100 | 72.2 | 53.5 |
| Lysinibacillus fusiformis | 58.4 | 72.2 | 72.2 | 100 | 51.2 |
| Clostridium perfringens str. 13 | 48.7 | 53.2 | 53.5 | 51.2 | 100 |

[1] EIJ77596.1
[2] EIJ83020.1

In other cases, variants having less than 100% identity of SEQ ID NO:1 can be generated by known variants of methanol dehydrogenases, such as described in the art. Such variants may provide increased catalytic activity in the fusion protein, such as increased conversion of methanol to formaldehyde, which is then subsequently converted into a ketose phosphate compound such as hexulose 6-phosphate, or fructose 6-phosphate due to the localization of HPS and/or PSI in the fusion protein.

Exemplary variants of *Bacillus methanolicus* MGA3 MeDH (SEQ ID NO: 1) are described in International Patent Application No. PCT/US2014/059135, the disclosure of which is incorporated herein. A fusion protein including a MeDH region of the current disclosure can include one or more amino acid substitutions based on these variants. Exemplary amino acid substitutions of SEQ ID NO: 1 include, but are not limited to, those as follows: S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I1163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K354M, N355D, N355I, N355K, E358G, V360A, V360G, V360K, V360R, V360S, C361N, C361R, Q363K, and K379M.

Other exemplary amino acid substitutions of SEQ ID NO: 1 include: D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I1163Q, D164N, Q267H, G270M, G270S, G270Y, K345E, N355D, V360G, V360K, V360R, V360S, C361R.

In exemplary embodiments a fusion protein including a MeDH region of the current disclosure includes one, two, three, or all four amino acid substitutions selected from the following group: V129M, V130I, G270S, and N355D. An exemplary MeDH variant is SEQ ID NO: 8 which is encoded by the nucleic acid sequence SEQ ID NO: 9.

Corresponding amino acid substitutions can also be made in other methanol dehydrogenase sequences based on alignment of SEQ ID NO: 1.

SEQ ID NO: 1, or an amino acid sequence with at least 50% or greater identity to SEQ ID NO: 1, can be used in any of the fusion proteins of the disclosure, including, but not limited to MeDH-PHI, MeDH-HPS, MeDH-HPS-PHI, MeDH-ACT-PHI, MeDH-ACT-HPS, HPS-MeDH, PHI-MeDH, HPS-MeDH-PHI, PHI-MeDH-HPS, PHI-MeDH-ACT, HPS-MeDH-ACT, ACT-MeDH-PHI-HPS, ACT-MeDH-HPS-PHI, HPS-PHI-MeDH-ACT, PHI-HPS-MeDH-ACT, MeDH(P1)-PHI-MeDH(P2), MeDH(P1)-HPS-PHI-MeDH(P2), and ACT-MeDH(P1)-HPS-MeDH (P2), including those fusion proteins having one or more linker sequences between regions/portions of the fusion protein. In another embodiment SEQ ID NO: 1, or an amino acid sequence with at least 50% or greater identity to SEQ ID NO: 1, can be used in any of the fusion proteins of the disclosure, including, but not limited to MeDH-DHAS, MeDH-F6PALD, MeDH-F6PALD-DHAS, MeDH-ACT-DHAS, MeDH-ACT-F6PALD, F6PALD-MeDH, DHAS-MeDH, F6PALD-MeDH-DHAS, DHAS-MeDH-F6PALD, DHAS-MeDH-ACT, F6PALD-MeDH-ACT, ACT-MeDH-DHAS-F6PALD, ACT-MeDH-F6PALD-DHAS, F6PALD-DHAS-MeDH-ACT, DHAS-F6PALD-MeDH-ACT, MeDH(P1)-DHAS-MeDH(P2), MeDH(P1)-F6PALD-DHAS-MeDH(P2), and ACT-MeDH(P1)-F6PALD-MeDH(P2), including those fusion proteins having one or more linker sequences between regions/portions of the fusion protein.

An exemplary MeDH having at least 50% or greater identity to SEQ ID NO: 1 is SEQ ID NO: 10 which is encoded by the nucleic acid sequence SEQ ID NO: 11.

The fusion protein can include a polypeptide sequence based on other methanol dehydrogenase sequences, including those known in the art. Methanol dehydrogenases are of the enzyme class (EC) 1.1.1. Other MeDH sequences include *Bacillus methanolicus* MGA3 MeDH (SEQ ID NO:1; 3EIJ77596.1); *Bacillus methanolicus* C1 MeDH (SEQ ID NO:13; AAA22593.1); *Bacillus methanolicus* PB1 MeDH (SEQ ID NO:14; EIJ77618.1); *Bacillus methanolicus* PB1 MeDH (SEQ ID NO:15; EIJ78790.1); *Bacillus methanolicus* MGA3 MeDH (SEQ ID NO:16; EIJ80770.1); *Bacillus methanolicus* PB1 MeDH (SEQ ID NO:17; EIJ78397.1); *Bacillus methanolicus* MGA3 MeDH (SEQ ID NO:18; EIJ83020.1); *Lysinibacillus fusiformis* MeDH (SEQ ID NO:19; EFI69743.1); *Bacillus coagulans* 36D1 MeDH (SEQ ID NO:20; YP_004860127.1); *Lysinibacillus sphaericus* MeDH (SEQ ID NO:21; YP_001699778.1); *Bacillus azotoformans* LMG 9581 MeDH (SEQ ID NO:22; ZP_11313277.1); *Burkholderia thailandensis* E264 MeDH (SEQ ID NO:23; ZP_05587334.1); *Cupriavidus necator* N-1 MeDH (SEQ ID NO:24; YP_004681552.1); uncultured organism MeDH (SEQ ID NO:25; AGF87161); *Geobacter bemidjiensis* Bem MeDH (SEQ ID NO:26; YP_002138168.1); *Carboxydothermus hydrogenoformans* Z-2901 MeDH (SEQ ID NO:27; YP_359772.1); *Actinobacillus succinogenes* 130Z MeDH (SEQ ID NO:28; YP_001343716.1); *Acinetobacter baumannii* Naval-82 MeDH (SEQ ID NO:29; ZP_16224338.1); *Clostridium pasteurianum* DSM 525 MeDH (SEQ ID NO:30; AAC45651.1); *Methanosarcina mazei* Tuc01 MeDH (SEQ ID NO:31; YP_007491369.1); *Desulfovibrio vulgaris* str. 'Miyazaki F' MeDH (SEQ ID NO:32; YP_002434746); *Desulfovibrio africanus* str. Walvis Bay MeDH (SEQ ID NO:33; YP_005052855); *Clostridium perfringens* str. 13 MeDH (SEQ ID NO:34; NP_561852.1); *Vibrio campbellii* ATCC BAA-1116 MeDH (SEQ ID NO:35; YP_001447544); *Desulfotomaculum reducens* MI-1 MeDH (SEQ ID NO:36; YP_001113612.1); *Desulfovibrio vulgaris* str. Hildenborough MeDH (SEQ ID NO:37; YP_011618); *Photobacterium profundum* 3TCK MeDH (SEQ ID NO:38; ZP_01220157.1); *Geobacillus* sp. Y4.1MC1 MeDH (SEQ ID NO:39; YP_003990729.1); *Desulfovibrio fructosovorans* JJ MeDH (SEQ ID NO:40; ZP_07335453.1); *Shewanella oneidensis* MR-1 MeDH (SEQ ID NO:41; NP_717107); *Sebaldella termitidis* ATCC 33386 MeDH (SEQ ID NO:42; YP_003310546.1); *Paenibacillus peoriae* KCTC 3763 MeDH (SEQ ID NO:43; ZP_10241531.1); *Klebsiella pneumoniae* subsp. *pneumoniae* MGH 78578 MeDH (SEQ ID NO:44; YP_001337153.1); *Escherichia coli* MeDH (SEQ ID NO:45; YP_026233.1); *Clostridium perfringens* ATCC 13124 MeDH (SEQ ID NO:46; YP_694908); *Ralstonia eutropha* H16 MeDH (SEQ ID NO:47; YP_725376.1); *Thermoanaerobacter* sp. X514 MeDH (SEQ ID NO:48; YP_001663549); human gut metagenome MeDH (SEQ ID NO:49; EKC54576); or *Geobacillus themodenitrificans*

NG80-2 MeDH (SEQ ID NO:50; YP_001126968.1). One of skill can modify the MeDH with one or more amino acids substitutions, deletions, and/or additions based on alignment of MeDH sequences, including those known in the art.

Any of these MeDH sequences, or an amino acid sequence with at least 50% or greater identity to these sequences, can be used in any of the fusion proteins of the disclosure, including, but not limited to MeDH-PHI, MeDH-HPS, MeDH-HPS-PHI, MeDH-ACT-PHI, MeDH-ACT-HPS, HPS-MeDH, PHI-MeDH, HPS-MeDH-PHI, PHI-MeDH-HPS, PHI-MeDH-ACT, HPS-MeDH-ACT, ACT-MeDH-PHI-HPS, ACT-MeDH-HPS-PHI, HPS-PHI-MeDH-ACT, PHI-HPS-MeDH-ACT, MeDH(P1)-PHI-MeDH(P2), MeDH(P1)-HPS-PHI-MeDH(P2), and ACT-MeDH(P1)-HPS-MeDH(P2), including those fusion proteins having one or more linker sequences between regions/portions of the fusion protein. In embodiments of MeDH with DHA Pathway enzymes, any of these MeDH sequences, or an amino acid sequence with at least 50% or greater identity to these sequences, can be used in any of the fusion proteins of the disclosure, including, but not limited to MeDH-DHAS, MeDH-F6PALD, MeDH-F6PALD-DHAS, MeDH-ACT-DHAS, MeDH-ACT-F6PALD, F6PALD-MeDH, DHAS-MeDH, F6PALD-MeDH-DHAS, DHAS-MeDH-F6PALD, DHAS-MeDH-ACT, F6PALD-MeDH-ACT, ACT-MeDH-DHAS-F6PALD, ACT-MeDH-F6PALD-DHAS, F6PALD-DHAS-MeDH-ACT, DHAS-F6PALD-MeDH-ACT, MeDH(P1)-DHAS-MeDH(P2), MeDH(P1)-F6PALD-DHAS-MeDH(P2), and ACT-MeDH(P1)-F6PALD-MeDH(P2), including those fusion proteins having one or more linker sequences between regions/portions of the fusion protein.

In some embodiments of the disclosure, an engineered cell can express one or more fusion proteins that include a MeDH region, in addition to a MeDH protein that is not fused to another protein (e.g., a MeDH protein in wild-type form). Expression of a non-fused MeDH protein, in combination with MeDH fusion proteins that include a 3-hexulose-6-phosphate dehydrogenase activity or 6-phospho-3-hexuloisomerase region can allow expression of desired amounts of polypeptide conferring MeDH, HPS, PHI, and ACT in the cell. As discussed herein, MeDH and MeDH fusion proteins can form a multi-protein complex and predetermined amounts of MeDH, HPS, PHI, and ACT can be present in the multi-protein complex to provide optimal conversion of methanol through d-arabino-3-hexulose-6-phosphate to fructose 6-phosphate. In embodiments of MeDH with the DHA Pathway enzymes of the disclosure, an engineered cell can express one or more fusion proteins that include a MeDH region, in addition to a MeDH protein that is not fused to another protein (e.g., a MeDH protein in wild-type form). Expression of a non-fused MeDH protein, in combination with MeDH fusion proteins that include a DHAS or F6PAld (or DHAK) region can allow expression of desired amounts of polypeptide conferring MeDH, DHAS, F6PAld (or DHAK), and ACT in the cell. As discussed herein, MeDH and MeDH fusion proteins can form a multi-protein complex and predetermined amounts of MeDH, DHAS, F6PAld (or DHAK), and ACT can be present in the multi-protein complex to provide optimal conversion of methanol through DHA and G3P to fructose 6-phosphate.

Other suitable methanol dehydrogenase sequences that can be used in the fusion protein of the disclosure include those that are "orthologs" of known methanol dehydrogenase sequences, such as SEQ ID NO: 1, can be identified and part or all of its sequence can be used to prepare the fusion proteins of the disclosure. An ortholog is a gene or genes that are related by vertical descent and are responsible for substantially the same or identical functions in different organisms. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 45% to 100% amino acid sequence identity, and more preferably about 60% to 100% amino acid sequence identity.

For example, genes sharing a desired amount of identity (e.g., 45%, 50%, 55%, or 60% or greater) to the NAD(P)-dependent methanol dehydrogenase from *Bacillus methanolicus* MGA3 (2315A), including orthologs and paralogs, can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor.

Computational approaches to sequence alignment and generation of sequence identity include global alignments and local alignments. Global alignment uses global optimization to forces alignment to span the entire length of all query sequences. Local alignments, by contrast, identify regions of similarity within long sequences that are often widely divergent overall. For understanding the identity of a target sequence to a known methanol dehydrogenase, such as For the *Bacillus methanolicus* MGA3 (2315A) template, a global alignment can be used. Optionally, amino terminal and/or carboxyl-terminal sequences of the target sequence that share little or no identity with the template sequence can be excluded for a global alignment and generation of an identity score.

Algorithms well known to those skilled in the art, such as Align, BLAST, Clustal W and others compare and determine a raw sequence similarity or identity, and also determine the presence or significance of gaps in the sequence which can be assigned a weight or score. Default parameters can be used for the alignment and BLOSUM62 as the scoring matrix.

Such algorithms also are known in the art and are similarly applicable for determining nucleotide sequence similarity or identity. Parameters for sufficient similarity to determine relatedness are computed based on well-known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 45% to 100% sequence identity. Proteins that are unrelated can have an identity which is essentially the same as would be expected to occur by chance, if a database of sufficient size is scanned (about 5%).

In some cases, it can be useful to use the Basic Local Alignment Search Tool (BLAST) algorithm to understand the sequence identity between an amino acid motif in a template sequence and a target sequence. Therefore, in preferred modes of practice, BLAST is used to identify or understand the identity of a shorter stretch of amino acids (e.g. a sequence motif) between a template and a target protein. BLAST finds similar sequences using a heuristic method that approximates the Smith-Waterman algorithm by locating short matches between the two sequences. The (BLAST) algorithm can identify library sequences that resemble the query sequence above a certain threshold. Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The enzyme 3-hexulose-6-phosphate synthase (HPS) can carry out the fixation of formaldehyde with ribulose 5-phosphate (Ru5P) to form d-arabino-3-hexulose-6-phosphate (Hu6P). The fusion protein can include a polypeptide sequence based on *Bacillus methanolicus* MGA HPS (Genbank Accession number AAR39392.1, 211 amino acids long; SEQ ID NO: 3).

The fusion protein of the disclosure can optionally have a 3-hexulose-6-phosphate synthase sequence that is less than 100% identical to *Bacillus methanolicus* MGA HPS (SEQ ID NO: 3). For example, the methanol dehydrogenase region in the fusion polypeptide can have 50% or greater, 60% or greater, 70% or greater, 80% or greater, 85% or greater, 90% or greater, 95% or greater, 96% or greater, 97% or greater, 98% or greater, or 99% or greater identity to SEQ ID NO: 3.

In some cases, variants having less than 100% identity of SEQ ID NO: 3 can be generated by sequence alignment of SEQ ID NO: 3 with other known 3-hexulose-6-phosphate synthase to identify regions that are conserved and/or important for enzymatic functioning of the protein. Once these regions are identified, the 3-hexulose-6-phosphate synthase can be modified at one or more amino acid locations outside of these conserved regions. Therefore, the 3-hexulose-6-phosphate synthase region of the fusion protein can have one or more amino acid substitutions, deletions, or additions which cause the sequence to vary from a native methanol dehydrogenase while retaining certain sequence features.

SEQ ID NO: 3, or an amino acid sequence with at least 50% or greater identity to SEQ ID NO: 3, can be used in fusion proteins of the disclosure, including, but not limited to MeDH-PHI, MeDH-HPS, MeDH-HPS-PHI, MeDH-ACT-PHI, MeDH-ACT-HPS, HPS-MeDH, PHI-MeDH, HPS-MeDH-PHI, PHI-MeDH-HPS, PHI-MeDH-ACT, HPS-MeDH-ACT, ACT-MeDH-PHI-HPS, ACT-MeDH-HPS-PHI, HPS-PHI-MeDH-ACT, PHI-HPS-MeDH-ACT, MeDH(P1)-HPS-PHI-MeDH(P2), ACT-MeDH(P1)-HPS-MeDH(P2), including those fusion proteins having one or more linker sequences between regions/portions of the fusion protein.

The fusion protein can include a polypeptide sequence based on other 3-hexulose-6-phosphate dehydrogenase sequences, including those known in the art. 3-hexulose-6-phosphate dehydrogenases are of the enzyme class (EC) 4.1.2.43. Other 3-hexulose-6-phosphate dehydrogenases include, but are not limited to, *Bacillus methanolicus* PB1 HPS (SEQ ID NO: 51; EIJ81375.1); *Methylobacillus flagellatus* HPS (SEQ ID NO: 52; YP_544362.1); *Methylobacillus flagellatus* HPS (SEQ ID NO:63; YP 544363.1); *Bacillus subtilis* HPS (SEQ ID NO: 53; NP_388228.1); *Methylophilus methylotrophus* HPS (SEQ ID NO: 54; WP_018986666.1); *Methylophilus methylotrophus* ATCC 53528 HPS (SEQ ID NO: 55; WP_018985298.1); *Aminomonas aminovorus* HPS (SEQ ID NO:64; AAG29505.1), *Amycolatopsis methanolica* 239 HPS (SEQ ID NO:65; AIJ24611.1); *Geobacillus* sp. GHHO1 HPS (SEQ ID NO:66; YP_007402409.1); *Geobacillus* sp. M10EXGHPS (SEQ ID NO:67; AAR91478.1); *Geobacillus* sp. Y4.1MC1 HPS (SEQ ID NO:68; YP_003990382.1); *Geobacillus thermodenitrificans* NG80-2 HPS (SEQ ID NO:69; WP_008879217.1); *Methylomonas aminofaciens* HPS (SEQ ID NO:70; BAA83096.1); *Methylovorus glucosetrophus* SIP3-4 HPS (SEQ ID NO:71; YP_003050044.1); *Methylovorus* sp. MP688 HPS (SEQ ID NO:72; YP_004038706.1); and *Mycobacterium gastri* HPS (SEQ ID NO: 62; BAA90546.1).

Any of these HPS sequences, or an amino acid sequence with at least 50% or greater identity to these sequences, can be used in fusion proteins of the disclosure, including, but not limited to MeDH-PHI, MeDH-HPS, MeDH-HPS-PHI, MeDH-ACT-PHI, MeDH-ACT-HPS, HPS-MeDH, PHI-MeDH, HPS-MeDH-PHI, PHI-MeDH-HPS, PHI-MeDH-ACT, HPS-MeDH-ACT, ACT-MeDH-PHI-HPS, ACT-MeDH-HPS-PHI, HPS-PHI-MeDH-ACT, PHI-HPS-MeDH-ACT, MeDH(P1)-HPS-PHI-MeDH(P2), ACT-MeDH(P1)-HPS-MeDH(P2), including those fusion proteins having one or more linker sequences between regions/portions of the fusion protein.

Other suitable 3-hexulose-6-phosphate dehydrogenase sequences that can be used in the fusion protein of the disclosure include those that are "orthologs" of known 3-hexulose-6-phosphate dehydrogenase sequences, such as orthologs of SEQ ID NO: 3, can be identified and part or all of its sequence can be used to prepare the fusion proteins of the disclosure.

One of skill can modify the HPS with one or more amino acid substitutions, deletions, and/or additions based on alignment of HPS sequences, including those known in the art. Tables 3A and 3B are tables of pairwise sequence identity of various 3 hexulose 6 phosphate dehydrogenase sequences including *Bacillus methanolicus* MGA HPS (SEQ ID NO: 3).

TABLE 3A

| HPS | Pairwise alignment (% ID) | | | | | | |
|---|---|---|---|---|---|---|---|
| | *Geobacillus thermodenitrificans* NG80-2 | *Bacillus methanolicus* MGA3 | *Bacillus methanolicus* PB1 | *Geobacillus* sp. GHH01 | *Geobacillus* sp. M10EXG | *Geobacillus* sp. γ4.1MC1 | *Methylophilus methylotrophus* |
| *Geobacillus thermodenitrificans* NG80-2 | 100 | 30.8 | 30.8 | 30.3 | 29.9 | 29.9 | 31.8 |
| *Bacillus methanolicus* MGA3 | 30.8 | 100 | 98.1 | 76.8 | 76.8 | 77.3 | 38.4 |
| *Bacillus methanolicus* PB1 | 30.8 | 98.1 | 100 | 76.3 | 76.3 | 76.8 | 37.9 |
| *Geobacillus* sp. GHH01 | 30.3 | 76.8 | 76.3 | 100 | 97.6 | 98.1 | 38.9 |
| *Geobacillus* sp. M10EXG | 29.9 | 76.8 | 76.3 | 97.6 | 100 | 99.5 | 38.4 |
| *Geobacillus* sp. γ4.1MC1 | 29.9 | 77.3 | 76.8 | 98.1 | 99.5 | 100 | 38.4 |
| *Methylophilus methylotrophus* | 31.8 | 38.4 | 37.9 | 38.9 | 38.4 | 38.4 | 100 |
| *Methylophilus methylotrophus* ATCC 53528 | 32.1 | 34.4 | 34 | 38.3 | 37.8 | 37.8 | 81.9 |
| *Methylobacillus flagellatus* | 33.2 | 37.5 | 37 | 40.9 | 40.4 | 40.4 | 83.7 |
| *Methylomonas aminofaciens* | 32.7 | 36.5 | 36.1 | 39.9 | 39.4 | 39.4 | 84.7 |
| *Methylovorus glucosetrophus* SIP3-4 | 31.5 | 37.2 | 36.7 | 38.2 | 37.7 | 37.7 | 80.4 |
| *Aminomonas aminovorus* | 31.3 | 37 | 36.5 | 37.9 | 37.4 | 37.4 | 76.1 |
| *Methylobacillus flagellatus* | 31.3 | 37 | 36.5 | 37.9 | 37.4 | 37.4 | 76.5 |
| *Amycolatopsis methanolica* 239 | 33.8 | 40 | 38.6 | 37.6 | 38.1 | 38.1 | 46.2 |
| *Mycobacterium gastri* | 32.7 | 39.4 | 39.9 | 39.4 | 38.9 | 38.9 | 46.6 |

TABLE 3B

| HPS | Pairwise alignment (% ID) | | | |
|---|---|---|---|---|
| | *Methylophilus methylotrophus* ATCC 53528 | *Methylobacillus flagellatus* | *Methylomonas aminofaciens* | *Methylovorus glucosetrophus* SIP3-4 |
| *Geobacillus thermodenitrificans* NG80-2 | 32.1 | 33.2 | 32.7 | 31.5 |
| *Bacillus methanolicus* MGA3 | 34.4 | 37.5 | 36.5 | 37.2 |
| *Bacillus methanolicus* PB1 | 34 | 37 | 36.1 | 36.7 |
| *Geobacillus* sp. GHH01 | 38.3 | 40.9 | 39.9 | 38.2 |
| *Geobacillus* sp. M10EXG | 37.8 | 40.4 | 39.4 | 37.7 |
| *Geobacillus* sp. γ4.1MC1 | 37.8 | 40.4 | 39.4 | 37.7 |
| *Methylophilus methylotrophus* | 81.9 | 83.7 | 84.7 | 80.4 |
| *Methylophilus methylotrophus* ATCC 53528 | 100 | 87.1 | 87.6 | 82 |
| *Methylobacillus flagellatus* | 87.1 | 100 | 97.1 | 88.2 |
| *Methylomonas aminofaciens* | 87.6 | 97.1 | 100 | 89.2 |
| *Methylovorus glucosetrophus* SIP3-4 | 82 | 88.2 | 89.2 | 100 |
| *Aminomonas aminovorus* | 83.3 | 87.6 | 86.1 | 90.5 |
| *Methylobacillus flagellatus* | 83.8 | 86.6 | 86.1 | 90.5 |
| *Amycolatopsis methanolica* 239 | 47.1 | 47.4 | 46.9 | 46.6 |
| *Mycobacterium gastri* | 47.1 | 47.1 | 45.7 | 45.6 |

| HPS | *Aminomonas aminovorus* | *Methylobacillus flagellatus* | *Amycolatopsis methanolica* 239 | *Mycobacterium gastri* |
|---|---|---|---|---|
| *Geobacillus thermodenitrificans* NG80-2 | 31.3 | 31.3 | 33.8 | 32.7 |
| *Bacillus methanolicus* MGA3 | 37 | 37 | 40 | 39.4 |
| *Bacillus methanolicus* PB1 | 36.5 | 36.5 | 38.6 | 39.9 |
| *Geobacillus* sp. GHH01 | 37.9 | 37.9 | 37.6 | 39.4 |
| *Geobacillus* sp. M10EXG | 37.4 | 37.4 | 38.1 | 38.9 |
| *Geobacillus* sp. γ4.1MC1 | 37.4 | 37.4 | 38.1 | 38.9 |
| *Methylophilus methylotrophus* | 76.1 | 76.5 | 46.2 | 46.6 |
| *Methylophilus methylotrophus* ATCC 53528 | 83.3 | 83.8 | 47.1 | 47.1 |
| *Methylobacillus flagellatus* | 87.6 | 86.6 | 47.4 | 47.1 |
| *Methylomonas aminofaciens* | 86.1 | 86.1 | 46.9 | 45.7 |
| *Methylovorus glucosetrophus* SIP3-4 | 90.5 | 90.5 | 46.6 | 45.6 |
| *Aminomonas aminovorus* | 100 | 97.4 | 47.6 | 47.1 |
| *Methylobacillus flagellatus* | 97.4 | 100 | 47.6 | 46.2 |
| *Amycolatopsis methanolica* 239 | 47.6 | 47.6 | 100 | 60.1 |
| *Mycobacterium gastri* | 47.1 | 46.2 | 60.1 | 100 |

6-phospho-3-hexuloisomerase activity (PHI), can carry out the isomerization of d-arabino-3-hexulose-6-phosphate (Hu6P) to fructose 6-phosphate (F6P). The fusion protein can include a polypeptide sequence based on *Bacillus methanolicus* MGA3 PHI (Genbank Accession number AAR39393.1, 184 amino acids long; SEQ ID NO: 4).

The fusion protein of the disclosure can optionally have a 6-phospho-3-hexuloisomerase sequence that is less than 100% identical to *Bacillus methanolicus* MGA3 PHI (SEQ ID NO: 4). For example, the methanol dehydrogenase region in the fusion polypeptide can have 50% or greater, 60% or greater, 70% or greater, 80% or greater, 85% or greater, 90% or greater, 95% or greater, 96% or greater, 97% or greater, 98% or greater, or 99% or greater identity to (SEQ ID NO: 4).

In some cases, variants having less than 100% identity of SEQ ID NO: 4 can be generated by sequence alignment of SEQ ID NO: 4 with other known 6-phospho-3-hexuloisomerase to identify regions that are conserved and/or important for enzymatic functioning of the protein. Once these regions are identified, the 6-phospho-3-hexuloisomerase can be modified at one or more amino acid locations outside of these conserved regions. Therefore, the 6-phospho-3-hexuloisomerase region of the fusion protein can have one or more amino acid substitutions, deletions, or additions which cause the sequence to vary from a native 6-phospho-3-hexuloisomerase while retaining certain sequence features.

SEQ ID NO: 4, or an amino acid sequence with at least 50% or greater identity to SEQ ID NO: 4, can be used in fusion proteins of the disclosure, including, but not limited to MeDH-PHI, MeDH-HPS-PHI, ACT-MeDH-HPS-PHI, PHI-MeDH, HPS-MeDH-PHI, PHI-MeDH-HPS, MeDH (P1)-PHI-MeDH(P2), MeDH(P1)-HPS-PHI-MeDH(P2), including those fusion proteins having one or more linker sequences between regions/portions of the fusion protein.

The fusion protein can include a polypeptide sequence based on other 6-phospho-3-hexuloisomerase activity sequences, including those known in the art. 6-phospho-3-hexuloisomerases are of the enzyme class (EC) 5.3.1.27. Other PHI sequences include, but are not limited to *Bacillus methanolicus* PB1 PHI (SEQ ID NO: 56; EIJ81376.1); *Mycobacterium gastri* PB1 PHI (SEQ ID NO: 57; BAA90545.1); *Methylobacillus flagellatus* KT PHI (SEQ ID NO: 58; YP 545762.1); *Bacillus subtilis* PHI (SEQ ID NO: 59; NP_388227.1); *Methylophilus methylotrophus* ATCC 53528 HPS (SEQ ID NO: 60; WP_018985297.1); *Amycolatopsis methanolica* 239 PHI (SEQ ID NO:73; AIJ24609.1); *Geobacillus* sp. GHH01 PHI (SEQ ID NO:74: YP_007402408.1); *Geobacillus* sp. Y4.1MC1 PHI (SEQ ID NO:75; YP_003990383.1); *Geobacillus thermodenitrificans* NG80-2 PHI (SEQ ID NO:76; WP_011887353.1); *Methylomonas aminofaciens* PHI (SEQ ID NO:77; BAA83098.1); *Methylovorus glucosetrophus* SIP3-4 PHI (SEQ ID NO:78; YP_003051269.1); and *Methylovorus* sp. MP688 PHI (SEQ ID NO:79: ADQ84715.1).

Any of these PHI sequences, or an amino acid sequence with at least 50% or greater identity to these sequences, can be used in fusion proteins of the disclosure, including, but not limited to MeDH-PHI, MeDH-HPS-PHI, ACT-MeDH-HPS-PHI, PHI-MeDH, HPS-MeDH-PHI, PHI-MeDH-HPS, MeDH(P1)-PHI-MeDH(P2), MeDH(P1)-HPS-PHI-MeDH (P2), including those fusion proteins having one or more linker sequences between regions/portions of the fusion protein.

One of skill can modify the PHI with one or more amino acid substitutions, deletions, and/or additions based on alignment of PHI sequences, including those known in the art. Tables 4A and 4B are tables of pairwise sequence identity of various 6-phospho-3-hexuloisomerase sequences including *Bacillus methanolicus* MGA3 PHI (SEQ ID NO: 4).

TABLE 4A

Pairwise alignment (% ID)

| PHI | *Methylobacillus flagellatus* KT | *Methylomonas aminofaciens* | *Methylophilus methylotrophus* ATCC 53528 | *Methylovorus glucosetrophus* SIP3-4 | *Geobacillus thermodenitrificans* NG80-2 |
|---|---|---|---|---|---|
| *Methylobacillus flagellatus* KT | 100 | 95.6 | 58.9 | 64.4 | 31.1 |
| *Methylomonas aminofaciens* | 95.6 | 100 | 59.4 | 65 | 30.6 |
| *Methylophilus methylotrophus* ATCC 53528 | 58.9 | 59.4 | 100 | 85.5 | 28 |
| *Methylovorus glucosetrophus* SIP3-4 | 64.4 | 65 | 86.5 | 100 | 29.7 |
| *Geobacillus thermodenitrificans* NG80-2 | 31.1 | 30.6 | 28 | 29.7 | 100 |
| *Bacillus methanolious* MGA3 | 32.4 | 33 | 32 | 33.1 | 37.2 |
| *Bacillus methanolious* PB1 | 32.4 | 33 | 32 | 33.1 | 37.2 |
| *Geobacillus* sp. GHH01 | 35 | 34.4 | 32.4 | 32.4 | 41.5 |
| *Geobacillus* sp. γ4.1MC1 | 33.9 | 34.4 | 33 | 33.5 | 39.9 |
| *Amycolatopsis methanolica* 239 | 31.3 | 31.9 | 27.1 | 27.6 | 36.6 |
| *Mycobacterium gastri* | 33 | 33 | 31.5 | 33.1 | 37.7 |

TABLE 4B

Pairwise alignment (% ID)

| PHI | *Bacillus methanolicus* MGA3 | *Bacillus methanolicus* PB1 | *Geobacillus* sp. GHH01 | *Geobacillus* sp. γ4.1MC1 | *Amycolatopsis methanolica* 239 | *Mycobacterium gastri* |
|---|---|---|---|---|---|---|
| *Methylobacillus flagellatus* KT | 32.4 | 32.4 | 35 | 33.9 | 31.3 | 33 |
| *Methylomonas aminofaciens* | 33 | 33 | 34.4 | 34.4 | 31.9 | 33 |
| *Methylophilus methylotrophus* ATCC 53528 | 32 | 32 | 32.4 | 33 | 27.1 | 31.5 |

TABLE 4B-continued

| PHI | Pairwise alignment (% ID) | | | | | |
|---|---|---|---|---|---|---|
| | Bacillus methanolicus MGA3 | Bacillus methanolicus PB1 | Geobacillus sp. GHH01 | Geobacillus sp. γ4.1MC1 | Amycolatopsis methanolica 239 | Mycobacterium gastri |
| Methylovorus glucosetrophus SIP3-4 | 33.1 | 33.1 | 32.4 | 33.5 | 27.6 | 33.1 |
| Geobacillus thermodenitrificans NG80-2 | 37.2 | 37.2 | 41.5 | 39.9 | 36.6 | 37.7 |
| Bacillus methanolicus MGA3 | 100 | 98.9 | 75.1 | 76.8 | 32.6 | 37.5 |
| Bacillus methanolicus PB1 | 98.9 | 100 | 74.6 | 76.2 | 32.6 | 38.6 |
| Geobacillus sp. GHH01 | 75.1 | 74.6 | 100 | 93 | 33 | 36.2 |
| Geobacillus sp. γ4.1MC1 | 76.8 | 76.2 | 93 | 100 | 32.6 | 38 |
| Amycolatopsis methanolica 239 | 32.6 | 32.6 | 33 | 32.6 | 100 | 47.7 |
| Mycobacterium gastri | 37.5 | 38.6 | 36.2 | 38 | 47.7 | 100 |

Engineered cells of the disclosure can also express MeDH-containing fusion proteins that include sequences of naturally-occurring HPS-PHI fusion proteins, or variants thereof.

The engineered fusion protein can include a polypeptide sequence based on natural HPS-PHI fusions, such as, a fusion from Methylococcus capsulatas (YP_115138.1); Methylomicrobium album BG8 (EIC30826.1); Pyrococcus abyssi (NP_127388.1); Pyrococcus furiosus (NP_577949.1); Pyrococcus horikoshii OT3 (NP_143767.1), or Thermococcus kodakaraensis (YP_182888.1). An exemplary HPS-PHI fusion is SEQ ID NO: 5.

Any of these HPS-PHI sequences, or an amino acid sequence with at least 50% or greater identity to these sequences, can be used in the fusion proteins of the disclosure, such as MeDH-PHI, MeDH-HPS-PHI, ACT-MeDH-HPS-PHI, and MeDH(P1)-HPS-PHI-MeDH(P2), including those fusion proteins having one or more linker sequences between regions/portions of the fusion protein.

Engineered cells of the disclosure (whether using HPA and PHI or using DHAS or F6PALd, or DHAS and DHAK) can also express MeDH-containing fusion proteins that include a MeDH activator sequence. A MeDH activator sequence can activate a MeDH enzyme by providing hydrolytic removal of a nicotinamide mononucleotide (NMN) moiety of the NAD cofactor. MeDH activator is active in the presence of magnesium ions and is also able to use ADP-ribose. (Kloosterman, H., et al. (2002) J Biol Chem. 277: 34785-34792).

The engineered fusion protein can include a polypeptide sequence based on MeDH activator sequences, such as, activators of Bacillus methanolicus MGA3 (WP_004435441.1; SEQ ID NO: 12) and Bacillus methanolicus PB1 (SEQ ID NO:80. WP_004437560.1).

These MeDH activator sequences, or an amino acid sequence with at least 50% or greater identity to SEQ ID NO: 12, can be used in the fusion proteins of the disclosure, such as MeDH-ACT-PHI, MeDH-ACT-HPS, HPS-MeDH-ACT, ACT-MeDH-PHI-HPS, ACT-MeDH-HPS-PHI, HPS-PHI-MeDH-ACT, PHI-HPS-MeDH-ACT, and ACT-MeDH(P1)-HPS-MeDH(P2).

One or more linker amino acid sequences can be present between regions in the fusion proteins of the disclosure. Linker sequence can provide desired functionality in the fusion protein. Some fusion proteins of the disclosure can be expressed as a single open reading frame without the introduction of linker(s), and some fusion proteins of the disclosure can include a linker sequence between one or more regions of the fusion protein, wherein the linker can allow the region to exhibit desired enzymatic activity. Linker sequences can generically be described as "rigid" or "flexible," with linker sequences of longer length generally considered to be more flexible. Rigid linkers frequently form alpha-helical structures. Linker sequences can be prepared to provide desired properties such as length, solubility, and protease sensitivity.

Exemplary linker sequences are from 1 to 150, 1 to 100, or 1 to 50 amino acids in length. Some linker sequences are short, such as from one to ten, or from two to six amino acids in length. Linker sequences may be referred to as "linkers," "linker peptides," "linker peptide sequences." The linker may include any amino acid, but preferably includes one or more amino acids that are selected from the group consisting of glycine, alanine, serine, and threonine. In some linker sequences the majority (>50%) of the amino acids residues are glycine. Some linker sequences may include acidic residues such as Asp or Glu, or basic residues, such as Lys, Arg. Linker sequences can be chosen to impart one or more particular properties to the fusion protein, such as improved stability or solubility properties. The amino acids may provide regions of flexibility between the MeDH, PHI, HPS, and/or ACT regions in the fusion proteins.

Exemplary linker sequence include, but are not limited to $(G)_n$ where n is 4-8; $(GS)_n$, $(GGS)_n$, $(GGGS)_n$, $(GGGGS)_n$, and $(GGGGGS)_n$, where n is 1-6, such as 1, 2, 3, 4, 5, or 6; $[(GGS)_x(GS)_y]n$ where x is 1-6, y is 1-6, and n is 1-4; $(GE)_n$, $(GGE)_n$, $(GGGE)_n$, and $(GGGGE)_n$, where n is 1-10; $(GD)_n$, $(GGD)_n$, $(GGGD)_n$, and $(GGGGD)_n$, where n is 1-10; $(GK)_n$, $(GGK)_n$, $(GGGK)_n$, and $(GGGGK)_n$, where n is 1-10; $(GR)_n$, $(GGR)_n$, $(GGGR)_n$, and $(GGGGR)_n$, where n is 1-10; $(EAAAK)_n$ where n is 1-10; $A(EAAAK)_nA$ where n is 1-10; $A(EAAAK)_4ALEA(EAAAK)_4A$; $(PAPAP)_n$ where n is 1-4; $(AEAAAKEAAAKA)_n$ where n is 1-4; $(AP)_n$ where n is 1-35; $(KP)_n$ where n is 1-35; $(EP)_n$ where n is 1-35; $(LE)_n$ where n is 1-35; $(GA_2PA_3PAKQEA_3PAPA_2KAEAPA_3PA_2KA)_n$ where n is 1-5; $(KESGSVSSEQLAQFRSLD)_n$ where n is 1-5; $(EGKSSGSGSESKST)_n$ where n is 1-5; $(GSAGSAAGSGEF)_n$ where n is 1-4; $[A(EAAAK)_nA]_y$ where n is 1-5 and y is 1-4; $(GGSGGSGSGSGGSGSGSGGS)_n$ where n is 1 or 2; and SSGWGSGG.

Preferably the linker is $[(GGS)_x(GS)_y(GGS)_z]_n$ (SEQ ID NO:91) where x is 1-6, y is 1-6, z is 0-3, and n is 1-4, preferably where x is 1-3, y is 1-3, z is 1-2, and n is 1-2.

Fusion protein formulas may optionally be described with reference to one or more SEQ ID NO(s). For example, a fusion protein of the general formula MeDH-L$^1$-HPS-L$^2$-PHI, may be more specifically described as SEQ ID NO:1-

L$^1$-SEQ ID NO:3-L$^2$-SEQ ID NO:4. If the fusion protein has a sequences with less than 100% identity to referenced sequences (e.g., 90% or greater identity), the fusion protein may described as follows: [SEQ ID NO:1, ≥90%]-L$^1$-[SEQ ID NO:3, ≥90%]-L$^2$-[SEQ ID NO:4, ≥90%]. Or for example, a fusion protein of the general formula MeDH-L$^1$-DHAS-L$^2$-F6PAld, may be more specifically described as SEQ ID NO:1-L$^1$-SEQ ID NO:X-L$^2$-SEQ ID NO:Y, where X and Y are a SEQ ID Number of a DHAS or F6PAld sequence, respectively, of which are exemplary sequences are described herein and below. If the fusion protein has a sequences with less than 100% identity to referenced sequences (e.g., 90% or greater identity), the fusion protein may described as follows: [SEQ ID NO:1≥90%]-L$^1$-[SEQ ID NO:X≥90%]-L$^2$-[SEQ ID NO:Y≥90%].

As another example, a fusion protein of the general formula ACT-L$^1$-MeDH-L$^2$-PHI-L$^3$-HPS, may be more specifically described as SEQ ID NO:12-L$^1$-SEQ ID NO:1-L$^2$-SEQ ID NO:4-L$^3$-SEQ ID NO:3. If certain regions of the fusion protein have sequences with less than 100% identity (e.g., 90% or greater identity, 85% or greater identity) to referenced sequences, the fusion protein may described as follows: SEQ ID NO:12-L$^1$-[SEQ ID NO:1≥90%]-L$^2$-SEQ ID NO:4-L$^3$-[SEQ ID NO:3≥85%].

As another example, a fusion protein of the general formula MeDH-L$^1$-HPS-PHI, wherein HPS-PHI is from a natural fusion protein, may be more specifically described as SEQ ID NO:1-L$^1$-SEQ ID NO:5, SEQ ID NO:6-L$^1$-SEQ ID NO:5, SEQ ID NO:8-L$^1$-SEQ ID NO:5, or SEQ ID NO: 10-L$^1$-SEQ ID NO:5. In some arrangements L$^1$ is SEQ ID NO:7. In some embodiments the fusion protein has 50% or greater, 60% or greater, 70% or greater, 80% or greater, 85% or greater, 90% or greater, 95% or greater, 96% or greater, 97% or greater, 98% or greater, or 99% or greater identity to SEQ ID NO: 1-SEQ ID NO:7-SEQ ID NO:5, SEQ ID NO:6-SEQ ID NO:7-SEQ ID NO:5, SEQ ID NO:8-SEQ ID NO:7-SEQ ID NO:5, or SEQ ID NO:10-SEQ ID NO:7-SEQ ID NO:5.

In some embodiments of the invention, fusion proteins are expressed in an engineered cell to provide a multi-protein complex including the fusion proteins. Formation of a multi-protein complex can be achieved through MeDH-MeDH interactions. MeDH is believed to be a homo-multimeric protein, frequently composed of 10 monomer subunits. It has been shown that MeDH from *Methylococcus capsulatus* (Bath) is primarily a dimer in solution, and an oligomeric species with a molecular mass of ~450-560 kDa forms at higher protein concentrations. (Culpepper M. A., Rosenzweig, A. C. (2014) Biochemistry 53:6211-6219). Therefore, a multi-protein complex can be formed in the cell by interactions between MeDH portions of fusion proteins, or between MeDH portions of fusion proteins and a non-fused MeDH, HPS, PHI, and/or ACT (e.g., wild type) proteins, or between MeDH portions of fusion proteins and a non-fused MeDH, DHAS, F6PAld (or DHAK) and/or ACT (e.g., wild type) proteins. The expression of desired fusion proteins, or combination of fusion proteins and unfused proteins, can produce a variety of heterodecamers or heteromultimers with activity optimized for methanol utilization, in some cases, subsequent bioproduct formation. For example, the cell can be engineered to provide a multi-protein complex that efficiently converts methanol to d-arabino-3-hexulose-6-phosphate to fructose 6-phosphate, which then can be further used as a precursor to a desired bioproduct.

A cell can be engineered in such a way to provide desired ratios of MeDH, HPS, PHI, and ACT sequences or to provide desired ratios of MeDH, DHAS, F6PAld (or DHAK) and ACT sequences. For example, the cell can include exogenous nucleic acids encoding the following fusion proteins: MeDH-PHI, MeDH-HPS, and MeDH-ACT, (or alternately MeDH-DHAS, MeDH-F6PAld and MeDH-ACT) and if the cell is engineered so that each of these fusion proteins is expressed in equal numbers, then the amount of MeDH sequence would be stoichiometrically greater (three times) greater than PHI, HPS, and ACT sequences (or alternatively DHAS, F6PALd and ACT sequences). Optionally, the cell can be engineered to express a MeDH (non-fusion) protein. The fusion proteins can assemble along with the non-fusion MeDH protein to form a multi-protein complex having a desired ratio of protein components which in turn can provide an optimal balance of methanol pathway activities to maximize methanol flux.

In some embodiments, the cell is engineered to provide a stoichiometric ratio of MeDH that is greater than any one of HPS, PHI, or ACT (MeDH>HPS, PHI, or ACT). For example, the ratio of MeDH to any one of HPS, PHI, or ACT can be in the range of 10:1 to 0.5:1, 6:1 to 1:1, or 3:1 to 1:1. Alternatively in some embodiments, the cell is engineered to provide a stoichiometric ratio of MeDH that is greater than any one of DHAS, F6PALd or ACT (MeDH>DHAS, F6PAld or ACT). For example, the ratio of MeDH to any one of DHAS, F6PAld or ACT can be in the range of 10:1 to 0.5:1, 6:1 to 1:1, or 3:1 to 1:1.

An expression vector or vectors can be constructed to include one or more fusion protein-encoding nucleic acids as exemplified herein, operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art.

The fusion protein can be co-expressed with one or more additional nucleic acids that may encode enzyme(s) useful for converting intermediates, such as fructose 6-phosphate (F6P) and other compounds downstream of F6P, to desired bioproducts. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The term "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid can utilize either or both a heterologous or homologous encoding nucleic acid.

It is understood that when more than one exogenous nucleic acid is included in a microbial organism, the more than one exogenous nucleic acid refers to the referenced encoding nucleic acid or biosynthetic activity, as discussed above. It is further understood, as disclosed herein, that more than one exogenous nucleic acid can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein, such as an exogenous nucleic acid that expresses a fusion protein of the disclosure, and one or more other enzymes that convert an intermediate from the RuMP pathway (or alternatively a DHA Pathway, preferably DHA Route 1) to a desired bioproduct.

In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

Exogenous fusion protein-encoding nucleic acid sequences can be introduced stably or transiently into a host cell using techniques well known in the art including, but not limited to, conjugation, electroporation, chemical transformation, transduction, transfection, and ultrasound transformation. Optionally, for exogenous expression in $E.\ coli$ or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in $E.\ coli$ (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

The terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

The term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments.

In some aspects a nucleic acid encoding the fusion protein is introduced into a cell with a gene disruption. The term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions. The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

A metabolic modification refers to a biochemical reaction that is altered from its naturally occurring state. Therefore, microorganisms may have genetic modifications to nucleic acids encoding metabolic polypeptides, or functional fragments thereof. Exemplary metabolic modifications are disclosed herein.

The microorganisms provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

A variety of microorganism may be suitable for incorporating nucleic acid encoding the fusion protein, optionally with one or more other transgenes Such organisms include both prokaryotic and eukaryotic organisms including, but not limited to, bacteria, including archaea and eubacteria, and eukaryotes, including yeast, plant, insect, animal, and mammal, including human. Exemplary species are reported in U.S. Patent Pub No. 2014/0058056 (Burgard et al.), which is incorporated herein by reference, and include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonasfluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcusfermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacterjejuni, Haemophilus influenzae, Serratia marcescens, Citrobacter amalonaticus, Myxococcus xanthus, Fusobacterium nuleatum, Penicillium chrysogenum, marine gamma proteobacterium, butyrate*-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. *paratuberculosis* K–10, *Mycobacterium marinum* M, *Tsukamurella paurometabola* DSM 20162, *Cyanobium* PCC7001, *Dictyostelium discoideum* AX4, as well as other exemplary species disclosed herein or available as source organisms for corresponding genes.

In certain embodiments, suitable organisms include *Acinetobacter baumannii* Naval-82, *Acinetobacter* sp. ADP1, *Acinetobacter* sp. strain M–1, *Actinobacillus succinogenes* 130Z, *Allochromatium vinosum* DSM 180, *Amycolatopsis methanolica, Arabidopsis thaliana, Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis* E264, *Burkholderiales* bacterium Joshi_001, Butyrate-producing bacterium $L^2$-50, *Campylobacterjejuni, Candida albicans, Candida boidinii, Candida methylica, Carboxydothermus hydrogenoformans, Carboxydothermus hydrogenoformans* Z-2901, *Caulobacter* sp. AP07, *Chloroflexus aggregans* DSM 9485, *Chloroflexus aurantiacus* J-10-fl, *Citrobacter freundii, Citrobacter koseri* ATCC BAA-895, *Citrobacter youngae, Clostridium, Clostridium acetobutylicum, Clostridium acetobutylicum* ATCC 824, *Clostridium acidurici, Clostridium aminobutyricum, Clostridium asparagiforme* DSM 15981, *Clostridium beijerinckii, Clostridium beijerinckii* NCIMB 8052, *Clostridium bolteae* ATCC BAA-613, *Clostridium carboxidivorans* P7, *Clostridium cellulovorans* 743B, *Clostridium difficile, Clostridium hiranonis* DSM 13275, *Clostridium hylemonae* DSM 15053, *Clostridium kluyveri, Clostridium kluyveri* DSM 555, *Clostridium* ljungdahli, *Clostridium ljungdahlii* DSM 13528, *Clostridium methylpentosum* DSM 5476, *Clostridium pasteurianum, Clostridium pasteurianum* DSM 525, *Clostridium perfringens, Clostridium perfringens* ATCC 13124, *Clostridium perfringens* str. 13, *Clostridium phytofermentans* ISDg, *Clostridium saccharobutylicum, Clostridium saccharoperbutylacetonicum, Clostridium saccharoperbutylacetonicum* NI–4, *Clostridium tetani, Corynebacterium glutamicum* ATCC 14067, *Corynebacterium glutamicum* R, *Corynebacterium* sp. U-96, *Corynebacterium* variabile, *Cupriavidus necator* N-1, *Cyanobium* PCC7001, *Desulfatibacillum alkenivorans* AK-01, *Desulfitobacterium hafniense*, *Desulfitobacterium metallireducens* DSM 15288, *Desulfotomaculum reducens* MI-1, *Desulfovibrio africanus* str. Walvis Bay, *Desulfovibrio* fructosovorans JJ, *Desulfovibrio vulgaris* str. Hildenborough, *Desulfovibrio vulgaris* str. 'Miyazaki F', *Dictyostelium discoideum* AX4, *Escherichia coli*, *Escherichia coli* K-12, *Escherichia coli* K-12 MG1655, *Eubacterium hallii* DSM 3353, *Flavobacterium frigoris*, *Fusobacterium nucleatum* subsp. *polymorphum* ATCC 10953, *Geobacillus* sp. Y4.1MC1, *Geobacillus themodenitrificans* NG80-2, *Geobacter bemidjiensis* Bem, *Geobacter sulfurreducens*, *Geobacter sulfurreducens* PCA, *Geobacillus stearothermophilus* DSM 2334, *Haemophilus influenzae*, *Helicobacter pylori*, *Homo sapiens*, *Hydrogenobacter thermophilus*, *Hydrogenobacter thermophilus* TK-6, *Hyphomicrobium denitrificans* ATCC 51888, *Hyphomicrobium zavarzinii*, *Klebsiella pneumoniae*, *Klebsiella pneumoniae* subsp. *pneumoniae* MGH 78578, *Lactobacillus brevis* ATCC 367, *Leuconostoc mesenteroides*, *Lysinibacillus fusiformis*, *Lysinibacillus sphaericus*, *Mesorhizobium loti* MAFF303099, *Metallosphaera sedula*, *Methanosarcina acetivorans*, *Methanosarcina acetivorans* C2A, *Methanosarcina barkeri*, *Methanosarcina mazei* Tuc01, *Methylobacter marinus*, *Methylobacterium extorquens*, *Methylobacterium extorquens* AM1, *Methylococcus* capsulatas, *Methylomonas* aminofaciens, *Moorella* thermoacetica, *Mycobacter* sp. strain JC1 DSM 3803, *Mycobacterium avium* subsp. *paratuberculosis* K-10, *Mycobacterium bovis* BCG, *Mycobacterium gastri*, *Mycobacterium marinum* M, *Mycobacterium smegmatis*, *Mycobacterium smegmatis* MC2 155, *Mycobacterium tuberculosis*, *Nitrosopumilus salaria* BD31, *Nitrososphaera gargensis* Ga9.2, *Nocardia farcinica* IFM 10152, *Nocardia iowensis* (sp. NRRL 5646), *Nostoc* sp. PCC 7120, *Ogataea angusta*, *Ogataea parapolymorpha* DL-1 (*Hansenula polymorpha* DL-1), *Paenibacillus peoriae* KCTC 3763, *Paracoccus denitrificans*, *Penicillium chrysogenum*, *Photobacterium profundum* 3TCK, *Phytofermentans* ISDg, *Pichia pastoris*, *Picrophilus torridus* DSM9790, *Porphyromonas gingivalis*, *Porphyromonas gingivalis* W83, *Pseudomonas aeruginosa* PA01, *Pseudomonas denitrificans*, *Pseudomonas knackmussii*, *Pseudomonas putida*, *Pseudomonas* sp, *Pseudomonas syringae* pv. *syringae* B728a, *Pyrobaculum islandicum* DSM 4184, *Pyrococcus abyssi*, *Pyrococcus furiosus*, *Pyrococcus horikoshii* OT3, *Ralstonia eutropha*, *Ralstonia eutropha* H16, *Rhodobacter capsulatus*, *Rhodobacter sphaeroides*, *Rhodobacter sphaeroides* ATCC 17025, *Rhodopseudomonas palustris*, *Rhodopseudomonas palustris* CGA009, *Rhodopseudomonas palustris* DX-1, *Rhodospirillum rubrum*, *Rhodospirillum rubrum* ATCC 11170, *Ruminococcus obeum* ATCC 29174, *Saccharomyces cerevisiae*, *Saccharomyces cerevisiae* S288c, *Salmonella enterica*, *Salmonella enterica* subsp. *enterica* serovar *Typhimurium* str. LT2, *Salmonella enterica typhimurium*, *Salmonella typhimurium*, *Schizosaccharomyces pombe*, *Sebaldella termitidis* ATCC 33386, *Shewanella oneidensis* MR-1, *Sinorhizobium meliloti* 1021, *Streptomyces coelicolor*, *Streptomyces griseus* subsp. *griseus* NBRC 13350, *Sulfolobus acidocalarius*, *Sulfolobus solfataricus* P-2, *Synechocystis* str. PCC 6803, *Syntrophobacter fumaroxidans*, *Thauera aromatica*, *Thermoanaerobacter* sp. X514, *Thermococcus kodakaraensis*, *Thermococcus litoralis*, *Thermoplasma acidophilum*, *Thermoproteus neutrophilus*, *Thermotoga maritima*, *Thiocapsa roseopersicina*, *Tolumonas auensis* DSM 9187, *Trichomonas vaginalis* G3, *Trypanosoma brucei*, *Tsukamurella paurometabola* DSM 20162, *Vibrio cholera*, *Vibrio harveyi* ATCC BAA-1116, *Xanthobacter autotrophicus* Py2, *Yersinia intermedia*, and *Zea mays*.

Therefore, the engineered cell including the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, can include one or more further genetic alterations, such as inserted transgenes, deletions, attenuation, mutations, etc., desired to increase levels of one or more intermediates or a product thereof, and include those genetic modifications as described in U.S. Patent Pub No. 2014/0058056 (Burgard et al.), which is incorporated herein by reference.

Target products obtained from, and product pathways suitable for producing in, host cells expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein include the following. Of particular interest are a target product obtained using pyruvate and acetyl-CoA as entry point or precursor to its product pathway(s), in part because the methanol metabolic pathway using the novel enzymes enables fixing the carbon of methanol into pathways to pyruvate and acetyl-CoA. Target products include (a) 1,4-butanediol and intermediates thereto, such as 4-hydroxybutanoic acid (4-hydroxybutanoate, 4-hydroxybutyrate, 4-HB), (b) butadiene and intermediates thereto, such as 1,4-butanediol, 1,3-butanediol, crotyl alcohol, 3-buten-2-ol (methyl vinyl carbinol) and 3-buten-1-ol, (c) 1,3-butanediol and intermediates thereto, such as 2,4-pentadienoate, crotyl alcohol or 3-buten-1-ol, (d) adipate, 6-aminocaproic acid, caprolactam, hexamethylenediamine and levulinic acid and their intermediates, e.g. 4-aminobutyryl-CoA, (e) methacrylic acid (2-methyl-2-propenoic acid) and its esters known collectively as methacrylates, such as methyl methacrylate, methyl methacrylate, 3-hydroxyisobutyrate and/or 2-hydroxyisobutyrate and their intermediates, (f) 1,2-propanediol (propylene glycol), n-propanol, 1,3-propanediol and glycerol, and their intermediates and (g) succinic acid and intermediates thereto.

In some aspects, a gene encoding a fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, is introduced into a cell engineered with increased of levels of 1,4-butanediol (BDO) or hydroxylbutyrate (4-HB) biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

With the complete genome sequence available for now more than 550 species (with more than half of these available on public databases such as the NCBI), including 395 microorganism genomes and a variety of yeast, fungi, plant, and mammalian genomes, the identification of genes encoding the requisite BDO or 4-HB biosynthetic pathway as well as other known biosynthetic pathways for 1,3-butanediol (13BDO), butadiene, 6-amino caproic acid (6ACA), hexamethyldiamine (HMDA), adipic acid or derivatives thereof, croytl alcohol, methyl vinyl carbinol, 3-buten-1-ol, succinic acid or derivatives thereof, n-propanol, isopropanol, propylene, methacrylic acid or derivatives thereof, methanol metabolic and/or formaldehyde assimilation activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of various target products including 1,3-butanediol (13BDO), 1,4-butanediol (BDO), 4-HB, butadiene, 6-amino caproic acid (6ACA), hexamethyldiamine (HMDA), adipic acid or derivatives thereof, croytl alcohol, methyl vinyl carbinol, 3-buten-1-ol, succinic acid or derivatives thereof, n-propanol, isopropanol, propylene, methacrylic acid or derivatives thereof, metabolism of methanol and/or assimilation of formaldehyde described herein with reference to a particular organism such as E. coli can be readily applied to other microorganisms, including prokaryotic and eukaryotic organisms alike. Given the teachings and guidance provided herein, those skilled in the art will know that a metabolic alteration exemplified in one organism can be applied equally to other organisms.

Exemplary alcohol metabolic pathway gene(s), such as described in U.S. Patent Pub No. 2014/0058056, encode a protein selected from the group consisting of: a formate dehydrogenase, a formaldehyde activating enzyme, a formaldehyde dehydrogenase, a S-(hydroxymethyl)glutathione synthase, a glutathione-dependent formaldehyde dehydrogenase, a S-formylglutathione hydrolase, a formate hydrogen lyase, and a hydrogenase, any or more can be coexpressed with the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, in the engineered cell.

Other exemplary alcohol metabolic pathway gene(s), such as described in U.S. Patent Pub No. 2014/0058056, encode an alcohol metabolic pathway gene(s) encoding a protein selected from the group consisting of a succinyl-CoA reductase (aldehyde forming), a 4-hydroxybutyrate (4-HB) dehydrogenase, a 4-HB kinase, a phosphotrans-4-hydroxybutyrylase, a 4-hydroxybutyryl-CoA reductase (aldehyde forming), a 1,4-butanediol dehydrogenase; a succinate reductase, a succinyl-CoA reductase (alcohol forming), 4-hydroxybutyryl-CoA transferase, a 4-hydroxybutyryl-CoA synthetase, a 4-HB reductase, and a 4-hydroxybutyryl-CoA reductase (alcohol forming), a succinyl-CoA transferase, and a succinyl-CoA synthetase, any or more can be co-expressed with the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, in the engineered cell.

1,4-butanediol and intermediates thereto, such as 4-hydroxybutanoic acid (4-hydroxybutanoate, 4-hydroxybutyrate, 4-HB), are target products that can be made by co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein with a product pathway described herein as well as in the following documents. Suitable product pathways and enzymes, methods for screening and methods for isolating are found herein as well as in the following documents, incorporated herein by reference: WO2008115840A2 published 25 Sep. 2008 entitled "Compositions and Methods for the Biosynthesis of 1,4-Butanediol and Its Precursors"; WO2010141780A1 published 9 Dec. 2010 entitled "Process of Separating Components of A Fermentation Broth"; WO2010141920A2 published 9 Dec. 2010 entitled "Microorganisms for the Production of 1,4-Butanediol and Related Methods"; WO2010030711A2 published 18 Mar. 2010 entitled "Microorganisms for the Production of 1,4-Butanediol"; WO2010071697A1 published 24 Jun. 2010 entitled "Microorganisms and Methods for Conversion of Syngas and Other Carbon Sources to Useful Products"; WO2009094485A1 published 30 Jul. 2009 entitled "Methods and Organisms for Utilizing Synthesis Gas or Other Gaseous Carbon Sources and Methanol"; WO2009023493A1 published 19 Feb. 2009 entitled "Methods and Organisms for the Growth-Coupled Production of 1,4-Butanediol"; WO2008115840A2 published 25 Sep. 2008 entitled "Compositions and Methods for the Biosynthesis of 1,4-Butanediol and Its Precursors"; and International Application No. PCT/US13/56725 filed 27 Aug. 2013 entitled "Microorganisms an Methods for Enhancing the Availability of Reducing Equivalents in the Presence of Methanol, and for Producing 1,4-Butanediol Related Thereto".

Butadiene and intermediates thereto, such as 1,4-butanediol, 1,3-butanediol, crotyl alcohol, 3-buten-2-ol (methyl vinyl carbinol) and 3-buten-1-ol, are target products that can be made by co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein with a product pathway described in the following documents. In addition to direct fermentation to produce butadiene, 1,3-butanediol, 1,4-butanediol, crotyl alcohol, 3-buten-2-ol (methyl vinyl carbinol) and 3-buten-1-ol can be separated, purified (for any use), and then dehydrated to butadiene in a second step involving metal-based catalysis. Suitable product pathways and enzymes, methods for screening and methods for isolating are found in the following documents, incorporated herein by reference: WO2011140171A2 published 10 Nov. 2011 lentitled "Microorganisms and Methods for the Biosynthesis of Butadiene"; WO2012018624A2 published 9 Feb. 2012 entitled "Microorganisms and Methods for the Biosynthesis of Aromatics, 2,4-Pentadienoate and 1,3-Butadiene"; WO201140171A2 published 10 Nov. 2011 entitled "Microorganisms and Methods for the Biosynthesis of Butadiene"; WO2013040383A1 published 21 Mar. 2013 entitled "Microorganisms and Methods for Producing Alkenes"; WO2012177710A1 published 27 Dec. 2012 entitled "Microorganisms for Producing Butadiene and Methods Related thereto"; WO2012106516A1 published 9 Aug. 2012 entitled "Microorganisms and Methods for the Biosynthesis of Butadiene"; WO2013028519A1 published 28 Feb. 2013 entitled "Microorganisms and Methods for Producing 2,4-

Pentadienoate, Butadiene, Propylene, 1,3-Butanediol and Related Alcohols"; and U.S. Patent Pub No. 2015/0050708.

1,3-butanediol and intermediates thereto, such as 2,4-pentadienoate, crotyl alcohol or 3-buten-1-ol, are target products that can be made by co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein with a product pathway described herein as well as in the following documents. Suitable product pathways and enzymes, methods for screening and methods for isolating are found herein as well as in the following documents, incorporated herein by reference: WO2011071682A1 published 16 Jun. 2011 entitled "Methods and Organisms for Converting Synthesis Gas or Other Gaseous Carbon Sources and Methanol to 1, 3-Butanediol"; WO2011031897A published 17 Mar. 2011 entitled "Microorganisms and Methods for the Co-Production of Isopropanol with Primary Alcohols, Diols and Acids"; WO2010127319A2 published 4 Nov. 2010 entitled "Organisms for the Production of 1,3-Butanediol"; WO2013071226A1 published 16 May 2013 entitled "Eukaryotic Organisms and Methods for Increasing the Availability of Cytosolic Acetyl-CoA, and for Producing 1,3-Butanediol"; WO2013028519A1 published 28 Feb. 2013 entitled "Microorganisms and Methods for Producing 2,4-Pentadienoate, Butadiene, Propylene, 1,3-Butanediol and Related Alcohols"; WO2013036764A1 published 14 Mar. 2013 entitled "Eukaryotic Organisms and Methods for Producing 1,3-Butanediol"; WO2013012975A1 published 24 Jan. 2013 entitled "Methods for Increasing Product Yields"; WO2012177619A2 published 27 Dec. 2012 entitled "Microorganisms for Producing 1,3-Butanediol and Methods Related Thereto"; and U.S. Patent Pub No. 2015/0050708.

Adipate, 6-aminocaproic acid, caprolactam, hexamethylenediamine and levulinic acid, and their intermediates, e.g. 4-aminobutyryl-CoA, are target products, useful for example for making nylon polymers, that can be made by co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein with a product pathway described herein as well as in the following documents. Suitable product pathways and enzymes, methods for screening and methods for isolating are found herein as well as in the following documents, incorporated herein by reference: WO2010129936A1 published 11 Nov. 2010 entitled "Microorganisms and Methods for the Biosynthesis of Adipate, Hexamethylenediamine and 6-Aminocaproic Acid"; WO2013012975A1 published 24 Jan. 2013 entitled "Methods for Increasing Product Yields"; WO2012177721A1 published 27 Dec. 2012 entitled "Microorganisms for Producing 6-Aminocaproic Acid"; WO2012099621A1 published 26 Jul. 2012 entitled "Methods for Increasing Product Yields"; and U.S. Patent Pub No. 2014/0329916 entitled "Microorganisms an Methods for Enhancing the Availability of Reducing Equivalents in the Presence of Methanol, and for Producing Adipate, 6-Aminocaproate, Hexamethylenediamine or Caprolactam Related Thereto".

Methacrylic acid (2-methyl-2-propenoic acid; used in the preparation of its esters known collectively as methacrylates, such as methyl methacrylate, which is used most notably in the manufacture of polymers), methacrylate ester such as methyl methacrylate, 3-hydroxyisobutyrate and/or 2-hydroxyisobutyrate and their intermediates are target products, useful for example for making polymers, that can be made by co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein with a product pathway described herein as well as in the following documents. Suitable product pathways and enzymes, methods for screening and methods for isolating are found herein as well as in the following documents, incorporated herein by reference: WO2012135789A2 published 4 Oct. 2012 entitled "Microorganisms for Producing Methacrylic Acid and Methacrylate Esters and Methods Related Thereto"; WO2009135074A2 published 5 Nov. 2009 entitled "Microorganisms for the Production of Methacrylic Acid"; and U.S. Patent Pub No. 2014/0288254 entitled "Microorganisms an Methods for Enhancing the Availability of Reducing Equivalents in the Presence of Methanol, and for Producing 3-Hydroxyisobutyate or Methacrylic Acid Related Thereto".

1,2-propanediol (propylene glycol), n-propanol, 1,3-propanediol and glycerol, and their intermediates are target products, useful for example for making polymers, that can be made by co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein with a product pathway described herein as well as in the following documents. Suitable product pathways and enzymes, methods for screening and methods for isolating are found herein as well as in the following documents, incorporated herein by reference: WO2009111672A1 published 9 Nov. 2009 entitled "Primary Alcohol Producing Organisms"; WO2011031897A1 17 Mar. 2011 entitled "Microorganisms and Methods for the Co-Production of Isopropanol with Primary Alcohols, Diols and Acids"; WO2012177599A2 published 27 Dec. 2012 entitled 'Microorganisms for Producing N-Propanol 1,3-Propanediol, 1,2-Propanediol or Glycerol and Methods Related Thereto"; and U.S. Patent Pub No. 2014/0302575 entitled "Microorganisms an Methods for Enhancing the Availability of Reducing Equivalents in the Presence of Methanol, and for Producing 1,2-Propanediol, n-Propanol, 1,3-Propanediol, or Glycerol Related Thereto".

Succinic acid and intermediates thereto (useful to produce products including polymers, e.g. PBS, 1,4-butanediol, tetrahydrofuran, pyrrolidone, solvents, paints, deicers, plastics, fuel additives, fabrics, carpets, pigments, and detergents) are target products that can be made by co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein with a product pathway described herein as well as in the following documents. Suitable product pathways and enzymes, methods for screening and methods for isolating are found herein as well as in the following documents, incorporated herein by reference: EP1937821A2 published 2 Jul. 2008 entitled "Methods and Organisms for the Growth-Coupled Production of Succinate"; and U.S. Patent Pub No. 2014/0302575 entitled "Microorganisms and Methods for Enhancing the Availability of Reducing Equivalents in the Presence of Methanol, and for Producing Succinate Related Thereto".

Target products obtained from, and product pathways suitable for producing in, host cells co-expressing the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, described herein include the following. Butadiene and intermediates thereto, such as 1,4-butanediol, 1,3-butanediol, crotyl alcohol, 3-buten-2-ol (methyl vinyl carbinol) and 3-buten-1-ol, are target products that can be made by co-expressing the fusion protein having at least (i) methanol dehydrogenase activity and (ii) 3-hexulose-6-phosphate dehydrogenase activity and/or 6-phospho-3-hexuloisomerase activity described herein with a product pathway described in the following documents. In addition to direct fermentation to produce butadiene, 1,3-butanediol, 1,4-butanediol, crotyl alcohol, 3-buten-2-ol (methyl vinyl carbinol) and 3-buten-1-ol can be separated, purified (for any use), and then dehydrated to butadiene in a second step involving metal-based catalysis. Suitable product pathways and enzymes, methods for screening and methods for isolating are found in: WO2011140171A2 published 10 Nov. 2011 entitled "Microorganisms and Methods for the Biosynthesis of Butadiene"; WO2012018624A2 published 9 Feb. 2012 entitled "Microorganisms and Methods for the Biosynthesis of Aromatics, 2,4-Pentadienoate and 1,3-Butadiene"; WO2011140171A2 published 10 Nov. 2011 entitled "Microorganisms and Methods for the Biosynthesis of Butadiene"; WO2013040383A1 published 21 Mar. 2013 entitled "Microorganisms and Methods for Producing Alkenes"; WO2012177710A1 published 27 Dec. 2012 entitled "Microorganisms for Producing Butadiene and Methods Related thereto"; WO2012106516A1 published 9 Aug. 2012 entitled "Microorganisms and Methods for the Biosynthesis of Butadiene"; WO2013028519A1 published 28 Feb. 2013 entitled "Microorganisms and Methods for Producing 2,4-Pentadienoate, Butadiene, Propylene, 1,3-Butanediol and Related Alcohols"; and U.S. Patent Pub No. 2015/0050708.

Figure 6:
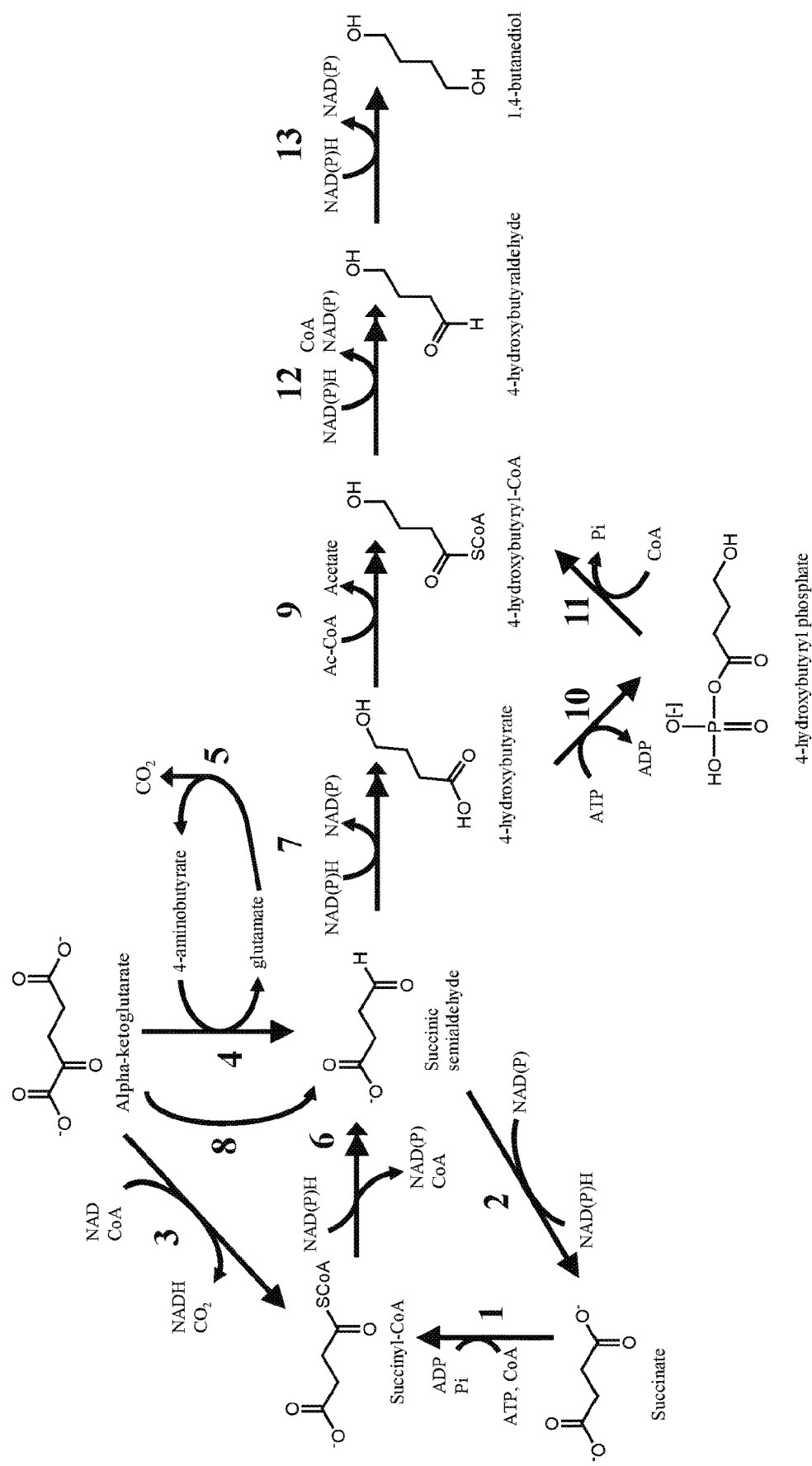
FIG. 6 illustrates an exemplary target product pathway, a 1,4-BDO product pathway, which can exploit acetyl-CoA available from methanol assimilation as disclosed herein. Enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA: acetyl-CoA transferase; (10) butyrate kinase; (11) phosphotransbutyrylase; (12) aldehyde dehydrogenase; (13) alcohol dehydrogenase.

Enzymes, genes and methods for engineering pathways from acetyl-CoA, succinate and succinyl-CoA to various products, such as BDO, into a microorganism, are now known in the art (see, e.g., U.S. Publ. No. 2011/0201089). A set of BDO pathway enzymes represents a group of enzymes that can convert succinate or alpha-ketoglutarate to BDO as shown in FIG. 6. For example, BDO can be produced from succinyl-CoA via previously disclosed pathways (see for example, Burk et al., WO 2008/115840). FIG. 6 presents exemplary pathways which can use the primary metabolites, e.g. acetyl-CoA, made available by the use of methanol as a carbon source as described herein. In FIG. 6, the organism comprises at least one exogenous nucleic acid encoding a BDO pathway enzyme expressed in a sufficient amount to produce BDO. In certain embodiments, the BDO pathway enzyme is selected from the group consisting of (1) a succinyl-CoA synthetase; (2) a CoA-independent succinic semialdehyde dehydrogenase; (3) a α-ketoglutarate dehydrogenase; (4) a glutamate:succinate semialdehyde transaminase; (5) a glutamate decarboxylase; (6) a CoA-dependent succinic semialdehyde dehydrogenase; (7) a 4-hydroxybutanoate dehydrogenase; (8) a α-ketoglutarate decarboxylase; (9) a 4-hydroxybutyryl CoA:acetyl-CoA transferase; (10) a butyrate kinase; (11) a phosphotransbutyrylase; (12) an aldehyde dehydrogenase; and (13) an alcohol dehydrogenase. Preferred pathways include those from alpha-ketoglutarate, e.g. steps 8, 7, 9, 12 and 13; steps 3, 6, 7, 9, 12 and 13; and steps 1, 6, 7, 9, 12, 13. In an alternative, a single protein can comprise the activities of steps 12 and 13. Specific enzymes, classes of enzymes and sources of enzymes and their genes can be found in WO2008115840, for example.

In some embodiments, the disclosure provides organisms comprising a fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, and that are engineered to improve the availability of reducing equivalents, which can be used for the production of target product molecules. It will be recognized by one skilled in the art that any product molecule that utilizes reducing equivalents in its production can exhibit enhanced production through other biosynthetic pathways.

In numerous engineered pathways, realization of maximum product yields based on carbohydrate feedstock is hampered by insufficient reducing equivalents or by loss of reducing equivalents to byproducts. Methanol is a relatively inexpensive organic feedstock that can be used to generate reducing equivalents by using the fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, and one or more metabolic enzymes. The reducing equivalents produced by the metabolism of methanol can then be used to power the glucose to BDO production pathways, for example, as shown in FIG. 6.

FIG. 6 presents exemplary pathways which can use the primary metabolites, e.g. acetyl-CoA, made available by the use of methanol as a carbon source as described herein. In FIG. 6, the organism comprises at least one exogenous nucleic acid encoding a BDO pathway enzyme expressed in a sufficient amount to produce BDO. In certain embodiments, the BDO pathway enzyme is selected from the group consisting of (1) a succinyl-CoA synthetase; (2) a CoA-independent succinic semialdehyde dehydrogenase; (3) a α-ketoglutarate dehydrogenase; (4) a glutamate:succinate semialdehyde transaminase; (5) a glutamate decarboxylase; (6) a CoA-dependent succinic semialdehyde dehydrogenase; (7) a 4-hydroxybutanoate dehydrogenase; (8) a α-ketoglutarate decarboxylase; (9) a 4-hydroxybutyryl CoA:acetyl-CoA transferase; (10) a butyrate kinase; (11) a phosphotransbutyrylase; (12) an aldehyde dehydrogenase; and (13) an alcohol dehydrogenase. Preferred pathways include those from alpha-ketoglutarate, e.g. steps 8, 7, 9, 12 and 13; steps 3, 6, 7, 9, 12 and 13; and steps 1, 6, 7, 9, 12, 13. In an alternative, a single protein can comprise the activities of steps 12 and 13. Specific enzymes, classes of enzymes and sources of enzymes and their genes can be found in WO2008115840A2, for example.

Enzymes, genes and methods for engineering pathways from succinate and succinyl-CoA to various products, such as BDO, into a microorganism, are now known in the art (see, e.g., U.S. Publ. No. 2011/0201089). A set of BDO pathway enzyme s represents a group of enzymes that can convert succinate or alpha-ketoglutarate to BDO as shown in FIG. 6. The additional reducing equivalents obtained from the MeDH pathway, as disclosed herein, improve the yields of all these products when utilizing carbohydrate-based feedstock. For example, BDO can be produced from succinyl-CoA via previously disclosed pathways (see for example, Burk et al., WO 2008/115840).

The maximum theoretical yield of BDO via the pathway shown in FIG. 6 supplemented with the reactions of the oxidative TCA cycle (e.g., citrate synthase, aconitase, isocitrate dehydrogenase, alpha-ketoglutarate dehydrogenase) is 1.09 mol/mol.

$$1C_6H_{12}O_6 \rightarrow 1.09C_4H_{10}O_2 + 1.64CO_2 + 0.55H_2O$$

When both feedstocks of sugar and methanol are available, the methanol can be utilized to generate reducing equivalents by employing one or more of enzymes. The reducing equivalents generated from methanol can be utilized to power the glucose to BDO production pathways, e.g., as shown in FIG. 6. Theoretically, all carbons in glucose will be conserved, thus resulting in a maximal theoretical yield to produce BDO from glucose at 2 mol BDO per mol of glucose under either aerobic or anaerobic conditions:

$$10CH_3OH + 3C_6H_{12}O_6 = 6C_4H_{10}O_2 + 8H_2O + 4CO_2$$

In a similar manner, the maximum theoretical yields of succinate and 4-HB can reach 2 mol/mol glucose:

$$C_6H_{12}O_6 + 0.667CH_3OH + 1.333CO_2 \rightarrow 2C_4H_6O_4 + 1.333H_2O$$

$$C_6H_{12}O_6 + 2CH_3OH \rightarrow 2C_4H_8O_3 + 2H_2O$$

In other embodiments, the organism having a fusion protein having at least (i) methanol dehydrogenase activity and (ii) 3-hexulose-6-phosphate dehydrogenase activity and/or 6-phospho-3-hexuloisomerase activity, or alternatively including the fusion protein having at least (i) methanol dehydrogenase activity and (ii) DHAS activity and/or F6PAld activity, either alone or in combination with a BDO pathway, as provided herein, may further comprise a second formaldehyde assimilation pathway (FAP). The second FAP can also utilizes formaldehyde, for example, formaldehyde that not utilized by the fusion protein, in the formation of intermediates of certain central metabolic pathways that can be used, for example, in the formation of biomass.

With reference to FIG. 5, in the second formaldehyde assimilation pathway, the organism comprises at least one exogenous nucleic acid encoding a formaldehyde assimilation pathway enzyme that is different than the MeDH, PSI, HPS, and ACT proteins. Enzymes of the second formaldehyde assimilation pathway can be expressed in a sufficient amount to produce an intermediate of glycolysis and/or a metabolic pathway that can be used in the formation of biomass. In one embodiment, the second formaldehyde assimilation pathway enzyme is expressed in a sufficient amount to produce an intermediate of glycolysis. In another embodiment, the second formaldehyde assimilation pathway enzyme is expressed in a sufficient amount to produce an intermediate of a metabolic pathway that can be used in the formation of biomass. In some of the embodiments, the second formaldehyde assimilation pathway comprises a dihydroxyacetone (DHA) synthase or a DHA kinase. The preferred DHA pathway is DHA Route 1 in FIG. 5, which is a combination of DHA (dihydroxyacetone) synthase, e.g. EC 2.2.1.3 (Step 6) and F6P (fructose-6-phosphate) aldolase (Step 7). In one embodiment, the intermediate is a DHA, a DHA phosphate, or a combination thereof. In certain embodiments, the organism comprises two exogenous nucleic acids, each encoding a second formaldehyde assimilation pathway enzyme.

In addition to the fusion protein having at least (i) methanol dehydrogenase activity and (ii) 3-hexulose-6-phosphate dehydrogenase activity and/or 6-phospho-3-hexuloisomerase activity, the cell can also possess a pathway that proceeds through dihydroxyacetone (DHA). Both the fusion protein of the RuMP pathway and the DHA pathway can be for the detoxification and assimilation of formaldehyde. As shown in FIG. 5, a transketolase first transfers a glycoaldehyde group from xylulose-5-phosphate to formaldehyde (Step 6, FIG. 5), resulting in the formation of DHA and G3P, which is an intermediate in glycolysis. The DHA obtained from DHA synthase is then further phosphorylated to form DHA phosphate (DHAP) by a DHA kinase. DHAP can be assimilated into glycolysis and several other pathways. Alternatively, DHA and G3P can be converted by fructose-6-phosphate aldolase to form fructose-6-phosphate (F6P) (FIG. 5, step 7).

In some embodiments, in addition to the fusion protein having at least (i) methanol dehydrogenase activity and (ii) DHAS and/or F6PAld activity, the cell can also possess a pathway that proceeds through hexose-6-phosphate (H6P) as depicted in FIG. 5. The pathway that proceeds through hexose-6-phosphate (H6P) can optionally use a MeDH fusion protein. For example, an engineered cell of the disclosure can include a MeDH fusion protein of the DHA pathway and a MeDH fusion protein of the RuMP pathway, which can be for the detoxification and assimilation of formaldehyde.

The DHA synthase in the engineered cell, which in some embodiments can be present as a fusion protein with MeDH, can be an exogenous DHA synthase, such as a DHA synthase from *Mycobacter* sp. strain JC1 DSM 3803 (SEQ ID NO:81; AAG12171.2); *Ogataea parapolymorpha* DL-1 (*Hansenula polymorpha* DL-1) (SEQ ID NO:82; EFW95760.1); or *Candida boidinii* (SEQ ID NO:83; AAC83349.1). DHA synthases are of the enzyme class (EC) 2.2.1.3. Table 5 is a table of pairwise sequence identity of various DHA synthase sequences.

TABLE 5

| | Pairwise alignment (% ID) | | |
|---|---|---|---|
| DHA Synthase | *Mycobacter* sp. strain JC1 DSM 3803 | *Ogataea parapolymorpha* DL-1 (*Hansenula polymorpha* DL-1) | *Candida boidinii* |
| *Mycobacter* sp. strain JC1 DSM 3803 | 100 | 29.8 | 30.9 |
| *Ogataea parapolymorpha* DL-1 (*Hansenula polymorpha* DL-1) | 29.8 | 100 | 70.7 |
| *Candida boidinii* | 30.9 | 70.7 | 100 |

The DHA kinase in the engineered cell, which in some embodiments can be present as a fusion protein with MeDH, can be an exogenous DHA kinase, such as a DHA kinase from *Pichia angusta* (AAC27705.1); *Saccharomyces cerevisiae* S288c (P54838.1); *Saccharomyces cerevisiae* S288c (P43550.1); *Citrobacter freundii* ATCC 8090 (ZP_16280678.1); *Klebsiella pneumoniae* subsp. *pneumoniae* WGLW3 (ZP_18488498.1); *Escherichia coli* K-12 MG1655 (NP_415718.6); *Escherichia coli* K-12 MG1655 (NP_415717.1); or *Escherichia coli* K-12 MG1655 (NP_415716.4). DHA kinases are of the enzyme class (EC) 2.7.1.121. Table 6 is a table of pairwise sequence identity of various DHA kinase sequences.

TABLE 6

Pairwise alignment (% ID)

| DHA kinase | Escherichia coli K-12 MG1655 | Escherichia coli K-12 MG1655 | Citrobacter freundii ATCC 8090 | Klebsiella pneumoniae subsp. pneumoniae WGLW3 |
|---|---|---|---|---|
| Escherichia coli K-12 MG1655 | 100 | 5.5 | 9.9 | 10.6 |
| Escherichia coli K-12 MG1655 | 5.5 | 100 | 11.4 | 11.2 |
| Citrobacter freundii ATCC 8090 | 9.9 | 11.4 | 100 | 86.2 |
| Klebsiella pneumoniae subsp. pneumoniae WGLW3 | 10.6 | 11.2 | 86.2 | 100 |
| Escherichia coli K-12 MG1655 | 11.1 | 5.2 | 26.9 | 27.2 |
| Saccharomyces cerevisiae S288c | 11 | 9.4 | 31.7 | 30.8 |
| Pichia angusta | 10.1 | 9.2 | 31.3 | 30.1 |
| Saccharomyces cerevisiae S288c | 9.5 | 10.3 | 29 | 29.1 |

| DHA kinase | Escherichia coli K-12 MG1655 | Saccharomyces cerevisiae S288c | Pichia angusta | Saccharomyces cerevisiae S288c |
|---|---|---|---|---|
| Escherichia coli K-12 MG1655 | 11.1 | 11 | 10.1 | 9.5 |
| Escherichia coli K-12 MG1655 | 5.2 | 9.4 | 9.2 | 10.3 |
| Citrobacter freundii ATCC 8090 | 26.9 | 31.7 | 31.3 | 29 |
| Klebsiella pneumoniae subsp. pneumoniae WGLW3 | 27.2 | 30.8 | 30.1 | 29.1 |
| Escherichia coli K-12 MG1655 | 100 | 32.7 | 33.1 | 32.6 |
| Saccharomyces cerevisiae S288c | 32.7 | 100 | 42.6 | 43.1 |
| Pichia angusta | 33.1 | 42.6 | 100 | 50.2 |
| Saccharomyces cerevisiae S288c | 32.6 | 43.1 | 50.2 | 100 |

The fructose-6-phosphate aldolase in the engineered cell, which in some embodiments can be present as a fusion protein with MeDH, can be an exogenous fructose-6-phosphate aldolase, such as a ructose-6-phosphate aldolase from *Amycolatopsis methanolica* 239 (SEQ ID NO:84. AIJ24623.1); *Bacillus methanolicus* MGA3 plasmid pBM19 (SEQ ID NO:85; WP_003349819.1); *Bacillus methanolicus* PB1 plasmid pBM20 (SEQ ID NO:86; WP_003352247.1); *Geobacillus thermodenitrificans* NG80-2 (SEQ ID NO:87; WP_008880720.1); *Geobacillus thermodenitrificans* NG80-2 (SEQ ID NO:88; WP_008880032.1); *Methylophilus methylotrophus* ATCC 53528 (SEQ ID NO:89; WP_018986971.1); and *Bacillus methanolicus* MGA3 (SEQ ID NO:90; WP_003346852.1). Fructose-6-phosphate aldolases are of the enzyme class (EC) 4. 1.2.

The fructose biphosphate aldolase in the engineered cell, which in some embodiments can be present as a fusion protein with MeDH, can be an exogenous fructose biphosphate aldolase. Fructose biphosphate aldolases are of the enzyme class (EC) 4.1.2.13.

Suitable purification and/or assays to test, e.g., for the production of BDO can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The BDO or other target molecules may be separated from other components in the culture using a variety of methods well known in the art. Such separation methods include, for example, extraction procedures as well as methods that include continuous liquid-liquid extraction, pervaporation, evaporation, filtration, membrane filtration (including reverse osmosis, nanofiltration, ultrafiltration, and microfiltration), membrane filtration with diafiltration, membrane separation, reverse osmosis, electrodialysis, distillation, extractive distillation, reactive distillation, azeotropic distillation, crystallization and recrystallization, centrifugation, extractive filtration, ion exchange chromatography, size exclusion chromatography, adsorption chromatography, carbon adsorption, hydrogenation, and ultrafiltration. All of the above methods are well known in the art.

Examples of target molecule isolation processes include distillation for 13BDO, 14BDO, butadiene, methyl vinyl carbinol, 3-buten-1-ol, n-propanol, isopropanol, propylene, and crotyl alcohol; crystallization for 6ACA (alternatively it can be converted to caprolactam and then purified via distillation as a final step), HMDA, adipic acid or derivatives thereof, succinic acid or derivatives thereof, or any of crystallization, distillation, or extraction for methacrylic acid or derivatives thereof.

Target molecules such as 13BDO, 14BDO, butadiene, methyl vinyl carbinol n-propanol, isopropanol, propylene, crotyl alcohol; 3-buten-1-ol, 6ACA, HMDA, adipic acid or derivatives thereof, succinic acid or derivatives thereof, or methacrylic acid or derivatives thereof are chemicals used in commercial and industrial applications. In some embodiments, BDO and/or 4-HB are used in various commercial and industrial applications. Non-limiting examples of such applications include production of plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Moreover, BDO and/or 4-HB are also used as a raw material in the production of a wide range of products including plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like.

Accordingly, in some embodiments, provided are biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising one or more bioderived BDO and/or 4-HB or bioderived BDO and/or 4-HB intermediate thereof produced by an organism provided herein or produced using a method disclosed herein.

As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the disclosure. A biobased or bioderived product is in contrast to a petroleum derived product, wherein such a product is derived from or synthesized from petroleum or a petrochemical feedstock.

In some embodiments, provided herein is a culture medium comprising bioderived BDO. In some embodiments, the bioderived BDO is produced by culturing an organism having a fusion protein and BDO pathway, as provided herein. In certain embodiments, the bioderived BDO has a carbon-12, carbon-13 and carbon-14 isotope ratio that reflects an atmospheric carbon dioxide uptake source. In one embodiment, the culture medium is separated from an organism having a fusion protein and BDO pathway.

In other embodiments, provided herein is a bioderived BDO. In some embodiments, the bioderived BDO is produced by culturing an organism having a fusion protein and BDO pathway, as provided herein. In some embodiments, the bioderived BDO has an Fm value of at least 80%, at least 85%, at least 90%, at least 95% or at least 98%. In certain embodiments, the bioderived BDO is a component of culture medium.

In certain embodiments, provided herein is a composition comprising a bioderived BDO provided herein, for example, a bioderived BDO produced by culturing an organism having a MeDH fusion protein and BDOP (BDO pathway), as provided herein. In some embodiments, the composition further comprises a compound other than said bioderived BDO. In certain embodiments, the compound other than said bioderived BDO is a trace amount of a cellular portion of an organism having a fusion protein and a BDO pathway, as provided herein.

In some embodiments, provided herein is a biobased product comprising a bioderived BDO provided herein. In certain embodiments, the biobased product is a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon. In certain embodiments, the biobased product comprises at least 5% bioderived BDO. In certain embodiments, the biobased product is (i) a polymer, THF or a THF derivative, or GBL or a GBL derivative; (ii) a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon; (iii) a polymer, a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (iv) a polymer, wherein the polymer comprises polybutylene terephthalate (PBT); (v) a polymer, wherein the polymer comprises PBT and the biobased product is a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (vi) a THF or a THF derivative, wherein the THF derivative is polytetramethylene ether glycol (PTMEG), a polyester ether (COPE) or a thermoplastic polyurethane; (viii) a THF derivative, wherein the THF derivative comprises a fiber; or (ix) a GBL or a GBL derivative, wherein the GBL derivative is a pyrrolidone. In certain embodiments, the biobased product comprises at least 10% bioderived BDO. In some embodiments, the biobased product comprises at least 20% bioderived BDO. In other embodiments, the biobased product comprises at least 30% bioderived BDO. In some embodiments, the biobased product comprises at least 40% bioderived BDO. In other embodiments, the biobased product comprises at least 50% bioderived BDO. In one embodiment, the biobased product comprises a portion of said bioderived BDO as a repeating unit. In another embodiment, provided herein is a molded product obtained by molding the biobased product provided herein. In other embodiments, provided herein is a process for producing a biobased product provided herein, comprising chemically reacting said bioderived-BDO with itself or another compound in a reaction that produces said biobased product. In certain embodiments, provided herein is a polymer comprising or obtained by converting the bioderived BDO. In other embodiments, provided herein is a method for producing a polymer, comprising chemically or enzymatically converting the bioderived BDO to the polymer. In yet other embodiments, provided herein is a composition comprising the bioderived BDO, or a cell lysate or culture supernatant thereof.

BDO is a valuable chemical for the production of high performance polymers, solvents, and fine chemicals. It is the basis for producing other high value chemicals such as tetrahydrofuran (THF) and gamma-butyrolactone (GBL). The value chain is comprised of three main segments including: (1) polymers, (2) THF derivatives, and (3) GBL derivatives. In the case of polymers, BDO is a comonomer for polybutylene terephthalate (PBT) production. PBT is a medium performance engineering thermoplastic used in automotive, electrical, water systems, and small appliance applications. Conversion to THF, and subsequently to polytetramethylene ether glycol (PTMEG), provides an intermediate used to manufacture spandex products such as LYCRA® fibers. PTMEG is also combined with BDO in the production of specialty polyester ethers (COPE). COPEs are high modulus elastomers with excellent mechanical properties and oil/environmental resistance, allowing them to operate at high and low temperature extremes. PTMEG and BDO also make thermoplastic polyurethanes processed on standard thermoplastic extrusion, calendaring, and molding equipment, and are characterized by their outstanding toughness and abrasion resistance. The GBL produced from BDO provides the feedstock for making pyrrolidones, as well as serving the agrochemical market. The pyrrolidones are used as high performance solvents for extraction processes of increasing use, including for example, in the electronics industry and in pharmaceutical production. Accordingly, provided herein is bioderived BDO produced according to the methods described herein and biobased products comprising or obtained using the bioderived BDO.

In some embodiments, the carbon feedstock and other cellular uptake sources such as phosphate, ammonia, sulfate, chloride and other halogens can be chosen to alter the isotopic distribution of the atoms present in BDO and/or 4-HB or any BDO and/or 4-HB pathway intermediate. The various carbon feedstock and other uptake sources enumerated above will be referred to herein, collectively, as "uptake sources." Uptake sources can provide isotopic enrichment for any atom present in the product BDO and/or 4-HB or BDO and/or 4-HB pathway intermediate, or for side products generated in reactions diverging away from a BDO and/or 4-HB pathway. Isotopic enrichment can be achieved for any target atom including, for example, carbon, hydrogen, oxygen, nitrogen, sulfur, phosphorus, chloride or other halogens. The same holds true for the MMPs and FAPs, as well as intermediates thereof, provided herein.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target isotopic ratio of an uptake source can be obtained by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

Accordingly, in some embodiments, provided are BDO and/or 4-HB or a BDO and/or 4-HB pathway intermediate thereof that has a carbon-12, carbon-13, and carbon-14 ratio that reflects an atmospheric carbon, also referred to as environmental carbon, uptake source.

Further, the disclosure relates, in part, to biologically produced BDO and/or 4-HB or BDO and/or 4-HB intermediate thereof as disclosed herein, and to the products derived therefrom, wherein the BDO and/or 4-HB or a BDO and/or 4-HB intermediate thereof has a carbon-12, carbon-13, and carbon-14 isotope ratio of about the same value as the $CO_2$ that occurs in the environment.

Those skilled in the art will understand that an organism can be engineered that secretes the biosynthesized compounds when grown on a carbon source such as a methanol alone or combined with other carbohydrates. Such compounds include, for example, BDO and any of the intermediate metabolites in the BDOP. All that is required is to engineer in one or more of the required enzyme or protein activities to achieve biosynthesis of the desired compound or intermediate including, for example, inclusion of some or all of the BDO biosynthetic pathways. Accordingly, provided herein is an organism that produces and/or secretes BDO when grown on a carbohydrate or other carbon source and produces and/or secretes any of the intermediate metabolites shown in the BDOP when grown on a carbohydrate or other carbon source. The BDO producing microbial organisms provided herein can initiate synthesis from an intermediate. The same holds true for intermediates in the formaldehyde assimilation.

In one embodiment, the carbon source is methanol or formate. In certain embodiments, methanol is used as a carbon source. In other embodiments, formate is used as a carbon source. In specific embodiments, methanol is used as a carbon source in the organisms provided herein, either alone or in combination with the product pathways provided herein.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth. In some embodiments, the sugar (e.g., glucose) is provided at a molar concentration ratio of methanol to sugar of from 200:1 to 1:200. In certain embodiments, the carbon source comprises formate and a sugar (e.g., glucose). In some embodiments, the sugar (e.g., glucose) is provided at a molar concentration ratio of formate to sugar of from 200:1 to 1:200. In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200.

Example 1: Preparation of MeDH Fusion Protein Constructs

Nucleic acid constructs for expression of various MeDH-containing fusion proteins were prepared, as well as control constructs without a fusion and a no insert control. Table 7 is a list of the nucleic acid constructs and Table 8 provides details of the genes used in the fusion protein constructs.

TABLE 7 pZS13S-p100-2315LS-linker-hps-phi
pZS13S-p100-2435A-linker-hps-phi
pZS13S-p100-2451A-linker-hps-phi
pZS13S-p108-2315LS-linker-hps-phi
pZS13S-p108-2435A-linker-hps-phi
pZS13S-p108-2451A-linker-hps-phi
pZS13S-p100-2435A-hps-phi
pZS13S-p100-2451A-hps-phi
pZS13S-p108-2315LS-hps-phi
pZS13S-p108-2435A-hps-phi
pZS13S-p108-2451A-hps-phi

TABLE 8

| Gene/region | CDS number | Identifier/SEQ ID NO | Source |
|---|---|---|---|
| MeDH | 2315LS | Variant of MGA3_17392 SEQ ID NO: 8 | Evolved variant of MeDH from *Bacillus Methanolicus* |
| MeDH | 2435A | ADH_2277 SEQ ID NO: 6 | *Desulfotomaculum reducens* MI-1 |
| MeDH | 2451A | ADH/KC157637 SEQ ID NO: 10 | Metalibrary sp |
| HPS-PHI | 2616A | rmpAB fusion SEQ ID NO: 5 | *Mycobacterium gastri* MB19 |
| Linker | | | |
| GGSGGSGSGSGGSGSGSGGS (SEQ ID NO: 7) | | | |

Nucleic acid constructs that express these MeDH-GGSGGSGSGSGGSGSGSGGS-2616A fusions were transformed into *E. coli* as described in Example 2.

Example 2: Preparation of Engineered *E. coli* Expressing MeDH Fusion Proteins and Analysis Nucleic acid constructs as listed in Table 7 were transformed into *E. coli*. *E. coli* tranformants that express MeDH-2616A fusions were assessed for expression of soluble protein, methanol dehydrogenase activity in lysates of *E. coli* cells, and ability to confer an engineered *E. coli* strain (ECKh-8665) the ability to grow on methanol as a carbon source. Several variables were tested to identify combinations that confer improved activity, including: promoter strength, different MeDH variants, and peptide linkers in MeDH and 2616 fusions.

Nucleic acid constructs were transformed into *E. coli* strain 7539 and grown overnight at 37° C. in 5 mL of LB+carb100 broth.

In vitro assay conditions were as follows. Lysis: 1 mL of cells harvested and lysed in 200 ul of BugBuster with lysozyme and benzonase (samples were all OD normalized during data normalization). Assay: 10 uL of lysate added to 100 ul of assay buffer, rate of NADH production monitored at 340 nm over 2 hours. Assay buffer: 100 mM Tris 8.5, 500 mM Methanol, 5 mM $MgCl_2$, 500 mM $NAD^+$.

Growth in Bioscreen instrument of *E. coli* host ECKh-8665 containing the denoted plasmid. The media was MM9 minimal media containing 2 g/L glycerol and 500 mM methanol. 3 replicates. See Table 9.

TABLE 9

| plasmid (pZS*13S-) | Growth rate estimation |
|---|---|
| P108__2451A-linker-2616A | 0.11 |
| P100__2435A | 0.11 |
| P100__2315LS | 0.10 |
| P107__2435A | 0.10 |

TABLE 9-continued

| plasmid (pZS*13S-) | Growth rate estimation |
|---|---|
| P108__2435A-linker-2616A | 0.09 |
| P108__2315LS | 0.09 |
| P108__2315LS-linker-2616A | 0.08 |
| P119__2435A | 0.04 |
| P108__2315LS-2616A | no growth |
| Empty Vector | no growth |

What is claimed is:

1. A fusion protein which converts methanol to a ketose phosphate, the fusion protein comprising:
   (1a) a first region comprising methanol dehydrogenase;
   (1b) a second region comprising 3-hexulose-6-phosphate dehydrogenase; and (1c) a third region comprising 6-phospho-3-hexuloisomerase;
   wherein the fusion protein comprises one or more linker amino acid sequence(s) positioned between two or more of the first, second, and third regions of the fusion protein; and
   wherein any of the methanol dehydrogenase, the 3-hexulose-6-phosphate dehydrogenase, or the 6-phospho-3-hexuloisomerase is a bacterial sequence; and
   wherein the fusion protein has a structure as follows:
   1a-$L^1$-1b-$L^2$-1c, 1a-$L^1$-1c-$L^2$-1b, 1b-$L^1$-1a-$L^2$-1c, 1b-$L^1$-1c-$L^2$-1a, 1c-$L^1$-1a-$L^2$-1b, or 1c-$L^1$-1b-$L^2$-1a,
   wherein $L^1$ and $L^2$ are independently selected from (—) (a covalent bond) and a linker amino acid sequence, wherein one or both of $L^1$ or $L^2$ is a linker amino acid sequence.

2. The fusion protein of claim 1 having a structure as follows:
   1a-$L^1$-1b-$L^2$-1c, wherein $L^1$ is a linker amino acid sequence and $L^2$ is (—) (a covalent bond) or a linker amino acid sequence.

3. The fusion protein of claim 1 wherein the methanol dehydrogenase, the 3-hexulose-6-phosphate dehydrogenase, or the 6-phospho-3-hexuloisomerase are from *Bacillus* sequences.

4. The fusion protein of claim 3 wherein one or more of the methanol dehydrogenase, the 3-hexulose-6-phosphate dehydrogenase, or the 6-phospho-3-hexuloisomerase is from *Bacillus methanolicus* MGA3 or *Bacillus methanolicus* PB1.

5. The fusion protein of claim 1, wherein the region comprising methanol dehydrogenase (MeDH) is from *Bacillus methanolicus* MGA3 MeDH (SEQ ID NO:1; EIJ77596.1); SEQ ID NO:6; SEQ ID NO:8; SEQ ID NO:10; *Bacillus methanolicus* C1 MeDH (SEQ ID NO:13; AAA22593.1); *Bacillus methanolicus* PB1 MeDH (SEQ ID NO:14; EIJ77618.1); *Bacillus methanolicus* PB1 MeDH (SEQ ID NO:15; EIJ78790.1); *Bacillus methanolicus* MGA3 MeDH (SEQ ID NO:16; EIJ80770.1); *Bacillus methanolicus* PB1 MeDH (SEQ ID NO:17; EIJ78397.1); *Bacillus methanolicus* MGA3 MeDH (SEQ ID NO:18; EIJ83020.1); *Lysinibacillus fusiformis* MeDH (SEQ ID NO:19; EFI69743.1); *Bacillus coagulans* 36D1 MeDH (SEQ ID NO:20; YP_004860127.1); *Lysinibacillus sphaericus* MeDH (SEQ ID NO:21; YP_001699778.1); *Bacillus azotoformans* LMG 9581 MeDH (SEQ ID NO:22; ZP_11313277.1); *Burkholderia thailandensis* E264 MeDH (SEQ ID NO:23; ZP_05587334.1); *Cupriavidus necator* N-1 MeDH (SEQ ID NO:24; YP_004681552.1); SEQ ID NO:25 AGF87161); *Geobacter bemidjiensis* Bem MeDH (SEQ ID NO:26; YP_002138168.1); *Carboxydothermus hydrogenoformans* Z-2901 MeDH (SEQ ID NO:27; YP_359772.1); *Actinobacillus succinogenes* 130Z MeDH (SEQ ID NO:28; YP_001343716.1); *Acinetobacter baumannii* Naval-82 MeDH (SEQ ID NO:29; ZP_16224338.1); *Clostridium pasteurianum* DSM 525 MeDH (SEQ ID NO:30; AAC45651.1); *Methanosarcina mazei* Tuc01 MeDH (SEQ ID NO:31; YP_007491369.1); *Desulfovibrio vulgaris* str 'Miyazaki F' MeDH (SEQ ID NO:32; YP_002434746); *Desulfovibrio africanus* str Walvis Bay MeDH (SEQ ID NO:33; YP_005052855); *Clostridium perfringens* str 13 MeDH (SEQ ID NO:34; NP_561852.1); *Vibrio campbellii* ATCC BAA-1116 MeDH (SEQ ID NO:35; YP_001447544); *Desulfotomaculum reducens* MI-1 MeDH (SEQ ID NO:36; YP_001113612.1); *Desulfovibrio vulgaris* str Hildenborough MeDH (SEQ ID NO:37; YP_011618); *Photobacterium profundum* 3TCK MeDH (SEQ ID NO:38; ZP_01220157.1); *Geobacillus* sp. Y4.1MC1 MeDH (SEQ ID NO:39; YP_003990729.1); *Desulfovibrio fructosovorans* JJ MeDH (SEQ ID NO:40; ZP_07335453.1); *Shewanella oneidensis* MR-1 MeDH (SEQ ID NO:41; NP_717107); *Sebaldella termitidis* ATCC 33386 MeDH (SEQ ID NO:42; YP_003310546.1); *Paenibacillus peoriae* KCTC 3763 MeDH (SEQ ID NO:43; ZP_10241531.1); *Klebsiella pneumoniae* subsp. *pneumoniae* MGH 78578 MeDH (SEQ ID NO:44; YP_001337153.1); *Escherichia coli* MeDH (SEQ ID NO:45; YP_026233.1); *Clostridium perfringens* ATCC 13124 MeDH (SEQ ID NO:46; YP_694908); *Ralstonia eutropha* H16 MeDH (SEQ ID NO:47; YP_725376.1); *Thermoanaerobacter* sp. X514 MeDH (SEQ ID NO:48; YP_001663549); human gut metagenome MeDH (SEQ ID NO:49; EKC54576); or *Geobacillus themodenitrificans* NG80-2 MeDH (SEQ ID NO:50; YP_001126968.1).

6. The fusion protein of claim 1, wherein the methanol dehydrogenase is *Bacillus methanolicus* MGA3 MeDH (SEQ ID NO:1, EIJ77596.1).

7. The fusion protein of claim 1, wherein the region comprising 3-hexulose-6-phosphate dehydrogenase (HPS) is from *Bacillus methanolicus* MGA3 HPS (SEQ ID NO: 3; AAR39392.1); *Bacillus methanolicus* PB1 HPS (SEQ ID NO: 51; EIJ81375.1); *Methylobacillus* flagellatus HPS (SEQ ID NO: 52; YP 544362.1; WP_011478618.1); *Bacillus subtilis* HPS (SEQ ID NO: 53; NP_388228.1); *Methylophilus methylotrophus* HPS (SEQ ID NO: 54; WP_018986666.1); *Methylophilus methylotrophus* ATCC 53528 HPS (SEQ ID NO: 55; WP_018985298.1); or *Mycobacterium* gastri HPS (SEQ ID NO: 62; BAA90546.1).

8. The fusion protein of claim 1, wherein the 3-hexulose-6-phosphate dehydrogenase (HPS) is *Bacillus methanolicus* MGA3 HPS (SEQ ID NO: 3, AAR39392.1).

9. The fusion protein of claim 1, wherein the 6-phospho-3-hexuloisomerase (PHI) is from *Bacillus methanolicus* MGA3 PHI (SEQ ID NO: 4; AAR39393.1); *Bacillus methanolicus* PB1 PHI (SEQ ID NO: 56; EIJ81376.1); *Mycobacterium* gastri PB1 PHI (SEQ ID NO: 57; BAA90545.1); *Methylobacillus flagellatus* KT PHI (SEQ ID NO: 58; YP 545762.1); *Bacillus subtilis* PHI (SEQ ID NO: 59; NP_388227.1); or *Methylophilus methylotrophus* ATCC 53528 HPS (SEQ ID NO: 60; WP_018985297.1).

10. The fusion protein of claim 1, wherein the 6-phospho-3-hexuloisomerase (PHI) is *Bacillus methanolicus* MGA3 PHI (SEQ ID NO: 4; AAR39393.1).

11. The fusion protein of claim 1, wherein $L^1$, $L^2$, or both $L^1$ and $L^2$:
   a) has or have a length in the range of 1-50 amino acid residues, or 1-20 amino acid residues, and comprise one or more amino acids selected from the group consisting of glycine, alanine, serine, and threonine;
   b) is or are $[(GGS)_x(GS)_y(GGS)_z]_n$ (SEQ ID NO:91), where x is 1-6, y is 1-6, z is 0-3, and n is 1-4; or
   c) is or are GGSGGSGSGSGGGSGSGSGGS (SEQ ID NO: 7).

12. An engineered cell comprising the fusion protein of claim 1.

13. The fusion protein of claim 2 wherein:
   $L^1$ is a linker amino acid sequence comprising one or more amino acids selected from the group consisting of glycine, alanine, serine, and threonine; and
   $L^2$ is (—) (a covalent bond) or a linker amino acid sequence comprising one or more amino acids selected from the group consisting of glycine, alanine, serine, and threonine.

\* \* \* \* \*

SEQUENCE LISTING

<160> NUMBER OF SEQ ID NOS: 91

<210> SEQ ID NO 1
<211> LENGTH: 382
<212> TYPE: PRT
<213> ORGANISM: Bacillus methanolicus MGA3

<400> SEQUENCE: 1

Met Thr Thr Asn Phe Phe Ile Pro Pro Ala Ser Val Ile Gly Arg Gly
1               5                   10                  15

Ala Val Lys Glu Val Gly Thr Arg Leu Lys Gln Ile Gly Ala Lys Lys
            20                  25                  30

Ala Leu Ile Val Thr Asp Ala Phe Leu His Ser Thr Gly Leu Ser Glu
        35                  40                  45

Glu Val Ala Lys Asn Ile Arg Glu Ala Gly Val Asp Val Ala Ile Phe
    50                  55                  60

Pro Lys Ala Gln Pro Asp Pro Ala Asp Thr Gln Val His Glu Gly Val
65                  70                  75                  80

Asp Val Phe Lys Gln Glu Asn Cys Asp Ser Leu Val Ser Ile Gly Gly
                85                  90                  95

Gly Ser Ser His Asp Thr Ala Lys Ala Ile Gly Leu Val Ala Ala Asn
            100                 105                 110

Gly Gly Arg Ile Asn Asp Tyr Gln Gly Val Asn Ser Val Glu Lys Pro
        115                 120                 125

Val Val Pro Val Val Ala Ile Thr Thr Thr Ala Gly Thr Gly Ser Glu
    130                 135                 140

Thr Thr Ser Leu Ala Val Ile Thr Asp Ser Ala Arg Lys Val Lys Met
145                 150                 155                 160

Pro Val Ile Asp Glu Lys Ile Thr Pro Thr Val Ala Ile Val Asp Pro
                165                 170                 175

Glu Leu Met Val Lys Lys Pro Ala Gly Leu Thr Ile Ala Thr Gly Met
            180                 185                 190

Asp Ala Leu Ser His Ala Ile Glu Ala Tyr Val Ala Lys Gly Ala Thr
        195                 200                 205

Pro Val Thr Asp Ala Phe Ala Ile Gln Ala Met Lys Leu Ile Asn Glu
    210                 215                 220

Tyr Leu Pro Lys Ala Val Ala Asn Gly Glu Asp Ile Glu Ala Arg Glu
225                 230                 235                 240

Lys Met Ala Tyr Ala Gln Tyr Met Ala Gly Val Ala Phe Asn Asn Gly
                245                 250                 255

Gly Leu Gly Leu Val His Ser Ile Ser His Gln Val Gly Gly Val Tyr
            260                 265                 270

Lys Leu Gln His Gly Ile Cys Asn Ser Val Asn Met Pro His Val Cys
        275                 280                 285

Ala Phe Asn Leu Ile Ala Lys Thr Glu Arg Phe Ala His Ile Ala Glu

Leu Leu Gly Glu Asn Val Ala Gly Leu Ser Thr Ala Ala Ala Glu
305                 310                 315                 320

Arg Ala Ile Val Ala Leu Glu Arg Ile Asn Lys Ser Phe Gly Ile Pro
            325                 330                 335

Ser Gly Tyr Ala Glu Met Gly Val Lys Glu Asp Ile Glu Leu Leu
            340                 345                 350

Ala Lys Asn Ala Tyr Glu Asp Val Cys Thr Gln Ser Asn Pro Arg Val
            355                 360                 365

Pro Thr Val Gln Asp Ile Ala Gln Ile Ile Lys Asn Ala Met
            370                 375                 380

<210> SEQ ID NO 2
<211> LENGTH: 1149
<212> TYPE: DNA
<213> ORGANISM: Bacillus methanolicus MGA3

<400> SEQUENCE: 2
atgacaacaa actttttcat tccaccagcc agcgtaattg acgcggtgc agtaaaggaa         60 gtaggaacaa gacttaagca aattggagct aagaaagcgc ttatcgttac agatgcattc      120
cttcacagca caggtttatc tgaagaagtt gctaaaaaca ttcgtgaagc tggcgttgat      180
gttgcgattt cccaaaaagc tcaaccagat ccagcagata cacaagttca tgaaggtgta      240
gatgtattca acaagaaaa ctgtgattca cttgtttcta tcggtggagg tagctctcac       300
gatacagcta agcaatcgg tttagttgca gcaaacggcg gaagaatcaa tgactatcaa      360
ggtgtaaaca gcgtagaaaa accagtcgtt ccagtagttg caatcactac aacagctggt      420
actggtagtg aaacaacatc tcttgcggtt attacagact ctgcacgtaa agtaaaaatg      480
cctgttattg atgagaaaat tactccaact gtagcaattg ttgacccaga attaatggtg      540
aaaaaaccag ctggattaac aatcgcaact ggtatggatg cattgtccca tgcaattgaa      600
gcatatgttg caaaggtgc tacaccagtt actgatgcat tgctattca gcaatgaaa        660 cttatcaatg aatacttacc aaaagcggtt gcgaacggag aagacatcga agcacgtgaa      720
aaaatggctt atgcacaata catggcagga gtggcattta caacggtgg tttaggacta      780 gttcactcta tttctcacca gtaggtgga gtttacaaat acaacacgg aatctgtaac        840 tcagttaata tgccacacgt ttgcgcattc aacctaattg ctaaaactga gcgcttcgca      900
cacattgctg agcttttagg tgagaatgtt gctggcttaa gcactgcagc agctgctgag      960
agagcaattg tagctcttga agaatcaac aaatccttcg gtatccatc tggctatgca       1020 gaaatgggcg tgaaagaaga ggatatcgaa ttattagcga aaaacgcata cgaagacgta     1080
tgtactcaaa gcaacccacg cgttcctact gttcaagaca ttgcacaaat catcaaaaac      1140
gctatgtaa                                                              1149

<210> SEQ ID NO 3
<211> LENGTH: 211
<212> TYPE: PRT
<213> ORGANISM: Bacillus methanolicus MGA3

<400> SEQUENCE: 3

Met Glu Leu Gln Leu Ala Leu Asp Leu Val Asn Ile Glu Glu Ala Lys
1               5                   10                  15

Gln Val Val Ala Glu Val Gln Glu Tyr Val Asp Ile Val Glu Ile Gly
            20                  25                  30

-continued

```
Thr Pro Val Ile Lys Ile Trp Gly Leu Gln Ala Val Lys Ala Val Lys
            35                  40                  45

Asp Ala Phe Pro His Leu Gln Val Leu Ala Asp Met Lys Thr Met Asp
 50                  55                  60

Ala Ala Ala Tyr Glu Val Ala Lys Ala Ala Glu His Gly Ala Asp Ile
 65                  70                  75                  80

Val Thr Ile Leu Ala Ala Glu Asp Val Ser Ile Lys Gly Ala Val
                    85                  90                  95

Glu Glu Ala Lys Lys Leu Gly Lys Lys Ile Leu Val Asp Met Ile Ala
                100                 105                 110

Val Lys Asn Leu Glu Glu Arg Ala Lys Gln Val Asp Glu Met Gly Val
            115                 120                 125

Asp Tyr Ile Cys Val His Ala Gly Tyr Asp Leu Gln Ala Val Gly Lys
        130                 135                 140

Asn Pro Leu Asp Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                    165                 170                 175

Ile Lys Ala Glu Pro Asp Leu Val Ile Val Gly Gly Ile Ala Asn
                180                 185                 190

Gln Thr Asp Lys Lys Ala Ala Glu Lys Ile Asn Lys Leu Val Lys
            195                 200                 205

Gln Gly Leu
    210

<210> SEQ ID NO 4
<211> LENGTH: 184
<212> TYPE: PRT
<213> ORGANISM: Bacillus methanolicus MGA3

<400> SEQUENCE: 4

Met Leu Thr Thr Glu Phe Leu Ala Glu Ile Val Lys Glu Leu Asn Ser
 1               5                  10                  15

Ser Val Asn Gln Ile Ala Asp Glu Glu Ala Glu Ala Leu Val Asn Gly
                20                  25                  30

Ile Leu Gln Ser Lys Lys Val Phe Val Ala Gly Ala Gly Arg Ser Gly
            35                  40                  45

Phe Met Ala Lys Ser Phe Ala Met Arg Met Met His Met Gly Ile Asp
 50                  55                  60

Ala Tyr Val Val Gly Glu Thr Val Thr Pro Asn Tyr Glu Lys Glu Asp
 65                  70                  75                  80

Ile Leu Ile Ile Gly Ser Gly Ser Gly Glu Thr Lys Ser Leu Val Ser
                    85                  90                  95

Met Ala Gln Lys Ala Lys Ser Ile Gly Gly Thr Ile Ala Ala Val Thr
                100                 105                 110

Ile Asn Pro Glu Ser Thr Ile Gly Gln Leu Ala Asp Ile Val Ile Lys
            115                 120                 125

Met Pro Gly Ser Pro Lys Asp Lys Ser Glu Ala Arg Glu Thr Ile Gln
        130                 135                 140

Pro Met Gly Ser Leu Phe Glu Gln Thr Leu Leu Phe Tyr Asp Ala
145                 150                 155                 160

Val Ile Leu Arg Phe Met Glu Lys Lys Gly Leu Asp Thr Lys Thr Met
                    165                 170                 175

Tyr Gly Arg His Ala Asn Leu Glu
                180
```

<210> SEQ ID NO 5
<211> LENGTH: 406
<212> TYPE: PRT
<213> ORGANISM: Artificial Sequence
<220> FEATURE:
<223> OTHER INFORMATION: HPS-PHI fusion

<400> SEQUENCE: 5

```
Met Lys Leu Gln Val Ala Ile Asp Leu Leu Ser Thr Glu Ala Ala Leu
1               5                   10                  15

Glu Leu Ala Gly Lys Val Ala Glu Tyr Val Asp Ile Ile Glu Leu Gly
            20                  25                  30

Thr Pro Leu Ile Lys Ala Glu Gly Leu Ser Val Ile Thr Ala Val Lys
        35                  40                  45

Lys Ala His Pro Asp Lys Ile Val Phe Ala Asp Met Lys Thr Met Asp
    50                  55                  60

Ala Gly Glu Leu Glu Ala Asp Ile Ala Phe Lys Ala Gly Ala Asp Leu
65                  70                  75                  80

Val Thr Val Leu Gly Ser Ala Asp Ser Thr Ile Ala Gly Ala Val
                85                  90                  95

Lys Ala Ala Gln Ala His Asn Lys Gly Val Val Asp Leu Ile Gly
            100                 105                 110

Ile Glu Asp Lys Ala Thr Arg Ala Gln Glu Val Arg Ala Leu Gly Ala
        115                 120                 125

Lys Phe Val Glu Met His Ala Gly Leu Asp Glu Gln Ala Lys Pro Gly
    130                 135                 140

Phe Asp Leu Asn Gly Leu Leu Ala Ala Gly Glu Lys Ala Arg Val Pro
145                 150                 155                 160

Phe Ser Val Ala Gly Gly Val Lys Val Ala Thr Ile Pro Ala Val Gln
                165                 170                 175

Lys Ala Gly Ala Glu Val Ala Val Ala Gly Gly Ala Ile Tyr Gly Ala
            180                 185                 190

Ala Asp Pro Ala Ala Ala Lys Glu Leu Arg Ala Ala Ile Ala Met
        195                 200                 205

Thr Gln Ala Ala Glu Ala Asp Gly Ala Val Lys Val Val Gly Asp Asp
    210                 215                 220

Ile Thr Asn Asn Leu Ser Leu Val Arg Asp Glu Val Ala Asp Thr Ala
225                 230                 235                 240

Ala Lys Val Asp Pro Glu Gln Val Ala Val Leu Ala Arg Gln Ile Val
                245                 250                 255

Gln Pro Gly Arg Val Phe Val Ala Gly Ala Gly Arg Ser Gly Leu Val
            260                 265                 270

Leu Arg Met Ala Ala Met Arg Leu Met His Phe Gly Leu Thr Val His
        275                 280                 285

Val Ala Gly Asp Thr Thr Thr Pro Ala Ile Ser Ala Gly Asp Leu Leu
    290                 295                 300

Leu Val Ala Ser Gly Ser Gly Thr Thr Ser Gly Val Val Lys Ser Ala
305                 310                 315                 320

Glu Thr Ala Lys Lys Ala Gly Ala Arg Ile Ala Ala Phe Thr Thr Asn
                325                 330                 335

Pro Asp Ser Pro Leu Ala Gly Leu Ala Asp Ala Val Val Ile Ile Pro
            340                 345                 350

Ala Ala Gln Lys Thr Asp His Gly Ser His Ile Ser Arg Gln Tyr Ala
        355                 360                 365
```

Gly Ser Leu Phe Glu Gln Val Leu Phe Val Val Thr Glu Ala Val Phe
    370                 375                 380

Gln Ser Leu Trp Asp His Thr Glu Val Glu Ala Glu Glu Leu Trp Thr
385                 390                 395                 400

Arg His Ala Asn Leu Glu
                405

<210> SEQ ID NO 6
<211> LENGTH: 388
<212> TYPE: PRT
<213> ORGANISM: Desulfotomaculum reducens MI-1

<400> SEQUENCE: 6

Met Thr Val Gly Glu Gln Val Phe Gly Tyr Phe Ile Pro Thr Val Asn
1               5                   10                  15

Leu Met Gly Val Gly Ala His Lys Glu Ile Pro Asp Gln Val Lys Val
            20                  25                  30

Leu Gly Gly Ser Asn Val Leu Ile Val Thr Asp Ala Phe Leu Gly Arg
        35                  40                  45

Pro Gly Gly Met Ala Asp Asp Ile Lys Gly Met Leu Glu Ala Glu Asn
    50                  55                  60

Ile Lys Val Thr Ile Tyr Ala Gly Ala Glu Pro Asn Pro Thr Asp Val
65                  70                  75                  80

Asn Val His Asp Gly Leu Lys Val Tyr Gln Glu Cys Gly Ala Asp Met
                85                  90                  95

Ile Leu Ser Leu Gly Gly Gly Ser Ser His Asp Cys Ala Lys Gly Ile
            100                 105                 110

Gly Ile Val Ala Thr Asn Gly Gly Asn Ile Arg Asp Tyr Glu Gly Ile
        115                 120                 125

Asn Lys Ser Ser Lys Ala Met Pro Pro Phe Ile Ala Val Asn Thr Thr
130                 135                 140

Ala Gly Thr Ala Ser Glu Met Thr Arg Phe Cys Ile Ile Thr Asn Thr
145                 150                 155                 160

Ser Asn His Val Lys Met Ala Ile Val Asp Trp Arg Cys Thr Pro Asn
                165                 170                 175

Ile Ala Ile Asn Asp Pro Leu Leu Met Ala Gly Met Pro Pro Ala Leu
            180                 185                 190

Thr Ala Ala Thr Gly Met Asp Ala Leu Thr His Ala Ile Glu Ala Tyr
        195                 200                 205

Val Ser Val Ala Ala Thr Pro Val Thr Asp Ser Ala Ala Leu Met Ala
    210                 215                 220

Ile Lys Leu Ile Ser Gln Tyr Leu Arg Ala Ala Val Ala Asn Gly Glu
225                 230                 235                 240

Asn Met Glu Ala Arg Asp Lys Met Ala Tyr Ala Glu Phe Leu Gly Gly
                245                 250                 255

Met Ala Phe Asn Asn Ala Ser Leu Gly Tyr Val His Ala Met Ala His
            260                 265                 270

Gln Leu Gly Gly Phe Tyr Asn Leu Pro His Gly Val Cys Asn Ala Ile
        275                 280                 285

Leu Leu Pro His Val Glu Ala Phe Asn Leu Ile Ala Cys Pro Glu Arg
    290                 295                 300

Phe Val Asp Ile Ala Val Ala Met Gly Glu Asn Val Glu Gly Leu Ser
305                 310                 315                 320

Val Arg Asp Ala Ala Asp Lys Ala Leu Ser Ala Ile Arg Lys Leu Ser

```
                    325                 330                 335
Ala Asp Val Gly Ile Pro Ala Gly Leu Thr Glu Leu Gly Val Lys Glu
                340                 345                 350

Glu Asp Leu Lys Thr Met Ala Glu Asn Ala Met Lys Asp Ala Cys Ala
                355                 360                 365

Leu Thr Asn Pro Arg Lys Ala Thr Leu Asn Asp Ile Val Gly Ile Tyr
            370                 375                 380

Lys Thr Ala Leu
385

<210> SEQ ID NO 7
<211> LENGTH: 20
<212> TYPE: PRT
<213> ORGANISM: Artificial Sequence
<220> FEATURE:
<223> OTHER INFORMATION: linker

<400> SEQUENCE: 7

Gly Gly Ser Gly Gly Ser Gly Ser Gly Gly Ser Gly Ser Gly
1               5                   10                  15

Ser Gly Gly Ser
            20

<210> SEQ ID NO 8
<211> LENGTH: 382
<212> TYPE: PRT
<213> ORGANISM: Artificial Sequence
<220> FEATURE:
<223> OTHER INFORMATION: MeDH variant

<400> SEQUENCE: 8

Met Thr Thr Asn Phe Phe Ile Pro Pro Ala Ser Val Ile Gly Arg Gly
1               5                   10                  15

Ala Val Lys Glu Val Gly Thr Arg Leu Lys Gln Ile Gly Ala Lys Lys
                20                  25                  30

Ala Leu Ile Val Thr Asp Ala Phe Leu His Ser Thr Gly Leu Ser Glu
            35                  40                  45

Glu Val Ala Lys Asn Ile Arg Glu Ala Gly Val Asp Val Ala Ile Phe
        50                  55                  60

Pro Lys Ala Gln Pro Asp Pro Ala Asp Thr Gln Val His Glu Gly Val
65                  70                  75                  80

Asp Val Phe Lys Gln Glu Asn Cys Asp Ser Leu Val Ser Ile Gly Gly
                85                  90                  95

Gly Ser Ser His Asp Thr Ala Lys Ala Ile Gly Leu Val Ala Ala Asn
                100                 105                 110

Gly Gly Arg Ile Asn Asp Tyr Gln Gly Val Asn Ser Val Glu Lys Pro
            115                 120                 125

Met Ile Pro Val Val Ala Ile Thr Thr Thr Ala Gly Thr Gly Ser Glu
        130                 135                 140

Thr Thr Ser Leu Ala Val Ile Thr Asp Ser Ala Arg Lys Val Lys Met
145                 150                 155                 160

Pro Val Ile Asp Glu Lys Ile Thr Pro Thr Val Ala Ile Val Asp Pro
                165                 170                 175

Glu Leu Met Val Lys Lys Pro Ala Gly Leu Thr Ile Ala Thr Gly Met
                180                 185                 190

Asp Ala Leu Ser His Ala Ile Glu Ala Tyr Val Ala Lys Gly Ala Thr
            195                 200                 205
```

```
Pro Val Thr Asp Ala Phe Ala Ile Gln Ala Met Lys Leu Ile Asn Glu
    210                 215                 220

Tyr Leu Pro Lys Ala Val Ala Asn Gly Glu Asp Ile Glu Ala Arg Glu
225                 230                 235                 240

Lys Met Ala Tyr Ala Gln Tyr Met Ala Gly Val Ala Phe Asn Asn Gly
                245                 250                 255

Gly Leu Gly Leu Val His Ser Ile Ser His Gln Val Gly Ser Val Tyr
                260                 265                 270

Lys Leu Gln His Gly Ile Cys Asn Ser Val Asn Met Pro His Val Cys
            275                 280                 285

Ala Phe Asn Leu Ile Ala Lys Thr Glu Arg Phe Ala His Ile Ala Glu
        290                 295                 300

Leu Leu Gly Glu Asn Val Ala Gly Leu Ser Thr Ala Ala Ala Ala Glu
305                 310                 315                 320

Arg Ala Ile Val Ala Leu Glu Arg Ile Asn Lys Ser Phe Gly Ile Pro
                325                 330                 335

Ser Gly Tyr Ala Glu Met Gly Val Lys Glu Glu Asp Ile Glu Leu Leu
            340                 345                 350

Ala Lys Asp Ala Tyr Glu Asp Val Cys Thr Gln Ser Asn Pro Arg Val
        355                 360                 365

Pro Thr Val Gln Asp Ile Ala Gln Ile Ile Lys Asn Ala Met
    370                 375                 380

<210> SEQ ID NO 9
<211> LENGTH: 1149
<212> TYPE: DNA
<213> ORGANISM: Artificial Sequence
<220> FEATURE:
<223> OTHER INFORMATION: MeDH variant

<400> SEQUENCE: 9
atgaccacca actttttcat cccaccagca tcagttatcg gtagaggcgc agttaaagaa      60
gttggcaccc gtctgaagca aatcggtgcg aagaaagctc tgattgttac cgacgcgttt     120
ctgcatagca ccggttttga gcgaagaagtg gcgaagaaca ttcgtgaagc gggcgtcgat     180
gtggcgattt cccgaaagc ccagccggac cctgccgata cgcaagtcca cgaaggtgtt     240
gatgtcttta acaggagaa ttgcgacagc ttggttagca tcggtggcgg ctcttcccat     300
gatacggcga aagcaattgg cctggtcgca gcaaatggtg gccgtatcaa tgactaccag     360
ggtgttaaca gcgtggagaa gccgatgatt ccggtggtcg cgatcacgac tacggcaggc     420
accggctccg aaaccaccag cttggcggtc atcacggata gcgcgcgtaa agtgaaaatg     480
ccggtgatcg atgagaaaat caccccgacc gtggcgattg cgatccgga gctgatggtg     540
aagaagccgc tggtttgac cattgcaacc ggtatgacg ccctgtctca cgccatcgaa     600
gcatacgtgg caaagggtgc gacgccggtg accgatgcgt cgccattca ggcaatgaaa     660
ctgattaatg agtatctgcc gaaggctgtt gcgaatggcg aggacatcga ggcacgcgag     720
aaaatggcgt atgctcaata catggccggt gtcgcgttca caatggtgg tctgggtctg     780
gtacacagca tcagccacca agtgggtagt gtgtacaaac tgcaacacgg catttgcaac     840
tccgtcaaca tgccgcacgt ttgtgcgttt aatctgattg ccaagaccga acgtttcgcc     900
catatcgctg agctgctggg tgagaacgtt gcaggcctga gcacggcggc tgcggcggag     960
cgcgcaattg tcgcgctgga acgcattaac aagagctttg gtatcccgag cggctatgcg    1020
gagatgggtg tgaaagaaga ggacattgaa ctgctggcta aggatgcgta cgaggacgtt    1080
```
tgtactcaga gcaacccgcg tgttccgacg gtccaggaca ttgcccagat tatcaagaac    1140
gcgatgtag                                                             1149

<210> SEQ ID NO 10
<211> LENGTH: 393
<212> TYPE: PRT
<213> ORGANISM: Unknown
<220> FEATURE:
<223> OTHER INFORMATION: Metalibrary sp

<400> SEQUENCE: 10

Met Ser Leu Val Asn Tyr Leu Gln Leu Ala Asp Arg Thr Asp Gly Phe
1               5                   10                  15

Phe Ile Pro Ser Val Thr Leu Val Gly Pro Gly Cys Val Lys Glu Val
            20                  25                  30

Gly Pro Arg Ala Lys Met Leu Gly Ala Lys Arg Ala Leu Ile Val Thr
        35                  40                  45

Asp Ala Gly Leu His Lys Met Gly Leu Ser Gln Glu Ile Ala Asp Leu
    50                  55                  60

Leu Arg Ser Glu Gly Ile Asp Ser Val Ile Phe Ala Gly Ala Glu Pro
65                  70                  75                  80

Asn Pro Thr Asp Ile Asn Val His Asp Gly Val Lys Val Tyr Gln Lys
                85                  90                  95

Glu Lys Cys Asp Phe Ile Val Ser Leu Gly Gly Gly Ser Ser His Asp
            100                 105                 110

Cys Ala Lys Gly Ile Gly Leu Val Thr Ala Gly Gly His Ile Arg
        115                 120                 125

Asp Tyr Glu Gly Val Asp Lys Ser Lys Val Pro Met Thr Pro Leu Ile
    130                 135                 140

Ala Ile Asn Thr Thr Ala Gly Thr Ala Ser Glu Met Thr Arg Phe Cys
145                 150                 155                 160

Ile Ile Thr Asn Thr Asp Thr His Val Lys Met Ala Ile Val Asp Trp
                165                 170                 175

Arg Cys Thr Pro Leu Val Ala Ile Asp Asp Pro Arg Leu Met Val Lys
            180                 185                 190

Met Pro Pro Ala Leu Thr Ala Thr Gly Met Asp Ala Leu Thr His
        195                 200                 205

Ala Val Glu Ala Tyr Val Ser Thr Ala Ala Thr Pro Ile Thr Asp Thr
    210                 215                 220

Cys Ala Glu Lys Ala Ile Glu Leu Ile Gly Gln Trp Leu Pro Lys Ala
225                 230                 235                 240

Val Ala Asn Gly Asp Trp Met Glu Ala Arg Ala Ala Met Cys Tyr Ala
                245                 250                 255

Gln Tyr Leu Ala Gly Met Ala Phe Asn Ala Ser Leu Gly Tyr Val
            260                 265                 270

His Ala Met Ala His Gln Leu Gly Gly Phe Tyr Asn Leu Pro His Gly
        275                 280                 285

Val Cys Asn Ala Ile Leu Leu Pro His Val Cys Gln Phe Asn Leu Ile
    290                 295                 300

Ala Ala Thr Glu Arg Tyr Ala Arg Ile Ala Ala Leu Leu Gly Val Asp
305                 310                 315                 320

Thr Ser Gly Met Glu Thr Arg Glu Ala Ala Leu Ala Ala Ile Ala Ala
                325                 330                 335

Ile Lys Glu Leu Ser Ser Ser Ile Gly Ile Pro Arg Gly Leu Ser Glu
            340                 345                 350

Leu Gly Val Lys Ala Ala Asp His Lys Val Met Ala Glu Asn Ala Gln
        355                 360                 365

Lys Asp Ala Cys Met Leu Thr Asn Pro Arg Lys Ala Thr Leu Glu Gln
        370                 375                 380

Val Ile Gly Ile Phe Glu Ala Ala Met
385                 390

<210> SEQ ID NO 11
<211> LENGTH: 1182
<212> TYPE: DNA
<213> ORGANISM: Unknown
<220> FEATURE:
<223> OTHER INFORMATION: Metalibrary sp

<400> SEQUENCE: 11
atgagcctgg ttaattatct gcagctggcc gatcgtaccg atggcttttt tatcccgagc      60
gttaccctgg ttggtccggg ttgtgttaaa gaagttggtc ctcgcgcaaa aatgctgggt     120
gcaaaacgtg cactgattgt taccgatgca ggtctgcaca aaatgggtct gagccaagaa     180
attgccgatc tgctgcgtag cgaaggtatt gatagcgtta ttttgccgg tgcagaaccg      240 aatccgaccg atatcaatgt tcatgatggt gtgaaagtgt atcagaaaga gaatgcgat     300 tttatcgtta gcctgggtgg tggtagcagc catgattgtg caaaaggtat tggtctggtt     360
accgcaggcg gtggtcatat tcgtgattat gaaggtgttg acaaaagcaa agttccgatg     420
acaccgctga ttgcaattaa taccaccgca ggcaccgcaa gcgaaatgac ccgttttgt      480 attattacca caccgatac ccatgtgaaa atggcaattg ttgattggcg ttgtactccg      540
ctggttgcca ttgatgatcc gcgtctgatg gttaaaatgc ctccggcact gaccgcagca     600
accggtatgg atgcactgac ccatgcagtt gaagcatatg tgagcaccgc agccaccccg     660
attaccgata cctgtgcaga aaaagcaatt gaactgattg gtcagtggct gccgaaagca     720
gttgcaaatg gtgattggat ggaagcacgt gcagcaatgt gttatgcaca gtatctggca     780
ggtatggcat tcaataatgc aagcctgggt tatgttcatg caatggcaca tcagctgggt     840
ggcttttata acctgccgca tggtgttttgt aatgcaattc tgctgcctca tgtttgccag     900
tttaatctga ttgcagccac cgaacgttat gcccgtattg cagcactgct gggtgttgat     960 accagccggta tggaaacccg tgaagcagca ctggcagcaa ttgccgcaat taaagaactg    1020
agcagcagca ttggtattcc gcgtggtctg agcgaactgg gtgttaaagc agccgatcat    1080
aaagttatgg cagaaaatgc acagaaagat gcatgtatgc tgacaaatcc gcgtaaagca    1140
accctggaac aggttattgg tatttttgaa gccgcaatgt ag                       1182

<210> SEQ ID NO 12
<211> LENGTH: 185
<212> TYPE: PRT
<213> ORGANISM: Bacillus methanolicus

<400> SEQUENCE: 12

Met Gly Lys Leu Phe Glu Glu Lys Thr Ile Lys Thr Glu Gln Ile Phe
1               5                   10                  15

Ser Gly Arg Val Val Lys Leu Gln Val Asp Asp Val Glu Leu Pro Asn
            20                  25                  30

Gly Gln Thr Ser Lys Arg Glu Ile Val Arg His Pro Gly Ala Val Ala
        35                  40                  45

Val Ile Ala Ile Thr Asn Glu Asn Lys Ile Val Met Val Glu Gln Tyr
    50                  55                  60

Arg Lys Pro Leu Glu Lys Ser Ile Val Glu Ile Pro Ala Gly Lys Leu
65                  70                  75                  80

Glu Lys Gly Glu Asp Pro Arg Ile Thr Ala Leu Arg Glu Leu Glu Glu
                85                  90                  95

Glu Thr Gly Tyr Glu Cys Glu Gln Met Glu Trp Leu Ile Ser Phe Ala
            100                 105                 110

Thr Ser Pro Gly Phe Ala Asp Glu Ile Ile His Ile Tyr Val Ala Lys
        115                 120                 125

Gly Leu Ser Lys Lys Glu Asn Ala Ala Gly Leu Asp Glu Asp Glu Phe
    130                 135                 140

Val Asp Leu Ile Glu Leu Thr Leu Asp Glu Ala Leu Gln Tyr Ile Lys
145                 150                 155                 160

Glu Gln Arg Ile Tyr Asp Ser Lys Thr Val Ile Ala Val Gln Tyr Leu
                165                 170                 175

Gln Leu Gln Glu Ala Leu Lys Asn Lys
        180                 185

<210> SEQ ID NO 13
<211> LENGTH: 381
<212> TYPE: PRT
<213> ORGANISM: Bacillus methanolicus C1

<400> SEQUENCE: 13

Met Thr Asn Phe Phe Ile Pro Pro Ala Ser Val Ile Gly Arg Gly Ala
1               5                   10                  15

Val Lys Glu Val Gly Thr Arg Leu Lys Gln Ile Gly Ala Lys Lys Ala
            20                  25                  30

Leu Ile Val Thr Asp Ala Phe Leu His Ser Thr Gly Leu Ser Glu Glu
        35                  40                  45

Val Ala Lys Asn Ile Arg Glu Ala Gly Leu Asp Val Ala Ile Phe Pro
    50                  55                  60

Lys Ala Gln Pro Asp Pro Ala Asp Thr Gln Val His Glu Gly Val Asp
65                  70                  75                  80

Val Phe Lys Gln Glu Asn Cys Asp Ala Leu Val Ser Ile Gly Gly Gly
                85                  90                  95

Ser Ser His Asp Thr Ala Lys Ala Ile Gly Leu Val Ala Ala Asn Gly
            100                 105                 110

Gly Arg Ile Asn Asp Tyr Gln Gly Val Asn Ser Val Glu Lys Pro Val
        115                 120                 125

Val Pro Val Val Ala Ile Thr Thr Thr Ala Gly Thr Gly Ser Glu Thr
    130                 135                 140

Thr Ser Leu Ala Val Ile Thr Asp Ser Ala Arg Lys Val Lys Met Pro
145                 150                 155                 160

Val Ile Asp Glu Lys Ile Thr Pro Thr Val Ala Ile Val Asp Pro Glu
                165                 170                 175

Leu Met Val Lys Lys Pro Ala Gly Leu Thr Ile Ala Thr Gly Met Asp
            180                 185                 190

Ala Leu Ser His Ala Ile Glu Ala Tyr Val Lys Gly Ala Thr Pro
        195                 200                 205

Val Thr Asp Ala Phe Ala Ile Gln Ala Met Lys Leu Ile Asn Glu Tyr
    210                 215                 220

Leu Pro Lys Ala Val Ala Asn Gly Glu Asp Ile Glu Ala Arg Glu Ala
225                 230                 235                 240

Met Ala Tyr Ala Gln Tyr Met Ala Gly Val Ala Phe Asn Asn Gly Gly

```
              245                 250                 255
Leu Gly Leu Val His Ser Ile Ser His Gln Val Gly Val Tyr Lys
        260                 265                 270

Leu Gln His Gly Ile Cys Asn Ser Val Asn Met Pro His Val Cys Ala
        275                 280                 285

Phe Asn Leu Ile Ala Lys Thr Glu Arg Phe Ala His Ile Ala Glu Leu
        290                 295                 300

Leu Gly Glu Asn Val Ser Gly Leu Ser Thr Ala Ala Ala Glu Arg
305                 310                 315                 320

Ala Ile Val Ala Leu Glu Arg Tyr Asn Lys Asn Phe Gly Ile Pro Ser
            325                 330                 335

Gly Tyr Ala Glu Met Gly Val Lys Glu Asp Ile Glu Leu Leu Ala
            340                 345                 350

Lys Asn Ala Phe Glu Asp Val Cys Thr Gln Ser Asn Pro Arg Val Ala
            355                 360                 365

Thr Val Gln Asp Ile Ala Gln Ile Ile Lys Asn Ala Leu
            370                 375                 380

<210> SEQ ID NO 14
<211> LENGTH: 383
<212> TYPE: PRT
<213> ORGANISM: Bacillus methanolicus PB1

<400> SEQUENCE: 14

Met Thr Gln Arg Asn Phe Phe Ile Pro Pro Ala Ser Val Ile Gly Arg
1               5                   10                  15

Gly Ala Val Lys Glu Val Gly Thr Arg Leu Lys Gln Ile Gly Ala Thr
            20                  25                  30

Lys Ala Leu Ile Val Thr Asp Ala Phe Leu His Gly Thr Gly Leu Ser
        35                  40                  45

Glu Glu Val Ala Lys Asn Ile Arg Glu Ala Gly Leu Asp Ala Val Ile
50                  55                  60

Phe Pro Lys Ala Gln Pro Asp Pro Ala Asp Thr Gln Val His Glu Gly
65                  70                  75                  80

Val Asp Ile Phe Lys Gln Glu Lys Cys Asp Ala Leu Val Ser Ile Gly
            85                  90                  95

Gly Gly Ser Ser His Asp Thr Ala Lys Ala Ile Gly Leu Val Ala Ala
        100                 105                 110

Asn Gly Gly Arg Ile Asn Asp Tyr Gln Gly Val Asn Ser Val Glu Lys
    115                 120                 125

Pro Val Val Pro Val Val Ala Ile Thr Thr Thr Ala Gly Thr Gly Ser
130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
            165                 170                 175

Pro Glu Leu Met Val Lys Lys Pro Ala Gly Leu Thr Ile Ala Thr Gly
            180                 185                 190

Met Asp Ala Leu Ser His Ala Ile Glu Ala Tyr Val Ala Lys Arg Ala
        195                 200                 205

Thr Pro Val Thr Asp Ala Phe Ala Ile Gln Ala Met Lys Leu Ile Asn
    210                 215                 220

Glu Tyr Leu Pro Arg Ala Val Ala Asn Gly Glu Asp Ile Glu Ala Arg
225                 230                 235                 240
```

Glu Ala Met Ala Tyr Ala Gln Tyr Met Ala Gly Val Ala Phe Asn Asn
            245                 250                 255

Gly Gly Leu Gly Leu Val His Ser Ile Ser His Gln Val Gly Gly Val
        260                 265                 270

Tyr Lys Leu Gln His Gly Ile Cys Asn Ser Val Asn Met Pro His Val
    275                 280                 285

Cys Gln Phe Asn Leu Ile Ala Arg Thr Glu Arg Phe Ala His Ile Ala
    290                 295                 300

Glu Leu Leu Gly Glu Asn Val Ser Gly Leu Ser Thr Ala Ser Ala Ala
305                 310                 315                 320

Glu Arg Ala Ile Val Ala Leu Gln Arg Tyr Asn Lys Asn Phe Gly Ile
            325                 330                 335

Pro Ser Gly Tyr Ala Glu Met Gly Val Lys Glu Glu Asp Ile Glu Leu
        340                 345                 350

Leu Ala Asn Asn Ala Tyr Gln Asp Val Cys Thr Leu Asp Asn Pro Arg
    355                 360                 365

Val Pro Thr Val Gln Asp Ile Ala Gln Ile Ile Lys Asn Ala Leu
    370                 375                 380

<210> SEQ ID NO 15
<211> LENGTH: 383
<212> TYPE: PRT
<213> ORGANISM: Bacillus methanolicus PB1

<400> SEQUENCE: 15

Met Thr Lys Thr Lys Phe Phe Ile Pro Ser Ser Thr Val Phe Gly Arg
1               5                   10                  15

Gly Ala Val Lys Glu Val Gly Ala Arg Leu Lys Ala Ile Gly Ala Thr
            20                  25                  30

Lys Ala Leu Ile Val Thr Asp Ala Phe Leu His Ser Thr Gly Leu Ser
        35                  40                  45

Glu Glu Val Ala Lys Asn Ile Arg Glu Ala Gly Leu Asp Val Val Ile
    50                  55                  60

Phe Pro Lys Ala Gln Pro Asp Pro Ala Asp Thr Gln Val His Glu Gly
65                  70                  75                  80

Val Glu Val Phe Lys Gln Glu Lys Cys Asp Ala Leu Val Ser Ile Gly
            85                  90                  95

Gly Gly Ser Ser His Asp Thr Ala Lys Gly Ile Gly Leu Val Ala Ala
        100                 105                 110

Asn Gly Gly Arg Ile Asn Asp Tyr Gln Gly Val Asn Ser Val Glu Lys
    115                 120                 125

Gln Val Val Pro Gln Ile Ala Ile Thr Thr Thr Ala Gly Thr Gly Ser
    130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
            165                 170                 175

Pro Glu Leu Met Val Lys Lys Pro Ala Gly Leu Thr Ile Ala Thr Gly
        180                 185                 190

Met Asp Ala Leu Ser His Ala Ile Glu Ala Tyr Val Ala Lys Arg Ala
    195                 200                 205

Thr Pro Val Thr Asp Ala Phe Ala Ile Gln Ala Met Lys Leu Ile Asn
    210                 215                 220

Glu Tyr Leu Pro Lys Ala Val Ala Asn Gly Glu Asp Ile Glu Ala Arg
225                 230                 235                 240

```
Glu Ala Met Ala Tyr Ala Gln Tyr Met Ala Gly Val Ala Phe Asn Asn
            245                 250                 255

Gly Gly Leu Gly Leu Val His Ser Ile Ser His Gln Val Gly Gly Val
            260                 265                 270

Tyr Lys Leu Gln His Gly Ile Cys Asn Ser Val Val Met Pro His Val
            275                 280                 285

Cys Gln Phe Asn Leu Ile Ala Arg Thr Glu Arg Phe Ala His Ile Ala
            290                 295                 300

Glu Leu Leu Gly Glu Asn Val Ser Gly Leu Ser Thr Ala Ser Ala Ala
305                 310                 315                 320

Glu Arg Thr Ile Ala Ala Leu Glu Arg Tyr Asn Arg Asn Phe Gly Ile
            325                 330                 335

Pro Ser Gly Tyr Lys Ala Met Gly Val Lys Glu Glu Asp Ile Glu Leu
            340                 345                 350

Leu Ala Asn Asn Ala Met Gln Asp Val Cys Thr Leu Asp Asn Pro Arg
            355                 360                 365

Val Pro Thr Val Gln Asp Ile Gln Gln Ile Ile Lys Asn Ala Leu
            370                 375                 380
```

<210> SEQ ID NO 16
<211> LENGTH: 385
<212> TYPE: PRT
<213> ORGANISM: Bacillus methanolicus MGA3

<400> SEQUENCE: 16

```
Met Lys Asn Thr Gln Ser Ala Phe Tyr Met Pro Ser Val Asn Leu Phe
1               5                   10                  15

Gly Ala Gly Ser Val Asn Glu Val Gly Thr Arg Leu Ala Gly Leu Gly
            20                  25                  30

Val Lys Lys Ala Leu Leu Val Thr Asp Ala Gly Leu His Ser Leu Gly
            35                  40                  45

Leu Ser Glu Lys Ile Ala Gly Ile Ile Arg Glu Ala Gly Val Glu Val
            50                  55                  60

Ala Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr
            85                  90                  95

Leu Gly Gly Gly Ser Ser His Asp Ala Gly Lys Ala Ile Ala Leu Val
            100                 105                 110

Ala Ala Asn Gly Gly Thr Ile His Asp Tyr Glu Gly Val Asp Val Ser
            115                 120                 125

Lys Lys Pro Met Val Pro Leu Ile Ala Ile Asn Thr Thr Ala Gly Thr
            130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
            165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
            195                 200                 205

Gly Ala Thr Pro Ile Thr Asp Ala Leu Ala Ile Gln Ala Ile Lys Ile
            210                 215                 220

Ile Ser Lys Tyr Leu Pro Arg Ala Val Ala Asn Gly Lys Asp Ile Glu
```

```
        225                 230                 235                 240
Ala Arg Glu Gln Met Ala Phe Ala Gln Ser Leu Ala Gly Met Ala Phe
                245                 250                 255
Asn Asn Ala Gly Leu Gly Tyr Val His Ala Ile Ala His Gln Leu Gly
                260                 265                 270
Gly Phe Tyr Asn Phe Pro His Gly Val Cys Asn Ala Ile Leu Leu Pro
                275                 280                 285
His Val Cys Arg Phe Asn Leu Ile Ser Lys Val Glu Arg Tyr Ala Glu
                290                 295                 300
Ile Ala Ala Phe Leu Gly Glu Asn Val Asp Gly Leu Ser Thr Tyr Glu
305                 310                 315                 320
Ala Ala Glu Lys Ala Ile Lys Ala Ile Glu Arg Met Ala Arg Asp Leu
                325                 330                 335
Asn Ile Pro Lys Gly Phe Lys Glu Leu Gly Ala Lys Glu Glu Asp Ile
                340                 345                 350
Glu Thr Leu Ala Lys Asn Ala Met Asn Asp Ala Cys Ala Leu Thr Asn
                355                 360                 365
Pro Arg Lys Pro Lys Leu Glu Glu Val Ile Gln Ile Ile Lys Asn Ala
                370                 375                 380
Met
385

<210> SEQ ID NO 17
<211> LENGTH: 385
<212> TYPE: PRT
<213> ORGANISM: Bacillus methanolicus PB1

<400> SEQUENCE: 17

Met Thr Asn Thr Gln Ser Ile Phe Tyr Ile Pro Ser Val Asn Leu Phe
1               5                   10                  15
Gly Pro Gly Ser Val Asn Glu Val Gly Thr Arg Leu Ala Gly Leu Gly
                20                  25                  30
Val Lys Lys Ala Leu Leu Val Thr Asp Ala Gly Leu His Gly Leu Gly
                35                  40                  45
Leu Ser Glu Lys Ile Ala Ser Ile Ile Arg Glu Ala Gly Val Glu Val
        50                  55                  60
Leu Ile Phe Pro Lys Ala Glu Pro Asn Pro Thr Asp Lys Asn Val Ala
65                  70                  75                  80
Glu Gly Leu Glu Val Tyr Asn Ala Glu Asn Cys Asp Ser Ile Val Thr
                85                  90                  95
Leu Gly Gly Gly Ser Ser His Asp Ala Gly Lys Gly Ile Ala Leu Val
                100                 105                 110
Ala Ala Asn Gly Gly Thr Ile Tyr Asp Tyr Glu Gly Val Asp Lys Ser
                115                 120                 125
Lys Lys Pro Met Val Pro Leu Ile Ala Ile Asn Thr Thr Ala Gly Thr
        130                 135                 140
Gly Ser Glu Leu Thr Arg Phe Thr Ile Ile Thr Asp Thr Glu Arg Lys
145                 150                 155                 160
Val Lys Met Ala Ile Val Asp Lys His Val Thr Pro Thr Leu Ser Ile
                165                 170                 175
Asn Asp Pro Glu Leu Met Val Gly Met Pro Pro Ser Leu Thr Ala Ala
                180                 185                 190
Thr Gly Leu Asp Ala Leu Thr His Ala Ile Glu Ala Tyr Val Ser Thr
                195                 200                 205
```

```
Ala Ala Thr Pro Ile Thr Asp Ala Leu Ala Ile Gln Ala Ile Lys Ile
    210             215                 220

Ile Ser Lys Tyr Leu Pro Arg Ala Phe Ala Asn Gly Lys Asp Met Glu
225                 230                 235                 240

Ala Arg Glu Gln Met Ala Phe Ala Gln Ser Leu Ala Gly Met Ala Phe
                245                 250                 255

Asn Asn Ala Ser Leu Gly Tyr Val His Ala Ile Ala His Gln Phe Gly
            260                 265                 270

Gly Phe Tyr Asn Phe Pro His Gly Val Cys Asn Ala Ile Leu Leu Pro
        275                 280                 285

His Val Cys Arg Phe Asn Leu Ile Ser Lys Val Glu Arg Phe Ala Glu
    290                 295                 300

Ile Ala Ala Leu Leu Gly Glu Asn Val Ala Gly Leu Ser Thr Arg Glu
305                 310                 315                 320

Ala Ala Glu Lys Gly Ile Lys Ala Ile Glu Arg Met Ala Lys Asp Leu
                325                 330                 335

Asn Ile Pro Arg Gly Phe Lys Glu Leu Gly Ala Lys Glu Glu Asp Ile
            340                 345                 350

Val Thr Leu Ala Glu Asn Ala Met Lys Asp Ala Thr Ala Leu Thr Asn
        355                 360                 365

Pro Arg Lys Pro Lys Leu Glu Glu Val Ile Gln Ile Ile Lys Asn Ala
    370                 375                 380

Met
385

<210> SEQ ID NO 18
<211> LENGTH: 385
<212> TYPE: PRT
<213> ORGANISM: Bacillus methanolicus MGA3

<400> SEQUENCE: 18

Met Thr Asn Thr Gln Ser Ala Phe Phe Met Pro Ser Val Asn Leu Phe
1               5                   10                  15

Gly Ala Gly Ser Val Asn Glu Val Gly Thr Arg Leu Ala Asp Leu Gly
                20                  25                  30

Val Lys Lys Ala Leu Leu Val Thr Asp Ala Gly Leu His Gly Leu Gly
            35                  40                  45

Leu Ser Glu Lys Ile Ser Ser Ile Ile Arg Ala Ala Gly Val Glu Val
    50                  55                  60

Ser Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr
                85                  90                  95

Leu Gly Gly Gly Ser Ser His Asp Ala Gly Lys Ala Ile Ala Leu Val
            100                 105                 110

Ala Ala Asn Gly Gly Lys Ile His Asp Tyr Glu Gly Val Asp Val Ser
        115                 120                 125

Lys Glu Pro Met Val Pro Leu Ile Ala Ile Asn Thr Thr Ala Gly Thr
    130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190
```

```
Thr Gly Leu Asp Ala Leu Thr His Ala Ile Glu Ala Tyr Val Ser Thr
        195                 200                 205

Gly Ala Thr Pro Ile Thr Asp Ala Leu Ala Ile Gln Ala Ile Lys Ile
210                 215                 220

Ile Ser Lys Tyr Leu Pro Arg Ala Val Ala Asn Gly Lys Asp Ile Glu
225                 230                 235                 240

Ala Arg Glu Gln Met Ala Phe Ala Gln Ser Leu Ala Gly Met Ala Phe
                245                 250                 255

Asn Asn Ala Gly Leu Gly Tyr Val His Ala Ile Ala His Gln Leu Gly
                260                 265                 270

Gly Phe Tyr Asn Phe Pro His Gly Val Cys Asn Ala Val Leu Leu Pro
                275                 280                 285

Tyr Val Cys Arg Phe Asn Leu Ile Ser Lys Val Glu Arg Tyr Ala Glu
                290                 295                 300

Ile Ala Ala Phe Leu Gly Glu Asn Val Asp Gly Leu Ser Thr Tyr Asp
305                 310                 315                 320

Ala Ala Glu Lys Ala Ile Lys Ala Ile Glu Arg Met Ala Lys Asp Leu
                325                 330                 335

Asn Ile Pro Lys Gly Phe Lys Glu Leu Gly Ala Lys Glu Glu Asp Ile
                340                 345                 350

Glu Thr Leu Ala Lys Asn Ala Met Lys Asp Ala Cys Ala Leu Thr Asn
                355                 360                 365

Pro Arg Lys Pro Lys Leu Glu Glu Val Ile Gln Ile Ile Lys Asn Ala
                370                 375                 380

Met
385

<210> SEQ ID NO 19
<211> LENGTH: 401
<212> TYPE: PRT
<213> ORGANISM: Lysinibacillus fusiformis

<400> SEQUENCE: 19

Met Ser Asp Val Leu Lys Gln Phe Val Met Pro Lys Thr Asn Leu Phe
1                   5                   10                  15

Gly Pro Gly Ala

```
                165                 170                 175
Asn Asp Pro Glu Leu Met Ile Gly Leu Pro Ala Leu Thr Ala Ala
            180                 185                 190

Thr Gly Val Asp Ala Leu Thr His Ala Ile Glu Ser Phe Val Ser Thr
            195                 200                 205

Asn Ala Thr Pro Ile Thr Asp Ala Cys Ala Glu Lys Val Leu Gln Leu
            210                 215                 220

Ile Pro Glu Tyr Leu Pro Arg Ala Tyr Ala Asn Gly Ala Asp Ile Glu
225                 230                 235                 240

Ala Arg Glu Gln Met Val Tyr Ala Gln Phe Leu Ala Gly Met Ala Phe
                245                 250                 255

Asn Asn Ala Ser Leu Gly Tyr Val His Ala Ile Ala His Gln Leu Gly
            260                 265                 270

Gly Phe Tyr Asn Leu Pro His Gly Val Cys Asn Ala Ile Leu Leu Pro
            275                 280                 285

His Val Cys Arg Phe Asn Val Thr Ala Arg Thr Glu Arg Phe Ala Arg
            290                 295                 300

Ile Ala Glu Leu Leu Gly Glu Asn Val Glu Gly Leu Ser Lys Arg Asp
305                 310                 315                 320

Ala Ala Glu Lys Ala Ile Thr Ala Ile Glu Lys Leu Ser Gln Asp Leu
                325                 330                 335

Asn Ile Pro Ser Gly Phe Arg Glu Leu Gly Ala Lys Asp Glu Asp Ile
            340                 345                 350

Glu Ile Leu Ala Lys Asn Ala Leu Leu Asp Val Cys Ala Glu Thr Asn
            355                 360                 365

Pro Arg Lys Ala Thr Leu Glu Asp Ile Lys Gln Ile Ile Thr Asn Ala
            370                 375                 380

Met Gly Pro Ile Val Lys Lys Glu Glu Ser Leu Glu Ala Val Ala Leu
385                 390                 395                 400

Ser

<210> SEQ ID NO 20
<211> LENGTH: 386
<212> TYPE: PRT
<213> ORGANISM: Bacillus coagulans 36D1

<400> SEQUENCE: 20

Met Leu Thr Gly Leu Arg Thr Asp Phe Gln Met Pro Ser Val Asn Leu
1               5                   10                  15

Phe Gly Gln Gly Thr Ala Glu Glu Ile Gly Asn Arg Leu Lys Asn Leu
                20                  25                  30

Gly Cys Arg Arg Pro Leu Ile Val Thr Asp Glu Gly Leu His Gln Leu
            35                  40                  45

Gly Tyr Ser Glu Lys Ile Ala Ala Tyr Ile Lys Glu Ala Gly Leu Glu
        50                  55                  60

Val Ala Ile Tyr Pro Lys Ala Glu Pro Asn Pro Thr Asp Lys Asn Val
65                  70                  75                  80

Glu Asp Gly Leu Lys Thr Tyr His Glu Asn Cys Asp Ser Ile Val
                85                  90                  95

Ser Leu Gly Gly Gly Ser Ala His Asp Cys Ala Lys Gly Ile Gly Leu
            100                 105                 110

Val Ala Ala Asn Gly Gly Lys Ile His Asp Tyr Glu Gly Leu Asp Arg
            115                 120                 125

Ser Glu Lys Pro Met Val Pro Leu Val Ala Ile Asn Thr Thr Ala Gly
```

```
    130                 135                 140

Thr Ala Ser Glu Met Thr Lys Phe Thr Ile Ile Thr Asp Thr Ser Arg
145                 150                 155                 160

Lys Val Lys Met Ala Ile Val Asp Lys His Val Thr Pro Val Leu Ser
                165                 170                 175

Ile Asn Asp Pro Leu Leu Met Val Gly Met Pro Pro Ser Leu Thr Ala
            180                 185                 190

Ala Thr Gly Leu Asp Ala Leu Thr His Ala Val Glu Ala Tyr Val Ser
        195                 200                 205

Thr Ala Ala Thr Pro Val Thr Asp Ala Cys Ala Ile Lys Ala Ile Gln
    210                 215                 220

Ile Ile Pro Gln Tyr Leu Pro Lys Ala Val Ala Asn Gly Asn Asp Met
225                 230                 235                 240

Glu Ala Arg Glu Gln Met Val Tyr Ala Gln Tyr Leu Ala Gly Met Ala
                245                 250                 255

Phe Asn Asn Ala Ser Leu Gly Tyr Val His Ala Ile Ala His Gln Phe
            260                 265                 270

Gly Gly Phe Tyr Asn Leu Pro His Gly Val Cys Asn Ala Ile Leu Leu
        275                 280                 285

Pro His Val Cys Arg Phe Asn Leu Ile Ala Arg Lys Glu Arg Phe Ala
    290                 295                 300

Glu Ile Ala Val Ala Leu Gly Glu Lys Thr Asp Ser Leu Ser Val Asp
305                 310                 315                 320

Glu Ala Ala Glu Lys Ala Ile Thr Ala Ile Glu Arg Leu Ala Ala Gln
                325                 330                 335

Leu Asn Ile Pro Lys Gly Phe Lys Glu Leu Gly Ala Lys Glu Glu Asp
            340                 345                 350

Ile Glu Ile Leu Ala Gln His Ala Met Gln Asp Ala Cys Ala Ala Thr
        355                 360                 365

Asn Pro Arg Lys Pro Thr Gln Lys Glu Val Glu Ala Ile Ile Lys Ala
    370                 375                 380

Ala Met
385

<210> SEQ ID NO 21
<211> LENGTH: 402
<212> TYPE: PRT
<213> ORGANISM: Lysinibacillus sphaericus

<400> SEQUENCE: 21

Met Ser Asp Val Leu Lys Gln Phe Val Met Pro Lys Lys Asn Leu Phe
1               5                   10                  15

Gly Pro Gly Ala Ile Gln Glu Val Gly Lys His Leu Asn Asp Leu Glu
            20                  25                  30

Val Lys Lys Thr Leu Ile Val Thr Asp Glu Gly Leu His Lys Leu Gly
        35                  40                  45

Leu Ser Glu Gln Ile Ala Asn Ile Ile Thr Ala Ala Gly Ile Asp Val
    50                  55                  60

Ala Ile Phe Pro Lys Ala Glu Pro Asn Pro Thr Asp Gln Asn Ile Glu
65                  70                  75                  80

Asp Gly Ile Ala Asp Tyr His Ala Glu Ser Cys Asp Ser Ile Val Ser
                85                  90                  95

Leu Gly Gly Gly Ser Ala His Asp Ala Ala Lys Gly Ile Gly Leu Ile
            100                 105                 110

Ala Ser Asn Gly Gly Arg Ile Gln Asp Tyr Glu Gly Val Asp Lys Ser
            115                 120                 125

Gln Asn Pro Leu Val Pro Leu Ile Ala Ile Asn Thr Thr Ala Gly Thr
130                 135                 140

Ala Ser Glu Met Thr Arg Phe Thr Ile Ile Thr Asp Thr Ala Arg Lys
145                 150                 155                 160

Val Lys Met Ala Ile Val Asp Lys His Val Thr Pro Leu Leu Ser Ile
                165                 170                 175

Asn Asp Ser Glu Leu Met Ile Gly Leu Pro Pro Ala Leu Thr Ala Ala
            180                 185                 190

Thr Gly Val Asp Ala Leu Thr His Ala Ile Glu Ser Phe Val Ser Thr
        195                 200                 205

Asn Ala Thr Pro Ile Thr Asp Ala Cys Ala Glu Lys Val Leu Gln Leu
210                 215                 220

Val Pro Glu Phe Leu Pro Arg Ala Tyr Ala Asn Gly Ala Asp Leu Glu
225                 230                 235                 240

Ala Arg Glu Gln Met Val Tyr Ala Gln Phe Leu Ala Gly Met Ala Phe
                245                 250                 255

Asn Asn Ala Ser Leu Gly Tyr Val His Ala Ile Ala His Gln Leu Gly
            260                 265                 270

Gly Tyr Tyr Asn Leu Pro His Gly Val Cys Asn Ala Ile Leu Leu Pro
        275                 280                 285

His Val Cys Arg Phe Asn Val Thr Ala Arg Thr Glu Arg Phe Ala Arg
        290                 295                 300

Ile Ala Glu Leu Leu Gly Glu Asn Val Thr Gly Leu Ser Lys Arg Asp
305                 310                 315                 320

Ala Ala Glu Lys Ala Ile Ser Ala Ile Glu Lys Leu Ser Lys Asp Leu
                325                 330                 335

Asn Ile Pro Ser Gly Phe Arg Glu Leu Gly Ala Lys Asp Glu Asp Ile
            340                 345                 350

Glu Ile Leu Ala Lys Asn Ala Met Leu Asp Val Cys Ala Glu Thr Asn
        355                 360                 365

Pro Arg Lys Ala Thr Leu Asp Asp Ile Lys Gln Ile Ile Thr Asn Ala
    370                 375                 380

Met Gly Pro Ile Val Lys Lys Glu Glu Ser Leu Glu Ala Val Ala Ala
385                 390                 395                 400

Leu Ser

<210> SEQ ID NO 22
<211> LENGTH: 386
<212> TYPE: PRT
<213> ORGANISM: Bacillus azotoformans LMG 9581

<400> SEQUENCE: 22

Met Ala Asn Gln Lys Val Tyr Gly Phe Phe Met Pro Thr Val Asn Leu
1               5                   10                  15

Met Gly Val Gly Ala Val Asn Glu Ala Gly Pro Arg Ile Lys Ala Leu
                20                  25                  30

Gly Cys Asn Lys Ser Leu Leu Val Thr Asp Lys Gly Leu Ser Lys Met
            35                  40                  45

Gly Val Ala Glu Glu Ile Ala Asn Ile Ile Gly Gln Ala Gly Val Glu
        50                  55                  60

Val Ser Ile Phe Asp Gly Ala Gly Pro Asn Pro Thr Asp Leu Asn Val
65                  70                  75                  80

Glu Ala Gly Leu Lys Gln Tyr Arg Glu Leu Gly Cys Asp Ser Ile Ile
                85                  90                  95

Ser Leu Gly Gly Gly Ser Ser His Asp Cys Ala Lys Gly Ile Gly Leu
            100                 105                 110

Val Ala Ser Asn Gly Gly Thr Ile His Asp Tyr Glu Gly Val Asp Met
            115                 120                 125

Ser Lys Glu Pro Met Ile Pro Leu Val Ala Ile Asn Thr Thr Ala Gly
        130                 135                 140

Thr Ala Ser Glu Met Thr Arg Phe Cys Ile Ile Thr Asp Thr Ser Arg
145                 150                 155                 160

Lys Ile Lys Met Ala Ile Val Asp Lys His Thr Thr Pro Leu Ile Ser
                165                 170                 175

Ile Asn Asp Pro Ile Leu Thr Val Lys Met Pro Ala Gly Leu Thr Ala
            180                 185                 190

Ala Thr Gly Met Asp Ala Leu Thr His Ala Ile Glu Ala Tyr Val Ser
            195                 200                 205

Thr Asp Ala Thr Pro Ile Thr Asp Ala Cys Ala Leu Gln Thr Ile Arg
        210                 215                 220

Leu Val Ser Gln Asn Leu Arg Ala Ala Val Ala Asn Gly Glu Asp Ile
225                 230                 235                 240

Asp Ala Arg Asn Asn Met Cys Tyr Ala Gln Phe Leu Gly Met Ala
                245                 250                 255

Phe Asn Asn Ala Ser Leu Gly Tyr Val His Ala Ile Ala His Gln Leu
            260                 265                 270

Gly Gly Phe Tyr Asn Leu Pro His Gly Val Cys Asn Ala Val Leu Leu
        275                 280                 285

Pro His Val Glu Arg Phe Asn Leu Ile Ala Lys Pro Glu Arg Phe Val
        290                 295                 300

Asp Ile Ala Ile Ala Leu Gly Glu Asn Val Ser Gly Leu Pro Thr Arg
305                 310                 315                 320

Ala Ala Ala Glu Ile Ala Leu Thr Ala Ile Glu Thr Leu Ala Lys Asp
                325                 330                 335

Val Gly Ile Pro Gly Ser Leu Thr Glu Leu Gly Val Lys Glu Glu Asp
            340                 345                 350

Ile Pro Leu Leu Ala Glu Asn Ala Met Arg Asp Ala Cys Ser Phe Thr
            355                 360                 365

Asn Pro Arg Lys Ala Thr Leu Asp Asp Val Gln Gly Met Ile Arg Ala
        370                 375                 380

Ala Leu
385

<210> SEQ ID NO 23
<211> LENGTH: 386
<212> TYPE: PRT
<213> ORGANISM: Burkholderia thailandensis E264

<400> SEQUENCE: 23

Met Ala Asn Gln Lys Val Tyr Gly Phe Phe Met Pro Thr Val Asn Leu
1               5                   10                  15

Met Gly Val Gly Ala Val Asn Glu Ala Gly Pro Arg Ile Lys Ala Leu
            20                  25                  30

Gly Cys Asn Lys Ser Leu Leu Val Thr Asp Lys Gly Leu Ser Lys Met
        35                  40                  45

Gly Val Ala Glu Glu Ile Ala Asn Ile Ile Gly Gln Ala Gly Val Glu
    50                  55                  60

Val Ser Ile Phe Asp Gly Ala Glu Pro Asn Pro Thr Asp Leu Asn Val
65                  70                  75                  80

Glu Ala Gly Leu Lys Gln Tyr Arg Glu Leu Gly Cys Asp Ser Ile Ile
            85                  90                  95

Ser Leu Gly Gly Gly Ser Ser His Asp Cys Ala Lys Gly Ile Gly Leu
        100                 105                 110

Val Ala Ser Asn Gly Gly Thr Ile His Asp Tyr Glu Gly Val Asp Met
    115                 120                 125

Ser Lys Glu Pro Met Ile Pro Leu Val Ala Ile Asn Thr Thr Ala Gly
130                 135                 140

Thr Ala Ser Glu Met Thr Arg Phe Cys Ile Ile Thr Asp Thr Ser Arg
145                 150                 155                 160

Lys Ile Lys Met Ala Ile Val Asp Lys His Thr Thr Pro Leu Ile Ser
                165                 170                 175

Ile Asn Asp Pro Ile Leu Thr Val Lys Met Pro Ala Gly Leu Thr Ala
            180                 185                 190

Ala Thr Gly Met Asp Ala Leu Thr His Ala Ile Glu Ala Tyr Val Ser
        195                 200                 205

Thr Asp Ala Thr Pro Ile Thr Asp Ala Cys Ala Leu Gln Thr Ile Arg
210                 215                 220

Leu Val Ser Gln Asn Leu Arg Ala Ala Val Ala Asn Gly Glu Asp Ile
225                 230                 235                 240

Asp Ala Arg Asn Asn Met Cys Tyr Ala Gln Phe Leu Gly Gly Met Ala
                245                 250                 255

Phe Asn Asn Ala Ser Leu Gly Tyr Val His Ala Ile Ala His Gln Leu
            260                 265                 270

Gly Gly Phe Tyr Asn Leu Pro His Gly Val Cys Asn Ala Val Leu Leu
        275                 280                 285

Pro His Val Glu Arg Phe Asn Leu Ile Ala Lys Pro Glu Arg Phe Val
290                 295                 300

Asp Ile Ala Ile Ala Leu Gly Glu Asn Val Ser Gly Leu Pro Thr Arg
305                 310                 315                 320

Ala Ala Ala Glu Ile Ala Leu Thr Ala Ile Glu Thr Leu Ala Lys Asp
                325                 330                 335

Val Gly Ile Pro Gly Ser Leu Thr Glu Leu Gly Val Lys Glu Glu Asp
            340                 345                 350

Ile Pro Leu Leu Ala Glu Asn Ala Met Arg Asp Ala Cys Ser Phe Thr
        355                 360                 365

Asn Pro Arg Lys Ala Thr Leu Asp Asp Val Gln Gly Met Ile Arg Ala
370                 375                 380

Ala Leu
385

<210> SEQ ID NO 24
<211> LENGTH: 390
<212> TYPE: PRT
<213> ORGANISM: Cupriavidus necator N-1

<400> SEQUENCE: 24

Met Thr His Leu Asn Ile Ala Asn Arg Val Asp Ser Phe Phe Ile Pro
1               5                   10                  15

Cys Val Thr Leu Phe Gly Pro Gly Cys Ala Arg Glu Thr Gly Ala Arg
            20                  25                  30

Ala Arg Ser Leu Gly Ala Arg Lys Ala Leu Ile Val Thr Asp Ala Gly

```
                35                  40                  45
Leu His Lys Met Gly Leu Ser Glu Val Ala Gly His Ile Arg Glu
 50                  55                  60

Ala Gly Leu Gln Ala Val Ile Phe Pro Gly Ala Glu Pro Asn Pro Thr
 65                  70                  75                  80

Asp Val Asn Val His Asp Gly Val Lys Leu Phe Glu Arg Glu Glu Cys
                 85                  90                  95

Asp Phe Ile Val Ser Leu Gly Gly Ser Ser His Asp Cys Ala Lys
                100                 105                 110

Gly Ile Gly Leu Val Thr Ala Gly Gly His Ile Arg Asp Tyr Glu
            115                 120                 125

Gly Ile Asp Lys Ser Thr Val Pro Met Thr Pro Leu Ile Ser Ile Asn
            130                 135                 140

Thr Thr Ala Gly Thr Ala Ala Glu Met Thr Arg Phe Cys Ile Ile Thr
145                 150                 155                 160

Asn Ser Ser Asn His Val Lys Met Ala Ile Val Asp Trp Arg Cys Thr
                165                 170                 175

Pro Leu Ile Ala Ile Asp Asp Pro Ser Leu Met Val Ala Met Pro Pro
            180                 185                 190

Ala Leu Thr Ala Ala Thr Gly Met Asp Ala Leu Thr His Ala Ile Glu
            195                 200                 205

Ala Tyr Val Ser Thr Ala Ala Thr Pro Ile Thr Asp Ala Cys Ala Glu
210                 215                 220

Lys Ala Ile Val Leu Ile Ala Glu Trp Leu Pro Lys Ala Val Ala Asn
225                 230                 235                 240

Gly Asp Ser Met Glu Ala Arg Ala Ala Met Cys Tyr Ala Gln Tyr Leu
                245                 250                 255

Ala Gly Met Ala Phe Asn Asn Ala Ser Leu Gly Tyr Val His Ala Met
                260                 265                 270

Ala His Gln Leu Gly Gly Phe Tyr Asn Leu Pro His Gly Val Cys Asn
            275                 280                 285

Ala Ile Leu Leu Pro His Val Ser Glu Phe Asn Leu Ile Ala Ala Pro
            290                 295                 300

Glu Arg Tyr Ala Arg Ile Ala Glu Leu Leu Gly Glu Asn Ile Gly Gly
305                 310                 315                 320

Leu Ser Ala His Asp Ala Ala Lys Ala Ala Val Ser Ala Ile Arg Thr
                325                 330                 335

Leu Ser Thr Ser Ile Gly Ile Pro Ala Gly Leu Ala Gly Leu Gly Val
                340                 345                 350

Lys Ala Asp Asp His Glu Val Met Ala Ser Asn Ala Gln Lys Asp Ala
            355                 360                 365

Cys Met Leu Thr Asn Pro Arg Lys Ala Thr Leu Ala Gln Val Met Ala
            370                 375                 380

Ile Phe Ala Ala Ala Met
385                 390

<210> SEQ ID NO 25
<211> LENGTH: 393
<212> TYPE: PRT
<213> ORGANISM: uncultured organism

<400> SEQUENCE: 25

Met Ser Leu Val Asn Tyr Leu Gln Leu Ala Asp Arg Thr Asp Gly Phe
 1               5                  10                  15
```

Phe Ile Pro Ser Val Thr Leu Val Gly Pro Gly Cys Val Lys Glu Val
             20                  25                  30

Gly Pro Arg Ala Lys Met Leu Gly Ala Lys Arg Ala Leu Ile Val Thr
         35                  40                  45

Asp Ala Gly Leu His Lys Met Gly Leu Ser Gln Glu Ile Ala Asp Leu
     50                  55                  60

Leu Arg Ser Glu Gly Ile Asp Ser Val Ile Phe Ala Gly Ala Glu Pro
 65                  70                  75                  80

Asn Pro Thr Asp Ile Asn Val His Asp Gly Val Lys Val Tyr Gln Lys
                 85                  90                  95

Glu Lys Cys Asp Phe Ile Val Ser Leu Gly Gly Ser Ser His Asp
            100                 105                 110

Cys Ala Lys Gly Ile Gly Leu Val Thr Ala Gly Gly His Ile Arg
        115                 120                 125

Asp Tyr Glu Gly Val Asp Lys Ser Lys Val Pro Met Thr Pro Leu Ile
    130                 135                 140

Ala Ile Asn Thr Thr Ala Gly Thr Ala Ser Glu Met Thr Arg Phe Cys
145                 150                 155                 160

Ile Ile Thr Asn Thr Asp Thr His Val Lys Met Ala Ile Val Asp Trp
                165                 170                 175

Arg Cys Thr Pro Leu Val Ala Ile Asp Asp Pro Arg Leu Met Val Lys
            180                 185                 190

Met Pro Pro Ala Leu Thr Ala Thr Gly Met Asp Ala Leu Thr His
        195                 200                 205

Ala Val Glu Ala Tyr Val Ser Thr Ala Ala Thr Pro Ile Thr Asp Thr
210                 215                 220

Cys Ala Glu Lys Ala Ile Glu Leu Ile Gly Gln Trp Leu Pro Lys Ala
225                 230                 235                 240

Val Ala Asn Gly Asp Trp Met Glu Ala Arg Ala Ala Met Cys Tyr Ala
                245                 250                 255

Gln Tyr Leu Ala Gly Met Ala Phe Asn Asn Ala Ser Leu Gly Tyr Val
            260                 265                 270

His Ala Met Ala His Gln Leu Gly Gly Phe Tyr Asn Leu Pro His Gly
        275                 280                 285

Val Cys Asn Ala Ile Leu Leu Pro His Val Cys Gln Phe Asn Leu Ile
290                 295                 300

Ala Ala Thr Glu Arg Tyr Ala Arg Ile Ala Ala Leu Leu Gly Val Asp
305                 310                 315                 320

Thr Ser Gly Met Glu Thr Arg Glu Ala Ala Leu Ala Ala Ile Ala Ala
                325                 330                 335

Ile Lys Glu Leu Ser Ser Ser Ile Gly Ile Pro Arg Gly Leu Ser Glu
            340                 345                 350

Leu Gly Val Lys Ala Ala Asp His Lys Val Met Ala Glu Asn Ala Gln
        355                 360                 365

Lys Asp Ala Cys Met Leu Thr Asn Pro Arg Lys Ala Thr Leu Glu Gln
    370                 375                 380

Val Ile Gly Ile Phe Glu Ala Ala Met
385                 390

<210> SEQ ID NO 26
<211> LENGTH: 387
<212> TYPE: PRT
<213> ORGANISM: Geobacter bemidjiensis Bem

<400> SEQUENCE: 26

```
Met Ala Leu Gly Glu Gln Thr Tyr Gly Phe Tyr Ile Pro Thr Val Ser
1               5                   10                  15

Leu Met Gly Ile Gly Ser Ala Lys Glu Thr Gly Gly Gln Ile Lys Ala
            20                  25                  30

Leu Gly Ala Ser Lys Ala Leu Ile Val Thr Asp Lys Gly Leu Ser Ala
            35                  40                  45

Met Gly Val Ala Asp Lys Ile Lys Ser Gln Val Glu Glu Ala Gly Val
        50                  55                  60

Ser Ala Val Ile Phe Asp Gly Ala Glu Pro Asn Pro Thr Asp Ile Asn
65                  70                  75                  80

Val His Asp Gly Val Lys Val Tyr Gln Asp Asn Gly Cys Asp Ala Ile
                85                  90                  95

Ile Ser Leu Gly Gly Gly Ser Ser His Asp Cys Ala Lys Gly Ile Gly
                100                 105                 110

Met Val Ile Gly Asn Gly Gly His Ile Arg Asp Leu Glu Gly Val Asn
            115                 120                 125

Lys Thr Thr Lys Pro Met Pro Ala Phe Val Ala Ile Asn Thr Thr Ala
130                 135                 140

Gly Thr Ala Ser Glu Met Thr Arg Phe Cys Ile Ile Thr Asn Thr Asp
145                 150                 155                 160

Thr His Val Lys Met Ala Ile Val Asp Trp Arg Cys Thr Pro Asn Val
                165                 170                 175

Ala Ile Asn Asp Pro Leu Leu Met Val Gly Lys Pro Ala Ala Leu Thr
                180                 185                 190

Ala Ala Thr Gly Met Asp Ala Leu Thr His Ala Val Glu Ala Tyr Val
            195                 200                 205

Ser Thr Ile Ala Thr Pro Ile Thr Asp Ala Cys Ala Ile Lys Ala Ile
210                 215                 220

Glu Leu Ile Ala Glu Phe Leu Ser Lys Ala Val Ala Asn Gly Glu Asp
225                 230                 235                 240

Leu Glu Ala Arg Asp Lys Met Ala Tyr Ala Glu Tyr Leu Ala Gly Met
                245                 250                 255

Ala Phe Asn Asn Ala Ser Leu Gly Tyr Val His Ser Met Ala His Gln
                260                 265                 270

Leu Gly Gly Phe Tyr Asn Leu Pro His Gly Val Cys Asn Ala Ile Leu
            275                 280                 285

Leu Pro Ala Val Ser Gln Tyr Asn Leu Ile Ala Cys Pro Lys Arg Phe
290                 295                 300

Ala Asp Ile Ala Lys Ala Leu Gly Glu Asn Ile Asp Gly Leu Ser Val
305                 310                 315                 320

Thr Glu Ala Gly Gln Lys Ala Ile Asp Arg Ile Arg Thr Leu Ser Ala
                325                 330                 335

Ser Ile Gly Ile Pro Thr Gly Leu Lys Ala Leu Asn Val Lys Glu Ala
            340                 345                 350

Asp Leu Thr Ile Met Ala Glu Asn Ala Lys Lys Asp Ala Cys Gln Phe
            355                 360                 365

Thr Asn Pro Arg Lys Ala Thr Leu Glu Gln Val Val Gln Ile Phe Lys
370                 375                 380

Asp Ala Met
385

<210> SEQ ID NO 27
<211> LENGTH: 383
```

```
<212> TYPE: PRT
<213> ORGANISM: Carboxydothermus hydrogenoformans Z-2901

<400> SEQUENCE: 27
```

| | | | | | | | | | | | | | | |
|---|---|---|---|---|---|---|---|---|---|---|---|---|---|---|
| Met | Lys | Thr | Tyr | Arg | Phe | Tyr | Met | Pro | Val | Ser | Leu | Met | Gly | Ile |
| 1 | | | | 5 | | | | | 10 | | | | | 15 |
| Gly | Cys | Leu | Lys | Glu | Ala | Gly | Glu | Glu | Ile | Lys | Lys | Leu | Gly | Phe | Lys |
| | | | 20 | | | | | 25 | | | | | 30 | |
| Lys | Ala | Leu | Ile | Val | Thr | Asp | Lys | Val | Leu | Val | Lys | Ile | Gly | Leu | Val |
| | | 35 | | | | | 40 | | | | | 45 | | |
| Asn | Lys | Leu | Thr | Glu | Ile | Leu | Asp | Asn | Glu | Gly | Ile | Glu | Tyr | Val | Ile |
| 50 | | | | | 55 | | | | | 60 | | | | |
| Phe | Asp | Glu | Thr | Lys | Pro | Asn | Pro | Thr | Val | Lys | Asn | Val | Glu | Asp | Gly |
| 65 | | | | | 70 | | | | | 75 | | | | | 80 |
| Leu | Lys | Met | Leu | Lys | Glu | Asn | Asn | Cys | Asp | Phe | Leu | Ile | Ser | Phe | Gly |
| | | | | 85 | | | | | 90 | | | | | 95 | |
| Gly | Gly | Ser | Pro | His | Asp | Cys | Ala | Lys | Gly | Ile | Gly | Leu | Val | Ala | Thr |
| | | | 100 | | | | | 105 | | | | | 110 | | |
| Asn | Gly | Gly | Ser | Ile | Lys | Asp | Tyr | Glu | Gly | Val | Asn | Lys | Ser | Ala | Lys |
| | | 115 | | | | | 120 | | | | | 125 | | | |
| Pro | Met | Leu | Pro | Leu | Val | Ala | Val | Asn | Thr | Thr | Ala | Gly | Thr | Ala | Ser |
| 130 | | | | | 135 | | | | | 140 | | | | | |
| Glu | Met | Thr | Arg | Phe | Ser | Ile | Ile | Thr | Asp | Glu | Asp | Arg | His | Val | Lys |
| 145 | | | | | 150 | | | | | 155 | | | | | 160 |
| Met | Ala | Ile | Val | Asp | Trp | His | Val | Thr | Pro | Ile | Met | Ala | Val | Asn | Asp |
| | | | | 165 | | | | | 170 | | | | | 175 | |
| Pro | Glu | Leu | Met | Val | Glu | Met | Pro | Lys | Ala | Leu | Thr | Ala | Ala | Thr | Gly |
| | | | 180 | | | | | 185 | | | | | 190 | | |
| Met | Asp | Ala | Leu | Thr | His | Ala | Ile | Glu | Ala | Tyr | Val | Ser | Ile | Asp | Ala |
| | | 195 | | | | | 200 | | | | | 205 | | | |
| Thr | Pro | Val | Thr | Asp | Ala | Ala | Leu | Lys | Ala | Ile | Glu | Leu | Ile | Phe |
| 210 | | | | | 215 | | | | | 220 | | | | |
| Lys | Tyr | Leu | Lys | Arg | Ala | Val | Glu | Asn | Gly | Lys | Asp | Ile | Glu | Ala | Arg |
| 225 | | | | | 230 | | | | | 235 | | | | | 240 |
| Asp | Lys | Met | Ala | Tyr | Ala | Glu | Tyr | Leu | Ala | Gly | Val | Ala | Phe | Asn | Asn |
| | | | | 245 | | | | | 250 | | | | | 255 | |
| Ala | Gly | Leu | Gly | Tyr | Val | His | Ala | Met | Ala | His | Gln | Leu | Gly | Gly | Phe |
| | | | 260 | | | | | 265 | | | | | 270 | | |
| Tyr | Asp | Leu | Pro | His | Gly | Val | Cys | Asn | Ala | Val | Leu | Leu | Pro | His | Val |
| | | 275 | | | | | 280 | | | | | 285 | | | |
| Gln | Ala | Tyr | Asn | Leu | Gln | Val | Val | Pro | Glu | Arg | Phe | Ile | Asp | Ile | Ala |
| 290 | | | | | 295 | | | | | 300 | | | | | |
| Lys | Ala | Met | Gly | Ile | Asn | Val | Glu | Asn | Leu | Thr | Ala | Lys | Glu | Ala | Gly |
| 305 | | | | | 310 | | | | | 315 | | | | | 320 |
| Glu | Lys | Val | Leu | Glu | Ala | Ile | Lys | Asn | Leu | Ser | Arg | Glu | Ile | Gly | Ile |
| | | | | 325 | | | | | 330 | | | | | 335 | |
| Pro | Ser | Gly | Leu | Lys | Glu | Leu | Gly | Val | Lys | Glu | Glu | Asp | Leu | Lys | Thr |
| | | | 340 | | | | | 345 | | | | | 350 | | |
| Leu | Ala | Glu | Asn | Ala | Leu | Lys | Asp | Ala | Cys | Gly | Phe | Thr | Asn | Pro | Lys |
| | | | 355 | | | | | 360 | | | | | 365 | | |
| Gln | Ala | Ser | Leu | Asp | Asp | Ile | Ile | Arg | Ile | Phe | Lys | Glu | Ala | Met |
| 370 | | | | | 375 | | | | | 380 | | | | |

```
<210> SEQ ID NO 28
```

```
<211> LENGTH: 385
<212> TYPE: PRT
<213> ORGANISM: Actinobacillus succinogenes 130Z

<400> SEQUENCE: 28
```

Met Ser Thr Tyr Tyr Phe Leu Pro Thr Arg Asn Val Phe Gly Glu Asn
1               5                   10                  15

Ala Val Glu Val Gly Thr Leu Met Lys Ser Leu Gly Gly Asn Asn
            20                  25                  30

Pro Leu Ile Val Thr Asp Ala Phe Leu Ala Lys Asn Gly Met Ala Asp
        35                  40                  45

Gln Leu Ala Ala Val Leu Ser Asn Ala Gly Leu Lys Pro Val Ile Phe
50                  55                  60

Gly Gly Ala Glu Pro Asn Pro Thr Asp Lys Asn Val Glu Glu Gly Ile
65                  70                  75                  80

Val Phe Tyr Asn Glu His Gly Cys Asp Ser Ile Ile Ser Leu Gly Gly
                85                  90                  95

Gly Ser Ser His Asp Cys Ala Lys Gly Ile Gly Leu Ile Ala Ser Asn
            100                 105                 110

Gly Gly Arg Ile Gln Asp Tyr Glu Gly Val Asp Arg Ser His Asn Ala
        115                 120                 125

Met Val Pro Leu Met Ala Val Asn Thr Thr Ala Gly Thr Ala Ser Glu
130                 135                 140

Ile Thr Arg Phe Cys Ile Ile Thr Asp Thr Ala Arg Lys Val Lys Met
145                 150                 155                 160

Ala Ile Val Asp Trp Arg Ile Thr Pro Gln Ile Ala Val Asn Asp Pro
                165                 170                 175

Leu Leu Met Lys Gly Met Pro Pro Ser Leu Thr Ala Ala Thr Gly Met
            180                 185                 190

Asp Ala Leu Thr His Ala Ile Glu Ala Tyr Val Ser Thr Ala Ala Asn
        195                 200                 205

Pro Leu Thr Asp Ala Ala Ala Leu Met Ala Ile Thr Met Ile Gln Gln
210                 215                 220

Tyr Leu Pro Lys Ala Val Ala Asn Gly Asp Tyr Met Lys Ala Arg Asp
225                 230                 235                 240

Lys Met Ala Tyr Ala Gln Tyr Leu Ala Gly Ile Ala Phe Asn Asn Ala
                245                 250                 255

Ser Leu Gly Tyr Val His Ala Met Ala His Gln Leu Gly Gly Phe Tyr
            260                 265                 270

Asn Leu Pro His Gly Val Cys Asn Ala Ile Leu Leu Pro Tyr Val Glu
        275                 280                 285

Glu Phe Asn Leu Ile Gly Asn Leu Asn Arg Phe Arg Asp Ile Ala Lys
290                 295                 300

Ala Met Gly Glu Asn Ile Asp Gly Leu Cys Thr Asp Ala Ala Leu
305                 310                 315                 320

Lys Ala Ile Gly Ala Ile Arg Arg Leu Ser Lys Gln Val Gly Ile Pro
                325                 330                 335

Ala Asn Leu Gln Leu Leu Gly Val Lys Pro Glu Asp Phe Asp Val Met
            340                 345                 350

Ala Glu Asn Ala Met Lys Asp Val Cys Met Leu Thr Asn Pro Arg Lys
        355                 360                 365

Ala Thr Lys Gln Gln Val Ile Glu Ile Phe Gln Arg Ala Tyr Asp Gly
370                 375                 380

Asp

<210> SEQ ID NO 29
<211> LENGTH: 390
<212> TYPE: PRT
<213> ORGANISM: Acinetobacter baumannii Naval-82

<400> SEQUENCE: 29

```
Met Ala Phe Lys Asn Ile Ala Asp Gln Thr Asn Gly Phe Tyr Ile Pro
1               5                   10                  15
Cys Val Ser Leu Phe Gly Pro Gly Cys Ala Lys Glu Ile Gly Thr Lys
                20                  25                  30
Ala Gln Asn Leu Gly Ala Lys Lys Ala Leu Ile Val Thr Asp Glu Gly
            35                  40                  45
Leu Phe Lys Phe Gly Val Ala Asp Leu Ile Ala Ser Tyr Leu Thr Glu
    50                  55                  60
Ala Gly Val Ala Ser His Ile Phe Pro Gly Ala Glu Pro Asn Pro Thr
65                  70                  75                  80
Asp Ile Asn Val His Asn Gly Val Asn Ala Tyr Asn Glu Asn Gly Cys
                85                  90                  95
Asp Phe Ile Val Ser Leu Gly Gly Gly Ser His Asp Cys Ala Lys
                100                 105                 110
Gly Ile Gly Leu Val Thr Ala Gly Gly His Ile Arg Asp Tyr Glu
            115                 120                 125
Gly Ile Asp Lys Ser Lys Val Pro Met Thr Pro Leu Ile Ala Val Asn
    130                 135                 140
Thr Thr Ala Gly Thr Ala Ser Glu Met Thr Arg Phe Cys Ile Ile Thr
145                 150                 155                 160
Asn Thr Asp Thr His Val Lys Met Ala Ile Val Asp Trp Arg Cys Thr
                165                 170                 175
Pro Leu Ile Ala Ile Asp Asp Pro Lys Leu Met Ile Ala Lys Pro Ala
            180                 185                 190
Gly Leu Thr Ala Ala Thr Gly Met Asp Ala Leu Thr His Ala Val Glu
    195                 200                 205
Ala Tyr Val Ser Thr Ala Ala Asn Pro Ile Thr Asp Ala Cys Ala Glu
210                 215                 220
Lys Ala Ile Thr Met Ile Ser Gln Trp Leu Gln Pro Ala Val Ala Asn
225                 230                 235                 240
Gly Glu Asn Ile Glu Ala Arg Asp Ala Met Ser Tyr Ala Gln Tyr Leu
                245                 250                 255
Ala Gly Met Ala Phe Asn Asn Ala Ser Leu Gly Tyr Val His Ala Met
            260                 265                 270
Ala His Gln Leu Gly Gly Phe Tyr Asn Leu Pro His Gly Val Cys Asn
    275                 280                 285
Ala Ile Leu Leu Pro His Val Cys Glu Phe Asn Leu Ile Ala Cys Pro
290                 295                 300
Asp Arg Tyr Ala Lys Ile Ala Glu Leu Met Gly Val Asn Thr His Gly
305                 310                 315                 320
Leu Thr Val Thr Glu Ala Ala Tyr Ala Ala Ile Asp Ala Ile Arg Lys
                325                 330                 335
Leu Ser Ser Leu Ile Gly Ile Pro Ser Gly Leu Thr Glu Leu Gly Val
            340                 345                 350
Lys Thr Glu Asp Leu Ala Val Met Ala Glu Asn Ala Gln Lys Asp Ala
    355                 360                 365
```

```
Cys Met Leu Thr Asn Pro Arg Lys Ala Asn His Ala Gln Val Val Glu
        370                 375                 380

Ile Phe Lys Ala Ala Leu
385                 390

<210> SEQ ID NO 30
<211> LENGTH: 385
<212> TYPE: PRT
<213> ORGANISM: Clostridium pasteurianum DSM 525

<400> SEQUENCE: 30

Met Arg Met Tyr Asp Phe Leu Ala Pro Asn Val Asn Phe Met Gly Ala
1               5                   10                  15

Gly Ala Ile Lys Leu Val Gly Glu Arg Cys Lys Ile Leu Gly Gly Lys
            20                  25                  30

Lys Ala Leu Ile Val Thr Asp Lys Phe Leu Arg Asn Met Glu Asp Gly
        35                  40                  45

Ala Val Ala Gln Thr Val Lys Tyr Ile Lys Glu Ala Gly Ile Asp Val
    50                  55                  60

Ala Phe Tyr Asp Asp Val Glu Pro Asn Pro Lys Asp Thr Asn Val Arg
65                  70                  75                  80

Asp Gly Leu Lys Val Tyr Arg Lys Glu Asn Cys Asp Leu Ile Val Thr
                85                  90                  95

Val Gly Gly Gly Ser Ser His Asp Cys Gly Lys Gly Ile Gly Ile Ala
            100                 105                 110

Ala Thr His Glu Gly Asp Leu Tyr Asp Tyr Ala Gly Ile Glu Thr Leu
        115                 120                 125

Thr Asn Pro Leu Pro Pro Ile Val Ala Val Asn Thr Thr Ala Gly Thr
    130                 135                 140

Gly Ser Glu Val Thr Arg His Cys Val Ile Thr Asn Thr Lys Thr Lys
145                 150                 155                 160

Ile Lys Phe Val Ile Val Ser Trp Arg Asn Leu Pro Leu Val Ser Ile
                165                 170                 175

Asn Asp Pro Ile Leu Met Ile Lys Lys Pro Ala Gly Leu Thr Ala Ala
            180                 185                 190

Thr Gly Met Asp Ala Leu Thr His Ala Ile Glu Ser Tyr Val Ser Lys
        195                 200                 205

Asp Ala Asn Pro Val Thr Asp Ala Leu Ala Ile Gln Ala Ile Lys Leu
    210                 215                 220

Ile Ala Asn Asn Leu Arg Gln Ala Val Ala Leu Gly Glu Asn Leu Glu
225                 230                 235                 240

Ala Arg Glu Asn Met Ala Tyr Ala Ser Leu Leu Ala Gly Met Ala Phe
                245                 250                 255

Asn Asn Ala Asn Leu Gly Tyr Val His Ala Met Ala His Gln Leu Gly
            260                 265                 270

Gly Leu Tyr Asp Met Ala His Gly Val Ala Asn Ala Met Leu Leu Pro
        275                 280                 285

His Val Glu Arg Tyr Asn Leu Ile Ser Asn Pro Lys Lys Phe Ala Asp
    290                 295                 300

Ile Ala Glu Phe Met Gly Glu Asn Ile Glu Gly Leu Ser Val Met Glu
305                 310                 315                 320

Ala Ala Glu Lys Ala Ile Asp Ala Met Phe Arg Leu Ser Lys Asp Val
                325                 330                 335

Gly Ile Pro Ala Ser Leu Lys Glu Met Gly Val Asn Glu Gly Asp Phe
            340                 345                 350
```

```
Glu Tyr Met Ala Lys Met Ala Leu Lys Asp Gly Asn Ala Phe Ser Asn
        355                 360                 365

Pro Arg Lys Gly Asn Glu Lys Asp Ile Val Lys Ile Phe Arg Glu Ala
    370                 375                 380

Phe
385

<210> SEQ ID NO 31
<211> LENGTH: 386
<212> TYPE: PRT
<213> ORGANISM: Methanosarcina mazei Tuc01

<400> SEQUENCE: 31

Met Ile Glu Lys Met Thr Tyr Thr Tyr Leu Asn Pro Lys Ile Ala Leu
1               5                   10                  15

Met Gly Pro Gly Cys Val Asn Gly Ile Gly Thr His Ala Lys Asp Leu
            20                  25                  30

Gly Gly Thr Lys Ala Leu Ile Val Ser Gly Lys Ser Arg His Gly Lys
        35                  40                  45

Glu Leu Ala Ala Asp Ile Arg Arg Ile Leu Glu Arg Ala Gly Ile Glu
    50                  55                  60

Ala Ala Ile Phe Pro Gly Ala Asp Pro Asn Pro Thr Asp Thr Ser Val
65                  70                  75                  80

Met Glu Gly Ala Asp Ile Tyr Arg Lys Glu Asn Cys Asn Met Ile Val
                85                  90                  95

Ala Val Gly Gly Gly Ser Pro Met Asp Cys Ala Lys Ala Ile Gly Ile
            100                 105                 110

Val Val Tyr Asn Gly Gly Arg Ile Asn Asp Tyr Glu Gly Val Gly Lys
        115                 120                 125

Val Thr Arg Gly Ile Pro Pro Leu Ile Thr Val Asn Thr Thr Ala Gly
    130                 135                 140

Thr Ala Ser Glu Met Thr Ser Phe Thr Ile Ile Thr Asp Thr Glu Arg
145                 150                 155                 160

His Ile Lys Met Ala Ile Val Asp Pro Arg Ile Thr Pro Asp Val Ala
                165                 170                 175

Val Asn Asp Pro Glu Leu Met Val Ser Met Pro Ala Leu Thr Ala
            180                 185                 190

Ala Thr Gly Met Asp Ala Leu Thr His Ala Val Glu Ala Tyr Val Ser
        195                 200                 205

Thr Met Ala Thr Pro Thr Thr Asp Ala Ala Ala Ile Lys Ala Ile Glu
    210                 215                 220

Leu Ile Ser Lys Tyr Leu Pro Glu Ala Val Leu His Gly Glu Asp Ile
225                 230                 235                 240

Arg Ala Arg Asp Met Met Ala His Ala Glu Tyr Leu Ala Gly Ile Ala
                245                 250                 255

Phe Asn Asn Ala Ser Leu Gly Tyr Val His Ser Met Ala His Gln Leu
            260                 265                 270

Gly Gly Phe Tyr Asp Leu Pro His Gly Val Cys Asn Ala Ile Leu Leu
        275                 280                 285

Pro Tyr Val Glu Met Tyr Asn Lys Gln Val Cys Pro Glu Arg Phe Ala
    290                 295                 300

Asp Ile Ala Lys Ala Met Gly Glu Lys Val Glu Gly Leu Ser Pro Glu
305                 310                 315                 320

Glu Ala Ala Asp Lys Ala Ile Glu Ala Ile Lys Lys Leu Ala Ala Glu
```

```
            325                 330                 335
Ile Gly Ile Pro Ser Gly Leu Lys Glu Leu Gly Ala Arg Glu Glu Asp
            340                 345                 350

Leu Glu Leu Leu Ala Glu Asn Ala Met Gln Asp Val Cys Arg Leu Thr
            355                 360                 365

Asn Pro Arg Glu Leu Ser Lys Glu Asp Ile Ile Glu Ile Tyr Arg Lys
370                 375                 380

Ala Leu
385

<210> SEQ ID NO 32
<211> LENGTH: 393
<212> TYPE: PRT
<213> ORGANISM: Desulfovibrio vulgaris str. 'Miyazaki F'

<400> SEQUENCE: 32

Met Ala Val Gln Glu Gln Val Tyr Gly Phe Phe Ile Pro Ser Val Thr
1               5                   10                  15

Leu Ile Gly Ile Gly Ala Ser Lys Ala Ile Pro Glu Lys Ile Lys Ala
            20                  25                  30

Leu Gly Gly Ser Lys Pro Leu Ile Val Thr Asp Met Gly Ile Val Lys
        35                  40                  45

Ala Gly Ile Leu Lys Gln Ile Thr Asp Leu Leu Asp Ala Ala Lys Met
    50                  55                  60

Ala Tyr Ser Val Tyr Asp Glu Thr Ile Pro Asn Pro Thr Asp Asp Asn
65                  70                  75                  80

Val His Lys Gly Val Glu Val Tyr Lys Lys Asn Lys Cys Asp Ser Leu
                85                  90                  95

Ile Thr Leu Gly Gly Gly Ser Ser His Asp Cys Gly Lys Gly Ile Gly
            100                 105                 110

Leu Val Ile Ala Asn Gly Gly Lys Ile His Asp Phe Glu Gly Val Asp
        115                 120                 125

Lys Ser Phe Lys Pro Met Pro Pro Tyr Val Ala Val Asn Thr Thr Ala
    130                 135                 140

Gly Thr Ala Ser Glu Met Thr Arg Phe Cys Ile Ile Thr Asp Thr Ser
145                 150                 155                 160

Arg Lys Val Lys Met Ala Ile Val Asp Trp Arg Val Thr Pro Ser Ile
                165                 170                 175

Ala Leu Asp Asp Pro Leu Leu Met Met Gly Met Pro Pro Ala Leu Thr
            180                 185                 190

Ala Ala Thr Gly Met Asp Ala Leu Thr His Ala Val Glu Ala Tyr Val
        195                 200                 205

Ser Thr Ile Ala Thr Pro Met Thr Asp Ala Cys Ala Glu Gln Ala Ile
    210                 215                 220

Thr Leu Ile Ala Thr Phe Leu Arg Arg Ala Val Ala Asn Gly Arg Asp
225                 230                 235                 240

Ile Glu Ala Arg Glu Arg Met Cys Phe Ala Gln Tyr Leu Ala Gly Met
                245                 250                 255

Ala Phe Asn Asn Ala Ser Leu Gly His Val His Ala Met Ala His Gln
            260                 265                 270

Leu Gly Gly Phe Tyr Asp Leu Pro His Gly Glu Cys Asn Ala Ile Leu
        275                 280                 285

Leu Pro His Val Ser Gln Phe Asn Leu Ile Ala Lys Leu Asp Arg Phe
    290                 295                 300
```

```
Ala Arg Ile Ala Glu Leu Met Gly Glu Asn Ile Ser Gly Leu Ser Val
305                 310                 315                 320

Arg Asp Ala Ala Glu Lys Ala Ile Cys Ala Ile Lys Arg Leu Ser Ala
                325                 330                 335

Asp Val Gly Ile Pro Ala Gly Leu Val Ala Leu Gly Lys Arg Tyr Gly
                340                 345                 350

Lys Asp Val Lys Ala Lys Asp Ile Ala Ile Met Thr Lys Asn Ala Gln
                355                 360                 365

Lys Asp Ala Cys Gly Leu Thr Asn Pro Arg Cys Pro Thr Asp Ala Asp
                370                 375                 380

Val Ala Ala Ile Tyr Glu Ala Ala Met
385                 390
```

<210> SEQ ID NO 33
<211> LENGTH: 393
<212> TYPE: PRT
<213> ORGANISM: Desulfovibrio africanus str. Walvis Bay

<400> SEQUENCE: 33

```
Met Ala Val Arg Glu Gln Val Tyr Gly Phe Phe Ile Pro Ser Val Thr
1               5                   10                  15

Leu Ile Gly Ile Gly Ala Ser Lys Glu Ile Pro Asn Lys Ile Arg Asp
                20                  25                  30

Leu Gly Gly Lys Pro Leu Ile Val Thr Asp Gln Gly Ile Val Lys
                35                  40                  45

Ala Gly Ile Leu Lys Met Ile Thr Asp His Met Asp Lys Ala Gly Met
            50                  55                  60

Gln Tyr Ser Val Tyr Asp Lys Thr Ile Pro Asn Pro Thr Asp Asn Asn
65              70                  75                  80

Val Ala Glu Gly Val Glu Val Tyr Lys Lys Glu Gly Cys Asp Ser Leu
                85                  90                  95

Ile Thr Leu Gly Gly Gly Ser Ser His Asp Cys Gly Lys Gly Val Gly
                100                 105                 110

Leu Val Val Ser Asn Gly Gly Lys Ile His Asp Tyr Glu Gly Val Asp
            115                 120                 125

Lys Ser Thr Lys Pro Leu Pro Pro Tyr Val Ala Val Asn Thr Thr Ala
130                 135                 140

Gly Thr Ala Ser Glu Met Thr Arg Phe Cys Ile Ile Thr Asp Thr Ser
145                 150                 155                 160

Arg Lys Val Lys Met Ala Ile Val Asp Trp Arg Val Thr Pro Gly Ile
                165                 170                 175

Ala Leu Asp Asp Pro Leu Leu Met Val Gly Met Pro Pro Ala Leu Thr
                180                 185                 190

Ala Ala Thr Gly Met Asp Ala Leu Thr His Ala Val Glu Ala Tyr Val
            195                 200                 205

Ser Thr Ile Ala Thr Pro Met Thr Asp Ala Cys Ala Glu Lys Ala Ile
        210                 215                 220

Ser Leu Ile Phe Thr Phe Leu Arg Arg Ala Thr Ala Asn Gly Gln Asp
225                 230                 235                 240

Ile Glu Ala Arg Glu Gly Met Cys Phe Ala Gln Tyr Leu Ala Gly Met
                245                 250                 255

Ala Phe Asn Asn Ala Ser Leu Gly His Val His Ala Met Ala His Gln
                260                 265                 270

Leu Gly Gly Phe Tyr Asp Leu Pro His Gly Glu Cys Asn Ala Ile Leu
                275                 280                 285
```

```
Leu Pro His Val Glu Lys Tyr Asn Leu Ile Ala Lys Val Glu Arg Phe
            290                 295                 300

Gly Lys Met Ala Glu Ile Met Gly Glu Asn Ile Gln Gly Met Ser Pro
305                 310                 315                 320

Arg Ala Ala Glu Lys Cys Leu Asp Ala Ile Arg Gln Leu Ser Gln
                325                 330                 335

Asp Val Gly Ile Pro Ser Gly Leu Ile Glu Leu Gly Lys Arg Tyr Gly
                340                 345                 350

Lys Asn Val Lys Lys Glu Asp Ile Asp Thr Met Thr Gly Asn Ala Gln
                355                 360                 365

Lys Asp Ala Cys Gly Phe Thr Asn Pro Arg Cys Pro Ser Asp Lys Asp
370                 375                 380

Val Lys Ala Ile Tyr Glu Ala Ala Leu
385                 390
```

<210> SEQ ID NO 34
<211> LENGTH: 385
<212> TYPE: PRT
<213> ORGANISM: Clostridium perfringens str. 13

<400> SEQUENCE: 34

```
Met Arg Met Tyr Asp Tyr Leu Val Pro Ser Val Asn Phe Met Gly Ala
1               5                   10                  15

Asn Ser Ile Ser Val Val Gly Glu Arg Cys Lys Ile Leu Gly Gly Lys
                20                  25                  30

Lys Ala Leu Ile Val Thr Asp Lys Phe Leu Arg Gly Leu Lys Gly Gly
            35                  40                  45

Ala Val Glu Leu Thr Glu Lys Tyr Leu Lys Glu Ala Gly Ile Glu Val
        50                  55                  60

Ala Tyr Tyr Asp Gly Val Glu Pro Asn Pro Lys Asp Thr Asn Val Lys
65                  70                  75                  80

Asp Gly Leu Lys Ile Phe Gln Asp Glu Asn Cys Asp Met Ile Val Thr
                85                  90                  95

Val Gly Gly Gly Ser Ser His Asp Cys Gly Lys Gly Ile Gly Ile Ala
                100                 105                 110

Ala Thr His Glu Gly Asp Leu Tyr Asp Tyr Ala Gly Ile Glu Thr Leu
            115                 120                 125

Thr Asn Pro Leu Pro Pro Ile Val Ala Val Asn Thr Thr Ala Gly Thr
        130                 135                 140

Ala Ser Glu Val Thr Arg His Cys Val Ile Thr Asn Thr Lys Thr Lys
145                 150                 155                 160

Val Lys Phe Val Ile Val Ser Trp Arg Asn Leu Pro Leu Val Ser Ile
                165                 170                 175

Asn Asp Pro Met Leu Met Val Gly Lys Pro Ala Gly Leu Thr Ala Ala
                180                 185                 190

Thr Gly Met Asp Ala Leu Thr His Ala Val Glu Ala Tyr Val Ser Lys
            195                 200                 205

Asp Ala Asn Pro Val Thr Asp Ala Ala Ala Ile Gln Ala Ile Lys Leu
        210                 215                 220

Ile Ser Ser Asn Leu Arg Gln Ala Val Ala Leu Gly Glu Asn Leu Val
225                 230                 235                 240

Ala Arg Glu Asn Met Ala Tyr Gly Ser Leu Leu Ala Gly Met Ala Phe
                245                 250                 255

Asn Asn Ala Asn Leu Gly Tyr Val His Ala Met Ala His Gln Leu Gly
```

```
            260                 265                 270
Gly Leu Tyr Asp Met Pro His Gly Val Ala Asn Ala Met Leu Leu Pro
            275                 280                 285

His Val Cys Lys Tyr Asn Leu Ile Ser Asn Pro Gln Lys Phe Ala Asp
            290                 295                 300

Ile Ala Glu Phe Met Gly Glu Asn Ile Glu Gly Leu Ser Val Met Asp
305                 310                 315                 320

Ala Ala Gln Lys Ala Ile Asp Ala Met Phe Arg Leu Ser Thr Asp Ile
            325                 330                 335

Gly Ile Pro Ala Lys Leu Arg Asp Met Gly Val Lys Glu Glu Asp Phe
            340                 345                 350

Gly Tyr Met Ala Glu Met Ala Leu Lys Asp Gly Asn Ala Phe Ser Asn
            355                 360                 365

Pro Arg Lys Gly Asn Glu Arg Asp Ile Val Glu Ile Phe Lys Ala Ala
            370                 375                 380

Phe
385

<210> SEQ ID NO 35
<211> LENGTH: 382
<212> TYPE: PRT
<213> ORGANISM: Vibrio campbellii ATCC BAA-1116

<400> SEQUENCE: 35

Met Thr Ser Ala Phe Phe Ile Pro Thr Val Asn Leu Met Gly Ala Gly
1               5                   10                  15

Cys Leu Lys Asp Ala Thr Asp Ser Ile Gln Ser Gln Gly Phe Lys Lys
            20                  25                  30

Gly Leu Ile Val Thr Asp Lys Ile Leu Asn Gln Ile Gly Val Val Lys
            35                  40                  45

Gln Val Gln Asp Leu Leu Ala Glu Arg Asp Val Glu Thr Val Val Phe
        50                  55                  60

Asp Gly Thr Gln Pro Asn Pro Thr Ile Ser Asn Val Asn Asp Gly Leu
65                  70                  75                  80

Ala Leu Leu Thr Asp Asn Glu Cys Asp Phe Val Ile Ser Leu Gly Gly
            85                  90                  95

Gly Ser Pro His Asp Cys Ala Lys Gly Ile Ala Leu Val Ala Ser Asn
            100                 105                 110

Gly Gly Lys Ile Ala Asp Tyr Glu Gly Val Asp Gln Ser Ala Lys Pro
            115                 120                 125

Met Met Pro Leu Ile Ala Ile Asn Thr Thr Ala Gly Thr Ala Ser Glu
130                 135                 140

Met Thr Arg Phe Cys Ile Ile Thr Asp Glu Glu Arg His Ile Lys Met
145                 150                 155                 160

Ala Ile Val Asp Lys His Thr Thr Pro Leu Ile Ser Val Asn Asp Pro
            165                 170                 175

Glu Leu Met Leu Ala Lys Pro Ala Ser Leu Thr Ala Ala Thr Gly Met
            180                 185                 190

Asp Ala Leu Thr His Ala Ile Glu Ala Tyr Val Ser Ile Ala Ala Thr
            195                 200                 205

Pro Ile Thr Asp Ala Val Ala Ile Lys Ala Ile Glu Leu Ile Gln Ala
            210                 215                 220

Tyr Leu Arg Thr Ala Val Lys Asn Gly Glu Asp Leu Glu Ala Arg Glu
225                 230                 235                 240
```

```
Gln Met Ala Tyr Ala Gln Phe Met Ala Gly Met Ala Phe Asn Asn Ala
                245                 250                 255

Ser Leu Gly Tyr Val His Ala Met Ala His Gln Leu Gly Gly Phe Tyr
            260                 265                 270

Asp Leu Pro His Gly Val Cys Asn Ala Ile Leu Pro His Val Gln
        275                 280                 285

Arg Tyr Asn Ala Gln Val Cys Pro Glu Arg Leu Arg Asp Val Ala Lys
        290                 295                 300

Ala Met Gly Val Asn Val Glu Asp Met Ser Ala Glu Ala Gly Ala Ala
305                 310                 315                 320

Ala Ala Ile Asp Ala Ile Val Thr Leu Ala Lys Asp Val Gly Ile Pro
                325                 330                 335

Ala Gly Ile Lys Glu Leu Gly Ala Lys Leu Glu Asp Ile Pro Thr Leu
            340                 345                 350

Ala Asp Asn Ala Leu Lys Asp Ala Cys Gly Phe Thr Asn Pro Lys Gln
        355                 360                 365

Ala Thr His Glu Glu Ile Ser Lys Ile Phe Glu Glu Ala Met
        370                 375                 380

<210> SEQ ID NO 36
<211> LENGTH: 388
<212> TYPE: PRT
<213> ORGANISM: Desulfotomaculum reducens MI-1

<400> SEQUENCE: 36

Met Thr Val Gly Glu Gln Val Phe Gly Tyr Phe Ile Pro Thr Val Asn
1               5                   10                  15

Leu Met Gly Val Gly Ala His Lys Glu Ile Pro Asp Gln Val Lys Val
            20                  25                  30

Leu Gly Gly Ser Asn Val Leu Ile Val Thr Asp Ala Phe Leu Gly Arg
        35                  40                  45

Pro Gly Met Ala Asp Asp Ile Lys Gly Met Leu Glu Ala Glu Asn
    50                  55                  60

Ile Lys Val Thr Ile Tyr Ala Gly Ala Glu Pro Asn Pro Thr Asp Val
65                  70                  75                  80

Asn Val His Asp Gly Leu Lys Val Tyr Gln Glu Cys Gly Ala Asp Met
                85                  90                  95

Ile Leu Ser Leu Gly Gly Gly Ser Ser His Asp Cys Ala Lys Gly Ile
            100                 105                 110

Gly Ile Val Ala Thr Asn Gly Gly Asn Ile Arg Asp Tyr Glu Gly Ile
        115                 120                 125

Asn Lys Ser Ser Lys Ala Met Pro Pro Phe Ile Ala Val Asn Thr Thr
    130                 135                 140

Ala Gly Thr Ala Ser Glu Met Thr Arg Phe Cys Ile Ile Thr Asn Thr
145                 150                 155                 160

Ser Asn His Val Lys Met Ala Ile Val Asp Trp Arg Cys Thr Pro Asn
                165                 170                 175

Ile Ala Ile Asn Asp Pro Leu Leu Met Ala Gly Met Pro Ala Leu
            180                 185                 190

Thr Ala Ala Thr Gly Met Asp Ala Leu Thr His Ala Ile Glu Ala Tyr
        195                 200                 205

Val Ser Val Ala Ala Thr Pro Val Thr Asp Ser Ala Ala Leu Met Ala
    210                 215                 220

Ile Lys Leu Ile Ser Gln Tyr Leu Arg Ala Ala Val Ala Asn Gly Glu
225                 230                 235                 240
```

```
Asn Met Glu Ala Arg Asp Lys Met Ala Tyr Ala Glu Phe Leu Gly Gly
                245                 250                 255

Met Ala Phe Asn Asn Ala Ser Leu Gly Tyr Val His Ala Met Ala His
            260                 265                 270

Gln Leu Gly Gly Phe Tyr Asn Leu Pro His Gly Val Cys Asn Ala Ile
        275                 280                 285

Leu Leu Pro His Val Glu Ala Phe Asn Leu Ile Ala Cys Pro Glu Arg
    290                 295                 300

Phe Val Asp Ile Ala Val Ala Met Gly Glu Asn Val Glu Gly Leu Ser
305                 310                 315                 320

Val Arg Asp Ala Ala Asp Lys Ala Leu Ser Ala Ile Arg Lys Leu Ser
                325                 330                 335

Ala Asp Val Gly Ile Pro Ala Gly Leu Thr Glu Leu Gly Val Lys Glu
            340                 345                 350

Glu Asp Leu Lys Thr Met Ala Glu Asn Ala Met Lys Asp Ala Cys Ala
        355                 360                 365

Leu Thr Asn Pro Arg Lys Ala Thr Leu Asn Asp Ile Val Gly Ile Tyr
    370                 375                 380

Lys Thr Ala Leu
385

<210> SEQ ID NO 37
<211> LENGTH: 393
<212> TYPE: PRT
<213> ORGANISM: Desulfovibrio vulgaris str. Hildenborough

<400> SEQUENCE: 37

Met Ala Val Gln Glu Gln Val Tyr Gly Phe Phe Ile Pro Arg Val Thr
1               5                   10                  15

Leu Ile Gly Ile Gly Ala Ser Lys Ala Ile Pro Glu Lys Ile Lys Ala
            20                  25                  30

Leu Gly Gly Ser Lys Pro Leu Ile Val Thr Asp Met Gly Ile Val Lys
        35                  40                  45

Ala Gly Ile Leu Lys Gln Ile Thr Asp Leu Leu Asp Ala Ala Lys Met
    50                  55                  60

Ala Tyr Ser Val Tyr Asp Glu Thr Ile Pro Asn Pro Thr Asp Asp Asn
65                  70                  75                  80

Val His Lys Gly Val Asp Val Tyr Lys Lys Asn Lys Cys Asp Ser Leu
                85                  90                  95

Ile Thr Leu Gly Gly Gly Ser Ser His Asp Cys Gly Lys Gly Ile Gly
            100                 105                 110

Leu Val Val Ala Asn Gly Gly Lys Ile His Asp Phe Glu Gly Val Asp
        115                 120                 125

Lys Ser Thr Gln Arg Met Pro Pro Tyr Leu Ala Val Asn Thr Thr Ala
    130                 135                 140

Gly Thr Ala Ser Glu Met Thr Arg Phe Cys Ile Ile Thr Asp Thr Ser
145                 150                 155                 160

Arg Lys Val Lys Met Ala Ile Val Asp Trp Arg Val Thr Pro Asn Ile
                165                 170                 175

Ala Leu Asp Asp Pro Leu Leu Met Leu Gly Met Pro Ala Leu Thr
            180                 185                 190

Ala Ala Thr Gly Met Asp Ala Leu Thr His Ala Val Glu Ala Tyr Val
        195                 200                 205

Ser Thr Ile Ala Thr Pro Met Thr Asp Ala Cys Ala Glu Gln Ala Ile
```

```
                    210                 215                 220
Thr Leu Ile Ala Thr Phe Leu Arg Arg Ala Val Ala Asn Gly Gln Asp
225                 230                 235                 240

Leu Glu Ala Arg Glu Arg Met Cys Phe Ala Gln Tyr Leu Ala Gly Met
                245                 250                 255

Ala Phe Asn Asn Ala Ser Leu Gly His Val His Ala Met Ala His Gln
            260                 265                 270

Leu Gly Gly Phe Tyr Asp Leu Pro His Gly Glu Cys Asn Ala Ile Leu
        275                 280                 285

Leu Pro His Val Ser Lys Phe Asn Leu Ile Ala Lys Leu Asp Arg Tyr
    290                 295                 300

Ala Arg Ile Ala Gln Leu Met Gly Glu Asn Ile Ala Gly Leu Ser Thr
305                 310                 315                 320

Arg Glu Ala Ala Glu Arg Ala Ile Ser Ala Ile Lys Cys Leu Ser Thr
                325                 330                 335

Asp Val Gly Ile Pro Ala Gly Leu Val Ala Leu Gly Lys Arg Tyr Gly
            340                 345                 350

Lys Asp Val Lys Ala Ala Asp Ile Ala Ile Met Thr Lys Asn Ala Gln
        355                 360                 365

Lys Asp Ala Cys Gly Leu Thr Asn Pro Arg Cys Pro Thr Asp Ala Asp
    370                 375                 380

Val Ala Ala Ile Tyr Glu Ala Ala Leu
385                 390

<210> SEQ ID NO 38
<211> LENGTH: 382
<212> TYPE: PRT
<213> ORGANISM: Photobacterium profundum 3TCK

<400> SEQUENCE: 38

Met Ser Ser Ala Phe Phe Ile Pro Ser Val Asn Leu Met Gly Ala Gly
1               5                   10                  15

Cys Leu Thr Glu Ala Ala Asp Ala Val Lys Ala His Gly Phe Lys Lys
                20                  25                  30

Ala Leu Ile Val Thr Asp Lys Val Leu Asn Gln Ile Gly Val Val Lys
            35                  40                  45

Gln Val Val Asp Leu Leu Ala Glu Arg Asn Val Glu Ala Val Val Phe
        50                  55                  60

Asp Gly Thr Gln Pro Asn Pro Thr Met Gly Asn Val Glu Ala Gly Leu
65                  70                  75                  80

Ala Leu Leu Lys Ala Asn Glu Cys Asp Phe Val Ile Ser Leu Gly Gly
                85                  90                  95

Gly Ser Pro His Asp Cys Ala Lys Gly Ile Ala Leu Val Ala Ser Asn
            100                 105                 110

Gly Gly Ser Ile Ser Asp Tyr Glu Gly Val Asp Val Ser Ala Lys Pro
        115                 120                 125

Gln Leu Pro Leu Val Ala Ile Asn Thr Thr Ala Gly Thr Ala Ser Glu
    130                 135                 140

Met Thr Arg Phe Cys Ile Ile Thr Asp Glu Ala Arg His Ile Lys Met
145                 150                 155                 160

Ala Ile Val Asp Lys Asn Thr Thr Pro Leu Met Ser Val Asn Asp Pro
                165                 170                 175

Glu Leu Met Leu Ala Lys Pro Ala Ser Leu Thr Ala Ala Thr Gly Met
            180                 185                 190
```

Asp Ala Leu Thr His Ala Ile Glu Ala Tyr Val Ser Thr Ala Ala Thr
            195                 200                 205

Pro Ile Thr Asp Ala Val Ala Ile Lys Ala Met Glu Leu Ile Gln Ala
210                 215                 220

His Leu Arg Thr Ala Val Asn Asp Gly Gln Asn Leu Glu Ala Arg Glu
225                 230                 235                 240

Gln Met Ala Tyr Ala Gln Phe Met Ala Gly Met Ala Phe Asn Asn Ala
                245                 250                 255

Ser Leu Gly Tyr Val His Ala Met Ala His Gln Leu Gly Gly Phe Tyr
            260                 265                 270

Asp Leu Pro His Gly Val Cys Asn Ala Val Leu Leu Pro His Val Gln
        275                 280                 285

Arg Tyr Asn Ala Lys Val Cys Pro Glu Arg Leu Arg Asp Val Ala Lys
290                 295                 300

Ala Met Gly Val Asn Val Glu Ala Met Thr Ala Asp Gln Gly Ala Asp
305                 310                 315                 320

Ala Ala Leu Glu Ala Ile Gln Val Leu Ser Lys Asp Val Gly Ile Pro
                325                 330                 335

Ala Gly Leu Lys Asp Leu Gly Ala Lys Asn Glu Asp Ile Ser Ile Leu
            340                 345                 350

Ala Asp Asn Ala Leu Lys Asp Ala Cys Gly Phe Thr Asn Pro Lys Gln
        355                 360                 365

Ala Thr His Glu Glu Ile Ser Glu Ile Phe Ala Ala Met
    370                 375                 380

<210> SEQ ID NO 39
<211> LENGTH: 384
<212> TYPE: PRT
<213> ORGANISM: Geobacillus sp. Y4.1MC1

<400> SEQUENCE: 39

Met Ser Asn Ala His Val Phe Tyr Val Pro Ser Thr Asn Leu Met Gly
1               5                   10                  15

Arg Gly Cys Leu Ala Lys Val Gly Pro Phe Ile Lys Glu Phe Gly Phe
            20                  25                  30

Lys Lys Ala Leu Val Val Thr Asp Lys Phe Leu His Lys Ser Gly Ile
        35                  40                  45

Ala Gly Lys Val Leu Ala Val Leu Asp Glu Ile Gly Val Asn Tyr Val
    50                  55                  60

Val Tyr Asp Asp Val Lys Pro Asn Pro Thr Thr Lys Asn Val Tyr Ala
65                  70                  75                  80

Gly Ala Asp Leu Phe Lys Lys Asn Glu Cys Asp Phe Leu Val Ser Val
                85                  90                  95

Gly Gly Gly Ser Pro Gln Asp Thr Ala Lys Ala Ile Gly Leu Tyr Val
            100                 105                 110

Thr Asn Gly Gly Asp Ile Arg Asp Tyr Glu Gly Val Asn Lys Thr Lys
        115                 120                 125

Asn Lys Ser Val Pro Ile Val Ala Val Asn Thr Thr Ala Gly Thr Ser
    130                 135                 140

Ser Glu Phe Thr Ile Asn Tyr Val Ile Thr Asp Glu Glu Arg Asn Val
145                 150                 155                 160

Lys Met Val Met Val Asp Lys Asn Ser Leu Val Thr Ile Ser Val Asn
                165                 170                 175

Asp Pro Glu Leu Met Val Asp Lys Pro Ala Ala Leu Thr Ala Ala Thr
            180                 185                 190

Gly Met Asp Ala Leu Thr His Ala Ile Glu Ala Val Val Thr Pro Gly
            195                 200                 205

Ser Tyr Thr Val Thr Asp Ala Thr Leu Ala Ala Ile Glu Ile Ile
    210                 215                 220

Phe Asn Tyr Leu Pro Arg Ala Val Lys Asn Gly His Asp Ile Glu Ala
225                 230                 235                 240

Arg Glu Gln Met Ala Tyr Ala Met Phe Leu Val Gly Ile Ala Phe Asn
                245                 250                 255

Asn Ala Gly Leu Gly Met Val His Ala Met His Gln Leu Gly Gly
            260                 265                 270

Met Tyr Asp Leu Pro His Gly Val Cys Asn Ala Met Leu Leu Pro Ile
            275                 280                 285

Val Glu Arg Glu Asn Ala Lys Arg Asp Pro Arg Lys Phe Arg Ala Ile
290                 295                 300

Ala Lys Ala Ala Gly Ile Asp Val Thr Gly Lys Thr Asp Glu Gln Cys
305                 310                 315                 320

Ala Glu Glu Val Ile Glu Ala Ile Lys Ala Leu Ser Arg Glu Ile Gly
                325                 330                 335

Ile Pro Ser Lys Leu Ser Glu Leu Gly Val Asp Glu Val Asp Leu Glu
            340                 345                 350

Lys Leu Ala Asn Asn Ala Leu Lys Asp Ala Cys Ala Pro Gly Asn Pro
            355                 360                 365

Phe Gln Pro Thr Lys Glu Glu Val Ile Ser Met Phe Lys Glu Ile Leu
            370                 375                 380

<210> SEQ ID NO 40
<211> LENGTH: 393
<212> TYPE: PRT
<213> ORGANISM: Desulfovibrio fructosovorans JJ

<400> SEQUENCE: 40

Met Ala Val Arg Glu Gln Val Tyr Gly Phe Phe Ile Pro Ser Val Thr
1               5                   10                  15

Leu Ile Gly Ile Gly Ala Ala Lys Gln Ile Pro Glu Lys Ile Lys Ala
            20                  25                  30

Leu Gly Gly Thr Lys Pro Leu Ile Val Thr Asp Lys Gly Val Val Lys
        35                  40                  45

Val Gly Val Cys Lys Met Ile Thr Asp Leu Leu Asp Ala Ala Gly Met
    50                  55                  60

Lys Tyr His Ile Tyr Asp Glu Thr Ile Pro Asn Pro Thr Asp Glu Asn
65                  70                  75                  80

Val His Lys Gly Val Glu Val Tyr Lys Lys Glu Gly Cys Asp Ser Leu
                85                  90                  95

Ile Thr Leu Gly Gly Gly Ser Ser His Asp Cys Gly Lys Gly Ile Gly
            100                 105                 110

Leu Val Ile Ser Asn Gly Gly Lys Ile His Asp Tyr Glu Gly Val Asp
        115                 120                 125

Lys Ser Ser Lys Pro Phe Met Pro Tyr Leu Ala Val Asn Thr Thr Ala
    130                 135                 140

Gly Thr Ala Ser Glu Met Thr Arg Phe Cys Ile Ile Thr Asp Leu Ser
145                 150                 155                 160

Arg His Val Lys Met Ala Ile Val Asp Trp Arg Val Thr Pro His Ile
                165                 170                 175

Ala Ile Asp Asp Pro Val Leu Met Val Gly Met Pro Pro Ala Leu Thr

```
                180             185                  190
Ala Ser Thr Gly Met Asp Ala Leu Thr His Ala Val Glu Ala Phe Val
            195                 200                 205
Ser Thr Ile Ala Asn Pro Met Thr Asp Ala Cys Ala Ile Glu Ala Ile
            210                 215                 220
Lys Leu Ile Phe Lys Tyr Leu Arg Lys Ala Val Ala Asn Gly Gln Asp
225                 230                 235                 240
Met Glu Ala Arg Glu Gly Met Cys Phe Ala Glu Tyr Leu Ala Gly Met
            245                 250                 255
Ala Phe Asn Asn Ala Ser Leu Gly His Val His Ala Met Ala His Gln
            260                 265                 270
Leu Gly Gly Phe Tyr Asp Leu Pro His Gly Glu Cys Asn Ala Ile Leu
            275                 280                 285
Leu Pro His Val Glu Ser Tyr Asn Leu Ile Ala Lys Val Glu Lys Phe
            290                 295                 300
Ala Glu Met Ala Lys Ile Met Gly Glu Asn Ile Glu Gly Met Ala Pro
305                 310                 315                 320
Arg Asp Ala Ala Glu Leu Cys Leu Lys Ala Ile Arg Gln Leu Ser Val
            325                 330                 335
Asp Val Gly Ile Pro Ala Gly Leu Val Glu Leu Gly Lys Arg Tyr Gly
            340                 345                 350
Lys Asp Val Lys Ala Ala Asp Ile Pro Thr Met Thr Gly Asn Ala Gln
            355                 360                 365
Lys Asp Ala Cys Gly Leu Thr Asn Pro Arg Cys Pro Thr Asp Lys Asp
            370                 375                 380
Val Ala Ala Ile Tyr Thr Ala Ala Leu
385                 390

<210> SEQ ID NO 41
<211> LENGTH: 382
<212> TYPE: PRT
<213> ORGANISM: Shewanella oneidensis MR-1

<400> SEQUENCE: 41

Met Ala Ala Lys Phe Phe Ile Pro Ser Val Asn Val Leu Gly Lys Gly
1               5                   10                  15
Ala Val Asp Asp Ala Ile Gly Asp Ile Lys Thr Leu Gly Phe Lys Arg
            20                  25                  30
Ala Leu Ile Val Thr Asp Lys Pro Leu Val Asn Ile Gly Leu Val Gly
            35                  40                  45
Glu Val Ala Glu Lys Leu Gly Gln Asn Gly Ile Thr Ser Thr Val Phe
            50                  55                  60
Asp Gly Val Gln Pro Asn Pro Thr Val Gly Asn Val Glu Ala Gly Leu
65                  70                  75                  80
Ala Leu Leu Lys Ala Asn Gln Cys Asp Phe Val Ile Ser Leu Gly Gly
            85                  90                  95
Gly Ser Pro His Asp Cys Ala Lys Gly Ile Ala Leu Val Ala Thr Asn
            100                 105                 110
Gly Gly Ser Ile Lys Asp Tyr Glu Gly Leu Asp Lys Ser Thr Lys Pro
            115                 120                 125
Gln Leu Pro Leu Val Ala Ile Asn Thr Thr Ala Gly Thr Ala Ser Glu
            130                 135                 140
Met Thr Arg Phe Cys Ile Ile Thr Asp Glu Ala Arg His Ile Lys Met
145                 150                 155                 160
```

```
Ala Ile Val Asp Lys His Thr Thr Pro Ile Leu Ser Val Asn Asp Pro
            165                 170                 175

Glu Leu Met Leu Lys Lys Pro Ala Ser Leu Thr Ala Ala Thr Gly Met
        180                 185                 190

Asp Ala Leu Thr His Ala Val Glu Ala Tyr Val Ser Ile Ala Ala Asn
        195                 200                 205

Pro Ile Thr Asp Ala Cys Ala Ile Lys Ala Ile Glu Leu Ile Gln Gly
        210                 215                 220

Asn Leu Val Asn Ala Val Lys Gln Gly Gln Asp Ile Glu Ala Arg Glu
225                 230                 235                 240

Gln Met Ala Tyr Ala Gln Phe Leu Ala Gly Met Ala Phe Asn Asn Ala
                245                 250                 255

Ser Leu Gly Tyr Val His Ala Met Ala His Gln Leu Gly Gly Phe Tyr
                260                 265                 270

Asp Leu Pro His Gly Val Cys Asn Ala Leu Leu Leu Pro His Val Gln
            275                 280                 285

Glu Tyr Asn Ala Lys Val Val Pro His Arg Leu Lys Asp Ile Ala Lys
        290                 295                 300

Ala Met Gly Val Asp Val Ala Lys Met Thr Asp Glu Gln Gly Ala Ala
305                 310                 315                 320

Ala Ala Ile Thr Ala Ile Lys Thr Leu Ser Val Ala Val Asn Ile Pro
                325                 330                 335

Glu Asn Leu Thr Leu Leu Gly Val Lys Ala Glu Asp Ile Pro Thr Leu
                340                 345                 350

Ala Asp Asn Ala Leu Lys Asp Ala Cys Gly Phe Thr Asn Pro Lys Gln
            355                 360                 365

Ala Thr His Ala Glu Ile Cys Gln Ile Phe Thr Asn Ala Leu
        370                 375                 380

<210> SEQ ID NO 42
<211> LENGTH: 384
<212> TYPE: PRT
<213> ORGANISM: Sebaldella termitidis ATCC 33386

<400> SEQUENCE: 42

Met Lys Val Ser Arg Arg Ile Tyr Trp Pro Ala Val Thr Leu Ile Gly
1               5                   10                  15

Pro Gly Cys Val Lys Glu Ile Gly Gly Asp Ile Lys Asp Leu Gly Leu
                20                  25                  30

Lys Lys Ala Leu Val Val Thr Asp Asn Val Leu Val Lys Ile Gly Val
            35                  40                  45

Val Lys Lys Val Thr Asp Val Leu Asp Glu Ser Gly Ile Asn Tyr Val
50                  55                  60

Val Val Asp Asp Ile Gln Pro Asn Pro Thr Met Lys Asn Ile His Asp
65                  70                  75                  80

Gly Leu Asn Thr Tyr Lys Ser Glu Asn Cys Asp Phe Val Ile Ser Ile
                85                  90                  95

Gly Gly Gly Ser Pro Gln Asp Ala Gly Lys Ala Ile Gly Leu Leu Ala
                100                 105                 110

Thr Asn Gly Gly Glu Ile Lys Asp Tyr Glu Gly Ile Asn Met Ser Lys
            115                 120                 125

His Lys Ser Val Pro Ile Ile Ala Ile Asn Thr Thr Ala Gly Thr Ala
        130                 135                 140

Ser Glu Val Thr Ile Asn Tyr Val Ile Thr Asn Glu Asp Thr His Ile
145                 150                 155                 160
```

```
Lys Met Val Met Val Asp Lys Asn Cys Leu Ala Ser Ile Ala Val Ser
                165                 170                 175

Asp Pro Glu Leu Met Thr Gly Lys Pro Ala Asp Leu Thr Ala Ala Thr
            180                 185                 190

Gly Met Asp Ala Leu Thr His Ala Ile Glu Ala Tyr Val Ser Thr Gly
        195                 200                 205

Ala Tyr Glu Leu Thr Asp Val Leu Ala Leu Glu Ala Val Lys Leu Ile
    210                 215                 220

Gly Glu Ser Leu Glu Asp Ala Val Lys Asp Gly Asn Asn Ile Glu Ala
225                 230                 235                 240

Arg Ser Lys Met Ala Tyr Ala Ser Tyr Ile Ala Gly Met Ser Phe Asn
                245                 250                 255

Asn Ala Gly Leu Gly Tyr Val His Ser Met Ala His Gln Leu Gly Gly
            260                 265                 270

Phe Tyr Asn Leu Pro His Gly Val Cys Asn Ala Ile Leu Leu Pro His
        275                 280                 285

Val Glu Lys Phe Asn Ser Ala Asn Thr Gly Asp Lys Leu Arg Lys Val
    290                 295                 300

Ala Glu Ile Leu Gly Glu Asn Val Glu Gly Leu Ser Val Glu Glu Ala
305                 310                 315                 320

Asn Ala Lys Ala Ile Glu Ala Ile Met Lys Leu Ser Glu Arg Val Gly
                325                 330                 335

Ile Pro Lys Gly Leu Lys Glu Leu Gly Val Lys Glu Glu Asp Phe Lys
            340                 345                 350

Val Met Ala Glu Asn Ala Leu Lys Asp Val Cys Ala Gly Thr Asn Pro
        355                 360                 365

Arg Glu Val Thr Leu Glu Asp Thr Ile Ala Leu Tyr Lys Glu Ala Leu
    370                 375                 380

<210> SEQ ID NO 43
<211> LENGTH: 384
<212> TYPE: PRT
<213> ORGANISM: Paenibacillus peoriae KCTC 3763

<400> SEQUENCE: 43

Met Thr Gly Thr Ser Lys Phe Met Met Pro Gly Met Ser Leu Met Gly
1               5                   10                  15

Ser Gly Ala Leu Ala Asp Ala Gly Thr Glu Ile Gly Lys Leu Gly Tyr
            20                  25                  30

Thr Asn Ala Leu Ile Val Thr Asp Lys Pro Leu Val Asp Ile Gly Ile
        35                  40                  45

Val Lys Lys Val Thr Ser Val Leu Glu Ser Ile Asn Val Lys Ser Val
    50                  55                  60

Val Tyr Ser Gly Thr Gln Pro Asn Pro Thr Val Thr Asn Val Asn Glu
65                  70                  75                  80

Gly Leu Glu Leu Leu Ser Gln Ser Lys Cys Asp Phe Ile Ile Ser Leu
                85                  90                  95

Gly Gly Gly Ser Pro His Asp Cys Ala Lys Gly Ile Ala Leu Leu Ala
            100                 105                 110

Ser Asn Gly Gly Gln Ile Gly Asp Tyr Glu Gly Val Asp Lys Ser Thr
        115                 120                 125

Lys Pro Ser Phe Pro Leu Ile Ala Ile Asn Thr Thr Ala Gly Thr Ala
    130                 135                 140

Ser Glu Met Thr Met Phe Cys Ile Ile Thr Asp Glu Glu Arg His Ile
```

```
                145                 150                 155                 160
Lys Met Ala Ile Val Asp Asn His Thr Thr Pro Leu Ile Ala Val Asn
                    165                 170                 175

Asp Pro Asp Leu Met Met Ala Met Pro Lys Ser Leu Thr Ala Ala Thr
                    180                 185                 190

Gly Met Asp Ala Leu Thr His Ser Ile Glu Ala Tyr Val Ser Thr Asn
                    195                 200                 205

Ala Thr Pro Ile Thr Asp Ala Cys Ala Ile Lys Ala Ile Glu Leu Ile
                    210                 215                 220

Arg Asp Asn Leu Ala Arg Ala Val Asp Gly Asn Asp Val Glu Ala
225                 230                 235                 240

Arg Ser Gln Met Ala Tyr Ala Glu Phe Leu Ala Gly Met Ala Phe Asn
                    245                 250                 255

Asn Ala Gly Leu Gly Phe Val His Ala Met Ala His Gln Leu Gly Gly
                    260                 265                 270

Phe Tyr Asn Leu Pro His Gly Val Cys Asn Ala Ile Leu Leu Pro His
                    275                 280                 285

Val Glu Arg Tyr Asn Ala Lys Ala Ser Ala Glu Arg Leu Thr Asp Ile
                    290                 295                 300

Ala Arg Ala Leu Gly Glu Asn Thr Asp Gly Val Thr Pro Glu Gln Gly
305                 310                 315                 320

Ala Asn Leu Ala Leu Gln Ala Ile Glu Lys Leu Ala Lys Arg Val Asn
                    325                 330                 335

Ile Pro Ser Gly Leu Glu Glu Leu Gly Val Lys Arg Glu Asp Phe Thr
                    340                 345                 350

Val Leu Ala Ala Asn Ala Leu Lys Asp Ala Cys Gly Val Thr Asn Pro
                    355                 360                 365

Val Gln Pro Thr Gln Gln Glu Val Ile Ala Ile Phe Glu Gln Ala Met
                    370                 375                 380

<210> SEQ ID NO 44
<211> LENGTH: 387
<212> TYPE: PRT
<213> ORGANISM: Klebsiella pneumoniae subsp. pneumoniae MGH 78578

<400> SEQUENCE: 44

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
                    20                  25                  30

Gly Lys Lys Ala Leu Leu Val Thr Asp Lys Gly Leu Arg Ala Ile Lys
                    35                  40                  45

Asp Gly Ala Val Asp Lys Thr Leu His Tyr Leu Arg Glu Ala Gly Ile
                    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                    85                  90                  95

Val Thr Val Gly Gly Gly Ser Pro His Asp Cys Gly Lys Gly Ile Gly
                    100                 105                 110

Ile Ala Ala Thr His Glu Gly Asp Leu Tyr Gln Tyr Ala Gly Ile Glu
                    115                 120                 125

Thr Leu Thr Asn Pro Leu Pro Pro Ile Val Ala Val Asn Thr Thr Ala
                    130                 135                 140
```

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Met Gln Ala Ile
    210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ile Thr Arg Leu Ser Met
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
    370                 375                 380

Gln Ala Phe
385

<210> SEQ ID NO 45
<211> LENGTH: 383
<212> TYPE: PRT
<213> ORGANISM: Escherichia coli

<400> SEQUENCE: 45

Met Ala Ala Ser Thr Phe Phe Ile Pro Ser Val Asn Val Ile Gly Ala
1               5                   10                  15

Asp Ser Leu Thr Asp Ala Met Asn Met Met Ala Asp Tyr Gly Phe Thr
            20                  25                  30

Arg Thr Leu Ile Val Thr Asp Asn Met Leu Thr Lys Leu Gly Met Ala
        35                  40                  45

Gly Asp Val Gln Lys Ala Leu Glu Glu Arg Asn Ile Phe Ser Val Ile
    50                  55                  60

Tyr Asp Gly Thr Gln Pro Asn Pro Thr Thr Glu Asn Val Ala Ala Gly
65                  70                  75                  80

Leu Lys Leu Leu Lys Glu Asn Asn Cys Asp Ser Val Ile Ser Leu Gly
                85                  90                  95

Gly Gly Ser Pro His Asp Cys Ala Lys Gly Ile Ala Leu Val Ala Ala
            100                 105                 110

Asn Gly Gly Asp Ile Arg Asp Tyr Glu Gly Val Asp Arg Ser Ala Lys
        115                 120                 125

-continued

Pro Gln Leu Pro Met Ile Ala Ile Asn Thr Thr Ala Gly Thr Ala Ser
130                 135                 140

Glu Met Thr Arg Phe Cys Ile Ile Thr Asp Glu Ala Arg His Ile Lys
145                 150                 155                 160

Met Ala Ile Val Asp Lys His Val Thr Pro Leu Leu Ser Val Asn Asp
                165                 170                 175

Ser Ser Leu Met Ile Gly Met Pro Lys Ser Leu Thr Ala Ala Thr Gly
                180                 185                 190

Met Asp Ala Leu Thr His Ala Ile Glu Ala Tyr Val Ser Ile Ala Ala
                195                 200                 205

Thr Pro Ile Thr Asp Ala Cys Ala Leu Lys Ala Val Thr Met Ile Ala
210                 215                 220

Glu Asn Leu Pro Leu Ala Val Glu Asp Gly Ser Asn Ala Lys Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Phe
                260                 265                 270

Tyr Asn Leu Pro His Gly Val Cys Asn Ala Val Leu Leu Pro His Val
                275                 280                 285

Gln Val Phe Asn Ser Lys Val Ala Ala Ala Arg Leu Arg Asp Cys Ala
290                 295                 300

Ala Ala Met Gly Val Asn Val Thr Gly Lys Asn Asp Ala Glu Gly Ala
305                 310                 315                 320

Glu Ala Cys Ile Asn Ala Ile Arg Glu Leu Ala Lys Lys Val Asp Ile
                325                 330                 335

Pro Ala Gly Leu Arg Asp Leu Asn Val Lys Glu Glu Asp Phe Ala Val
                340                 345                 350

Leu Ala Thr Asn Ala Leu Lys Asp Ala Cys Gly Phe Thr Asn Pro Ile
                355                 360                 365

Gln Ala Thr His Glu Glu Ile Val Ala Ile Tyr Arg Ala Ala Met
                370                 375                 380

<210> SEQ ID NO 46
<211> LENGTH: 382
<212> TYPE: PRT
<213> ORGANISM: Clostridium perfringens ATCC 13124

<400> SEQUENCE: 46

Met Ser Tyr Lys Phe Phe Met Pro Ala Ile Ser Leu Met Gly Ala Asp
1               5                   10                  15

Cys Leu Lys Asp Ala Gly Asp Gln Val Gly Glu Leu Gly Phe Lys Lys
                20                  25                  30

Ala Leu Ile Val Thr Asp Lys Val Leu Gly Gln Ile Gly Ile Val Lys
                35                  40                  45

Lys Val Thr Asp Val Leu Asp Asn Lys Asn Ile Glu Tyr Ala Ile Tyr
                50                  55                  60

Asp Glu Thr Lys Pro Asn Pro Thr Val Lys Asn Val Asn Asp Gly Leu
65                  70                  75                  80

Ala Leu Leu Lys Glu Lys Glu Cys Asp Phe Val Ile Ser Leu Gly Gly
                85                  90                  95

Gly Ser Ala His Asp Cys Ala Lys Gly Ile Ala Leu Leu Ala Thr Asn
                100                 105                 110

Gly Gly Glu Ile Lys Asp Tyr Glu Gly Val Asp Lys Ser Lys Lys Pro

```
            115                 120                 125
Gln Leu Pro Met Val Gly Ile Asn Thr Thr Ala Gly Thr Gly Ser Glu
    130                 135                 140

Met Thr Leu Phe Ala Ile Ile Thr Asp Glu Glu Arg His Ile Lys Met
145                 150                 155                 160

Ala Leu Val Asp Lys His Leu Thr Pro Ile Ala Val Asn Asp Pro
                165                 170                 175

Ile Leu Met Leu Ala Met Pro Lys Ser Leu Thr Ala Ala Thr Gly Met
            180                 185                 190

Asp Ala Leu Thr His Ala Ile Glu Ala Tyr Val Ser Thr Ala Ala Thr
        195                 200                 205

Pro Ile Thr Asp Ala Cys Ala Glu Lys Ala Ile Glu Leu Ile Ser Asn
    210                 215                 220

Tyr Leu Val Asn Ala Val Glu Asn Gly Gln Asp Val Glu Ala Arg Asp
225                 230                 235                 240

Met Met Ala Tyr Ala Glu Tyr Leu Ala Gly Met Ala Phe Asn Asn Ala
                245                 250                 255

Ser Leu Gly Tyr Val His Ala Met Ala His Gln Leu Gly Gly Phe Tyr
            260                 265                 270

Asn Leu Pro His Gly Val Cys Asn Ala Ile Leu Leu Pro His Val Gln
        275                 280                 285

Glu Tyr Asn Lys Ser Thr Ser Ala Ser Arg Leu Ala Lys Ile Ala Lys
    290                 295                 300

Ile Met Gly Gly Asn Ile Glu Gly Leu Thr Asp Glu Gln Gly Ala Asp
305                 310                 315                 320

Leu Cys Ile Asp Met Ile Lys Ser Leu Ser Gln Thr Ile Gly Ile Pro
                325                 330                 335

Glu Gly Leu Gly Val Leu Gly Val Lys Glu Ser Asp Phe Glu Thr Leu
            340                 345                 350

Ala Thr Asn Ala Leu Asn Asp Ala Cys Ser Leu Thr Asn Pro Arg Lys
        355                 360                 365

Gly Asn Leu Glu Glu Val Ile Ala Ile Phe Lys Lys Ala Met
    370                 375                 380

<210> SEQ ID NO 47
<211> LENGTH: 366
<212> TYPE: PRT
<213> ORGANISM: Ralstonia eutropha H16

<400> SEQUENCE: 47

Met Arg Ala Arg Pro Ala Arg Ala Pro Lys Arg Lys Ala Gln Glu Arg
1               5                   10                  15

Pro Ser Ser Ser Arg Met Pro Ala Cys Thr Arg Trp Gly Tyr Pro Lys
            20                  25                  30

Pro Ser Arg Gly Thr Ser Ala Arg Gln Gly Phe Arg Pro Leu Ile Phe
        35                  40                  45

Pro Gly Ala Glu Pro Asn Pro Thr Asp Val Asn Val His Asp Gly Val
    50                  55                  60

Lys Leu Phe Glu Gln Glu Gly Cys Asp Phe Ile Val Ser Leu Gly Gly
65                  70                  75                  80

Gly Ser Ser His Asp Cys Ala Lys Gly Ile Gly Leu Val Thr Ala Gly
                85                  90                  95

Gly Gly His Ile Arg Asp Tyr Glu Gly Ile Asp Lys Ser Thr Val Pro
            100                 105                 110
```

```
Met Thr Pro Leu Ile Ser Ile Asn Thr Thr Ala Gly Thr Ala Ala Glu
            115                 120                 125

Met Thr Arg Phe Cys Ile Ile Thr Asn Ser Ser Asn His Val Lys Met
130                 135                 140

Ala Ile Val Asp Trp Arg Cys Thr Pro Leu Ile Ala Ile Asp Asp Pro
145                 150                 155                 160

Arg Leu Met Val Ala Met Pro Pro Ala Leu Thr Ala Thr Gly Met
            165                 170                 175

Asp Ala Leu Thr His Ala Val Glu Ala Tyr Val Ser Thr Ala Ala Thr
            180                 185                 190

Pro Ile Thr Asp Ala Cys Ala Glu Lys Ala Ile Ala Leu Ile Gly Glu
            195                 200                 205

Trp Leu Pro Lys Ala Val Ala Asn Gly Asn Ser Leu Glu Ala Arg Ala
210                 215                 220

Ala Met Cys Tyr Ala Gln Tyr Leu Ala Gly Met Ala Phe Asn Asn Ala
225                 230                 235                 240

Ser Leu Gly Tyr Val His Ala Met Ala His Gln Leu Gly Gly Leu Tyr
            245                 250                 255

Asn Leu Pro His Gly Val Cys Asn Ala Ile Leu Leu Pro His Val Ser
            260                 265                 270

Glu Phe Asn Leu Ile Ala Ala Pro Glu Arg Phe Ala Lys Ile Ala Glu
            275                 280                 285

Leu Leu Gly Glu Asn Val Ala Ser Leu Ser Thr Ser Asp Ala Ala Lys
            290                 295                 300

Ala Ala Ile Ser Ala Ile Arg Ala Leu Ala Ala Ser Ile Gly Ile Pro
305                 310                 315                 320

Ala Gly Leu Ala Ser Leu Gly Val Lys Ala Glu Asp His Glu Val Met
            325                 330                 335

Ala His Asn Ala Gln Lys Asp Ala Cys Met Leu Thr Asn Pro Arg Arg
            340                 345                 350

Ala Thr Thr Ala Gln Val Ile Ala Ile Phe Ala Ala Ala Met
            355                 360                 365

<210> SEQ ID NO 48
<211> LENGTH: 389
<212> TYPE: PRT
<213> ORGANISM: Thermoanaerobacter sp. X514

<400> SEQUENCE: 48

Met Lys Ile Phe Lys Phe His Met Pro Pro Ile Asn Leu Ile Gly Val
1               5                   10                  15

Gly Cys Leu Lys Asp Val Gly Arg Glu Ile Lys Lys Leu Gly Phe Lys
            20                  25                  30

Lys Gly Ile Ile Val Thr Asp Lys Val Leu Val Arg Ala Gly Leu Val
            35                  40                  45

Asn Asn Val Ile Ser Val Leu Glu Glu Glu Gly Ile Glu Tyr Val Val
            50                  55                  60

Phe Asp Glu Thr Lys Pro Asn Pro Thr Ile Lys Asn Val Thr Asn Gly
65                  70                  75                  80

Leu Lys Leu Leu Ile Glu Asn Lys Cys Asp Phe Ile Ile Ser Cys Gly
                85                  90                  95

Gly Gly Ser Ala His Asp Cys Ala Lys Gly Ile Gly Leu Ile Ala Lys
            100                 105                 110

Glu Lys Asn Phe Ile Asp Glu Val Glu Arg Leu Asp Lys Val Lys Cys
            115                 120                 125
```

```
Gly Gly Trp Asn Ser Ala Leu Leu Pro Leu Val Ala Ile Asn Thr
            130                 135                 140

Thr Ala Gly Thr Gly Ser Glu Val Thr Lys Phe Ala Ile Ile Thr Asp
145                 150                 155                 160

Glu Glu Lys Arg Ile Lys Met Pro Ile Val Asp Trp Arg Ile Thr Pro
                165                 170                 175

Leu Ile Ala Val Asn Asp Pro Leu Leu Met Ile Gly Met Pro Lys Ser
                180                 185                 190

Leu Thr Ala Ala Ser Gly Met Asp Ala Leu Thr His Ala Ile Glu Ala
            195                 200                 205

Tyr Ile Ser Ile Asp Ala Asn Pro Phe Thr Asp Ala Leu Ala Leu Lys
210                 215                 220

Ala Ile Glu Ile Ile Phe Asn Tyr Leu Lys Arg Ala Val Glu Asn Gly
225                 230                 235                 240

Asn Asp Ile Glu Ala Arg Glu Lys Met Ala Tyr Ala Glu Phe Leu Ala
                245                 250                 255

Gly Ile Ala Phe Asn Asn Ala Gly Leu Gly Tyr Val His Ala Met Ala
            260                 265                 270

His Gln Leu Gly Gly Phe Tyr Asp Leu Pro His Gly Val Cys Asn Ala
        275                 280                 285

Val Leu Leu Pro His Val Leu Glu Tyr Asn Leu Glu Ala Val Gln Asn
290                 295                 300

Lys Leu Ile Tyr Ile Ala Lys Ala Met Gly Ile Asp Val Asp Lys Leu
305                 310                 315                 320

Thr Thr Lys Glu Ile Gly Gly Lys Ile Ile Glu Ser Ile Asn Gln Leu
                325                 330                 335

Ser Gln Glu Ile Gly Ile Pro Ser Arg Leu Lys Glu Leu Gly Val Lys
            340                 345                 350

Glu Glu Asp Ile Lys Glu Leu Ser Gln Asn Ala Leu Lys Asp Val Cys
        355                 360                 365

Gly Phe Thr Asn Pro Lys Lys Ala Thr Leu Glu Asp Ile Ile Asn Ile
370                 375                 380

Phe Lys Ser Ala Met
385

<210> SEQ ID NO 49
<211> LENGTH: 384
<212> TYPE: PRT
<213> ORGANISM: human gut metagenome

<400> SEQUENCE: 49

Met Gly Asn Arg Ile Ile Leu Asn Gly Thr Ser Tyr Phe Gly Arg Gly
1               5                   10                  15

Ala Arg Glu Asn Val Ile Thr Glu Leu Arg Asn Arg Asn Phe Thr Lys
                20                  25                  30

Ala Leu Val Val Thr Asp Lys Asn Leu Leu Asp Ala His Val Thr Asn
            35                  40                  45

Leu Val Thr Asp Val Leu Asp Lys Asn Asp Phe Ser Tyr Gln Ile Tyr
        50                  55                  60

Ser Asp Ile Lys Pro Asn Pro Thr Thr Leu Asn Val Gln Glu Gly Val
65                  70                  75                  80

Thr Phe Cys Arg Asn Ser Lys Ala Asp Val Ile Ala Val Gly Gly
                85                  90                  95

Gly Ser Ala Ile Asp Thr Ala Lys Ala Ile Ser Ile Ile Met Thr Asn
```

```
                  100                 105                 110
Pro Glu His Phe Asp Val Ile Ser Leu Asp Gly Ala Val Glu Thr Lys
            115                 120                 125

Asn Ala Gly Met Pro Ile Ile Ala Leu Pro Thr Thr Ala Gly Thr Ala
130                 135                 140

Ala Glu Val Thr Ile Asn Tyr Val Ile Thr Asn Pro Val Gly Pro Lys
145                 150                 155                 160

Lys Met Val Cys Val Asp Pro His Asp Ile Pro Ile Val Ala Ile Ile
                165                 170                 175

Asp Gln Asp Leu Met Glu Lys Met Pro Lys Ser Leu Ala Ala Ser Thr
            180                 185                 190

Gly Met Asp Ala Leu Thr His Ala Met Glu Gly Tyr Thr Thr Lys Ala
        195                 200                 205

Ala Trp Leu Met Thr Asp Met Phe His Leu Asn Ala Met Ala Leu Ile
    210                 215                 220

Tyr Lys Asn Leu Glu Lys Ala Val Asn Leu Lys Asp Arg Asp Ala Ile
225                 230                 235                 240

Asp Asn Val Gly Tyr Gly Gln Tyr Ile Ala Gly Met Gly Phe Ser Asn
                245                 250                 255

Val Gly Leu Gly Ile Val His Ser Met Ala His Ser Leu Gly Ala Phe
            260                 265                 270

Phe Asp Thr Pro His Gly Leu Ala Asn Ala Leu Leu Leu Pro His Val
        275                 280                 285

Leu Lys Phe Asn Gly Lys Ile Cys Pro Asp Leu Phe Arg Asn Met Gly
    290                 295                 300

Arg Ala Met Gly Leu Asp Met Asp Asn Leu Thr Asp Asp Glu Ala Val
305                 310                 315                 320

Asp Lys Val Val Asp Ala Val Arg Ser Leu Ala Ile Lys Ile Gly Ile
                325                 330                 335

Pro Gln Thr Leu Lys Glu Ile Gly Ile Lys Lys Glu Asp Leu Pro Met
            340                 345                 350

Leu Ala His Gln Ala Ile Asp Asp Val Cys Thr Ala Gly Asn Pro Arg
        355                 360                 365

Asn Val Thr Glu Gln Asp Ile Leu Ala Leu Tyr Gln Glu Ala Tyr Glu
    370                 375                 380

<210> SEQ ID NO 50
<211> LENGTH: 387
<212> TYPE: PRT
<213> ORGANISM: Geobacillus themodenitrificans NG80-2

<400> SEQUENCE: 50

Met Gln Asn Phe Thr Phe Arg Asn Pro Thr Lys Leu Ile Phe Gly Arg
1               5                   10                  15

Gly Gln Ile Glu Gln Leu Lys Glu Val Pro Lys Tyr Gly Lys Lys
            20                  25                  30

Val Leu Leu Val Tyr Gly Gly Ser Ile Lys Arg Asn Gly Leu Tyr
        35                  40                  45

Asp Glu Val Met Ser Leu Leu Thr Asp Ile Gly Ala Glu Val Val Glu
    50                  55                  60

Leu Pro Gly Val Glu Pro Asn Pro Arg Leu Ser Thr Val Lys Lys Gly
65                  70                  75                  80

Val Asp Ile Cys Arg Arg Glu Gly Ile Glu Phe Leu Leu Ala Val Gly
                85                  90                  95
```

```
Gly Gly Ser Val Ile Asp Cys Thr Lys Ala Ile Ala Ala Gly Ala Lys
                100                 105                 110

Phe Asp Gly Asp Pro Trp Glu Phe Ile Thr Lys Lys Ala Thr Val Thr
            115                 120                 125

Glu Ala Leu Pro Phe Gly Thr Val Leu Thr Leu Ala Ala Thr Gly Ser
        130                 135                 140

Glu Met Asn Ala Gly Ser Val Ile Thr Asn Trp Glu Thr Lys Glu Lys
145                 150                 155                 160

Tyr Gly Trp Gly Ser Pro Val Thr Phe Pro Gln Phe Ser Ile Leu Asp
                165                 170                 175

Pro Thr Tyr Thr Met Thr Val Pro Lys Asp His Thr Val Tyr Gly Ile
            180                 185                 190

Val Asp Met Met Ser His Val Phe Glu Gln Tyr Phe His His Thr Pro
        195                 200                 205

Asn Thr Pro Leu Gln Asp Arg Met Cys Glu Ala Val Leu Lys Thr Val
    210                 215                 220

Ile Glu Ala Ala Pro Lys Leu Val Asp Leu Glu Asn Tyr Glu Leu
225                 230                 235                 240

Arg Glu Thr Ile Met Tyr Ser Gly Thr Ile Ala Leu Asn Gly Phe Leu
                245                 250                 255

Gln Met Gly Val Arg Gly Asp Trp Ala Thr His Asp Ile Glu His Ala
            260                 265                 270

Val Ser Ala Val Tyr Asp Ile Pro His Ala Gly Leu Ala Ile Leu
        275                 280                 285

Phe Pro Asn Trp Met Lys His Val Leu Asp Glu Asn Val Ser Arg Phe
290                 295                 300

Ala Gln Leu Ala Val Arg Val Phe Asp Val Asp Pro Thr Gly Lys Thr
305                 310                 315                 320

Glu Arg Asp Val Ala Leu Gly Ile Glu Arg Leu Arg Ala Phe Trp
                325                 330                 335

Ser Ser Leu Gly Ala Pro Ser Arg Leu Ala Asp Tyr Gly Ile Gly Glu
            340                 345                 350

Glu Asn Leu Glu Leu Met Ala Asp Lys Ala Met Ala Phe Gly Glu Phe
        355                 360                 365

Gly Arg Phe Lys Thr Leu Asn Arg Asp Asp Val Leu Ala Ile Leu Arg
    370                 375                 380

Ala Ser Leu
385

<210> SEQ ID NO 51
<211> LENGTH: 211
<212> TYPE: PRT
<213> ORGANISM: Bacillus methanolicus PB1

<400> SEQUENCE: 51

Met Gln Leu Gln Leu Ala Leu Asp Leu Val Asn Ile Glu Glu Ala Lys
1               5                   10                  15

Gln Val Val Ser Glu Val Gln Glu Tyr Val Asp Ile Val Glu Ile Gly
            20                  25                  30

Thr Pro Val Ile Lys Ile Trp Gly Leu Gln Ala Val Lys Ala Val Lys
        35                  40                  45

Asp Ala Phe Pro His Leu Gln Val Leu Ala Asp Met Lys Thr Met Asp
    50                  55                  60

Ala Ala Ala Tyr Glu Val Ala Lys Ala Ala Glu His Gly Ala Asp Ile
65                  70                  75                  80
```

```
Val Thr Ile Leu Ala Ala Glu Asp Val Ser Ile Lys Gly Ala Val
                85                  90                  95

Glu Glu Ala Lys Lys Leu Gly Lys Lys Ile Leu Val Asp Met Ile Ala
            100                 105                 110

Ile Lys Asn Leu Glu Glu Arg Ala Lys Gln Val Asp Glu Met Gly Val
            115                 120                 125

Asp Tyr Ile Cys Val His Ala Gly Tyr Asp Leu Gln Ala Val Gly Lys
    130                 135                 140

Asn Pro Leu Glu Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                165                 170                 175

Ile Lys Ala Glu Pro Asp Leu Val Ile Val Gly Gly Gly Ile Ala Asn
            180                 185                 190

Gln Thr Asp Lys Lys Ala Ala Ala Glu Lys Ile Asn Lys Leu Val Lys
            195                 200                 205

Gln Gly Leu
    210

<210> SEQ ID NO 52
<211> LENGTH: 228
<212> TYPE: PRT
<213> ORGANISM: Methylobacillus flagellatus

<400> SEQUENCE: 52

Met Ala Lys Pro Leu Val Gln Met Ala Leu Asp Ser Leu Asp Phe Asp
1               5                   10                  15

Gln Thr Val Ala Leu Ala Thr Thr Val Ala Pro His Val Asp Ile Leu
            20                  25                  30

Glu Ile Gly Thr Pro Cys Ile Lys Tyr Asn Gly Ile Lys Leu Leu Glu
        35                  40                  45

Thr Leu Arg Ala Lys Phe Pro Asn Asn Lys Ile Leu Val Asp Leu Lys
    50                  55                  60

Thr Met Asp Ala Gly Phe Tyr Glu Ala Glu Pro Phe Tyr Lys Ala Gly
65                  70                  75                  80

Ala Asp Ile Val Thr Val Leu Gly Thr Ala Asp Ile Gly Thr Ile Lys
                85                  90                  95

Gly Val Ile Asp Val Ala Asn Lys Tyr Gly Lys Lys Ala Gln Val Asp
            100                 105                 110

Leu Ile Asn Val Thr Asp Lys Ala Ala Arg Thr Lys Glu Val Ala Lys
            115                 120                 125

Leu Gly Ala His Ile Ile Gly Val His Thr Gly Leu Asp Gln Gln Ala
    130                 135                 140

Ala Gly Gln Thr Pro Phe Ala Asp Leu Asn Leu Val Ser Ser Leu Asn
145                 150                 155                 160

Leu Gly Val Asp Ile Ser Val Ala Gly Gly Val Lys Ala Thr Thr Ala
                165                 170                 175

Lys Gln Val Val Asp Ala Gly Ala Thr Ile Val Val Ala Gly Ala Ala
            180                 185                 190

Ile Tyr Gly Ala Ala Asp Pro Ala Ala Ala Ala Glu Ile Ser Ala
            195                 200                 205

Ala Ala Lys Gly Thr Gln Ser Ser Gly Gly Leu Phe Gly Trp Leu Lys
210                 215                 220

Lys Leu Phe Ser
```

-continued

```
<210> SEQ ID NO 53
<211> LENGTH: 210
<212> TYPE: PRT
<213> ORGANISM: Bacillus subtilis

<400> SEQUENCE: 53

Met Glu Leu Gln Leu Ala Leu Asp Leu Val Asn Ile Pro Glu Ala Ile
1               5                   10                  15

Glu Leu Val Lys Glu Val Glu Gln Tyr Ile Asp Val Val Glu Ile Gly
            20                  25                  30

Thr Pro Val Ile Asn Glu Gly Leu Arg Ala Val Lys Glu Ile Lys
        35                  40                  45

Glu Ala Phe Pro Gln Leu Lys Val Leu Ala Asp Leu Lys Ile Met Asp
    50                  55                  60

Ala Gly Gly Tyr Glu Ile Met Lys Ala Ser Glu Ala Gly Ala Asp Ile
65                  70                  75                  80

Ile Thr Val Leu Gly Ala Thr Asp Ala Thr Ile Lys Gly Ala Val
                85                  90                  95

Glu Glu Ala Lys Lys Gln Lys Lys Ile Leu Val Asp Met Ile Asn
            100                 105                 110

Val Lys Asp Ile Glu Ser Arg Ala Lys Glu Ile Asp Ala Leu Gly Val
        115                 120                 125

Asp Tyr Ile Cys Val His Thr Gly Tyr Asp Leu Gln Ala Glu Gly Lys
    130                 135                 140

Asn Ser Phe Glu Glu Leu Thr Thr Ile Lys Asn Thr Val Lys Asn Ala
145                 150                 155                 160

Lys Thr Ala Ile Ala Gly Gly Ile Lys Leu Asp Thr Leu Pro Glu Val
                165                 170                 175

Ile Gln Gln Lys Pro Asp Leu Val Ile Val Gly Gly Gly Ile Thr Ser
            180                 185                 190

Ala Ala Asp Lys Ala Glu Thr Ala Ser Lys Met Lys Gln Leu Ile Val
        195                 200                 205

Gln Gly
    210

<210> SEQ ID NO 54
<211> LENGTH: 293
<212> TYPE: PRT
<213> ORGANISM: Methylophilus methylotrophus

<400> SEQUENCE: 54

Met Ala Gln Thr Gln Met Ala Leu Asp Ser Leu Asp Phe Asp Ala Thr
1               5                   10                  15

Ile Ala Leu Ala Ala Lys Val Ala Pro His Val Asp Ile Leu Glu Ile
            20                  25                  30

Gly Thr Pro Cys Ile Lys His Asn Gly Ile Glu Leu Leu Lys Ala Leu
        35                  40                  45

Arg Ser Lys Phe Pro Asn Asn Lys Ile Leu Val Asp Leu Lys Thr Met
    50                  55                  60

Asp Ala Gly Phe Tyr Glu Ala Glu Pro Phe Tyr Lys Ala Gly Ala Asp
65                  70                  75                  80

Ile Cys Thr Val Leu Gly Thr Ala Asp Ile Gly Thr Ile Lys Gly Val
                85                  90                  95

Ile Asp Ala Ala Asn Lys Tyr Gly Lys Glu Ala Gln Ile Asp Leu Ile
```

```
                100                 105                 110
Asn Val Lys Asp Lys Ala Arg Thr Leu Glu Val Lys Leu Gly
            115                 120                 125

Ala His Ile Ile Gly Val His Thr Gly Leu Asp Gln Gln Ala Ala Gly
        130                 135                 140

Gln Thr Pro Phe Ala Asp Leu Gly Leu Val Ser Gly Leu Lys Thr Gly
145                 150                 155                 160

Ala Lys Val Ser Val Ala Gly Gly Val Lys Ala Ala Thr Thr Lys Gln
                165                 170                 175

Val Val Asp Ala Gly Ala Asp Ile Val Val Gly Ala Ala Ile Tyr
            180                 185                 190

Gly Ala Ala Asp Pro Ala Ala Ala Asn Glu Ile Thr Lys Ile Ala
        195                 200                 205

His Gly Ser Gly Ala Ala Lys Gly Gly Asn Lys Leu Leu Pro Trp
        210                 215                 220

Ile Ile Ala Ala Val Ala Ala Val Leu Val Phe Ser Leu Leu Gly Lys
225                 230                 235                 240

Lys Ser Glu Glu Ala Ala Pro Ala Ala Glu Ala Pro Ala Ala Glu Glu
                245                 250                 255

Ala Ala Pro Ala Glu Ala Ala Pro Ala Ala Glu Ala Pro Ala Ala Glu
                260                 265                 270

Glu Ala Ala Pro Ala Glu Ala Ala Pro Ala Glu Ala Ala Pro Ala
            275                 280                 285

Thr Glu Gly Ala Asn
    290

<210> SEQ ID NO 55
<211> LENGTH: 210
<212> TYPE: PRT
<213> ORGANISM: Methylophilus methylotrophus

<400> SEQUENCE: 55

Met Ala Leu Thr Gln Met Ala Leu Asp Ser Leu Asp Phe Asp Ala Thr
1               5                   10                  15

Ile Ala Leu Ala Glu Lys Val Ala Pro His Val Asp Ile Leu Glu Ile
                20                  25                  30

Gly Thr Pro Cys Ile Lys His Asn Gly Ile Lys Leu Leu Glu Thr Leu
            35                  40                  45

Arg Ala Lys Phe Pro Asn Asn Lys Ile Leu Val Asp Leu Lys Thr Met
        50                  55                  60

Asp Ala Gly Glu Tyr Glu Ser Glu Pro Phe Tyr Lys Ala Gly Ala Asp
65                  70                  75                  80

Ile Cys Val Val Leu Gly Val Ser Asp Ile Gly Thr Ile Lys Gly Val
                85                  90                  95

Ile Lys Ala Ala Asn Lys Tyr Gly Lys Lys Ala Gln Val Asp Leu Ile
            100                 105                 110

Ser Val Glu Asp Lys Val Ala Arg Thr Lys Glu Val Ala Ala Ala Gly
        115                 120                 125

Ala His Ile Ile Gly Ile His Thr Gly Leu Asp Gln Gln Ala Ala Gly
        130                 135                 140

Gln Thr Pro Phe Ala Asp Leu Ala Ala Val Ala Gly Leu Asn Leu Gly
145                 150                 155                 160

Val Asp Ile Ser Val Ala Gly Gly Val Lys Ala Thr Ala Ala Gln
                165                 170                 175
```

```
Val Arg Asp Ala Gly Ala Thr Ile Ile Val Ala Gly Ala Ala Ile Tyr
            180                 185                 190

Gly Ala Ala Asp Pro Ala Ala Ala Glu Ile Thr Ala Ile Ala
        195                 200                 205

His Ala
    210

<210> SEQ ID NO 56
<211> LENGTH: 184
<212> TYPE: PRT
<213> ORGANISM: Bacillus methanolicus PB1

<400> SEQUENCE: 56

Met Leu Thr Thr Glu Phe Leu Ser Glu Ile Val Lys Glu Leu Asn Ser
1               5                   10                  15

Ser Val Asn Gln Ile Ala Asp Glu Glu Ala Glu Ala Leu Val Asn Gly
            20                  25                  30

Ile Leu Gln Ser Lys Lys Val Phe Val Ala Gly Ala Gly Arg Ser Gly
        35                  40                  45

Phe Met Ala Lys Ser Phe Ala Met Arg Met Met His Met Gly Ile Asp
    50                  55                  60

Ala Tyr Val Val Gly Glu Thr Val Thr Pro Asn Tyr Glu Lys Glu Asp
65                  70                  75                  80

Ile Leu Ile Ile Gly Ser Gly Ser Gly Glu Thr Lys Gly Leu Val Ser
                85                  90                  95

Met Ala Gln Lys Ala Lys Ser Ile Gly Gly Thr Ile Ala Ala Val Thr
            100                 105                 110

Ile Asn Pro Glu Ser Thr Ile Gly Gln Leu Ala Asp Ile Val Ile Lys
        115                 120                 125

Met Pro Gly Ser Pro Lys Asp Lys Ser Glu Ala Arg Glu Thr Ile Gln
    130                 135                 140

Pro Met Gly Ser Leu Phe Glu Gln Thr Leu Leu Leu Phe Tyr Asp Ala
145                 150                 155                 160

Val Ile Leu Arg Phe Met Glu Lys Lys Gly Leu Asp Thr Lys Thr Met
                165                 170                 175

Tyr Gly Arg His Ala Asn Leu Glu
            180

<210> SEQ ID NO 57
<211> LENGTH: 199
<212> TYPE: PRT
<213> ORGANISM: Mycobacterium gastri

<400> SEQUENCE: 57

Met Thr Gln Ala Ala Glu Ala Asp Gly Ala Val Lys Val Val Gly Asp
1               5                   10                  15

Asp Ile Thr Asn Asn Leu Ser Leu Val Arg Asp Glu Val Ala Asp Thr
            20                  25                  30

Ala Ala Lys Val Asp Pro Glu Val Ala Val Leu Ala Arg Gln Ile
        35                  40                  45

Val Gln Pro Gly Arg Val Phe Val Ala Gly Ala Gly Arg Ser Gly Leu
    50                  55                  60

Val Leu Arg Met Ala Ala Met Arg Leu Met His Phe Gly Leu Thr Val
65                  70                  75                  80

His Val Ala Gly Asp Thr Thr Thr Pro Ala Ile Ser Ala Gly Asp Leu
                85                  90                  95
```

```
Leu Leu Val Ala Ser Gly Ser Gly Thr Thr Ser Gly Val Val Lys Ser
            100                 105                 110

Ala Glu Thr Ala Lys Lys Ala Gly Ala Arg Ile Ala Ala Phe Thr Thr
        115                 120                 125

Asn Pro Asp Ser Pro Leu Ala Gly Leu Ala Asp Ala Val Val Ile Ile
    130                 135                 140

Pro Ala Ala Gln Lys Thr Asp His Gly Ser His Ile Ser Arg Gln Tyr
145                 150                 155                 160

Ala Gly Ser Leu Phe Glu Gln Val Leu Phe Val Val Thr Glu Ala Val
                165                 170                 175

Phe Gln Ser Leu Trp Asp His Thr Glu Val Glu Ala Glu Leu Trp
                180                 185                 190

Thr Arg His Ala Asn Leu Glu
        195

<210> SEQ ID NO 58
<211> LENGTH: 181
<212> TYPE: PRT
<213> ORGANISM: Methylobacillus flagellatus KT

<400> SEQUENCE: 58

Met Asn Lys Tyr Gln Glu Leu Val Val Asn Lys Leu Thr Asn Val Ile
1               5                   10                  15

Asn Asn Thr Ala Glu Gly Tyr Asp Asp Lys Ile Leu Ser Met Val Asp
            20                  25                  30

Ala Ala Gly Arg Thr Phe Leu Gly Gly Ala Gly Arg Ser Leu Leu Val
        35                  40                  45

Ser Arg Phe Phe Ala Met Arg Leu Val His Ala Gly Tyr Gln Val Ser
    50                  55                  60

Met Val Gly Glu Val Val Thr Pro Ser Ile Gln Ala Gly Asp Leu Phe
65                  70                  75                  80

Ile Val Ile Ser Gly Ser Gly Ser Thr Glu Thr Leu Met Pro Leu Val
                85                  90                  95

Arg Lys Ala Lys Ser Gln Gly Ala Lys Val Ile Val Ile Ser Met Lys
            100                 105                 110

Ala Gln Ser Pro Met Ala Glu Leu Ala Asp Leu Val Val Pro Ile Gly
        115                 120                 125

Gly Asn Asp Ala His Ala Phe Asp Lys Thr His Gly Met Pro Met Gly
    130                 135                 140

Thr Ile Phe Glu Leu Ser Thr Leu Trp Phe Leu Glu Ala Thr Ile Ala
145                 150                 155                 160

Lys Leu Ile Asp Gln Lys Gly Leu Thr Glu Glu Gly Met Arg Ala Ile
                165                 170                 175

His Ala Asn Leu Glu
        180

<210> SEQ ID NO 59
<211> LENGTH: 185
<212> TYPE: PRT
<213> ORGANISM: Bacillus subtilis

<400> SEQUENCE: 59

Met Lys Thr Thr Glu Tyr Val Ala Glu Ile Leu Asn Glu Leu His Asn
1               5                   10                  15

Ser Ala Ala Tyr Ile Ser Asn Glu Glu Ala Asp Gln Leu Ala Asp His
            20                  25                  30
```

```
Ile Leu Ser Ser His Gln Ile Phe Thr Ala Gly Ala Gly Arg Ser Gly
         35                  40                  45

Leu Met Ala Lys Ser Phe Ala Met Arg Leu Met His Met Gly Phe Asn
 50                  55                  60

Ala His Ile Val Gly Glu Ile Leu Thr Pro Pro Leu Ala Glu Gly Asp
 65                  70                  75                  80

Leu Val Ile Ile Gly Ser Gly Ser Gly Glu Thr Lys Ser Leu Ile His
                 85                  90                  95

Thr Ala Ala Lys Ala Lys Ser Leu His Gly Ile Val Ala Ala Leu Thr
                100                 105                 110

Ile Asn Pro Glu Ser Ser Ile Gly Lys Gln Ala Asp Leu Ile Ile Arg
                115                 120                 125

Met Pro Gly Ser Pro Lys Asp Gln Ser Asn Gly Ser Tyr Lys Thr Ile
130                 135                 140

Gln Pro Met Gly Ser Leu Phe Glu Gln Thr Leu Leu Phe Tyr Asp
145                 150                 155                 160

Ala Val Ile Leu Lys Leu Met Glu Lys Lys Gly Leu Asp Ser Glu Thr
                165                 170                 175

Met Phe Thr His His Ala Asn Leu Glu
                180                 185

<210> SEQ ID NO 60
<211> LENGTH: 178
<212> TYPE: PRT
<213> ORGANISM: Methylophilus methylotrophus

<400> SEQUENCE: 60

Met Asp His Gln Gln Phe Ile Leu Asp Asn Leu Lys Arg Ile Leu Asp
 1                   5                  10                  15

Val Thr Asp Lys Ser Lys Ala Ala Glu Leu Leu Lys Leu Val Asp Glu
                 20                  25                  30

Ala Gly Ser Thr Phe Ile Gly Gly Ala Gly Arg Ser Leu Leu Val Ser
                 35                  40                  45

Arg Phe Phe Ala Met Arg Leu Val His Ser Gly Tyr Ser Val Tyr Met
 50                  55                  60

Ile Gly Glu Val Val Thr Pro Ala Ile Lys Lys Gly Asp Leu Leu Ile
 65                  70                  75                  80

Leu Val Ser Gly Ser Gly Gly Thr Ala Thr Leu Leu Pro Phe Val Lys
                 85                  90                  95

Lys Ala Lys Glu Val Gly Ala Lys Leu Val Val Ile Ser Met Lys Lys
                100                 105                 110

Thr Ser Ala Met Ala Asp Val Ala Asp Leu Val Ile Gln Ile Gly Gln
                115                 120                 125

Asp Asp Ser Phe Pro Leu Val Lys Gly Met Pro Met Gly Gly Gln Phe
130                 135                 140

Glu Leu Ser Thr Leu Val Phe Leu Glu Gly Ala Ile Ser Glu Leu Ile
145                 150                 155                 160

His Ala Lys Gly Leu Thr Glu Glu Gly Met Arg Ala Leu His Ala Asn
                165                 170                 175

Leu Glu

<210> SEQ ID NO 61
<211> LENGTH: 185
<212> TYPE: PRT
<213> ORGANISM: Bacillus methanolicus MGA3
```

<400> SEQUENCE: 61

Met Gly Lys Leu Phe Glu Glu Lys Thr Ile Lys Thr Glu Gln Ile Phe
1               5                   10                  15

Ser Gly Arg Val Val Lys Leu Gln Val Asp Asp Val Glu Leu Pro Asn
            20                  25                  30

Gly Gln Thr Ser Lys Arg Glu Ile Val Arg His Pro Gly Ala Val Ala
        35                  40                  45

Val Ile Ala Ile Thr Asn Glu Asn Lys Ile Val Met Val Glu Gln Tyr
50                  55                  60

Arg Lys Pro Leu Glu Lys Ser Ile Val Glu Ile Pro Ala Gly Lys Leu
65                  70                  75                  80

Glu Lys Gly Glu Asp Pro Arg Val Thr Ala Leu Arg Glu Leu Glu Glu
                85                  90                  95

Glu Thr Gly Tyr Glu Cys Glu Gln Met Glu Trp Leu Ile Ser Phe Ala
            100                 105                 110

Thr Ser Pro Gly Phe Ala Asp Glu Ile Ile His Leu Tyr Val Ala Lys
        115                 120                 125

Gly Leu Ser Lys Lys Glu Asn Ala Ala Gly Leu Asp Glu Asp Glu Phe
130                 135                 140

Val Asp Leu Ile Glu Leu Thr Leu Asp Glu Ala Leu Gln Tyr Ile Lys
145                 150                 155                 160

Glu Lys Arg Ile Tyr Asp Ser Lys Thr Val Ile Ala Val Gln Tyr Leu
                165                 170                 175

Gln Leu Gln Glu Ala Leu Lys His Lys
            180                 185

<210> SEQ ID NO 62
<211> LENGTH: 207
<212> TYPE: PRT
<213> ORGANISM: Mycobacterium gastri

<400> SEQUENCE: 62

Met Lys Leu Gln Val Ala Ile Asp Leu Leu Ser Thr Glu Ala Ala Leu
1               5                   10                  15

Glu Leu Ala Gly Lys Val Ala Glu Tyr Val Asp Ile Ile Glu Leu Gly
            20                  25                  30

Thr Pro Leu Ile Glu Ala Glu Gly Leu Ser Val Ile Thr Ala Val Lys
        35                  40                  45

Lys Ala His Pro Asp Lys Ile Val Phe Ala Asp Met Lys Thr Met Asp
50                  55                  60

Ala Gly Glu Leu Glu Ala Asp Ile Ala Phe Lys Ala Gly Ala Asp Leu
65                  70                  75                  80

Val Thr Val Leu Gly Ser Ala Asp Asp Ser Thr Ile Ala Gly Ala Val
                85                  90                  95

Lys Ala Ala Gln Ala His Asn Lys Gly Val Val Asp Leu Ile Gly
            100                 105                 110

Ile Glu Asp Lys Ala Thr Arg Ala Gln Glu Val Arg Ala Leu Gly Ala
        115                 120                 125

Lys Phe Val Glu Met His Ala Gly Leu Asp Glu Gln Ala Lys Pro Gly
130                 135                 140

Phe Asp Leu Asn Gly Leu Leu Ala Ala Gly Glu Lys Ala Arg Val Pro
145                 150                 155                 160

Phe Ser Val Ala Gly Gly Val Lys Val Ala Thr Ile Pro Ala Val Gln
                165                 170                 175

```
Lys Ala Gly Ala Glu Val Ala Val Ala Gly Gly Ala Ile Tyr Gly Ala
            180                 185                 190

Ala Asp Pro Ala Ala Ala Lys Glu Leu Arg Ala Ala Ile Ala
        195                 200                 205

<210> SEQ ID NO 63
<211> LENGTH: 198
<212> TYPE: PRT
<213> ORGANISM: Methylobacillus flagellatus

<400> SEQUENCE: 63

Met Thr Ala Met Arg Asn Ala Glu Val Ser Arg Asn Thr Leu Glu Thr
1               5                   10                  15

Lys Ile Ala Val Ala Ile Asn Leu Asp Gly Thr Gly Ile Ser Arg Leu
            20                  25                  30

Asn Ser Gly Val Gly Phe Phe Asp His Met Leu Asp Gln Ile Ala Arg
        35                  40                  45

His Gly Met Met Asp Ile Ser Val Glu Cys Gln Gly Asp Leu His Ile
    50                  55                  60

Asp Ala His His Thr Val Glu Asp Val Gly Ile Ala Leu Gly Gln Ala
65                  70                  75                  80

Phe Ser Lys Ala Leu Gly Asp Lys Lys Gly Ile Arg Arg Tyr Ala His
                85                  90                  95

Ala Tyr Val Pro Leu Asp Glu Ala Leu Ser Arg Val Val Leu Asp Ile
            100                 105                 110

Ser Gly Arg Pro Gly Leu Glu Phe Asn Val Glu Phe Thr Arg Ala Arg
        115                 120                 125

Ile Gly Glu Phe Asp Val Asp Leu Val Ser Glu Phe Phe Gln Gly Phe
    130                 135                 140

Val Asn His Ala Ala Ile Thr Leu His Ile Asp Asn Leu Arg Gly Lys
145                 150                 155                 160

Asn Ala His His Gln Ala Glu Thr Ile Phe Lys Ala Phe Gly Arg Ala
                165                 170                 175

Leu Arg Ala Ala Val Glu Leu Asp Pro Arg Met Val Gly Ile Met Pro
            180                 185                 190

Ser Thr Lys Gly Ser Leu
        195

<210> SEQ ID NO 64
<211> LENGTH: 228
<212> TYPE: PRT
<213> ORGANISM: Aminomonas aminovorus

<400> SEQUENCE: 64

Met Ala Lys Pro Leu Val Gln Met Ala Leu Asp Ser Leu Asp Phe Asp
1               5                   10                  15

Gln Thr Val Ala Leu Ala Thr Thr Val Ala Pro His Val Asp Ile Leu
            20                  25                  30

Glu Ile Gly Thr Pro Cys Ile Lys Tyr Asn Gly Ile Lys Leu Leu Glu
        35                  40                  45

Thr Leu Arg Ala Lys Phe Pro Asn Asn Lys Ile Leu Val Asp Leu Lys
    50                  55                  60

Thr Met Asp Ala Gly Phe Tyr Glu Ala Glu Pro Phe Phe Lys Ala Gly
65                  70                  75                  80

Ala Asp Ile Val Thr Val Leu Gly Thr Ala Asp Ile Gly Thr Ile Lys
                85                  90                  95
```

```
Gly Val Ile Asp Val Ala Asn Lys Tyr Gly Lys Lys Ala Gln Val Asp
                100                 105                 110

Leu Ile Asn Val Val Asp Lys Ala Ala Arg Thr Lys Glu Val Ala Lys
        115                 120                 125

Leu Gly Ala His Ile Ile Gly Val His Thr Gly Leu Asp Gln Gln Ala
130                 135                 140

Ala Gly Gln Thr Pro Phe Ala Asp Leu Gly Leu Val Ser Gly Leu Asn
145                 150                 155                 160

Leu Gly Val Asp Ile Ser Val Ala Gly Gly Val Lys Ser Thr Thr Ala
                165                 170                 175

Lys Gln Val Val Asp Ala Gly Ala Thr Ile Val Val Ala Gly Ala Ala
        180                 185                 190

Ile Tyr Gly Ala Ala Asp Pro Ala Ala Ala Ala Glu Ile Ser Ala
            195                 200                 205

Ala Ala Lys Gly Thr Gln Ser Ser Gly Gly Val Phe Gly Trp Leu Lys
210                 215                 220

Lys Leu Phe Ser
225

<210> SEQ ID NO 65
<211> LENGTH: 209
<212> TYPE: PRT
<213> ORGANISM: Amycolatopsis methanolica 239

<400> SEQUENCE: 65

Met Glu Leu Gln Val Ala Leu Asp Val Leu Asp Leu Pro Ala Ala Leu
1               5                   10                  15

Thr Leu Ala Arg Gln Val Ala Glu His Val Asp Ile Leu Glu Leu Gly
            20                  25                  30

Thr Pro Leu Val Lys Ser Ala Gly Ile Ala Ala Val Thr Ala Val Lys
        35                  40                  45

Ala Ala His Pro Asp Lys Gln Val Phe Val Asp Leu Lys Thr Ala Asp
50                  55                  60

Ala Gly Glu Leu Glu Ala Ala Leu Ala Phe Glu Ala Gly Ala Asp Leu
65                  70                  75                  80

Val Thr Val Met Gly Ala Ala Asp Asp Thr Val Arg Gly Ala Val
                85                  90                  95

Ala Ala Gly Arg Lys Tyr Gly Lys Lys Val Val Ala Asp Met Ile Thr
            100                 105                 110

Val Thr Asp Asn Arg Val Gln Arg Ile Arg Glu Val Ala Lys Leu Gly
        115                 120                 125

Val Ala Phe Val Glu Ile His Ala Gly Leu Asp Glu Gln Ala Arg Pro
130                 135                 140

Gly Tyr Thr Ile Asp Thr Leu Leu Arg Asp Gly Arg Glu Ala Gly Val
145                 150                 155                 160

Pro Phe Ser Ile Ala Gly Gly Ile Lys Ala Asp Thr Ile Thr Ala Val
                165                 170                 175

Arg Asp Ala Gly Ala Thr Val Ala Val Ala Gly Gly Ala Ile Tyr Asn
        180                 185                 190

Ala Pro Asp Pro Ala Thr Ala Ala Arg Glu Leu Lys His His Ala Thr
195                 200                 205

His

<210> SEQ ID NO 66
<211> LENGTH: 211
```

<212> TYPE: PRT
<213> ORGANISM: Geobacillus sp. GHH01

<400> SEQUENCE: 66

```
Met Glu Leu Gln Leu Ala Leu Asp Leu Val Asn Ile Pro Glu Ala Lys
1               5                   10                  15

Gln Leu Val Lys Glu Val Glu Gly Tyr Val Asp Ile Val Glu Ile Gly
            20                  25                  30

Thr Pro Val Ile Ile Asn Glu Gly Leu Arg Ala Val Lys Glu Ile Lys
        35                  40                  45

Gln Glu Phe Pro His Leu Lys Val Leu Ala Asp Leu Lys Ile Met Asp
50                  55                  60

Ala Ala Ala Tyr Glu Val Met Lys Ala Ser Glu Ala Gly Ala Asp Ile
65                  70                  75                  80

Ile Thr Ile Leu Gly Val Ala Glu Asp Leu Ser Ile Lys Gly Ala Val
                85                  90                  95

Glu Glu Ala Lys Lys Gln Gly Lys Lys Ile Leu Val Asp Met Ile Gly
            100                 105                 110

Val Lys Asn Leu Glu Glu Arg Ala Lys Glu Val Asp Gly Phe Gly Val
        115                 120                 125

Asp Tyr Ile Cys Val His Thr Gly Tyr Asp Leu Gln Ala Val Gly Lys
    130                 135                 140

Asn Ser Leu Glu Asp Leu Ala Thr Ile Lys Arg Val Val Lys Asn Ala
145                 150                 155                 160

Lys Thr Ala Ile Ala Gly Gly Ile Lys Leu Asn Thr Leu Pro Glu Val
                165                 170                 175

Ile Lys Ala Lys Pro Asp Leu Ile Ile Val Gly Gly Gly Ile Thr Gly
            180                 185                 190

Gln Glu Asp Lys Arg Ala Val Ala Ala Glu Met Lys Lys Met Ile Gln
        195                 200                 205

Gln Gly Glu
210
```

<210> SEQ ID NO 67
<211> LENGTH: 211
<212> TYPE: PRT
<213> ORGANISM: Geobacillus sp. M10EXG

<400> SEQUENCE: 67

```
Met Glu Leu Gln Leu Ala Leu Asp Leu Val Asn Ile Pro Glu Ala Lys
1               5                   10                  15

Lys Leu Val Lys Glu Val Glu Gly Tyr Val Asp Ile Val Glu Ile Gly
            20                  25                  30

Thr Pro Ala Ile Ile Asn Glu Gly Leu Arg Ala Val Lys Glu Ile Lys
        35                  40                  45

Glu Glu Phe Pro His Leu Lys Val Leu Ala Asp Leu Lys Ile Met Asp
50                  55                  60

Ala Ala Ala Tyr Glu Val Met Lys Ala Ser Glu Ala Gly Ala Asp Ile
65                  70                  75                  80

Ile Thr Ile Leu Gly Val Ala Glu Asp Leu Ser Ile Lys Gly Ala Val
                85                  90                  95

Glu Glu Ala Lys Lys Gln Gly Lys Lys Ile Leu Val Asp Met Ile Gly
            100                 105                 110

Val Lys Asn Leu Glu Glu Arg Ala Lys Glu Val Asp Glu Phe Gly Val
        115                 120                 125
```

```
Asp Tyr Ile Cys Val His Thr Gly Tyr Asp Leu Gln Ala Val Gly Lys
            130                 135                 140

Asn Ser Leu Glu Asp Leu Ala Thr Ile Lys Arg Val Val Lys Asn Ala
145                 150                 155                 160

Lys Thr Ala Ile Ala Gly Gly Ile Lys Leu Asn Thr Leu Pro Glu Val
                165                 170                 175

Ile Lys Ala Lys Pro Asp Leu Ile Ile Val Gly Gly Ile Thr Asn
                180                 185                 190

Gln Glu Asp Lys Arg Ala Val Ala Ala Glu Met Lys Lys Met Ile Gln
            195                 200                 205

Gln Gly Glu
    210

<210> SEQ ID NO 68
<211> LENGTH: 211
<212> TYPE: PRT
<213> ORGANISM: Geobacillus sp. Y4.1MC1

<400> SEQUENCE: 68

Met Glu Leu Gln Leu Ala Leu Asp Leu Val Asn Ile Pro Glu Ala Lys
1               5                   10                  15

Lys Leu Val Lys Glu Val Glu Gly Tyr Val Asp Ile Val Glu Ile Gly
                20                  25                  30

Thr Pro Val Ile Ile Asn Glu Gly Leu Arg Ala Val Lys Glu Ile Lys
                35                  40                  45

Glu Glu Phe Pro His Leu Lys Val Leu Ala Asp Leu Lys Ile Met Asp
    50                  55                  60

Ala Ala Ala Tyr Glu Val Met Lys Ala Ser Glu Ala Gly Ala Asp Ile
65                  70                  75                  80

Ile Thr Ile Leu Gly Val Ala Glu Asp Leu Ser Ile Lys Gly Ala Val
                85                  90                  95

Glu Glu Ala Lys Lys Gln Gly Lys Lys Ile Leu Val Asp Met Ile Gly
                100                 105                 110

Val Lys Asn Leu Glu Glu Arg Ala Lys Glu Val Asp Glu Phe Gly Val
            115                 120                 125

Asp Tyr Ile Cys Val His Thr Gly Tyr Asp Leu Gln Ala Val Gly Lys
            130                 135                 140

Asn Ser Leu Glu Asp Leu Ala Thr Ile Lys Arg Val Val Lys Asn Ala
145                 150                 155                 160

Lys Thr Ala Ile Ala Gly Gly Ile Lys Leu Asn Thr Leu Pro Glu Val
                165                 170                 175

Ile Lys Ala Lys Pro Asp Leu Ile Ile Val Gly Gly Ile Thr Asn
                180                 185                 190

Gln Glu Asp Lys Arg Ala Val Ala Ala Glu Met Lys Lys Met Ile Gln
            195                 200                 205

Gln Gly Glu
    210

<210> SEQ ID NO 69
<211> LENGTH: 215
<212> TYPE: PRT
<213> ORGANISM: Geobacillus thermodenitrificans NG80-2 HPS

<400> SEQUENCE: 69

Met Tyr Ile Gln Leu Ala Leu Asp Arg Met Asp Ile Asn Gln Ala Ile
1               5                   10                  15
```

Gln Ile Thr Gln Gln Val Glu Glu Tyr Ile Asp Trp Ile Glu Val Gly
            20                  25                  30

Thr Ser Leu Ile Lys Glu Phe Gly Ile Lys Ser Ile Glu Ala Ile Lys
        35                  40                  45

Arg Ala Phe Pro Gly Lys Met Ile Val Ala Asp Thr Lys Thr Met Asp
50                  55                  60

Asn Ala Val Tyr Glu Cys Asn Leu Cys Phe Glu Ala Gly Ala Asp Val
65                  70                  75                  80

Met Thr Val Met Gly Val Ala Pro Leu Met Thr Val Glu Ala Cys Leu
                85                  90                  95

Lys Glu Ala Ser Ile Arg Gly Lys Lys Val Met Ile Asp Leu Leu Asn
            100                 105                 110

Thr Asn Glu Ser Val Arg Gln Gln Leu Leu Gln Tyr Lys Glu Ala Ile
        115                 120                 125

Phe Cys Ile His Val Ser Lys Asp Glu Gln Glu Phe Ala Gln Gln His
130                 135                 140

Lys Asn Phe Asn Phe Ala His Phe His Arg Pro Thr Gly Cys Asn Leu
145                 150                 155                 160

Ala Val Ala Gly Gly Ile Ser Ala Ala Thr Met Lys Gln Ile Gln Pro
                165                 170                 175

Leu His Pro Ser Ile Val Ile Gly Ser Ala Ile Thr Arg Ala Glu
            180                 185                 190

His Pro Glu Arg Ala Ala Arg Glu Leu Arg Gln Leu Val Arg Asn Arg
        195                 200                 205

Gly Ile Asp Asp Ala Ser Asn
210                 215

<210> SEQ ID NO 70
<211> LENGTH: 209
<212> TYPE: PRT
<213> ORGANISM: Methylomonas aminofaciens

<400> SEQUENCE: 70

Met Ala Leu Thr Gln Met Ala Leu Asp Ser Leu Asp Phe Asp Ala Thr
1               5                   10                  15

Val Ala Leu Ala Glu Lys Val Ala Pro His Val Asp Ile Leu Glu Ile
            20                  25                  30

Gly Thr Pro Cys Ile Lys His Asn Gly Ile Lys Leu Leu Glu Thr Leu
        35                  40                  45

Arg Ala Lys Phe Pro Asn Asn Lys Ile Leu Val Asp Leu Lys Thr Met
50                  55                  60

Asp Ala Gly Phe Tyr Glu Ala Glu Pro Phe Tyr Lys Ala Gly Ala Asp
65                  70                  75                  80

Ile Thr Thr Val Leu Gly Val Ala Asp Leu Gly Thr Ile Lys Gly Val
                85                  90                  95

Ile Asp Ala Ala Asn Lys Tyr Gly Lys Lys Ala Gln Ile Asp Leu Ile
            100                 105                 110

Asn Val Gly Asp Lys Ala Ala Arg Thr Lys Glu Val Ala Lys Leu Gly
        115                 120                 125

Ala His Ile Ile Gly Val His Thr Gly Leu Asp Gln Gln Ala Ala Gly
130                 135                 140

Gln Thr Pro Phe Ala Asp Leu Ala Thr Val Thr Gly Leu Asn Leu Gly
145                 150                 155                 160

Leu Glu Val Ser Val Ala Gly Gly Val Lys Pro Ala Thr Val Ala Gln
                165                 170                 175

```
Val Lys Asp Ala Gly Ala Thr Ile Ile Val Ala Gly Ala Ala Ile Tyr
            180                 185                 190

Gly Ala Ala Asp Pro Ala Ala Ala Ala Glu Ile Thr Gly Leu Ala
        195                 200                 205

Lys

<210> SEQ ID NO 71
<211> LENGTH: 221
<212> TYPE: PRT
<213> ORGANISM: Methylovorus glucosetrophus SIP3-4

<400> SEQUENCE: 71

Met Ala Leu Asp Ser Leu Asp Phe Asp Ala Thr Val Ala Leu Ala Thr
1               5                   10                  15

Lys Val Ala Pro His Val Asp Ile Leu Glu Ile Gly Thr Pro Cys Ile
            20                  25                  30

Lys Tyr Asn Gly Ile Lys Leu Leu Gln Thr Leu Arg Ala Lys Phe Pro
        35                  40                  45

Asn Asn Lys Ile Leu Val Asp Leu Lys Thr Met Asp Ala Gly Tyr Tyr
50                  55                  60

Glu Ala Glu Pro Phe Tyr Lys Ala Gly Ala Asp Ile Cys Thr Val Leu
65                  70                  75                  80

Gly Thr Ala Asp Ile Gly Thr Ile Lys Gly Val Ile Asp Val Ala Asn
                85                  90                  95

Lys Tyr Gly Lys Glu Ala Gln Ile Asp Leu Ile Asn Val Ala Asp Lys
            100                 105                 110

Ala Ala Arg Thr Lys Glu Val Ala Lys Leu Gly Ala His Ile Ile Gly
        115                 120                 125

Val His Thr Gly Leu Asp Gln Gln Ala Ala Gly Gln Thr Pro Phe Ala
130                 135                 140

Asp Leu Gly Leu Val Ser Ser Leu Asn Leu Gly Val Lys Val Ser Val
145                 150                 155                 160

Ala Gly Gly Ile Lys Pro Ala Thr Val Lys Gln Val Asp Ala Gly
                165                 170                 175

Ala Asn Ile Val Val Ala Gly Ala Ala Ile Tyr Gly Ala Ala Asp Pro
            180                 185                 190

Ala Ala Ala Ala Ala Glu Ile Ser Gly Leu Ala Lys Gly Ser Thr Ser
        195                 200                 205

Ser Gly Gly Val Phe Gly Trp Leu Lys Lys Leu Phe Ser
210                 215                 220

<210> SEQ ID NO 72
<211> LENGTH: 221
<212> TYPE: PRT
<213> ORGANISM: Methylovorus sp. MP688

<400> SEQUENCE: 72

Met Ala Leu Asp Ser Leu Asp Phe Asp Ala Thr Val Ala Leu Ala Thr
1               5                   10                  15

Lys Val Ala Pro His Val Asp Ile Leu Glu Ile Gly Thr Pro Cys Ile
            20                  25                  30

Lys Tyr Asn Gly Ile Lys Leu Leu Gln Thr Leu Arg Ala Lys Phe Pro
        35                  40                  45

Asn Asn Lys Ile Leu Val Asp Leu Lys Thr Met Asp Ala Gly Tyr Tyr
50                  55                  60
```

```
Glu Ala Glu Pro Phe Tyr Lys Ala Gly Ala Asp Ile Cys Thr Val Leu
 65                  70                  75                  80

Gly Thr Ala Asp Ile Gly Thr Ile Lys Gly Val Ile Asp Val Ala Asn
                 85                  90                  95

Lys Tyr Gly Lys Glu Ala Gln Ile Asp Leu Ile Asn Val Ala Asp Lys
                100                 105                 110

Ala Ala Arg Thr Lys Glu Val Ala Lys Leu Gly Ala His Ile Ile Gly
            115                 120                 125

Val His Thr Gly Leu Asp Gln Gln Ala Ala Gly Gln Thr Pro Phe Ala
    130                 135                 140

Asp Leu Gly Leu Val Ser Ser Leu Asn Leu Gly Val Lys Val Ser Val
145                 150                 155                 160

Ala Gly Gly Ile Lys Pro Ala Thr Val Lys Gln Val Val Asp Ala Gly
                165                 170                 175

Ala Asn Ile Val Val Ala Gly Ala Ile Tyr Gly Ala Ala Asp Pro
                180                 185                 190

Ala Ala Ala Ala Ala Glu Ile Ser Gly Leu Ala Lys Gly Ser Thr Ser
            195                 200                 205

Ser Gly Gly Val Phe Gly Trp Leu Lys Lys Leu Phe Ser
210                 215                 220

<210> SEQ ID NO 73
<211> LENGTH: 195
<212> TYPE: PRT
<213> ORGANISM: Amycolatopsis methanolica 239

<400> SEQUENCE: 73

Met Thr Lys Ser Leu Ser Arg Lys Leu Asp Ala Asp His Phe Leu Asp
 1               5                  10                  15

Ala Thr Arg Ala Val Val Gly Glu Val Asp Lys Val Arg Ala Gly Val
             20                  25                  30

Asp Ser Pro Ser Trp Ile Arg Ala Ala Glu Leu Leu Leu Glu Ala Pro
         35                  40                  45

His Val Phe Thr Ile Gly Thr Gly Arg Ser Gly Leu Ala Leu Gln Met
     50                  55                  60

Ala Ala Met Arg Phe Met His Leu Gly Leu Ala Thr His Val Val Gly
 65                  70                  75                  80

Glu Thr Thr Ala Pro Ala Ile Gly Ala Arg Asp Val Leu Val Ala Ala
                 85                  90                  95

Ser Gly Ser Gly Lys Thr Ala Arg Val Val Arg Ala Ala Gln Thr Ala
                100                 105                 110

Arg Asp Gln Gly Ala Asp Val Ile Ala Leu Thr Thr Ala Ala Asp Ser
            115                 120                 125

Pro Leu Ala Lys Leu Ala Thr Glu Val Leu Ile Val Pro Ala Ala Asp
    130                 135                 140

Lys Gln Asp Phe Asp Gly Asn Thr Ser Val Gln Tyr Ala Gly Ser Leu
145                 150                 155                 160

Phe Glu Gln Ser Val Leu Leu Ile Thr Asp Ala Leu Phe His Thr Leu
                165                 170                 175

Trp Lys Thr Gly Gly Ser Gln Ala Arg Glu Leu Trp Arg Arg His Ala
                180                 185                 190

Asn Leu Glu
    195

<210> SEQ ID NO 74
```

```
<211> LENGTH: 185
<212> TYPE: PRT
<213> ORGANISM: Geobacillus sp. GHH01

<400> SEQUENCE: 74

Met Gln Ala Thr Gln Tyr Leu Gly Glu Ile Ile Lys Glu Leu Asn Arg
1               5                   10                  15

Thr Ala Asp Leu Ile Ala Ala Gly Glu Ala Glu Lys Leu Val Asn Glu
            20                  25                  30

Ile Leu Lys Ala Lys Lys Ile Phe Val Ala Gly Ala Gly Arg Ser Gly
        35                  40                  45

Phe Met Ser Lys Ser Phe Ala Met Arg Met Met His Met Gly Leu Asp
    50                  55                  60

Ala Tyr Val Val Gly Glu Thr Ile Thr Pro Asn Leu Glu Gln Asp Asp
65                  70                  75                  80

Ile Leu Ile Ile Gly Ser Gly Ser Gly Glu Thr Arg Ser Leu Val Ser
                85                  90                  95

Met Ala Glu Lys Ala Lys Ser Leu Gly Ala Thr Val Ala Leu Val Thr
            100                 105                 110

Ile Phe Pro Glu Ser Thr Ile Gly Gln Leu Ala Asp Ile Thr Val Lys
        115                 120                 125

Leu Pro Gly Ser Pro Lys Asp Gln Ser Asp Asn Gly Tyr Lys Thr Ile
    130                 135                 140

Gln Pro Met Gly Ser Leu Phe Glu Gln Thr Leu Leu Leu Phe Tyr Asp
145                 150                 155                 160

Ala Ile Ile Leu Arg Cys Met Glu Lys Lys Gly Leu Asp Ser Asn Thr
                165                 170                 175

Met Phe Lys Arg His Ala Asn Leu Glu
            180                 185

<210> SEQ ID NO 75
<211> LENGTH: 187
<212> TYPE: PRT
<213> ORGANISM: Geobacillus sp. Y4.1MC1

<400> SEQUENCE: 75

Met Met Met Gln Thr Thr Gln Tyr Leu Gly Glu Ile Leu Gln Glu Leu
1               5                   10                  15

Asn Arg Thr Ala Asp Phe Ile Ala Asp Glu Glu Ala Glu Lys Leu Val
            20                  25                  30

Asn Gly Ile Leu Gln Ala Lys Lys Ile Phe Val Ala Gly Ala Gly Arg
        35                  40                  45

Ser Gly Phe Met Ser Lys Ser Phe Ala Met Arg Met Met His Met Gly
    50                  55                  60

Leu Asp Ala Tyr Val Val Gly Glu Thr Ile Thr Pro Asn Leu Glu Gln
65                  70                  75                  80

Asp Asp Ile Leu Ile Ile Gly Ser Gly Ser Gly Glu Thr Arg Ser Leu
                85                  90                  95

Val Ser Met Ala Glu Lys Ala Lys Ser Leu Gly Ala Thr Ile Ala Leu
            100                 105                 110

Val Thr Ile Phe Pro Ala Ser Thr Ile Gly Lys Leu Ala Asp Ile Thr
        115                 120                 125

Val Lys Leu Pro Gly Ser Pro Lys Asp Gln Ala Asp Asn Gly Tyr Lys
    130                 135                 140

Thr Ile Gln Pro Met Gly Ser Leu Phe Glu Gln Thr Leu Leu Leu Phe
145                 150                 155                 160
```

Tyr Asp Ala Val Ile Leu Arg Cys Met Glu Lys Lys Gly Leu Asp Ser
            165                 170                 175

Asn Thr Met Phe Lys Arg His Ala Asn Leu Glu
            180                 185

<210> SEQ ID NO 76
<211> LENGTH: 183
<212> TYPE: PRT
<213> ORGANISM: Geobacillus thermodenitrificans NG80-2

<400> SEQUENCE: 76

Met Met His Pro Ile Glu Val Ile Phe Ser Glu Ile Glu Gln Val Phe
1               5                   10                  15

Ala Glu Phe Asp His Met Ser Ile Glu Cys Val Ala Met Arg Leu Ala
            20                  25                  30

Lys Ala Lys Arg Ile Phe Val Ala Gly Glu Gly Arg Ser Gly Phe Met
        35                  40                  45

Gly Lys Ala Phe Ala Met Arg Leu Met His Leu Gly Ala Thr Val Tyr
    50                  55                  60

Ala Val Gly Glu Thr Val Thr Pro Ser Leu Gln Ser Gly Asp Thr Leu
65                  70                  75                  80

Ile Ala Ile Ser Gly Ser Gly Val Thr Lys Gln Thr Val Trp Ile Ala
                85                  90                  95

Glu Lys Ala Lys Gln Leu Gly Cys Glu Val Ile Ala Val Thr Thr Asp
            100                 105                 110

Leu Ser Ser Ala Leu Ala Asn Ile Ala Ser Leu Thr Val His Ile Pro
        115                 120                 125

Ala Ala Thr Lys Tyr Arg Arg Gly His Glu Thr Gln Ser Lys Gln Pro
    130                 135                 140

Leu Gly Ser Leu Phe Asp Gln Cys Thr His Leu Ile Leu Asp Ala Ile
145                 150                 155                 160

Cys Leu Gln Tyr Ala Asn Asn Gln Gln Val Gly His Gly Lys Ala Phe
                165                 170                 175

Gln Arg His Ser Asn Leu Glu
            180

<210> SEQ ID NO 77
<211> LENGTH: 181
<212> TYPE: PRT
<213> ORGANISM: Methylomonas aminofaciens PHI

<400> SEQUENCE: 77

Met Asn Lys Tyr Gln Glu Leu Val Val Ser Lys Leu Thr Asn Val Ile
1               5                   10                  15

Asn Asn Thr Ala Glu Gly Tyr Asp Asp Lys Ile Leu Ser Leu Val Asp
            20                  25                  30

Ala Ala Gly Arg Thr Phe Ile Gly Gly Ala Gly Arg Ser Leu Leu Val
        35                  40                  45

Ser Arg Phe Phe Ala Met Arg Leu Val His Ala Gly Tyr Gln Val Ser
    50                  55                  60

Met Val Gly Glu Val Val Thr Pro Ser Ile Gln Ala Gly Asp Leu Phe
65                  70                  75                  80

Ile Val Ile Ser Gly Ser Gly Ser Thr Glu Thr Leu Met Pro Leu Val
                85                  90                  95

Lys Lys Ala Lys Ser Gln Gly Ala Lys Ile Ile Val Ile Ser Met Lys
            100                 105                 110

```
Ala Gln Ser Pro Met Ala Glu Leu Ala Asp Leu Val Val Pro Val Gly
            115                 120                 125

Gly Asn Asp Ala Asn Ala Phe Asp Lys Thr His Gly Met Pro Met Gly
        130                 135                 140

Thr Ile Phe Glu Leu Ser Thr Leu Trp Phe Leu Glu Ala Thr Ile Ala
145                 150                 155                 160

Lys Leu Val Asp Gln Lys Gly Leu Thr Glu Glu Gly Met Arg Ala Ile
                165                 170                 175

His Ala Asn Leu Glu
            180

<210> SEQ ID NO 78
<211> LENGTH: 178
<212> TYPE: PRT
<213> ORGANISM: Methylovorus glucosetrophus SIP3-4

<400> SEQUENCE: 78

Met Asp His Gln Gln Phe Ile Leu Asp Lys Leu Ser Gly Ile Leu Asn
1               5                   10                  15

Val Thr Asp Lys Thr Lys Gly Ala Glu Leu Leu Lys Leu Val Glu Ala
            20                  25                  30

Ala Gly Arg Thr Phe Ile Gly Gly Ala Gly Arg Ser Leu Leu Val Ser
        35                  40                  45

Arg Phe Phe Ala Met Arg Leu Val His Ala Gly Tyr Asn Val Ser Met
    50                  55                  60

Val Gly Glu Val Val Thr Pro Ala Ile Lys Ser Gly Asp Leu Leu Ile
65                  70                  75                  80

Leu Val Ser Gly Ser Gly Gly Thr Glu Thr Leu Leu Pro Phe Val Lys
                85                  90                  95

Lys Ala Lys Ser Leu Gly Ala Lys Leu Val Val Ile Ser Met Lys Lys
            100                 105                 110

Thr Ser Pro Met Ala Asp Ala Ala Asp Leu Val Ile Gln Ile Gly Gln
            115                 120                 125

Asp Asp Ser Phe Pro Leu Thr Lys Gly Met Pro Met Gly Ser Gln Phe
        130                 135                 140

Glu Leu Ser Thr Leu Ile Phe Leu Glu Gly Val Ile Ser Glu Leu Ile
145                 150                 155                 160

His Ala Lys Gly Leu Thr Glu Glu Gly Met Arg Ala Ile His Ala Asn
                165                 170                 175

Leu Glu

<210> SEQ ID NO 79
<211> LENGTH: 178
<212> TYPE: PRT
<213> ORGANISM: Methylovorus sp. MP688

<400> SEQUENCE: 79

Met Asp His Gln Gln Phe Ile Leu Asp Lys Leu Ser Gly Ile Leu Asn
1               5                   10                  15

Val Thr Asp Lys Thr Lys Gly Ala Glu Leu Leu Lys Leu Val Glu Ala
            20                  25                  30

Ala Gly Arg Thr Phe Ile Gly Gly Ala Gly Arg Ser Leu Leu Val Ser
        35                  40                  45

Arg Phe Phe Ala Met Arg Leu Val His Ala Gly Tyr Asn Val Ser Met
    50                  55                  60
```

```
Val Gly Glu Val Val Thr Pro Ala Ile Lys Ser Gly Asp Leu Leu Ile
 65                  70                  75                  80

Leu Val Ser Gly Ser Gly Gly Thr Glu Thr Leu Leu Pro Phe Val Lys
                 85                  90                  95

Lys Ala Lys Ser Leu Gly Ala Lys Leu Val Val Ile Ser Met Lys Lys
            100                 105                 110

Thr Ser Pro Met Ala Asp Ala Ala Asp Leu Val Ile Gln Ile Gly Gln
        115                 120                 125

Asp Asp Ser Phe Pro Leu Thr Lys Gly Met Pro Met Gly Ser Gln Phe
130                 135                 140

Glu Leu Ser Thr Leu Ile Phe Leu Glu Gly Val Ile Ser Glu Leu Ile
145                 150                 155                 160

His Ala Lys Gly Leu Thr Glu Glu Gly Met Arg Ala Ile His Ala Asn
                165                 170                 175

Leu Glu
```

<210> SEQ ID NO 80
<211> LENGTH: 185
<212> TYPE: PRT
<213> ORGANISM: Bacillus methanolicus PB1

<400> SEQUENCE: 80

```
Met Gly Lys Leu Phe Glu Glu Lys Thr Ile Lys Thr Glu Gln Ile Phe
1               5                   10                  15

Ser Gly Arg Val Val Lys Leu Gln Val Asp Asp Val Glu Leu Pro Asn
            20                  25                  30

Gly Gln Thr Ser Lys Arg Glu Ile Val Arg His Pro Gly Ala Val Ala
        35                  40                  45

Val Ile Ala Val Thr Asn Glu Asn Lys Ile Val Met Val Glu Gln Tyr
    50                  55                  60

Arg Lys Pro Leu Glu Lys Ser Ile Val Glu Ile Pro Ala Gly Lys Leu
65                  70                  75                  80

Glu Lys Gly Glu Asp Pro Arg Ile Thr Ala Leu Arg Glu Leu Glu Glu
                85                  90                  95

Glu Thr Gly Tyr Gln Cys Glu Gln Met Glu Trp Leu Ile Ser Phe Ala
            100                 105                 110

Thr Ser Pro Gly Phe Ala Asp Glu Ile Ile His Leu Tyr Val Ala Lys
        115                 120                 125

Gly Leu Ser Lys Lys Glu Asn Ala Ala Gly Leu Asp Glu Asp Glu Phe
    130                 135                 140

Val Asp Leu Ile Glu Leu Thr Leu Glu Glu Ala Leu Gln Tyr Ile Lys
145                 150                 155                 160

Glu Gln Arg Ile Tyr Asp Ser Leu Thr Val Ile Ala Val Gln Tyr Leu
                165                 170                 175

Gln Leu Gln Glu Ala Leu Lys Asn Lys
            180                 185
```

<210> SEQ ID NO 81
<211> LENGTH: 730
<212> TYPE: PRT
<213> ORGANISM: Mycobacter sp. strain JC1 DSM 3803

<400> SEQUENCE: 81

```
Met Arg Pro Pro Glu Ala Asp Glu Pro Lys Gly Arg Asn Arg Asp Ser
1               5                   10                  15

Asp Ser Arg Cys Asp Pro Cys Arg Ala Gln Phe Asp Thr Val Gly Val
```

-continued

```
                20                  25                  30
Glu Leu Asp Asn Arg Gly Pro Ala Cys Arg Gly His Arg Pro Gly Ala
             35                  40                  45
Gly Arg Gly Cys Val Glu Lys Val Gly Asn Gly His Pro Gly Thr Ala
 50                  55                  60
Met Ser Leu Ala Pro Ala Ala Tyr Leu Leu Phe Gln Lys Leu Met Arg
 65                  70                  75                  80
His Asp Pro Arg Asp Pro Asp Trp Val Gly Gly Asp Arg Phe Ile Leu
                 85                  90                  95
Ser Pro Gly His Ser Ser Val Thr Leu Tyr Ile Gln Leu Phe Leu Ala
                100                 105                 110
Gly Tyr Gly Leu Glu Leu Glu Asp Leu Lys Ser Phe Arg Thr Trp Gly
            115                 120                 125
Ser Leu Thr Pro Gly His Pro Glu Tyr Lys His Thr Lys Gly Val Glu
130                 135                 140
Ile Thr Thr Gly Pro Leu Gly Gln Gly Leu Ala Ser Ser Val Gly Phe
145                 150                 155                 160
Ala Tyr Ser Gln Arg Arg Met Arg Gly Leu Leu Asp Pro Asp Ala Ala
                165                 170                 175
Pro Gly Thr Ser Pro Phe Asp His Thr Ile Trp Val Ile Ala Ser Asp
            180                 185                 190
Gly Asp Leu Gln Glu Gly Val Thr Ser Glu Ala Ser Ser Leu Ala Gly
            195                 200                 205
His Gln Glu Leu Gly Asn Leu Val Val Tyr Asp Glu Asn His Ile
            210                 215                 220
Ser Ile Glu Asp Asp Thr Asp Ile Ser Phe Thr Glu Asp Val Leu Gly
225                 230                 235                 240
Arg Tyr Glu Ser Tyr Gly Trp His Val Gln Arg Val Asp Trp Thr Arg
                245                 250                 255
Thr Gly Glu Tyr Arg Glu Asp Val Glu Glu Leu Phe Ala Ala Leu Leu
            260                 265                 270
Ala Arg Arg Lys Pro Arg Ser Arg Pro Ser Phe Val Arg Thr Ile
            275                 280                 285
Ile Gly Tyr Pro Ala Pro Lys Lys Gln Asn Thr Gly Lys Ile His Gly
            290                 295                 300
Ser Ala Leu Gly Ala Glu Glu Val Ala Ala Val Lys Glu Val Leu Gly
305                 310                 315                 320
Phe Asp Pro Ala Lys Ser Phe Asp Val Asp Pro Ala Ile Leu Ala His
                325                 330                 335
Ala Arg Ala Ala Ile Asp Arg Gly Ala Ala Ala Arg Ser Glu Trp Asp
            340                 345                 350
Glu Ser Phe Gln Ser Trp Gln Ala Ala Asn Pro Asp Ala Ala Leu
            355                 360                 365
Leu Arg Arg Ile Glu Ala Arg Gln Leu Pro Asp Gly Val Asp Ala Val
            370                 375                 380
Leu Pro Val Phe Glu Ala Gly Lys Asp Val Ser Thr Arg Ala Ala Ser
385                 390                 395                 400
Gly Lys Val Leu Asn Ala Leu Gly Pro Val Leu Pro Glu Leu Trp Gly
                405                 410                 415
Gly Ser Ala Asp Leu Ala Glu Ser Asn Asn Thr Thr Ile Glu Gly Ser
            420                 425                 430
Pro Ser Phe Ile Pro Val Ser Arg Ser Ala Asn Ala Trp Lys Gly Asn
            435                 440                 445
```

-continued

Pro Tyr Gly Arg Val Leu His Phe Gly Ile Arg Glu Gln Leu Pro Arg
        450                 455                 460

Ser Ile Val Asn Gly Ile Ser Leu His Gly Pro Thr Arg Ala Phe Ser
465                 470                 475                 480

Gly Thr Phe Leu Ile Phe Ser Asp Tyr Gln Arg Pro Ala Ile Arg Leu
                485                 490                 495

Ser Ala Leu Met Gly Val Pro Ser Val Tyr Val Trp Ser His Asp Ser
            500                 505                 510

Ile Gly Leu Gly Glu Asp Gly Pro Thr His Gln Pro Val Glu Gln Leu
        515                 520                 525

Ser Thr Leu Arg Ala Ile Pro Gly Leu Asp Val Val Gly Pro Gly Asp
    530                 535                 540

Ala Asn Glu Val Gly Ile Ala Trp Lys Thr Ile Leu Glu Asn His Glu
545                 550                 555                 560

Asn Pro Ala Gly Val Val Leu Thr Arg Gln Asn Ile Pro Thr Phe Ala
                565                 570                 575

Arg Gly Glu Gly Ala Ala Glu Gly Asp Thr Phe Ala Ser Ala Ala Gly
            580                 585                 590

Val Ala Lys Gly Gly Tyr Val Leu Ala Glu Ala Ser Arg Asp Gly Ala
        595                 600                 605

Thr Val Pro Ala Gln Val Leu Leu Ile Ala Thr Gly Ser Glu Val Gln
    610                 615                 620

Leu Ala Val Gln Ala Arg Glu Ala Leu Gln Ala Glu Gly Ile Pro Thr
625                 630                 635                 640

Arg Val Ile Ser Met Pro Cys Val Glu Trp Phe Asn Lys Gln Asp Ala
                645                 650                 655

Ala Tyr Arg Glu Ser Val Leu Pro Ala Ala Val Thr Ala Arg Val Ser
            660                 665                 670

Val Glu Ala Gly Leu Ala Leu Gly Trp Lys Glu Phe Val Gly Asp Ala
        675                 680                 685

Gly Arg Ser Val Ser Leu Glu His Phe Gly Ala Ser Ala Asp Tyr Lys
    690                 695                 700

Arg Leu Phe Gln Glu Phe Gly Ile Thr Ala Asp Ala Val Val Ala Ala
705                 710                 715                 720

Ala Lys Asp Ser Ile Thr Ala Ala Gly Asn
                725                 730

<210> SEQ ID NO 82
<211> LENGTH: 710
<212> TYPE: PRT
<213> ORGANISM: Ogataea parapolymorpha DL-1

<400> SEQUENCE: 82

Met Ser Met Arg Ile Pro Lys Ala Ala Ser Val Asn Asp Glu Gln His
1               5                   10                  15

Gln Arg Ile Ile Lys Tyr Gly Arg Ala Leu Val Leu Asp Ile Val Glu
            20                  25                  30

Gln Tyr Gly Gly Gly His Pro Gly Ser Ala Met Gly Ala Met Ala Ile
        35                  40                  45

Gly Ile Ala Leu Trp Lys Tyr Thr Leu Lys Tyr Ala Pro Asn Asp Pro
    50                  55                  60

Asn Tyr Phe Asn Arg Asp Arg Phe Val Leu Ser Asn Gly His Val Cys
65                  70                  75                  80

Leu Phe Gln Tyr Ile Phe Gln His Leu Tyr Gly Leu Lys Ser Met Thr

-continued

```
                85                  90                  95
Met Ala Gln Leu Lys Ser Tyr His Ser Asn Asp Phe His Ser Leu Cys
            100                 105                 110

Pro Gly His Pro Glu Ile Glu His Asp Ala Val Glu Val Thr Thr Gly
            115                 120                 125

Pro Leu Gly Gln Gly Ile Ser Asn Ser Val Gly Leu Ala Ile Ala Thr
130                 135                 140

Lys Asn Leu Ala Ala Thr Tyr Asn Lys Pro Gly Phe Asp Ile Ile Thr
145                 150                 155                 160

Asn Lys Val Tyr Cys Met Val Gly Asp Ala Cys Leu Gln Glu Gly Pro
                165                 170                 175

Ala Leu Glu Ser Ile Ser Leu Ala Gly His Met Gly Leu Asp Asn Leu
            180                 185                 190

Ile Val Leu Tyr Asp Asn Asn Gln Val Cys Cys Asp Gly Ser Val Asp
            195                 200                 205

Ile Ala Asn Thr Glu Asp Ile Ser Ala Lys Phe Lys Ala Cys Asn Trp
            210                 215                 220

Asn Val Ile Glu Val Glu Asn Ala Ser Glu Asp Val Ala Thr Ile Val
225                 230                 235                 240

Lys Ala Leu Glu Tyr Ala Gln Ala Glu Lys His Arg Pro Thr Leu Ile
                245                 250                 255

Asn Cys Arg Thr Val Ile Gly Ser Gly Ala Ala Phe Glu Asn His Cys
            260                 265                 270

Ala Ala His Gly Ser Ala Leu Gly Glu Asp Gly Val Arg Glu Leu Lys
            275                 280                 285

Ile Lys Tyr Gly Met Asn Pro Ala Gln Lys Phe Tyr Ile Pro Gln Asp
290                 295                 300

Val Tyr Asp Phe Phe Lys Glu Lys Pro Ala Glu Gly Asp Lys Leu Val
305                 310                 315                 320

Ala Glu Trp Lys Ser Leu Val Ala Lys Tyr Val Lys Glu Tyr Pro Glu
                325                 330                 335

Glu Gly Gln Glu Phe Leu Ala Arg Val Arg Gly Glu Leu Pro Lys Asn
            340                 345                 350

Trp Lys Ser Phe Leu Pro Gln Gln Glu Phe Thr Gly Asp Ala Pro Thr
            355                 360                 365

Arg Ala Ala Arg Glu Leu Val Arg Ala Leu Gly Gln Asn Cys Lys
            370                 375                 380

Ser Val Leu Ala Gly Cys Ala Asp Leu Ser Val Ser Val Asn Leu Gln
385                 390                 395                 400

Trp Pro Gly Val Lys Tyr Phe Met Asp Pro Thr Leu Ser Thr Gln Cys
                405                 410                 415

Gly Leu Ser Gly Asp Tyr Ser Gly Arg Tyr Ile Glu Tyr Gly Ile Arg
            420                 425                 430

Glu His Ala Met Cys Ala Ile Ala Asn Gly Leu Ala Tyr Asn Lys
            435                 440                 445

Gly Thr Phe Leu Pro Ile Thr Ser Thr Phe Phe Met Phe Tyr Leu Tyr
            450                 455                 460

Ala Ala Pro Ala Ile Arg Met Ala Gly Leu Gln Glu Leu Lys Ala Ile
465                 470                 475                 480

His Ile Gly Thr His Asp Ser Ile Asn Glu Gly Glu Asn Gly Pro Thr
                485                 490                 495

His Gln Pro Val Glu Thr Pro Ala Leu Phe Arg Ala Met Pro Asn Ile
            500                 505                 510
```

Tyr Tyr Met Arg Pro Val Asp Ser Ala Glu Val Phe Gly Leu Phe Gln
            515                 520                 525

Lys Ala Val Glu Leu Pro Phe Ser Ser Ile Leu Ser Leu Ser Arg Asn
        530                 535                 540

Glu Val Leu Gln Tyr Pro Gly Gln Ser Ser Ala Glu Lys Ala Gln Arg
545                 550                 555                 560

Gly Gly Tyr Ile Leu Glu Asp Ala Glu Asn Ala Glu Val Gln Ile Ile
                565                 570                 575

Gly Val Gly Ala Glu Met Glu Phe Ala Tyr Lys Ala Ala Lys Ile Leu
                580                 585                 590

Gly Arg Lys Phe Arg Thr Arg Val Leu Ser Ile Pro Cys Thr Arg Leu
                595                 600                 605

Phe Asp Glu Gln Ser Ile Gly Tyr Arg Arg Ser Val Leu Arg Lys Asp
                610                 615                 620

Gly Arg Gln Val Pro Thr Val Val Asp Gly His Val Ala Phe Gly
625                 630                 635                 640

Trp Glu Arg Tyr Ala Thr Ala Ser Tyr Cys Met Asn Thr Tyr Gly Lys
                645                 650                 655

Ser Leu Pro Pro Glu Val Ile Tyr Glu Tyr Phe Gly Tyr Asn Pro Ala
                660                 665                 670

Thr Ile Ala Lys Lys Val Glu Ser Tyr Val Arg Ala Cys Gln Arg Asp
                675                 680                 685

Pro Leu Leu Leu His Asp Phe Leu Asp Leu Lys Glu Lys Pro Lys His
                690                 695                 700

Asp Lys Val Asn Lys Leu
705                 710

<210> SEQ ID NO 83
<211> LENGTH: 706
<212> TYPE: PRT
<213> ORGANISM: Candida boidinii

<400> SEQUENCE: 83

Met Ala Leu Ala Lys Ala Ala Ser Ile Asn Asp Asp Ile His Asp Leu
1               5                   10                  15

Thr Met Arg Ala Phe Arg Cys Tyr Val Leu Asp Leu Val Glu Gln Tyr
                20                  25                  30

Glu Gly Gly His Pro Gly Ser Ala Met Gly Met Val Ala Met Gly Ile
                35                  40                  45

Ala Leu Trp Lys Tyr Thr Met Lys Tyr Ser Thr Asn Asp Pro Thr Trp
        50                  55                  60

Phe Asn Arg Asp Arg Phe Val Leu Ser Asn Gly His Val Cys Leu Phe
65                  70                  75                  80

Gln Tyr Leu Phe Gln His Leu Ser Gly Leu Lys Ser Met Thr Glu Lys
                85                  90                  95

Gln Leu Lys Ser Tyr His Ser Ser Asp Tyr His Ser Lys Cys Pro Gly
                100                 105                 110

His Pro Glu Ile Glu Asn Glu Ala Val Glu Val Thr Thr Gly Pro Leu
                115                 120                 125

Gly Gln Gly Ile Ser Asn Ser Val Gly Leu Ala Ile Ala Ser Lys Asn
                130                 135                 140

Leu Gly Ala Leu Tyr Asn Lys Pro Gly Tyr Glu Val Val Asn Asn Thr
145                 150                 155                 160

Thr Tyr Cys Ile Val Gly Asp Ala Cys Leu Gln Glu Gly Pro Ala Leu

```
                165                 170                 175
Glu Ser Ile Ser Phe Ala Gly His Leu Gly Leu Asp Asn Leu Val Val
                180                 185                 190

Ile Tyr Asp Asn Asn Gln Val Cys Cys Asp Gly Ser Val Asp Ile Ala
                195                 200                 205

Asn Thr Glu Asp Ile Ser Ala Lys Phe Arg Ala Cys Asn Trp Asn Val
            210                 215                 220

Ile Glu Val Glu Asp Gly Ala Arg Asp Val Ala Thr Ile Val Lys Ala
225                 230                 235                 240

Leu Glu Leu Ala Gly Ala Glu Lys Asn Arg Pro Thr Leu Ile Asn Val
                245                 250                 255

Arg Thr Ile Ile Gly Thr Asp Ser Ala Phe Gln Asn His Cys Ala Ala
            260                 265                 270

His Gly Ser Ala Leu Gly Glu Glu Gly Ile Arg Glu Leu Lys Ile Lys
            275                 280                 285

Tyr Gly Phe Asn Pro Ser Gln Lys Phe His Phe Pro Gln Glu Val Tyr
            290                 295                 300

Asp Phe Phe Ser Asp Ile Pro Ala Lys Gly Asp Glu Tyr Val Ser Asn
305                 310                 315                 320

Trp Asn Lys Leu Val Ser Ser Tyr Val Lys Glu Phe Pro Glu Leu Gly
                325                 330                 335

Ala Glu Phe Gln Ser Arg Val Lys Gly Glu Leu Pro Lys Asn Trp Lys
                340                 345                 350

Ser Leu Leu Pro Asn Asn Leu Pro Asn Glu Asp Thr Ala Thr Arg Thr
            355                 360                 365

Ser Ala Arg Ala Met Val Arg Ala Leu Ala Lys Asp Val Pro Asn Val
            370                 375                 380

Ile Ala Gly Ser Ala Asp Leu Ser Val Ser Val Asn Leu Pro Trp Pro
385                 390                 395                 400

Gly Ser Lys Tyr Phe Glu Asn Pro Gln Leu Ala Thr Gln Cys Gly Leu
                405                 410                 415

Ala Gly Asp Tyr Ser Gly Arg Tyr Val Glu Phe Gly Ile Arg Glu His
                420                 425                 430

Cys Met Cys Ala Ile Ala Asn Gly Leu Ala Ala Phe Asn Lys Gly Thr
            435                 440                 445

Phe Leu Pro Ile Thr Ser Ser Phe Tyr Met Phe Tyr Leu Tyr Ala Ala
            450                 455                 460

Pro Ala Leu Arg Met Ala Ala Leu Gln Glu Leu Lys Ala Ile His Ile
465                 470                 475                 480

Ala Thr His Asp Ser Ile Gly Ala Gly Glu Asp Gly Pro Thr His Gln
                485                 490                 495

Pro Ile Ala Gln Ser Ala Leu Trp Arg Ala Met Pro Asn Phe Tyr Tyr
            500                 505                 510

Met Arg Pro Gly Asp Ala Ser Glu Val Arg Gly Leu Phe Glu Lys Ala
            515                 520                 525

Val Glu Leu Pro Leu Ser Thr Leu Phe Ser Leu Ser Arg His Glu Val
            530                 535                 540

Pro Gln Tyr Pro Gly Lys Ser Ser Ile Glu Leu Ala Lys Arg Gly Gly
545                 550                 555                 560

Tyr Val Phe Glu Asp Ala Lys Asp Ala Asp Ile Gln Leu Ile Gly Ala
                565                 570                 575

Gly Ser Glu Leu Glu Gln Ala Val Lys Thr Ala Arg Ile Leu Arg Ser
            580                 585                 590
```

Arg Gly Leu Lys Val Arg Ile Leu Ser Phe Pro Cys Gln Arg Leu Phe
            595                 600                 605

Asp Glu Gln Ser Val Gly Tyr Arg Arg Ser Val Leu Gln Arg Gly Lys
            610                 615                 620

Val Pro Thr Val Val Ile Glu Ala Tyr Val Ala Tyr Gly Trp Glu Arg
625                 630                 635                 640

Tyr Ala Thr Ala Gly Tyr Thr Met Asn Thr Phe Gly Lys Ser Leu Pro
            645                 650                 655

Val Glu Asp Val Tyr Glu Tyr Phe Gly Phe Asn Pro Ser Glu Ile Ser
            660                 665                 670

Lys Lys Ile Glu Gly Tyr Val Arg Ala Val Lys Ala Asn Pro Asp Leu
            675                 680                 685

Leu Tyr Glu Phe Ile Asp Leu Thr Glu Lys Pro Lys His Asp Gln Asn
            690                 695                 700

His Leu
705

<210> SEQ ID NO 84
<211> LENGTH: 325
<212> TYPE: PRT
<213> ORGANISM: Amycolatopsis methanolica 239

<400> SEQUENCE: 84

Met Ser Ala Leu Asn Lys Ile Ala Arg Thr Met Val Ser Asn Arg Arg
1               5                   10                  15

Gly Ile Leu Ala Ala Asp Glu Ser Ile Gly Thr Met Ser Ser Arg Leu
            20                  25                  30

Glu Gln Val Gly Val Glu Pro Thr Glu Glu Asn Arg Arg Val Tyr Arg
        35                  40                  45

Glu Leu Ile Val Thr Thr Pro Arg Leu Ala Asp Ser Ile Ser Gly Val
    50                  55                  60

Ile Leu Ala Asp Glu Thr Phe Arg Gln Lys Leu Ser Asp Gly Arg Thr
65                  70                  75                  80

Phe Pro Gln Tyr Leu Asp Asp Ile Gly Val Leu Ala Gly Ile Lys Val
            85                  90                  95

Asp Thr Gly Ala Lys Pro Leu Ala Gly Ala Pro Gly Glu Lys Val Thr
            100                 105                 110

Glu Gly Leu Asp Gly Leu Arg Glu Arg Val Ala Glu Tyr Val Arg Leu
        115                 120                 125

Gly Ala Thr Phe Ala Lys Trp Arg Ala Val Ile Thr Ile Gly Glu Asn
    130                 135                 140

Thr Pro Thr Asp Arg Ala Val Arg Ala Asn Val His Ala Leu Ala Arg
145                 150                 155                 160

Tyr Ala Gly Leu Cys Gln Glu Gly Gly Leu Val Pro Ile Val Glu Pro
            165                 170                 175

Glu Val Leu Met Asp Gly Ala His Ser Leu Thr Arg Cys Arg Glu Val
            180                 185                 190

Thr Thr Phe Val Leu Gln Val Leu Phe Ala Glu Leu Asp Val Met Glu
        195                 200                 205

Val Glu Leu Asp Gly Ile Val Leu Lys Pro Asn Met Val Val Ala Gly
    210                 215                 220

Ala Asp Ser Pro Glu Gln Pro Ser Val Glu Val Ala Arg Ala Thr
225                 230                 235                 240

Val Glu Thr Leu Arg Ala Thr Val Pro Glu Ser Val Pro Gly Ile Ala

```
                        245                 250                 255
Phe Leu Ser Gly Gly Gln Arg Pro Glu Val Ala Thr Ala His Leu Gly
            260                 265                 270

Ala Met Gln Ser Leu Asp Pro Leu Pro Trp Glu Leu Thr Tyr Ser Phe
            275                 280                 285

Gly Arg Ala Leu Val Gly Pro Ala Leu Glu Thr Trp Arg Gly Asp Asn
            290                 295                 300

Ser Lys Trp Thr Ala Ala Gln Asp Ala Leu Ser Glu Arg Ala Val Ala
305                 310                 315                 320

Asn Ala Ala Ala Arg
                325

<210> SEQ ID NO 85
<211> LENGTH: 284
<212> TYPE: PRT
<213> ORGANISM: Bacillus methanolicus MGA3

<400> SEQUENCE: 85

Met Pro Leu Val Ser Met Lys Asp Met Leu Asn His Gly Lys Glu Asn
1               5                   10                  15

Gly Tyr Ala Val Gly Gln Phe Asn Ile Asn Asn Leu Glu Phe Gly Gln
            20                  25                  30

Ala Ile Leu Gln Ala Ala Glu Glu Lys Ser Pro Val Ile Ile Gly
            35                  40                  45

Val Ser Val Gly Ala Ala Asn Tyr Met Gly Gly Phe Lys Leu Ile Val
        50                  55                  60

Asp Met Val Lys Ser Leu Met Asp Ser Tyr Asn Val Thr Val Pro Val
65                  70                  75                  80

Ala Ile His Leu Asp His Gly Pro Ser Leu Glu Lys Cys Val Gln Ala
                85                  90                  95

Ile His Ala Gly Phe Thr Ser Val Met Ile Asp Gly Ser His Leu Pro
            100                 105                 110

Leu Glu Glu Asn Ile Glu Leu Thr Lys Arg Val Val Glu Ile Ala His
            115                 120                 125

Ser Val Gly Val Ser Val Glu Ala Glu Leu Gly Arg Ile Gly Gly Gln
        130                 135                 140

Glu Asp Asp Val Val Ala Glu Ser Phe Tyr Ala Ile Pro Ser Glu Cys
145                 150                 155                 160

Glu Gln Leu Val Arg Glu Thr Gly Val Asp Cys Phe Ala Pro Ala Leu
                165                 170                 175

Gly Ser Val His Gly Pro Tyr Lys Gly Glu Pro Lys Leu Gly Phe Asp
            180                 185                 190

Arg Met Glu Glu Ile Met Lys Leu Thr Gly Val Pro Leu Val Leu His
            195                 200                 205

Gly Gly Thr Gly Ile Pro Thr Lys Asp Ile Gln Lys Ala Ile Ser Leu
        210                 215                 220

Gly Thr Ala Lys Ile Asn Val Asn Thr Glu Ser Gln Ile Ala Ala Thr
225                 230                 235                 240

Lys Ala Val Arg Glu Val Leu Asn Asn Asp Ala Lys Leu Phe Asp Pro
                245                 250                 255

Arg Lys Phe Leu Ala Pro Ala Arg Glu Ala Ile Lys Glu Thr Ile Lys
            260                 265                 270

Gly Lys Met Arg Glu Phe Gly Ser Ser Gly Lys Ala
            275                 280
```

<210> SEQ ID NO 86
<211> LENGTH: 284
<212> TYPE: PRT
<213> ORGANISM: Bacillus methanolicus PB1

<400> SEQUENCE: 86

Met Pro Leu Val Ser Met Lys Asp Met Leu Asn Arg Gly Lys Glu Asn
1               5                   10                  15

Gly Tyr Ala Val Gly Gln Phe Asn Ile Asn Asn Leu Glu Phe Gly Gln
            20                  25                  30

Ala Ile Leu Gln Ala Ala Glu Glu Lys Ser Pro Val Ile Ile Gly
        35                  40                  45

Val Ser Val Gly Ala Ala Asn Tyr Met Gly Gly Phe Lys Leu Ile Val
    50                  55                  60

Asp Met Val Lys Ser Leu Met Asp Ala Tyr Asn Val Thr Val Pro Val
65                  70                  75                  80

Ala Ile His Leu Asp His Gly Pro Ser Leu Glu Lys Cys Val Gln Ala
                85                  90                  95

Ile His Ala Gly Phe Thr Ser Val Met Ile Asp Gly Ser His Leu Pro
            100                 105                 110

Leu Glu Glu Asn Ile Glu Leu Thr Lys Arg Val Val Glu Ile Ala His
        115                 120                 125

Ala Val Gly Val Ser Val Glu Ala Glu Leu Gly Arg Ile Gly Gly Gln
    130                 135                 140

Glu Asp Asp Val Ala Glu Ser Phe Tyr Ala Val Pro Ser Glu Cys
145                 150                 155                 160

Glu Gln Leu Val Arg Glu Thr Gly Val Asp Cys Phe Ala Pro Ala Leu
                165                 170                 175

Gly Ser Val His Gly Pro Tyr Lys Gly Glu Pro Asn Leu Gly Phe Asp
            180                 185                 190

Arg Met Lys Glu Ile Met Glu Leu Thr Gly Val Pro Leu Val Leu His
        195                 200                 205

Gly Gly Thr Gly Ile Pro Thr Lys Asp Ile Gln Lys Ala Ile Ser Leu
    210                 215                 220

Gly Thr Ala Lys Ile Asn Val Asn Thr Glu Ser Gln Ile Ala Ala Thr
225                 230                 235                 240

Lys Ala Val Arg Glu Val Leu Asn Asn Asp Ala Lys Leu Phe Asp Pro
                245                 250                 255

Arg Lys Phe Leu Thr Pro Ala Arg Glu Ala Ile Lys Glu Thr Ile Lys
            260                 265                 270

Gly Lys Met Arg Glu Phe Gly Ser Ser Gly Lys Ala
        275                 280

<210> SEQ ID NO 87
<211> LENGTH: 287
<212> TYPE: PRT
<213> ORGANISM: Geobacillus thermodenitrificans NG80-2

<400> SEQUENCE: 87

Met Pro Leu Val Ser Met Lys Glu Met Leu Asn Glu Ala Leu Arg Gly
1               5                   10                  15

Lys Tyr Ala Val Gly Gln Phe Asn Ile Asn Asn Leu Glu Trp Thr Gln
            20                  25                  30

Ala Ile Leu Ala Ala Ala Glu Glu Glu Lys Ser Pro Val Ile Leu Gly
        35                  40                  45

Val Ser Glu Gly Ala Ala Arg Tyr Met Gly Gly Phe Lys Thr Val Val
    50                  55                  60

Asn Met Val Lys Gly Leu Met Glu Asp Met Asn Ile Thr Val Pro Val
65                  70                  75                  80

Ala Ile His Leu Asp His Gly Ser Ser Phe Glu Lys Cys Lys Ala Ala
                85                  90                  95

Ile Asp Ala Gly Phe Thr Ser Val Met Ile Asp Ala Ser His His Pro
            100                 105                 110

Phe Glu Glu Asn Val Arg Ile Thr Ser Gln Val Val Glu Tyr Ala His
            115                 120                 125

Ala Arg Gly Val Ser Val Glu Ala Glu Leu Gly Ile Val Gly Gly Gln
130                 135                 140

Glu Asp Asp Val Ile Gly Glu Gly Val Ile Tyr Ala Asp Pro Lys Glu
145                 150                 155                 160

Cys Glu Glu Leu Val Lys Arg Thr Gly Ile Asp Cys Leu Ala Pro Ala
                165                 170                 175

Leu Gly Ser Val His Gly Pro Tyr Lys Gly Glu Pro Lys Leu Gly Phe
            180                 185                 190

Ala Glu Met Glu Gln Ile Arg Asp Leu Thr Gly Ile Pro Leu Val Leu
        195                 200                 205

His Gly Gly Thr Gly Ile Pro Thr Glu Gln Ile Gln Arg Ala Ile Ser
    210                 215                 220

Leu Gly Thr Ser Lys Ile Asn Val Asn Thr Glu Asn Gln Ile Ala Phe
225                 230                 235                 240

Thr Lys Val Val Arg Glu Leu Leu Ala Lys Asp Ala Asn Val Tyr Asp
                245                 250                 255

Pro Arg Lys Ile Ile Gly Pro Gly Arg Asp Ala Ile Lys Ala Thr Val
            260                 265                 270

Ile Gly Lys Met Arg Glu Phe Gly Ser Ser Gly Lys Ala Ala Gln
        275                 280                 285

<210> SEQ ID NO 88
<211> LENGTH: 295
<212> TYPE: PRT
<213> ORGANISM: Geobacillus thermodenitrificans NG80-2

<400> SEQUENCE: 88

Met Pro Leu Val Ser Met Lys Glu Met Leu Gln Cys Ala Leu Gln Gly
1               5                   10                  15

Asn Tyr Ala Val Gly His Phe Asn Val Asn Asn Leu Glu Phe Ala Gln
            20                  25                  30

Ala Ile Leu Leu Gly Ala Glu Glu Glu Ala Pro Val Ile Leu Ala
        35                  40                  45

Val Ser Pro Gly Tyr Ile Gly His Leu Gly Gly Leu Arg Thr Ala Ala
    50                  55                  60

Ala Met Val Lys Glu Leu Val Lys Glu Tyr Arg Ile Thr Val Pro Val
65                  70                  75                  80

Ala Leu His Leu Asp His Gly Ser Ser Tyr Glu Gln Cys Leu Glu Ala
                85                  90                  95

Met Glu Ala Gly Phe Thr Ser Val Met Ile Asp Ala Ser His Phe Pro
            100                 105                 110

Leu Glu Glu Asn Ile Ser Met Thr Lys Lys Val Val Glu Ala Ala Arg
        115                 120                 125

Phe Phe Gly Val Ser Val Glu Ala Glu Val Gly Arg Ile Gly Gly Gln
130                 135                 140

Glu Asp Asp Val Val Asp Glu Ala Glu Ala Met Tyr Ala Ile Pro
145                 150                 155                 160

Glu Glu Cys Glu Arg Leu Val Lys Glu Thr Gly Val Asp Cys Leu Ala
                165                 170                 175

Pro Ala Leu Gly Ser Val His Gly Pro Tyr Lys Gly Lys Pro Lys Leu
            180                 185                 190

Gly Phe Ala Gln Met Glu Gln Ile Gln Arg Leu Thr Gly Val Pro Leu
            195                 200                 205

Val Leu His Gly Gly Thr Gly Ile Pro Leu Glu Asp Ile Arg Arg Ala
210                 215                 220

Ile Ser Leu Gly Thr Ala Lys Ile Asn Val Asn Thr Glu Asn Gln Leu
225                 230                 235                 240

Ala Phe Thr Arg Gly Val Arg Ser Leu Leu Asn Glu Asn Asn Gly Leu
            245                 250                 255

Tyr Asp Pro Arg Lys Tyr Leu Gly Ala Gly Arg Glu Glu Val Lys Gln
            260                 265                 270

Thr Val Arg Gln Lys Ile Arg Glu Phe Gly Ser Val Gly Lys Ala Lys
            275                 280                 285

Glu Gly Val Leu Ser Ser Leu
    290                 295

<210> SEQ ID NO 89
<211> LENGTH: 344
<212> TYPE: PRT
<213> ORGANISM: Methylophilus methylotrophus

<400> SEQUENCE: 89

Met Ala Leu Ile Ser Leu Arg Gln Leu Leu Asp His Ala Ala Glu His
1               5                   10                  15

Ser Tyr Gly Tyr Pro Ala Phe Asn Ile Asn Asn Met Glu Gln Ile Leu
            20                  25                  30

Ser Ile Met Lys Ala Ala Asp Glu Val Asp Ser Ala Val Ile Leu Gln
        35                  40                  45

Ala Ser Ala Gly Ala Arg Gly Tyr Ala Gly Glu Ser Phe Leu Arg Lys
50                  55                  60

Met Val Glu Ala Ala Ile Glu Gln Tyr Pro His Ile Pro Val Cys Met
65                  70                  75                  80

His Gln Asp His Gly Thr Ser Pro Lys Ile Cys Gln Met Ala Ile Arg
                85                  90                  95

Ser Gly Phe Ser Ser Val Met Met Asp Gly Ser Leu Lys Glu Asp His
            100                 105                 110

Lys Thr Pro Ala Ser Tyr Asp Tyr Asn Val Asp Val Thr Arg Arg Val
        115                 120                 125

Val Glu Phe Ala His Ala Val Gly Val Ser Val Glu Gly Glu Leu Gly
130                 135                 140

Val Leu Gly Ser Leu Glu Thr Gly Met Ala Gly Glu Glu Asp Gly Val
145                 150                 155                 160

Gly Ala Glu Gly Lys Leu Asp Glu Ser Gln Leu Leu Thr Asp Pro Asp
            165                 170                 175

Glu Ala Ala Ala Phe Val Glu Ala Thr Lys Val Asp Ala Leu Ala Ile
            180                 185                 190

Ala Ile Gly Thr Ser His Gly Ala Tyr Lys Phe Thr Arg Pro Pro Ser
        195                 200                 205

Ala Asp Thr Leu Ser Ile Glu Arg Ile Arg Glu Ile His Ala Lys Ile

```
                    210                 215                 220
Pro Asn Thr His Leu Val Met His Gly Ser Ser Val Pro Gln Ser
225                 230                 235                 240

Leu Leu Glu Gln Ile Arg His Tyr Gly Gly Asn Ile Lys Glu Thr Tyr
                    245                 250                 255

Gly Val Pro Val Ser Gln Ile Val Glu Gly Ile Lys Asn Gly Val Arg
                260                 265                 270

Lys Val Asn Ile Asp Thr Asp Ile Arg Leu Ala Met Thr Ala Ala Ile
            275                 280                 285

Arg Ala His Leu Ala Glu Tyr Pro Glu Gln Phe Asp Pro Arg Gln Tyr
        290                 295                 300

Phe Lys Glu Ala Thr Ile Ala Ala Gln His Leu Cys Lys Glu Arg Phe
305                 310                 315                 320

Glu Ala Phe Gly Ser Ala Gly Gln Ala Ser Lys Ile Lys Val Val Pro
                325                 330                 335

Leu Glu Lys Met Ala Ala Ile Tyr
                340

<210> SEQ ID NO 90
<211> LENGTH: 285
<212> TYPE: PRT
<213> ORGANISM: Bacillus methanolicus MGA3

<400> SEQUENCE: 90

Met Pro Leu Val Ser Met Thr Glu Met Leu Asn Lys Ala Lys Ala Glu
1               5                   10                  15

Gly Tyr Ala Val Gly Gln Phe Asn Leu Asn Asn Leu Glu Phe Thr Gln
            20                  25                  30

Ala Ile Leu Leu Ala Ala Glu Glu Lys Ser Pro Val Ile Leu Gly
        35                  40                  45

Val Ser Glu Gly Ala Gly Arg Tyr Met Gly Gly Phe Lys Thr Val Val
    50                  55                  60

Asn Met Val Lys Gly Leu Met Glu Asp Tyr Lys Ile Thr Val Pro Val
65                  70                  75                  80

Ala Ile His Leu Asp His Gly Ser Ser Phe Glu Lys Cys Lys Glu Val
                85                  90                  95

Ile Asp Ala Gly Phe Thr Ser Val Met Ile Asp Ala Ser His His Pro
            100                 105                 110

Phe Glu Glu Asn Val Glu Val Thr Lys Lys Val Val Glu Tyr Ala His
        115                 120                 125

Ala Arg Gly Val Ser Val Glu Ala Leu Gly Thr Val Gly Gly Gln
    130                 135                 140

Glu Asp Asp Val Ile Ala Asp Gly Val Ile Tyr Ala Asp Pro Lys Glu
145                 150                 155                 160

Cys Glu Glu Leu Val Lys Arg Thr Gly Ile Asp Cys Leu Ala Pro Ala
                165                 170                 175

Leu Gly Ser Val His Gly Pro Tyr Lys Gly Glu Pro Asn Leu Gly Phe
            180                 185                 190

Lys Glu Met Glu Glu Ile Gly Arg Ile Thr Gly Val Pro Leu Val Leu
        195                 200                 205

His Gly Gly Thr Gly Ile Pro Thr Lys Asp Ile Gln Arg Ala Ile Ser
    210                 215                 220

Leu Gly Thr Ala Lys Ile Asn Val Asn Thr Glu Asn Gln Ile Ala Ser
225                 230                 235                 240
```

```
Ala Lys Lys Val Arg Glu Val Leu Ala Glu Asn Pro Asn Met Tyr Asp
                245                 250                 255

Pro Arg Lys Tyr Leu Gly Pro Ala Arg Asp Ala Ile Lys Glu Thr Val
                260                 265                 270

Ile Gly Lys Met Arg Glu Phe Gly Ser Ser Gly Lys Ala
                275                 280             285

<210> SEQ ID NO 91
<211> LENGTH: 8
<212> TYPE: PRT
<213> ORGANISM: Artificial Sequence
<220> FEATURE:
<223> OTHER INFORMATION: linker

<400> SEQUENCE: 91

Gly Gly Ser Gly Ser Gly Gly Ser
1               5
```